(12) United States Patent
Fan et al.

(10) Patent No.: US 12,325,696 B2
(45) Date of Patent: Jun. 10, 2025

(54) INDAZOLE DERIVATIVE, PREPARATION METHOD THEREFOR, AND PHARMACEUTICAL APPLICATION THEREOF

(71) Applicants: JIANGSU HENGRUI MEDICINE CO., LTD., Lianyungang (CN); SHANGHAI HENGRUI PHARMACEUTICAL CO., LTD., Shanghai (CN)

(72) Inventors: Xing Fan, Shanghai (CN); Fanglong Yang, Shanghai (CN); Jingjing Yan, Shanghai (CN); Xiao Wu, Shanghai (CN); Feng He, Shanghai (CN); Weikang Tao, Shanghai (CN)

(73) Assignees: JIANGSU HENGRUI MEDICINE CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 725 days.

(21) Appl. No.: 17/618,767

(22) PCT Filed: Jun. 18, 2020

(86) PCT No.: PCT/CN2020/096744
§ 371 (c)(1),
(2) Date: Dec. 13, 2021

(87) PCT Pub. No.: WO2020/253762
PCT Pub. Date: Dec. 24, 2020

(65) Prior Publication Data
US 2022/0267304 A1    Aug. 25, 2022

(30) Foreign Application Priority Data
Jun. 19, 2019    (CN) .......................... 201910530981.3

(51) Int. Cl.
| C07D 401/14 | (2006.01) |
| C07D 401/06 | (2006.01) |
| C07D 405/14 | (2006.01) |
| C07D 413/14 | (2006.01) |

(52) U.S. Cl.
CPC ......... *C07D 401/14* (2013.01); *C07D 401/06* (2013.01); *C07D 405/14* (2013.01); *C07D 413/14* (2013.01)

(58) Field of Classification Search
CPC .. C07D 401/14; C07D 401/06; C07D 405/14; C07D 413/14; A61K 31/416; A61K 31/4439; A61K 31/4545; A61K 31/5377; A61P 35/00
See application file for complete search history.

(56) References Cited

U.S. PATENT DOCUMENTS

| 2016/0347717 A1 | 12/2016 | Bock et al. |
| 2018/0141913 A1 | 5/2018 | Bock et al. |

FOREIGN PATENT DOCUMENTS

| WO | 201196342 A1 | 12/2016 | |
| WO | 2016196346 A1 | 12/2016 | |
| WO | 2018098251 A1 | 5/2018 | |
| WO | 2018098305 A1 | 5/2018 | |
| WO | WO-2018091153 A1 * | 5/2018 | ......... A61K 31/4025 |

OTHER PUBLICATIONS

Yeo HL, Song YS, Ryu JH, Kim HD. Design, synthesis, and biological evaluation of cyclopropyl analogues of stilbene with raloxifene side chain as subtype-selective ligands for estrogen receptor. Arch Pharm Res. Sep. 2013;36(9):1096-103. doi: 10.1007/s12272-013-0134-2. Epub Apr. 24, 2013. PMID: 23613312. (Year: 2013).*

(Continued)

*Primary Examiner* — Joseph K McKane
*Assistant Examiner* — Annie Grace Kuckla
(74) *Attorney, Agent, or Firm* — Morgan, Lewis & Bockius LLP

(57) ABSTRACT

An indazole derivative, a preparation method therefor, and a pharmaceutical application thereof. In particular, the present invention relates to an indazole derivative represented by general formula (I), a preparation method therefor, a pharmaceutical composition comprising the derivative, and a use of the derivative as an estrogen receptor modulator in the prevention and/or treatment of an estrogen receptor mediated or dependent disease or condition, the disease being particularly preferably breast cancer. The definition of each substituent in the general formula (I) is the same as that in the description.

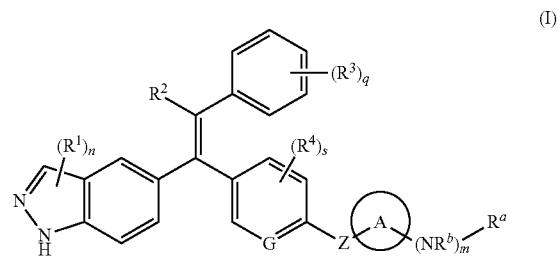

20 Claims, No Drawings
Specification includes a Sequence Listing.

(56) References Cited

OTHER PUBLICATIONS

Lindsey A. Torre, MSPH et al., Global Cancer Statistics, 2012, CA Cancer J Clin, Mar./Apr. 2015, pp. 87-108, vol. 65, No. 2 (22 pages).
Hitisha K. Patel et al., Selective estrogen receptor modulators (SERMs) and selective estrogen receptor degraders (SERDs) in cancer treatment, Pharmacology & Therapeutics 186, Dec. 28, 2017, pp. 1-24, Elsevier Inc., U.S. (24 pages).
Rinath Jeselsohn et al., ESR1 mutations—a mechanism for acquired endocrine resistance in breast cancer, Nature Reviews Clinical Oncology, Jun. 30, 2015, pp. 1-11, 2015 Macmillan Publishers Limited, U.S. (11 pages).
Weiyi Toy et al., ESR1 ligand-binding domain mutations in hormone-resistant breast cancer, Nature Genetics, Dec. 2013, vol. 45, No. 12, pp. 1439-1447, Nature America, Inc., U.S. (9 pages).
Xiaoling Puyang et al., Discovery of Selective Estrogen Receptor Covalent Antagonists for the Treatment of ERαWT and ERαMUT Breast Cancer, American Association for Cancer Research, Jul. 10, 2018, pp. 1176-1194, U.S. (19 pages).
Steven P. Govek et al, Optimization of an indazole series of selective estrogen receptor degraders: Tumor regression in a tamoxifen-resistant breast cancer xenograft, Bioorganic & Medicinal Chemistry Letters 25, Oct. 15, 2015, pp. 5163-5167, Elsevier Inc., U.S. (5 pages).

\* cited by examiner

SEQUENCE LISTING

```
<160> NUMBER OF SEQ ID NOS: 4

<210> SEQ ID NO 1
<211> LENGTH: 39
<212> TYPE: DNA
<213> ORGANISM: Artificial sequence
<220> FEATURE:
<223> OTHER INFORMATION: Synthetic Sequence_vY537S-F

<400> SEQUENCE: 1
aagaacgtgg tgcccctctc tgacctgctg ctggagatg                    39

<210> SEQ ID NO 2
<211> LENGTH: 39
<212> TYPE: DNA
<213> ORGANISM: Artificial sequence
<220> FEATURE:
<223> OTHER INFORMATION: Synthetic Sequence_Y537S-R

<400> SEQUENCE: 2
catctccagc agcaggtcag agaggggcac cacgttctt                    39

<210> SEQ ID NO 3
<211> LENGTH: 39
<212> TYPE: DNA
<213> ORGANISM: Artificial sequence
<220> FEATURE:
<223> OTHER INFORMATION: Synthetic Sequence_D538G-F

<400> SEQUENCE: 3
aacgtggtgc ccctctatgg cctgctgctg gagatgctg                    39

<210> SEQ ID NO 4
<211> LENGTH: 39
<212> TYPE: DNA
<213> ORGANISM: Artificial sequence
<220> FEATURE:
<223> OTHER INFORMATION: Synthetic Sequence_D538G-R

<400> SEQUENCE: 4
cagcatctcc agcagcaggc catagagggg caccacgtt                    39
```

INDAZOLE DERIVATIVE, PREPARATION METHOD THEREFOR, AND PHARMACEUTICAL APPLICATION THEREOF

CROSS-REFERENCE TO RELATED APPLICATIONS

The present application is the national stage of International Patent Application No. PCT/CN2020/096744, filed on Jun. 18, 2020, which claims the benefit of and priority to Chinese Patent Application No. CN201910530981.3 filed on Jun. 19, 2019.

SEQUENCE LISTING

The instant application contains a Sequence Listing which has been submitted electronically in ASCII format and is hereby incorporated by reference in its entirety. Said ASCII copy, created on Jun. 19, 2019, is named "702056CPUS_126268-5028-US_Sequence_Listing.TXT" and is 2 kilobytes in size.

TECHNICAL FIELD

The present disclosure belongs to the field of medicine, and relates to an indazole derivative, a method for preparing the same, and a use thereof in medicine. The present disclosure discloses a use of the indazole derivative as an estrogen receptor modulator for preventing and/or treating estrogen receptor-mediated or estrogen receptor-dependent disease or disorder, wherein the disease is particularly preferably breast cancer.

BACKGROUND

Breast cancer is one of the most common malignant tumors in women. According to GLOBALCAN statistics in 2012 (CA CANCER J CLIN 2015; 65:87-108), there are approximately 1.7 million new cases and 520,000 deaths in the world each year. Regardless of morbidity and mortality, breast cancer ranks first among female malignancies. According to the China Cancer Registry Annual Report (2017) released by the National Cancer Center of China, breast cancer ranks first in the incidence of female malignant tumors, with about 279,000 new cases each year, and an annual increase of about 2%.

About 70% of breast cancer patients are suffered from estrogen receptor (ER)-positive breast cancer. Among the therapies for these breast cancer patients, endocrine therapy occupies an important position. There are three main types of endocrine therapy, that is, aromatase inhibitor (AI), which can inhibit the conversion of androgens into estrogen and reduce the level of estrogen in the body; selective estrogen receptor modulator (SERM), which antagonizes the activity of estrogen receptor; and selective estrogen receptor degrader (SERD), which can not only antagonize the activity of estrogen receptor, but also promote the degradation of the receptor (Pharmacol Ther. Dec. 28, 2017). Although endocrine therapy is the first choice for estrogen receptor-positive breast cancer, about 30% of patients receiving adjuvant therapy will relapse, and almost all patients with metastatic breast cancer will develop resistance and progress. There are two main types of mechanisms for the resistance to endocrine therapy. One type of mechanism focuses on the estrogen receptor signaling pathway itself, including activating mutation and amplification of the ESR1 gene encoding estrogen receptor, fusion of the ESR1 gene encoding estrogen receptor with other genes, disturbance of estrogen receptor co-mediating factor and downstream factors that control cell cycle, etc. Another type of mechanism includes activation of signaling pathways that cross-react with the estrogen receptor signaling pathway, such as the growth factor receptor pathway (Nat Rev Clin Oncol. 2015 October; 12(10):573-83).

Two studies carried out in 2013 showed that ESR1 gene mutation was found in 11 to 55% of estrogen receptor-positive metastatic breast cancer patients who have received aromatase inhibitor therapy. Further studies found that the mutant receptor can be phosphorylated independently of estrogen and provide a transcription effect, so that the tumor inoculated with estrogen-dependent MCF7 can grow in the body without relying on estrogen. Moreover, the mutated receptor will reduce the activity of SERM tamoxifen and SERD fulvestrant. Therefore, ESR1 gene mutation may be one of the mechanisms of drug resistance in estrogen receptor-positive breast cancer (Nat Rev Clin Oncol. 2015 October; 12(10):573-83 and Nat Genet 2013; 45:1439-45). In subsequent studies, a certain proportion of ESR1 gene mutations were found in patients with estrogen receptor-positive metastatic breast cancer, and the mutation proportion was about 30%. In the BOLERO-2 clinical trial, ER Y537S and ER D538G mutations were found in the ctDNA of 29% of patients with estrogen receptor-positive metastatic breast cancer who progressed after AIs treatment. In the exemestane-only group, the progression free survival (PFS) and overall survival (OS) of patients with mutations were shorter than those of patients without mutations (Nat Genet 2013; 45:1446-51).

In summary, ESR1 gene mutation mostly occurs in patients with metastatic estrogen receptor-positive breast cancer who have progressed after AIs treatment. These patients are no longer sensitive to AIs treatment. Therefore, there is a need to develop estrogen receptor antagonists that target ESR1 gene mutation.

The first-in-class estrogen receptor covalent binding antagonist H3B-6545 developed by Eisai has strong inhibitory activity on wild-type and mutant estrogen receptors, and can exert a prolonged efficacy by covalently binding with the receptor. It is currently undergoing phase I and II clinical trials. Currently published patent applications related to estrogen receptor antagonists targeting ESR1 gene mutation include WO2016196346 and WO2016196342.

SUMMARY OF THE INVENTION

The object of the present disclosure is to provide a compound of formula (I) or a tautomer, mesomer, racemate, enantiomer, diastereomer thereof, or mixture thereof, or a pharmaceutically acceptable salt thereof:

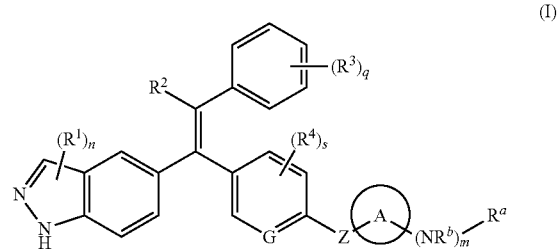

wherein:

G is CH or N;

Z is selected from the group consisting of a bond, $CR^5R^6$, —O—$(CH_2)t$- and —$NR^7$—$(CH_2)t$-;

ring A is selected from the group consisting of cycloalkyl and heterocyclyl;

$R^a$ is selected from the group consisting of —$CH_2CH$=$CHC(O)NR^8R^9$, —$C(O)CH$=$CR^{10}R^{11}$ and —$C(O)C$≡$CR^{12}$;

$R^b$ is selected from the group consisting of hydrogen atom and alkyl;

each $R^1$ is identical or different and each is independently selected from the group consisting of hydrogen atom, halogen, alkyl, haloalkyl, hydroxyalkyl, cycloalkyl, heterocyclyl, aryl and heteroaryl;

$R^2$ is selected from the group consisting of hydrogen atom, halogen, alkyl, haloalkyl, alkoxy, amino, cyano, nitro, carboxy, formyl, hydroxy, hydroxyalkyl, cycloalkyl, aryl and heteroaryl;

each $R^3$ is identical or different and each is independently selected from the group consisting of hydrogen atom, halogen, alkyl, haloalkyl, alkoxy, cyano, amino, nitro, carboxy, formyl, hydroxy, hydroxyalkyl, $NR^{13}C(O)R^{14}$, $C(O)NR^{13}R^{14}$, $SO_2R^{15}$, cycloalkyl, heterocyclyl, aryl and heteroaryl;

each $R^4$ is identical or different and each is independently selected from the group consisting of hydrogen atom, halogen, alkyl, haloalkyl, alkoxy, cyano, amino, nitro, carboxy, formyl, hydroxy, hydroxyalkyl, cycloalkyl, heterocyclyl, aryl and heteroaryl;

$R^5$ and $R^6$ are identical or different and are each independently selected from the group consisting of hydrogen atom, halogen, alkyl, haloalkyl, alkoxy, cyano, amino, nitro, carboxy, formyl, hydroxy, hydroxyalkyl, cycloalkyl, heterocyclyl, aryl and heteroaryl;

$R^7$ is selected from the group consisting of hydrogen atom, alkyl, haloalkyl, hydroxyalkyl, cycloalkyl, heterocyclyl, aryl and heteroaryl;

$R^8$ and $R^9$ are identical or different and are each independently selected from the group consisting of hydrogen atom, alkyl, haloalkyl, hydroxyalkyl, cycloalkyl, heterocyclyl, aryl and heteroaryl;

or, $R^8$ and $R^9$ together with the nitrogen atom to which they are attached form a heterocyclyl, wherein the heterocyclyl optionally contains one to two identical or different heteroatoms selected from the group consisting of N, O and S in addition to the said nitrogen atom, and the said heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

$R^{10}$ and $R^{11}$ are identical or different and are each independently selected from the group consisting of hydrogen atom, halogen, alkyl, haloalkyl, alkoxy, cyano, amino, nitro, carboxy, formyl, hydroxy, hydroxyalkyl, cycloalkyl, heterocyclyl, aryl and heteroaryl;

$R^{12}$ is selected from the group consisting of hydrogen atom, alkyl, haloalkyl, hydroxyalkyl, cycloalkyl, heterocyclyl, aryl and heteroaryl;

$R^{13}$ and $R^{14}$ are identical or different and are each independently selected from the group consisting of hydrogen atom, halogen, alkyl, haloalkyl, alkoxy, cyano, amino, nitro, carboxy, formyl, hydroxy, hydroxyalkyl, cycloalkyl, heterocyclyl, aryl and heteroaryl;

$R^{15}$ is selected from the group consisting of hydrogen atom, alkyl, haloalkyl, hydroxyalkyl, cycloalkyl, heterocyclyl, aryl and heteroaryl;

m is 0 or 1;

n is 0, 1, 2 or 3;

q is 0, 1, 2, 3, 4 or 5;

s is 0, 1, 2 or 3; and t is 0, 1, 2, 3, 4, 5 or 6.

In a preferred embodiment of the present disclosure, in the compound of formula (I) or the tautomer, mesomer, racemate, enantiomer, diastereomer thereof, or mixture thereof, or the pharmaceutically acceptable salt thereof, ring A is selected from the group consisting of $C_3$-$C_6$ cycloalkyl and 3 to 6 membered heterocyclyl, wherein the heterocyclyl contains one to three heteroatoms selected from the group consisting of N, O and S.

In another preferred embodiment of the present disclosure, in the compound of formula (I) or the tautomer, mesomer, racemate, enantiomer, diastereomer thereof, or mixture thereof, or the pharmaceutically acceptable salt thereof, ring A is selected from the group consisting of cyclopropyl, cyclopentyl, cyclohexyl, tetrahydropyrrolyl and piperidinyl.

In another preferred embodiment of the present disclosure, in the compound of formula (I) or the tautomer, mesomer, racemate, enantiomer, diastereomer thereof, or mixture thereof, or the pharmaceutically acceptable salt thereof, ring A is selected from the group consisting of

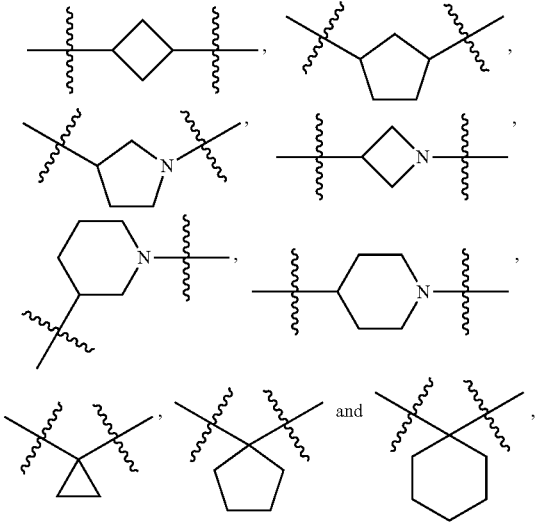

and, and preferably selected from the group consisting of

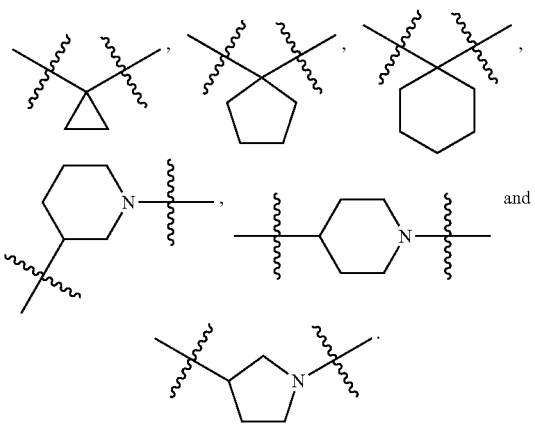

In a preferred embodiment of the present disclosure, the compound of formula (I) or the tautomer, mesomer, racemate, enantiomer, diastereomer thereof, or mixture thereof, or the pharmaceutically acceptable salt thereof is a compound of formula (II) or a tautomer, mesomer, racemate, enantiomer, diastereomer thereof, or mixture thereof, or a pharmaceutically acceptable salt thereof:

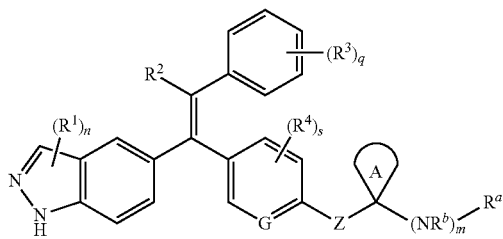

(II)

wherein
ring A, G, Z, $R^1$, $R^2$, $R^3$, $R^4$, $R^a$, $R^b$, n, m, s and q are as defined in formula (I).

In another preferred embodiment of the present disclosure, the compound of formula (I) or the tautomer, mesomer, racemate, enantiomer, diastereomer thereof, or mixture thereof, or the pharmaceutically acceptable salt thereof, is a compound of formula (III) or a tautomer, mesomer, racemate, enantiomer, diastereomer thereof, or mixture thereof, or a pharmaceutically acceptable salt thereof:

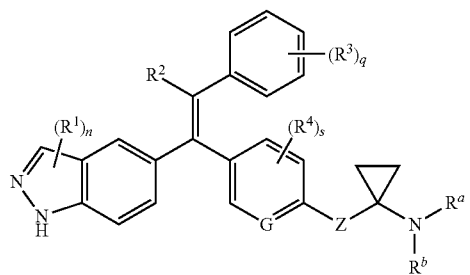

(III)

wherein: G, Z, $R^1$, $R^2$, $R^3$, $R^4$, $R^a$, $R^b$, n, m, s and q are as defined in formula (I).

In another preferred embodiment of the present disclosure, the compound of formula (I) or the tautomer, mesomer, racemate, enantiomer, diastereomer thereof, or mixture thereof, or the pharmaceutically acceptable salt thereof, is a compound of formula (IV) or a tautomer, mesomer, racemate, enantiomer, diastereomer thereof, or mixture thereof, or a pharmaceutically acceptable salt thereof:

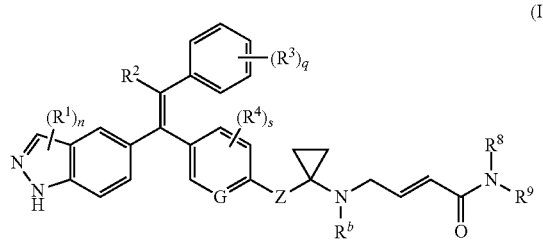

(IV)

wherein:
G, Z, $R^1$, $R^2$, $R^3$, $R^4$, $R^8$, $R^9$, $R^b$, n, s and q are as defined in formula (I); preferably, $R^8$ and $R^9$ together with the nitrogen atom to which they are attached form a heterocyclyl, wherein the heterocyclyl optionally contains one to two identical or different heteroatoms selected from the group consisting of N, O and S in addition to the said nitrogen atom, and the said heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl; more preferably, the heterocyclyl is optionally substituted by hydroxy or hydroxyalkyl; and further preferably, the heterocyclyl is optionally substituted by hydroxy.

In another preferred embodiment of the present disclosure, in the compound of formula (I) or the tautomer, mesomer, racemate, enantiomer, diastereomer thereof, or mixture thereof, or the pharmaceutically acceptable salt thereof, G is an N atom.

In another preferred embodiment of the present disclosure, in the compound of formula (I) or the tautomer, mesomer, racemate, enantiomer, diastereomer thereof, or mixture thereof, or the pharmaceutically acceptable salt thereof, $R^1$ is selected from the group consisting of halogen and hydrogen atom.

In another preferred embodiment of the present disclosure, in the compound of formula (I) or the tautomer, mesomer, racemate, enantiomer, diastereomer thereof, or mixture thereof, or the pharmaceutically acceptable salt thereof, $R^2$ is a haloalkyl, preferably $C_1$-$C_6$ haloalkyl, and more preferably —$CH_2CF_3$.

In another preferred embodiment of the present disclosure, in the compound of formula (I) or the tautomer, mesomer, racemate, enantiomer, diastereomer thereof, or mixture thereof, or the pharmaceutically acceptable salt thereof, $R^3$ is selected from the group consisting of hydrogen atom, halogen, alkyl, cyano, haloalkyl, $NR^{13}C(O)R^{14}$, $C(O)NR^{13}R^{14}$ and $SO_2R^{15}$; $R^{13}$ and $R^{14}$ are identical or different and are each independently selected from the group consisting of hydrogen atom and alkyl; and $R^{15}$ is selected from the group consisting of hydrogen atom and alkyl.

In another preferred embodiment of the present disclosure, in the compound of formula (I) or the tautomer, mesomer, racemate, enantiomer, diastereomer thereof, or mixture thereof, or the pharmaceutically acceptable salt thereof, each $R^4$ is identical or different and each is independently selected from the group consisting of hydrogen atom, halogen, alkyl and alkoxy, and preferably hydrogen.

In another preferred embodiment of the present disclosure, in the compound of formula (I) or the tautomer, mesomer, racemate, enantiomer, diastereomer thereof, or mixture thereof, or the pharmaceutically acceptable salt thereof, Z is selected from the group consisting of a bond, —O—, —O—$CH_2$— and —NH—.

In another preferred embodiment of the present disclosure, in the compound of formula (I) or the tautomer, mesomer, racemate, enantiomer, diastereomer thereof, or mixture thereof, or the pharmaceutically acceptable salt thereof, $R^a$ is selected from the group consisting of —$CH_2$CH=CHC(O)$NR^8R^9$, —C(O)CH=$CR^{10}R^{11}$ and —C(O)C≡$CR^{12}$; $R^8$ and $R^9$ are identical or different and are each independently selected from the group consisting of hydrogen atom, alkyl, cycloalkyl and heterocyclyl; or, $R^8$ and $R^9$ together with the nitrogen atom to which they are attached form a heterocyclyl, wherein the heterocyclyl optionally contains one to two identical or different heteroatoms selected from the group consisting of N, O and S in addition to one nitrogen atom, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl; $R^{10}$ and $R^{11}$ are identical or different and are each independently selected from the group consisting of hydrogen atom and alkyl; and $R^{12}$ is selected from the group consisting of hydrogen atom and alkyl.

In another preferred embodiment of the present disclosure, in the compound of formula (I) or the tautomer, mesomer, racemate, enantiomer, diastereomer thereof, or mixture thereof, or the pharmaceutically acceptable salt thereof, $R^a$ is selected from the group consisting of —CH$_2$CH═CHC(O)N(CH$_3$)$_2$, —CH$_2$CH═CHC(O)NH (CH$_3$), —CH$_2$CH═CHC(O)NHC(CH$_3$)$_3$, —C(O)CH═CH$_2$, —C(O)C≡CCH$_3$,

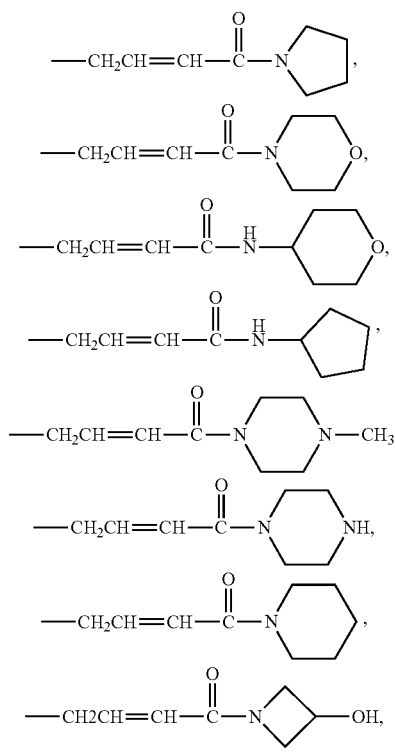

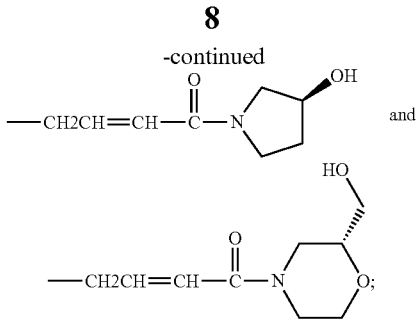

preferably, $R^a$ is selected from the group consisting of —CH$_2$CH═CHC(O)N(CH$_3$)$_2$, —CH$_2$CH═CHC(O)NH (CH$_3$), —CH$_2$CH═CHC(O)NHC(CH$_3$)$_3$, —C(O)CH═CH$_2$, —C(O)C≡CCH$_3$,

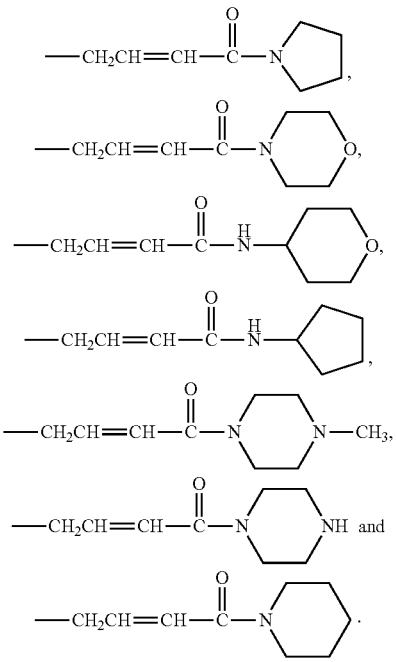

Typical compounds of formula (I) include, but are not limited to:

| Example No. | Structure and name of the compound | |
|---|---|---|
| 1 | ![structure] (E)-1-Morpholino-4-((1-(((5-((Z)-4,4-trifluoro-1-(3-fluoro-1H-indazol-5-yl)-2-phenylbut-1-en-1-yl)pyridin-2-yl)oxy)methyl)cyclopropyl)amino)but-2-en-1-one | 1 |

| Example No. | Structure and name of the compound | |
|---|---|---|
| 2 | 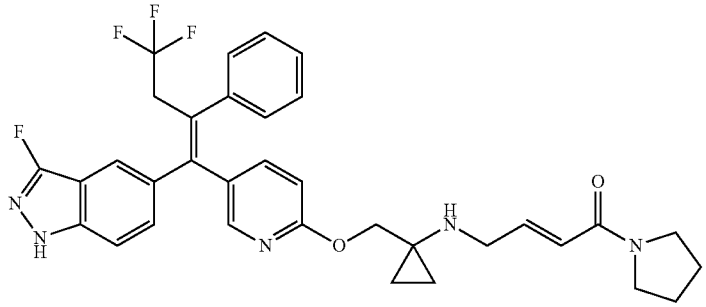 [SMILES: O=C(/C=C/CNC1(COc2ccc(/C(=C(/CC(F)(F)F)c3ccccc3)c3ccc4[nH]nc(F)c4c3)cn2)CC1)N1CCCC1]<br>(E)-1-(Pyrrolidin-1-yl)-4-((1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)but-2-en-1-one 2 | 2 |
| 3 | 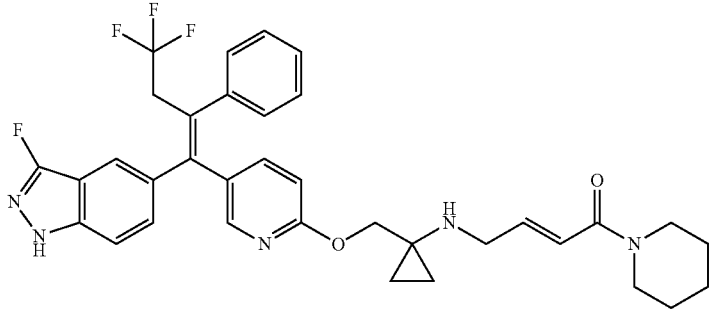 [SMILES: O=C(/C=C/CNC1(COc2ccc(/C(=C(/CC(F)(F)F)c3ccccc3)c3ccc4[nH]nc(F)c4c3)cn2)CC1)N1CCCCC1]<br>(E)-1-(Piperidin-1-yl)-4-((1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)but-2-en-1-one 3 | 3 |
| 4 | 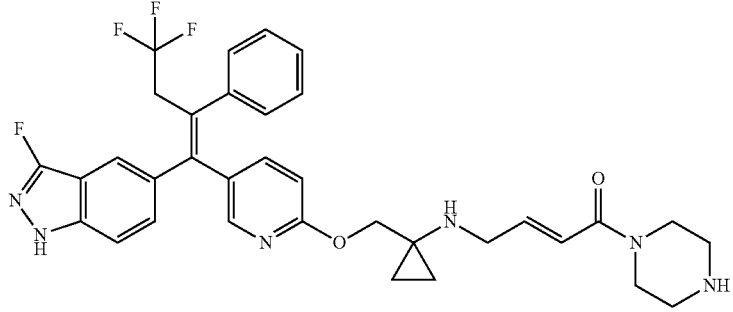 [SMILES: O=C(/C=C/CNC1(COc2ccc(/C(=C(/CC(F)(F)F)c3ccccc3)c3ccc4[nH]nc(F)c4c3)cn2)CC1)N1CCNCC1]<br>(E)-1-(Piperazin-1-yl)-4-((1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)but-2-en-1-one 4 | 4 |
| 5 | 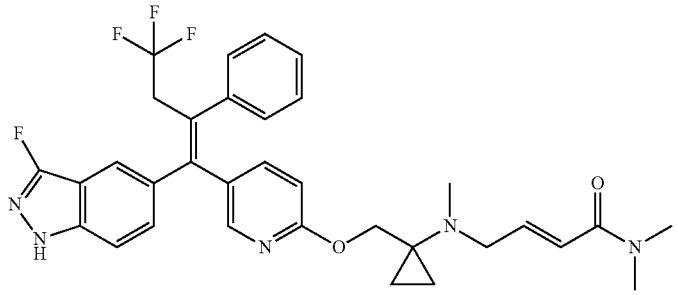 [SMILES: CN(C)C(=O)/C=C/CN(C)C1(COc2ccc(/C(=C(/CC(F)(F)F)c3ccccc3)c3ccc4[nH]nc(F)c4c3)cn2)CC1]<br>(E)-N,N-Dimethyl-4-(methyl(1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)but-2-enamide 5 | 5 |

| Example No. | Structure and name of the compound | |
|---|---|---|
| 6 | 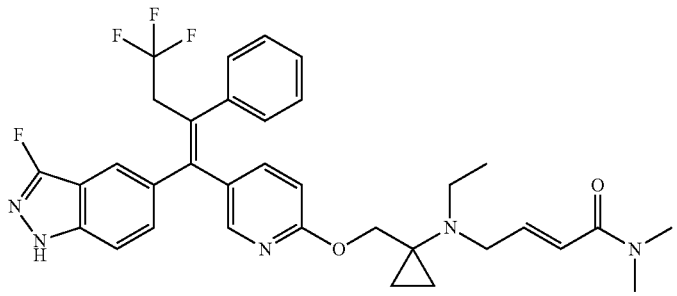 [SMILES: CCN(C/C=C/C(=O)N(C)C)C1(COc2ccc(/C(=C(/CC(F)(F)F)c3ccccc3)c3ccc4[nH]nc(F)c4c3)cn2)CC1]<br>(E)-4-(Ethyl(1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)-N,N-dimethylbut-2-enamide 6 | 6 |
| 7 | 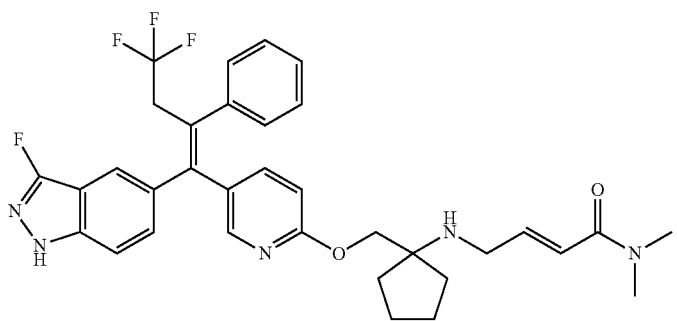 [SMILES: CN(C)C(=O)/C=C/CNC1(COc2ccc(/C(=C(/CC(F)(F)F)c3ccccc3)c3ccc4[nH]nc(F)c4c3)cn2)CCCC1]<br>(E)-N,N-Dimethyl-4-((1-(((5-((Z)-4,4,4-trifluoro-1-(3-fluoro-1H-indazol-5-yl)-2-phenylbut-1-en-1-yl)pyridin-2-yl)oxy)methyl)cyclopentyl)amino)but-2-enamide 7 | 7 |
| 8 | 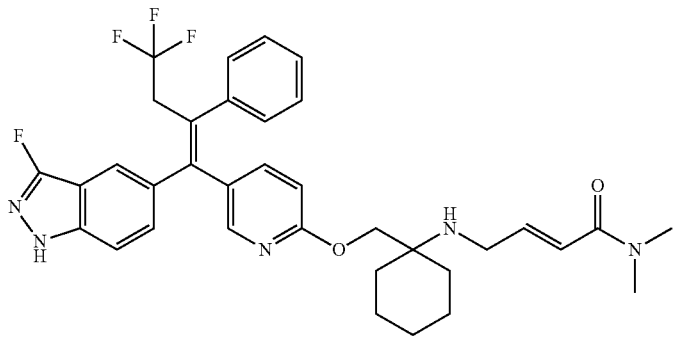 [SMILES: CN(C)C(=O)/C=C/CNC1(COc2ccc(/C(=C(/CC(F)(F)F)c3ccccc3)c3ccc4[nH]nc(F)c4c3)cn2)CCCCC1]<br>(E)-N,N-Dimethyl-4-((1-(((5-((Z)-4,4,4-trifluoro-1-(3-fluoro-1H-indazol-5-yl)-2-phenylbut-1-en-1-yl)pyridin-2-yl)oxy)methyl)cyclohexyl)amino)but-2-enamide 8 | 8 |
| 9 | 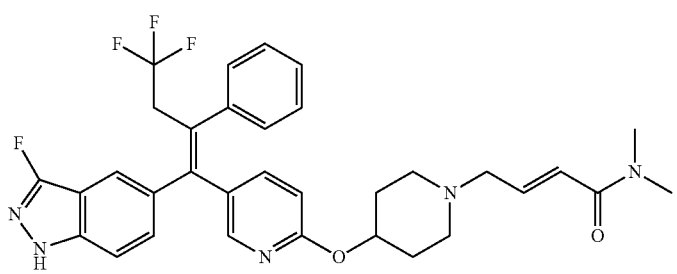 [SMILES: CN(C)C(=O)/C=C/CN1CCC(Oc2ccc(/C(=C(/CC(F)(F)F)c3ccccc3)c3ccc4[nH]nc(F)c4c3)cn2)CC1]<br>(E)-N,N-Dimethyl-4-(4-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide 9 | 9 |

-continued

| Example No. | Structure and name of the compound | |
|---|---|---|
| 10 | 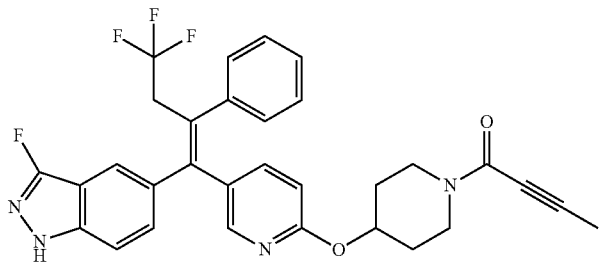 [SMILES: CC#CC(=O)N1CCC(Oc2ccc(/C(=C(/CC(F)(F)F)c3ccccc3)c3ccc4[nH]nc(F)c4c3)cn2)CC1]<br>(Z)-1-(4-((5-(4,4,4-Trifluoro-1-(3-fluoro-1H-indazol-5-yl)-2-phenylbut-1-en-1-yl)pyridin-2-yl)oxy)piperidin-1-yl)but-2-yn-1-one 10 | 10 |
| 11 | 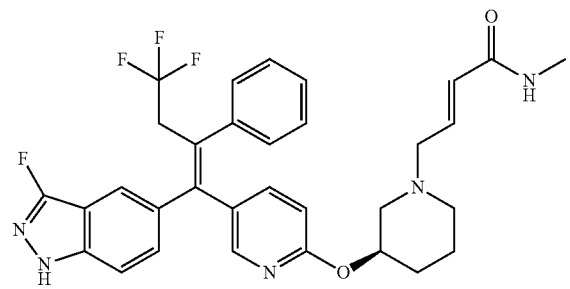<br>(E)-N-Methyl-4-((R)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide 11 | 11 |
| 12 | 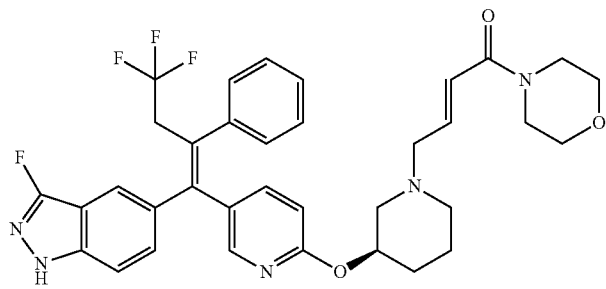 [SMILES: O=C(/C=C/CN1CCC[C@@H](Oc2ccc(/C(=C(/CC(F)(F)F)c3ccccc3)c3ccc4[nH]nc(F)c4c3)cn2)C1)N1CCOCC1]<br>(E)-1-Morpholino-4-((R)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-en-1-one 12 | 12 |
| 13 | 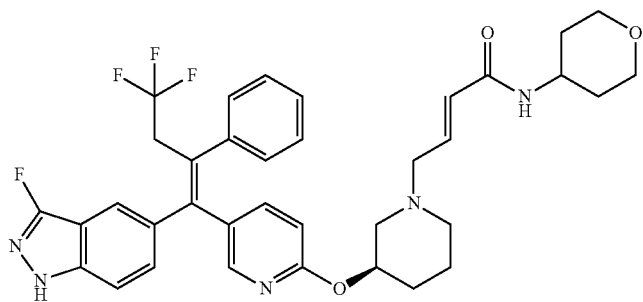 [SMILES: O=C(/C=C/CN1CCC[C@@H](Oc2ccc(/C(=C(/CC(F)(F)F)c3ccccc3)c3ccc4[nH]nc(F)c4c3)cn2)C1)NC1CCOCC1]<br>(E)-N-(Tetrahydro-2H-pyran-4-yl)-4-((R)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide 13 | 13 |

| Example No. | Structure and name of the compound |
|---|---|
| 14 | 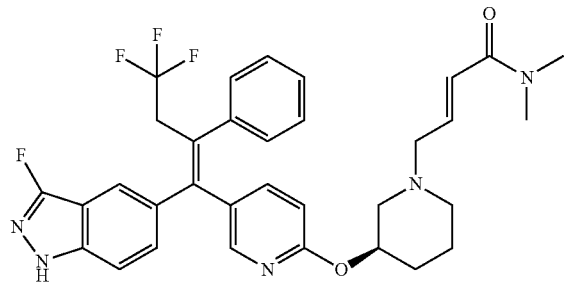 [SMILES: CN(C)C(=O)/C=C/CN1CCC[C@@H](Oc2ccc(/C(=C(/CC(F)(F)F)c3ccccc3)c3ccc4[nH]nc(F)c4c3)cn2)C1]<br>(E)-N,N-Dimethyl-4-((R)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide 14 |
| 15 | 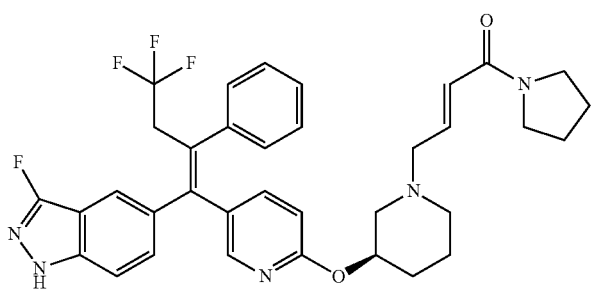 [SMILES: O=C(/C=C/CN1CCC[C@@H](Oc2ccc(/C(=C(/CC(F)(F)F)c3ccccc3)c3ccc4[nH]nc(F)c4c3)cn2)C1)N1CCCC1]<br>(E)-1-(Pyrrolidin-1-yl)-4-((R)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-en-1-one 15 |
| 16 | 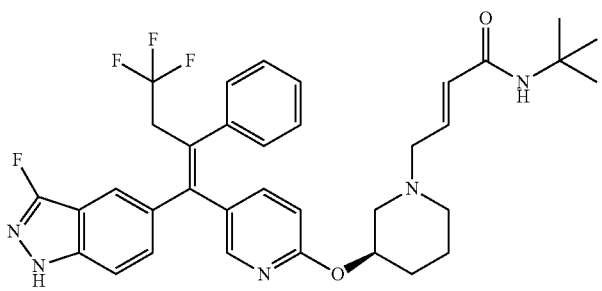 [SMILES: CC(C)(C)NC(=O)/C=C/CN1CCC[C@@H](Oc2ccc(/C(=C(/CC(F)(F)F)c3ccccc3)c3ccc4[nH]nc(F)c4c3)cn2)C1]<br>(E)-N-(Tert-butyl)-4-((R)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide 16 |
| 17 | 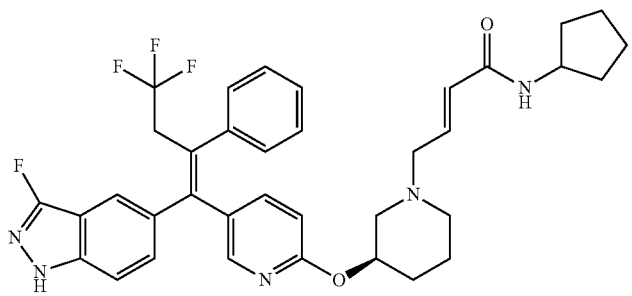 [SMILES: O=C(/C=C/CN1CCC[C@@H](Oc2ccc(/C(=C(/CC(F)(F)F)c3ccccc3)c3ccc4[nH]nc(F)c4c3)cn2)C1)NC1CCCC1]<br>(E)-N-Cyclopentyl-4-((R)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide 17 |

| Example No. | Structure and name of the compound |
|---|---|
| 18 | 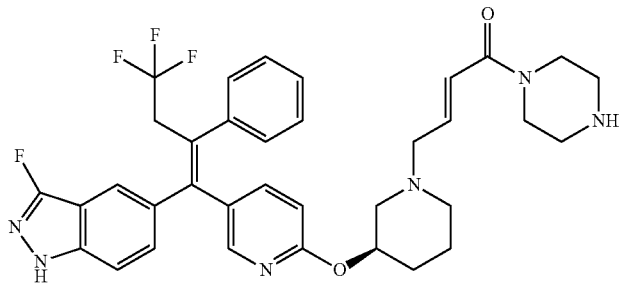 [SMILES: O=C(/C=C/CN1CCC[C@@H](Oc2ccc(/C(=C(/CC(F)(F)F)c3ccccc3)c3ccc4[nH]nc(F)c4c3)cn2)C1)N1CCNCC1]<br>(E)-1-(Piperazin-1-yl)-4-((R)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-en-1-one 18 |
| 19 | 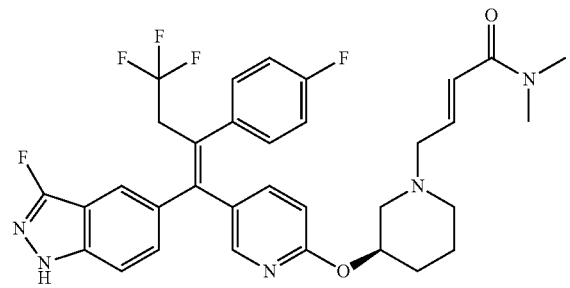 [SMILES: CN(C)C(=O)/C=C/CN1CCC[C@@H](Oc2ccc(/C(=C(/CC(F)(F)F)c3ccc(F)cc3)c3ccc4[nH]nc(F)c4c3)cn2)C1]<br>(E)-N,N-Dimethyl-4-((R)-3-((5-((Z)-4,4,4-trifluoro-1-(3-fluoro-1H-indazol-5-yl)-2-(4-fluorophenyl)but-1-en-1-yl)pyridin-2-yl)oxy)piperidin-1-yl)but-2-enamide 19 |
| 20 | 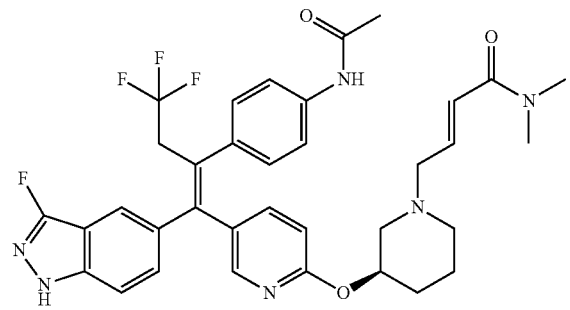 [SMILES: CC(=O)Nc1ccc(/C(CC(F)(F)F)=C(\c2ccc(O[C@@H]3CCCN(C/C=C/C(=O)N(C)C)C3)nc2)c2ccc3[nH]nc(F)c3c2)cc1]<br>(E)-4-((R)-3-((5-((Z)-2-(4-Acetamidophenyl)-4,4,4-trifluoro-1-(3-fluoro-1H-indazol-5-yl)but-1-en-1-yl)pyridin-2-yl)oxy)piperidin-1-yl)-N,N-dimethylbut-2-enamide 20 |
| 21 | 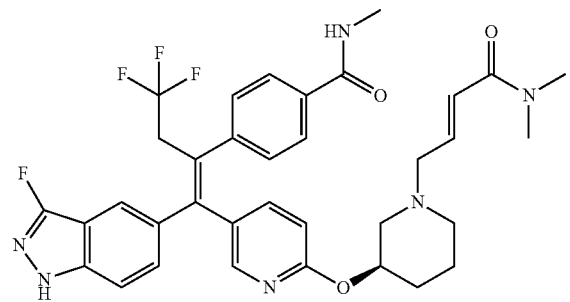 [SMILES: CNC(=O)c1ccc(/C(CC(F)(F)F)=C(\c2ccc(O[C@@H]3CCCN(C/C=C/C(=O)N(C)C)C3)nc2)c2ccc3[nH]nc(F)c3c2)cc1]<br>4-((Z)-1-(6-(((R)-1-((E)-4-(Dimethylamino)-4-oxobut-2-en-1-yl)piperidin-3-yl)oxy)pyridin-3-yl)-4,4,4-trifluoro-1-(3-fluoro-1H-indazol-5-yl)but-1-en-2-yl)-N-methylbenzamide 21 |

| Example No. | Structure and name of the compound |
|---|---|
| 22 | 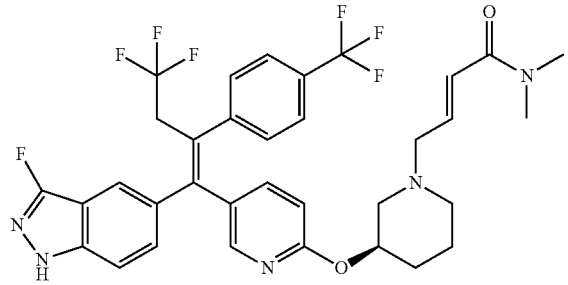 [SMILES: CN(C)C(=O)/C=C/CN1CCC[C@@H](Oc2ccc(/C(=C(/CC(F)(F)F)c3ccc(C(F)(F)F)cc3)c3ccc4[nH]nc(F)c4c3)cn2)C1]<br>(E)-N,N-Dimethyl-4-((R)-3-((5-((Z)-4,4,4-trifluoro-1-(3-fluoro-1H-indazol-5-yl)-2-(4-(trifluoromethyl)phenyl)but-1-en-1-yl)pyridin-2-yl)oxy)piperidin-1-yl)but-2-enamide 22 |
| 23 | 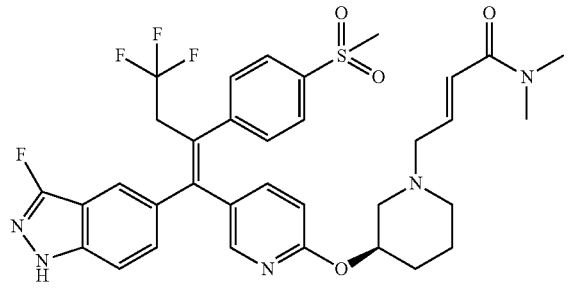 [SMILES: CN(C)C(=O)/C=C/CN1CCC[C@@H](Oc2ccc(/C(=C(/CC(F)(F)F)c3ccc(S(C)(=O)=O)cc3)c3ccc4[nH]nc(F)c4c3)cn2)C1]<br>(E)-N,N-Dimethyl-4-((R)-3-((5-((Z)-4,4,4-trifluoro-1-(3-fluoro-1H-indazol-5-yl)-2-(4-(methylsulfonyl)phenyl)but-1-en-1-yl)pyridin-2-yl)oxy)piperidin-1-yl)but-2-enamide 23 |
| 24 | 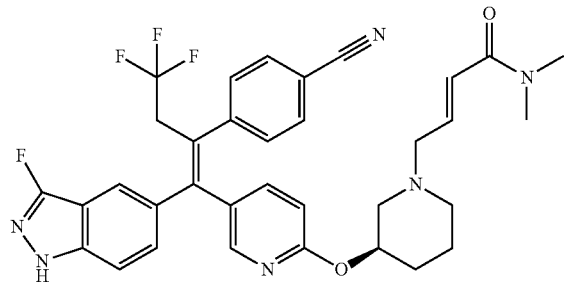 [SMILES: CN(C)C(=O)/C=C/CN1CCC[C@@H](Oc2ccc(/C(=C(/CC(F)(F)F)c3ccc(C#N)cc3)c3ccc4[nH]nc(F)c4c3)cn2)C1]<br>(E)-4-((R)-3-((5-((Z)-2-(4-Cyanophenyl)-4,4,4-trifluoro-1-(3-fluoro-1H-indazol-5-yl)but-1-en-1-yl)pyridin-2-yl)oxy)piperidin-1-yl)-N,N-dimethylbut-2-enamide 24 |
| 25 | 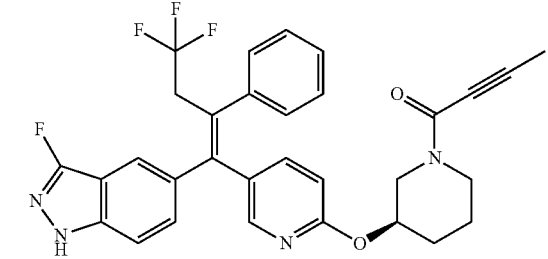 [SMILES: CC#CC(=O)N1CCC[C@@H](Oc2ccc(/C(=C(/CC(F)(F)F)c3ccccc3)c3ccc4[nH]nc(F)c4c3)cn2)C1]<br>(R,Z)-1-(3-((5-(4,4,4-Trifluoro-1-(3-fluoro-1H-indazol-5-yl)-2-phenylbut-1-en-1-yl)pyridin-2-yl)oxy)piperidin-1-yl)but-2-yn-1-one 25 |

| Example No. | Structure and name of the compound | |
|---|---|---|
| 26 | 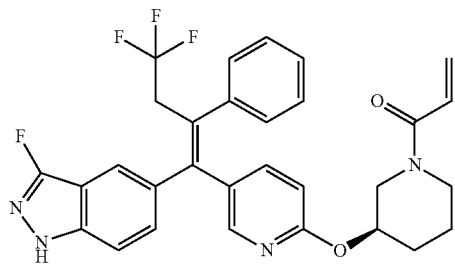 [SMILES: C=CC(=O)N1CCC[C@@H](Oc2ccc(/C(=C(/CC(F)(F)F)c3ccccc3)c3ccc4[nH]nc(F)c4c3)cn2)C1]<br>(R,Z)-1-(3-((5-(4,4,4-Trifluoro-1-(3-fluoro-1H-indazol-5-yl)-2-phenylbut-1-en-1-yl)pyridin-2-yl)oxy)piperidin-1-yl)prop-2-en-1-one | 26 |
| 27 | 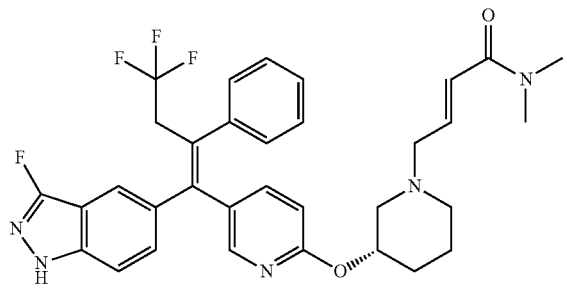 [SMILES: CN(C)C(=O)/C=C/CN1CCC[C@H](Oc2ccc(/C(=C(/CC(F)(F)F)c3ccccc3)c3ccc4[nH]nc(F)c4c3)cn2)C1]<br>(E)-N,N-Dimethyl-4-((S)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide | 27 |
| 28 | 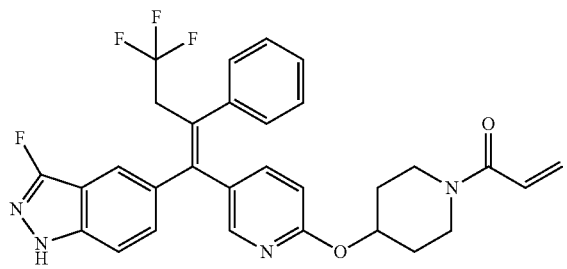 [SMILES: C=CC(=O)N1CCC(Oc2ccc(/C(=C(/CC(F)(F)F)c3ccccc3)c3ccc4[nH]nc(F)c4c3)cn2)CC1]<br>(Z)-1-(4-((5-(4,4,4-Trifluoro-1-(3-fluoro-1H-indazol-5-yl)-2-phenylbut-1-en-1-yl)pyridin-2-yl)oxy)piperidin-1-yl)prop-2-en-1-one | 28 |
| 29 | 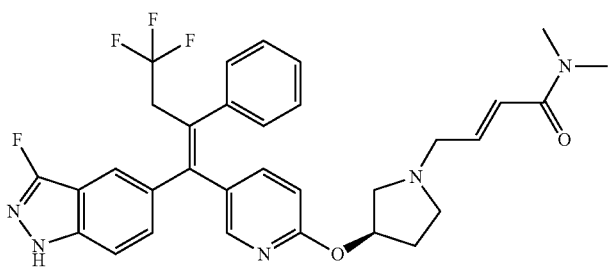 [SMILES: CN(C)C(=O)/C=C/CN1CC[C@@H](Oc2ccc(/C(=C(/CC(F)(F)F)c3ccccc3)c3ccc4[nH]nc(F)c4c3)cn2)C1]<br>(E)-N,N-Dimethyl-4-((R)-3-((5-((Z)-4,4,4-trifluoro-1-(3-fluoro-1H-indazol-5-yl)-2-phenylbut-1-en-1-yl)pyridin-2-yl)oxy)pyrrolidin-1-yl)but-2-enamide | 29 |

| Example No. | Structure and name of the compound | |
|---|---|---|
| 30 | 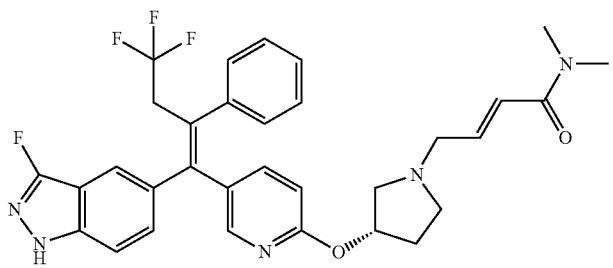 [SMILES: CN(C)C(=O)/C=C/CN1CC[C@H](Oc2ccc(/C(=C(/CC(F)(F)F)c3ccccc3)c3ccc4[nH]nc(F)c4c3)cn2)C1]<br>(E)-N,N-Dimethyl-4-((S)-3-((5-((Z)-4,4,4-trifluoro-1-(3-fluoro-1H-indazol-5-yl)-2-phenylbut-1-en-1-yl)pyridin-2-yl)oxy)pyrrolidin-1-yl)but-2-enamide | 30 |
| 31 | 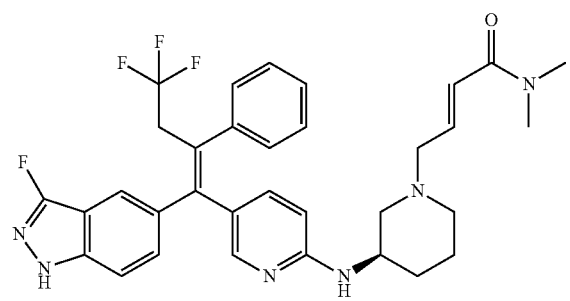 [SMILES: CN(C)C(=O)/C=C/CN1CCC[C@@H](Nc2ccc(/C(=C(/CC(F)(F)F)c3ccccc3)c3ccc4[nH]nc(F)c4c3)cn2)C1]<br>(E)-N,N-Dimethyl-4-((R)-3-((5-((Z)-4,4,4-trifluoro-1-(3-fluoro-1H-indazol-5-yl)-2-phenylbut-1-en-1-yl)pyridin-2-yl)amino)piperidin-1-yl)but-2-enamide | 31 |
| 32 | 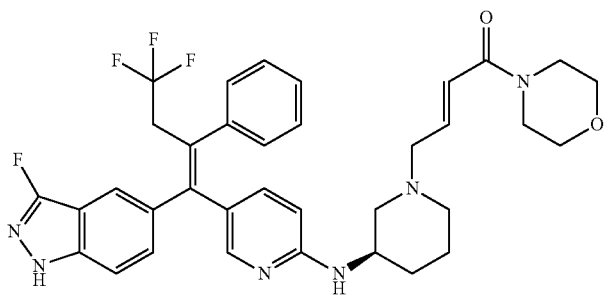 [SMILES: O=C(/C=C/CN1CCC[C@@H](Nc2ccc(/C(=C(/CC(F)(F)F)c3ccccc3)c3ccc4[nH]nc(F)c4c3)cn2)C1)N1CCOCC1]<br>(E)-1-Morpholino-4-((R)-3-((5-((Z)-4,4,4-trifluoro-1-(3-fluoro-1H-indazol-5-yl)-2-phenylbut-1-en-1-yl)pyridin-2-yl)amino)piperidin-1-yl)but-2-en-1-one | 32 |
| 33 | 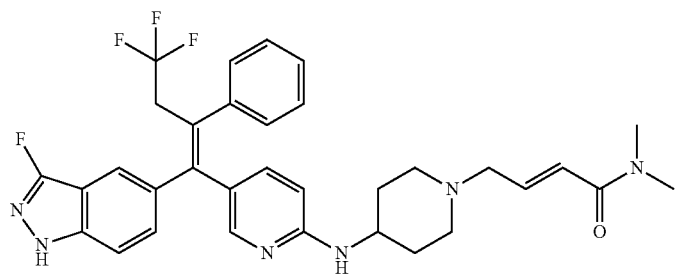 [SMILES: CN(C)C(=O)/C=C/CN1CCC(Nc2ccc(/C(=C(/CC(F)(F)F)c3ccccc3)c3ccc4[nH]nc(F)c4c3)cn2)CC1]<br>(E)-N,N-Dimethyl-4-(4-((5-((Z)-4,4,4-trifluoro-1-(3-fluoro-1H-indazol-5-yl)-2-phenylbut-1-en-1-yl)pyridin-2-yl)amino)piperidin-1-yl)but-2-enamide | 33 |

| Example No. | Structure and name of the compound | |
|---|---|---|
| 34 | 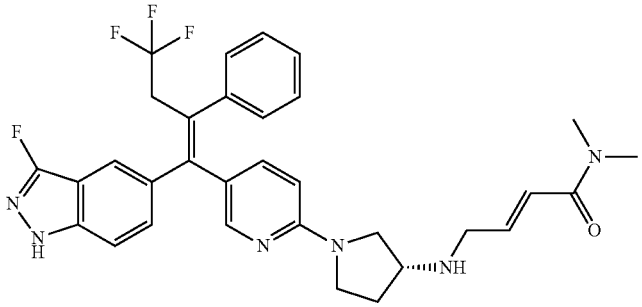 [SMILES: CN(C)C(=O)/C=C/CN[C@@H]1CCN(c2ccc(/C(=C(/CC(F)(F)F)c3ccccc3)c3ccc4[nH]nc(F)c4c3)cn2)C1]<br>(E)-N,N-Dimethyl-4-(((R)-1-(5-((Z)-4,4,4-trifluoro-1-(3-fluoro-1H-indazol-5-yl)-2-phenylbut-1-en-1-yl)pyridin-2-yl)pyrrolidin-3-yl)amino)but-2-enamide | 34 |
| 35 | 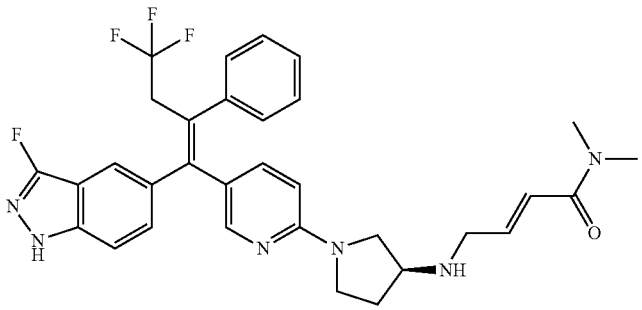 [SMILES: CN(C)C(=O)/C=C/CN[C@H]1CCN(c2ccc(/C(=C(/CC(F)(F)F)c3ccccc3)c3ccc4[nH]nc(F)c4c3)cn2)C1]<br>(E)-N,N-Dimethyl-4-(((S)-1-(5-((Z)-4,4,4-trifluoro-1-(3-fluoro-1H-indazol-5-yl)-2-phenylbut-1-en-1-yl)pyridin-2-yl)pyrrolidin-3-yl)amino)but-2-enamide | 35 |
| 36 | 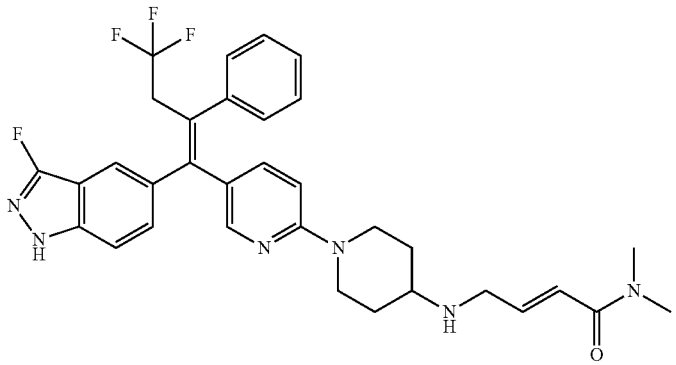 [SMILES: CN(C)C(=O)/C=C/CNC1CCN(c2ccc(/C(=C(/CC(F)(F)F)c3ccccc3)c3ccc4[nH]nc(F)c4c3)cn2)CC1]<br>(E)-N,N-Dimethyl-4-((1-(5-((Z)-4,4,4-trifluoro-1-(3-fluoro-1H-indazol-5-yl)-2-phenylbut-1-en-1-yl)pyridin-2-yl)piperidin-4-yl)amino)but-2-enamide | 36 |
| 37 | 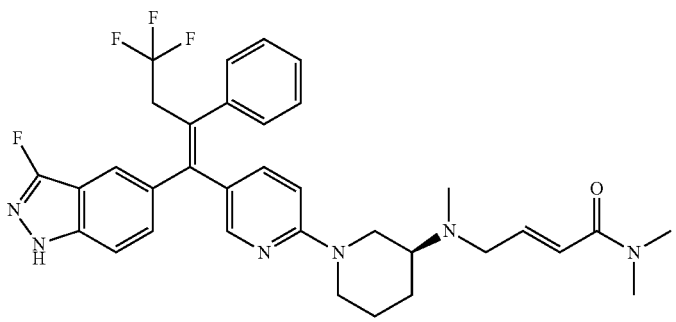 [SMILES: CN(C)C(=O)/C=C/CN(C)[C@H]1CCCN(c2ccc(/C(=C(/CC(F)(F)F)c3ccccc3)c3ccc4[nH]nc(F)c4c3)cn2)C1]<br>(E)-N,N-Dimethyl-4-(methyl((S)-1-(5-((Z)-4,4,4-trifluoro-1-(3-fluoro-1H-indazol-5-yl)-2-phenylbut-1-en-1-yl)pyridin-2-yl)piperidin-3-yl)amino)but-2-enamide | 37 |

| Example No. | Structure and name of the compound | |
|---|---|---|
| 38 | 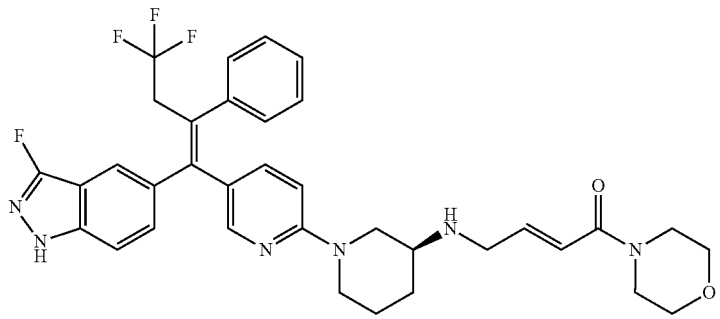 [SMILES: O=C(/C=C/CN[C@H]1CCCN(c2ccc(/C(=C(/CC(F)(F)F)c3ccccc3)c3ccc4[nH]nc(F)c4c3)cn2)C1)N1CCOCC1]<br>(E)-1-Morpholino-4-(((S)-1-(5-((Z)-4,4,4-trifluoro-1-(3-fluoro-1H-indazol-5-yl)-2-phenylbut-1-en-1-yl)pyridin-2-yl)piperidin-3-yl)amino)but-2-en-1-one 38 | 38 |
| 39 | 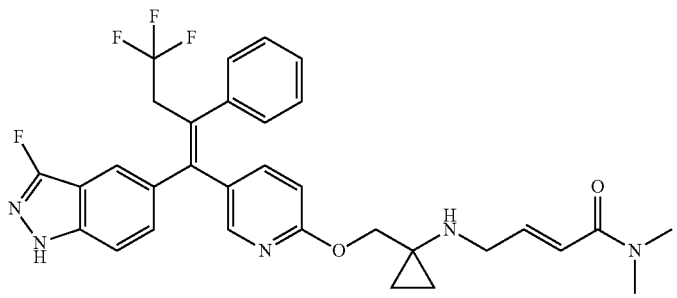 [SMILES: CN(C)C(=O)/C=C/CNC1(COc2ccc(/C(=C(/CC(F)(F)F)c3ccccc3)c3ccc4[nH]nc(F)c4c3)cn2)CC1]<br>(E)-N,N-Dimethyl-4-((1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)but-2-enamide 39 | 39 |
| 40 | 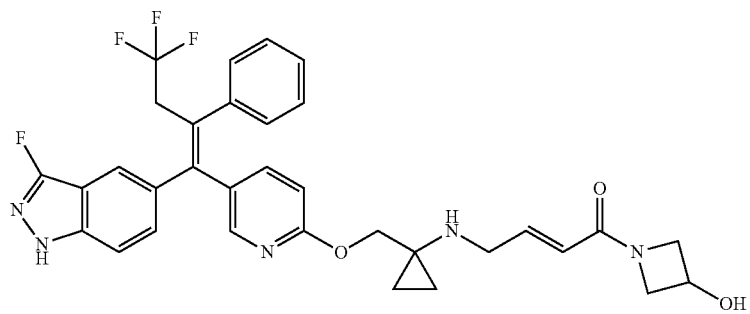 [SMILES: O=C(/C=C/CNC1(COc2ccc(/C(=C(/CC(F)(F)F)c3ccccc3)c3ccc4[nH]nc(F)c4c3)cn2)CC1)N1CC(O)C1]<br>(E)-1-(3-Hydroxyazetidin-1-yl)-4-((1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)but-2-en-1-one 40 | 40 |
| 41 | 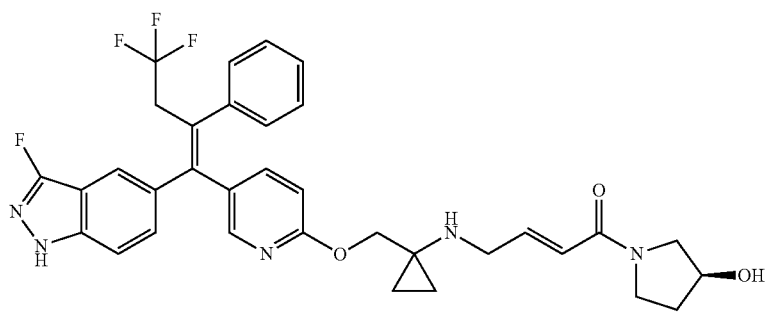 [SMILES: O=C(/C=C/CNC1(COc2ccc(/C(=C(/CC(F)(F)F)c3ccccc3)c3ccc4[nH]nc(F)c4c3)cn2)CC1)N1CC[C@H](O)C1]<br>(E)-1-((S)-3-Hydroxypyrrolidin-1-yl)-4-((1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)but-2-en-1-one 41 | 41 |

| Example No. | Structure and name of the compound |
|---|---|
| 42 | 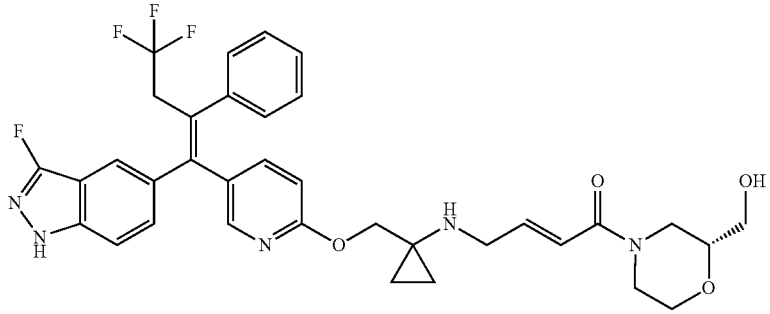 [SMILES: O=C(/C=C/CNC1(COc2ccc(/C(=C(/CC(F)(F)F)c3ccccc3)c3ccc4[nH]nc(F)c4c3)cn2)CC1)N1CCO[C@@H](CO)C1]
(E)-1-((R)-2-(Hydroxymethyl)morpholino)-4-((1-(((5-((Z)-4,4-trifluoro-1-(3-fluoro-1H-indazol-5-yl)-2-phenylbut-1-en-1-yl)pyridin-2-yl)oxy)methyl)cyclopropyl)amino)but-2-en-1-one 42 | or a tautomer, mesomer, racemate, enantiomer, diastereomer thereof, or mixture thereof, or a pharmaceutically acceptable salt thereof.

In another aspect, the present disclosure provides a compound of formula (IA) or a tautomer, mesomer, racemate, enantiomer, diastereomer thereof, or mixture thereof, or a pharmaceutically acceptable salt thereof,

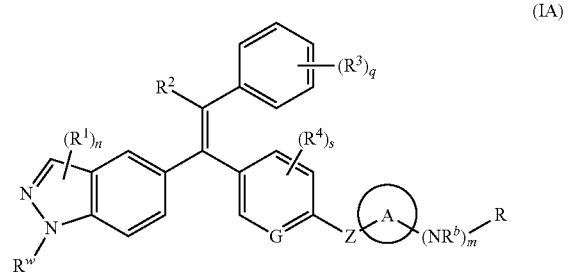

(IA)

which is an intermediate for synthesizing the compound of formula (I), wherein:

$R^w$ is an amino protecting group, and preferably tetrahydropyranyl;

R is selected from the group consisting of —$CH_2CH=CHC(O)NR^8R^9$, —$C(O)CH=CR^{10}R^{11}$ and —$C(O)C\equiv CR^{12}$;

$R^8$ and $R^9$ are identical or different and are each independently selected from the group consisting of hydrogen atom, alkyl, haloalkyl, hydroxyalkyl, cycloalkyl, heterocyclyl, aryl and heteroaryl;

or, $R^8$ and $R^9$ together with the nitrogen atom to which they are attached form a heterocyclyl, wherein the heterocyclyl optionally contains one to two identical or different heteroatoms selected from the group consisting of N, O and S in addition to one nitrogen atom, and the heterocyclyl is optionally substituted by one or more substituents selected from the group consisting of alkyl, alkoxy, halogen, amino, cyano, nitro, hydroxy, hydroxyalkyl, —$COOR^{16}$—, cycloalkyl, heterocyclyl, aryl and heteroaryl;

$R^{10}$ and $R^{11}$ are identical or different and are each independently selected from the group consisting of hydrogen atom, halogen, alkyl, haloalkyl, alkoxy, cyano, amino, nitro, carboxy, formyl, hydroxy, hydroxyalkyl, cycloalkyl, heterocyclyl, aryl and heteroaryl;

$R^{12}$ is selected from the group consisting of hydrogen atom, alkyl, haloalkyl, hydroxyalkyl, cycloalkyl, heterocyclyl, aryl and heteroaryl;

$R^{16}$ is selected from the group consisting of hydrogen atom, alkyl, haloalkyl and hydroxyalkyl;

ring A, G, Z, $R^1$, $R^2$, $R^3$, $R^4$, $R^b$, n, m, s and q are as defined in formula (I).

In another aspect, the present disclosure provides a compound of formula (IIA) or a tautomer, mesomer, racemate, enantiomer, diastereomer thereof, or mixture thereof, or a pharmaceutically acceptable salt thereof,

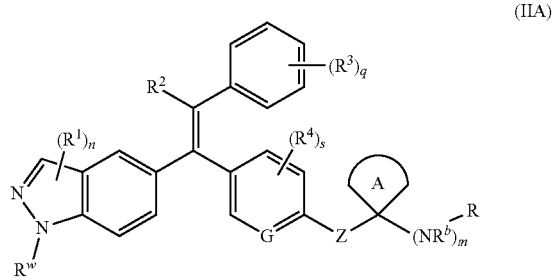

(IIA)

which is an intermediate for synthesizing the compound of formula (II), wherein:

$R^w$ is an amino protecting group, and preferably tetrahydropyranyl;

R is as defined in formula (IA);

ring A, G, Z, $R^1$, $R^2$, $R^3$, $R^4$, $R^b$, n, m, s and q are as defined in formula (II).

In another aspect, the present disclosure provides a compound of formula (IIIA) or a tautomer, mesomer, racemate, enantiomer, diastereomer thereof, or mixture thereof, or a pharmaceutically acceptable salt thereof,

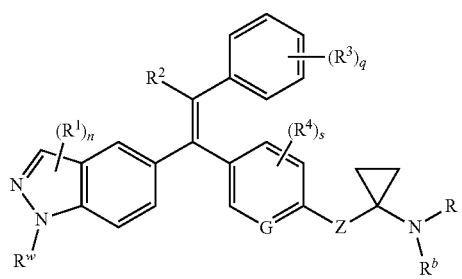

(IIIA)

which is an intermediate for synthesizing the compound of formula (III), wherein:

$R^w$ is an amino protecting group, and preferably tetrahydropyranyl;

R is as defined in formula (IA);

G, Z, $R^1$, $R^2$, $R^3$, $R^4$, $R^b$, n, s and q are as defined in formula (III).

In another aspect, the present disclosure provides a compound of formula (IVA) or a tautomer, mesomer, racemate, enantiomer, diastereomer thereof, or mixture thereof, or a pharmaceutically acceptable salt thereof,

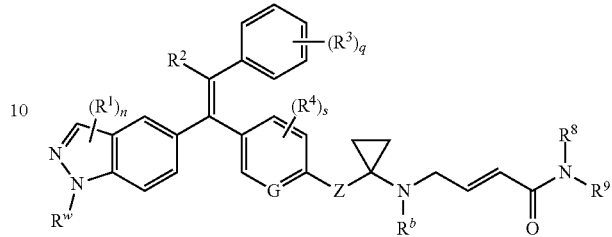

(IVA)

which is an intermediate for synthesizing the compound of formula (IV), wherein:

$R^w$ is an amino protecting group, and preferably tetrahydropyranyl;

G, Z, $R^1$, $R^2$, $R^3$, $R^4$, $R^b$, $R^8$, $R^9$, n, s and q are as defined in formula (IV).

Typical compounds of formula (IA) include, but are not limited to:

| Example No. | Structure and name of the compound | |
|---|---|---|
| 1i | ![structure] (E)-1-Morpholino-4-((1-(((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-en-1-one 1i | 1i |
| 2b | ![structure] (E)-1-(Pyrrolidin-1-yl)-4-((1-(((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-en-1-one 2b | 2b |

| Example No. | Structure and name of the compound | |
|---|---|---|
| 3b | 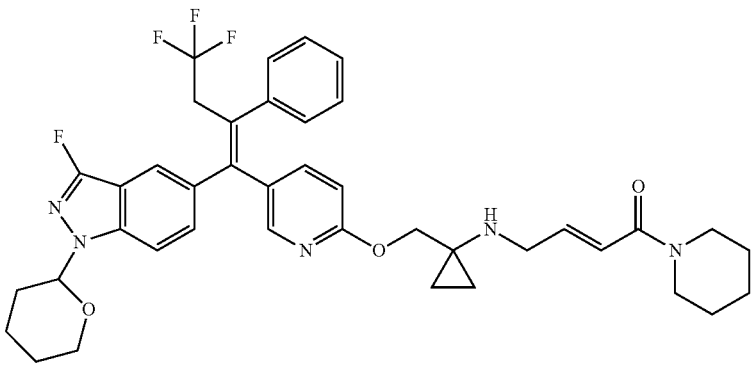 [SMILES: O=C(/C=C/CNC1(COc2ccc(/C(=C(/CC(F)(F)F)c3ccccc3)c3ccc4c(c3)c(F)nn4C3CCCCO3)cn2)CC1)N1CCCCC1] (E)-1-(Piperidin-1-yl)-4-((1-(((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-en-1-one 3b | 3b |
| 4b | 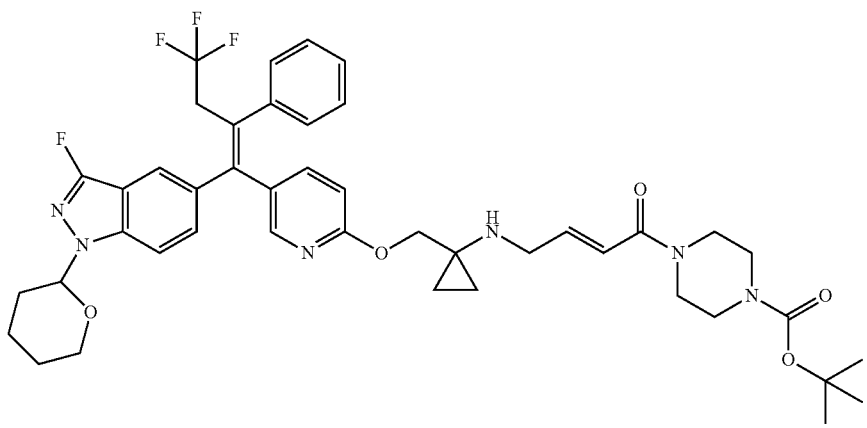 [SMILES: CC(C)(C)OC(=O)N1CCN(C(=O)/C=C/CNC2(COc3ccc(/C(=C(/CC(F)(F)F)c4ccccc4)c4ccc5c(c4)c(F)nn5C4CCCCO4)cn3)CC2)CC1] Tert-butyl 4-((E)-4-((1-(((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-enoyl)piperazine-1-carboxylate 4b | 4b |
| 5e | 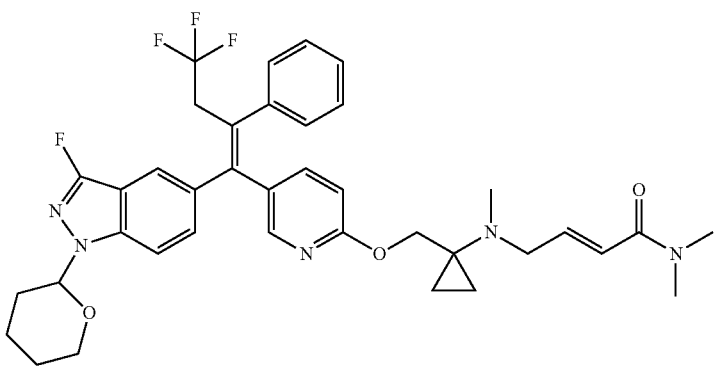 [SMILES: CN(C)C(=O)/C=C/CN(C)C1(COc2ccc(/C(=C(/CC(F)(F)F)c3ccccc3)c3ccc4c(c3)c(F)nn4C3CCCCO3)cn2)CC1] (E)-N,N-Dimethyl-4-(methyl(1-(((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-enamide 5e | 5e |

| Example No. | Structure and name of the compound |
|---|---|
| 6d | 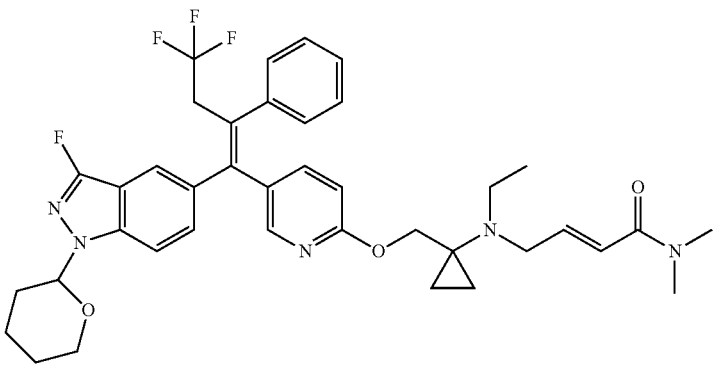 [SMILES: CCN(C/C=C/C(=O)N(C)C)C1(COc2ccc(/C(=C(/CC(F)(F)F)c3ccccc3)c3ccc4c(c3)c(F)nn4C3CCCCO3)cn2)CC1]<br>(E)-4-(Ethyl(1-(((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)-N,N-dimethylbut-2-enamide 6d |
| 7d | 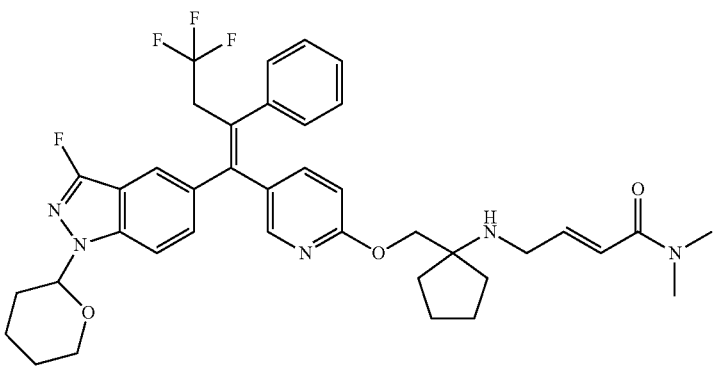 [SMILES: CN(C)C(=O)/C=C/CNC1(COc2ccc(/C(=C(/CC(F)(F)F)c3ccccc3)c3ccc4c(c3)c(F)nn4C3CCCCO3)cn2)CCCC1]<br>(E)-N,N-Dimethyl-4-((1-(((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopentyl)amino)but-2-enamide 7d |
| 8d | 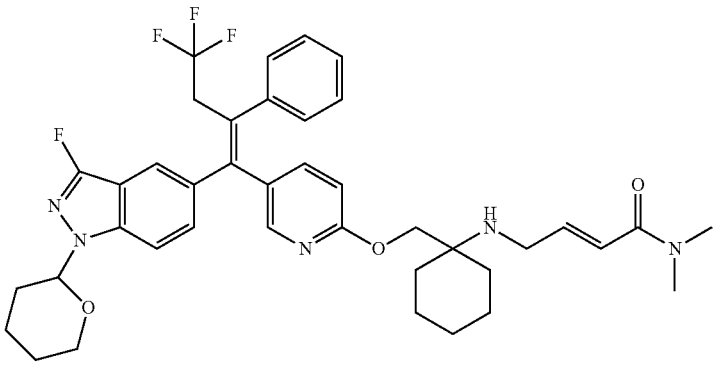 [SMILES: CN(C)C(=O)/C=C/CNC1(COc2ccc(/C(=C(/CC(F)(F)F)c3ccccc3)c3ccc4c(c3)c(F)nn4C3CCCCO3)cn2)CCCCC1]<br>(E)-N,N-Dimethyl-4-((1-(((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclohexyl)amino)but-2-enamide 8d |

| Example No. | Structure and name of the compound | |
|---|---|---|
| 9e | 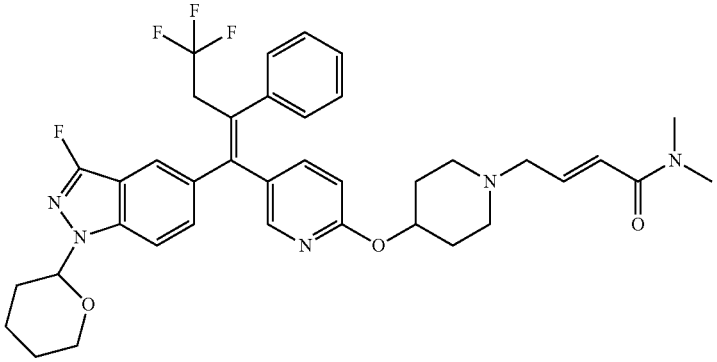 [SMILES: CN(C)C(=O)/C=C/CN1CCC(Oc2ccc(/C(=C(/CC(F)(F)F)c3ccccc3)c3ccc4c(c3)c(F)nn4C3CCCCO3)cn2)CC1]<br>(E)-N,N-Dimethyl-4-(4-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-enamide 9e | 9e |
| 10b | 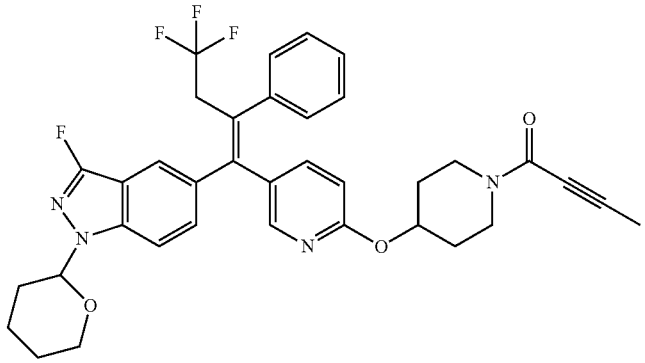 [SMILES: CC#CC(=O)N1CCC(Oc2ccc(/C(=C(/CC(F)(F)F)c3ccccc3)c3ccc4c(c3)c(F)nn4C3CCCCO3)cn2)CC1]<br>(Z)-1-(4-((5-(4,4,4-Trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-yn-1-one 10b | 10b |
| 11g | 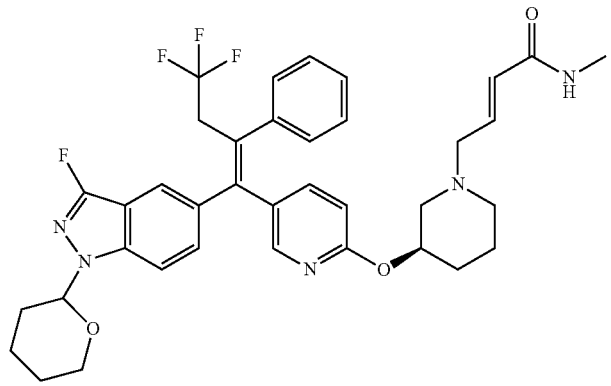 [SMILES: CNC(=O)/C=C/CN1CCC[C@@H](Oc2ccc(/C(=C(/CC(F)(F)F)c3ccccc3)c3ccc4c(c3)c(F)nn4C3CCCCO3)cn2)C1]<br>(E)-N-Methyl-4-((3R)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-enamide 11g | 11g |

| Example No. | Structure and name of the compound |
|---|---|
| 12a | 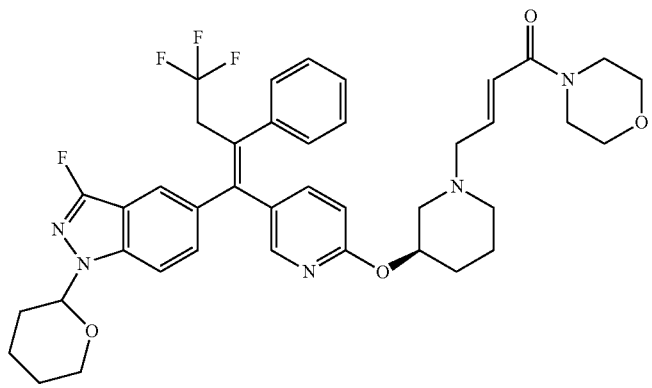 [SMILES: O=C(/C=C/CN1CCC[C@@H](Oc2ccc(/C(=C(/CC(F)(F)F)c3ccccc3)c3ccc4c(c3)c(F)nn4C3CCCCO3)cn2)C1)N1CCOCC1]<br>(E)-1-Morpholino-4-((3R)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-en-1-one 12a |
| 13b | 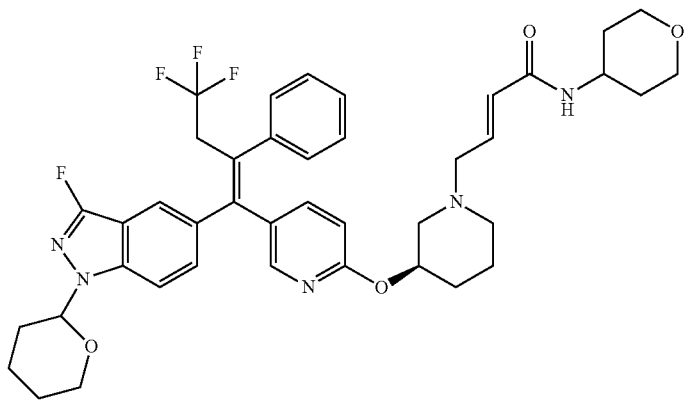 [SMILES: O=C(/C=C/CN1CCC[C@@H](Oc2ccc(/C(=C(/CC(F)(F)F)c3ccccc3)c3ccc4c(c3)c(F)nn4C3CCCCO3)cn2)C1)NC1CCOCC1]<br>(E)-N-(Tetrahydro-2H-pyran-4-yl)-4-((3R)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-enamide 13b |
| 14a | 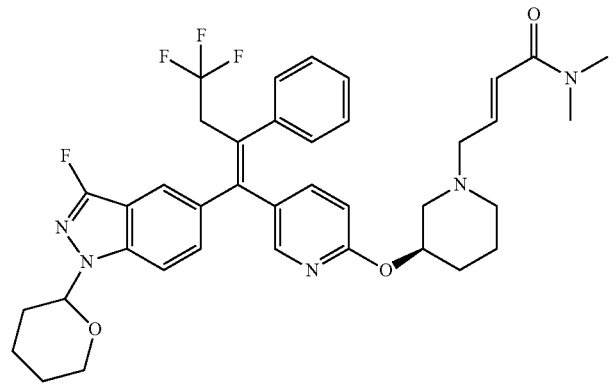 [SMILES: CN(C)C(=O)/C=C/CN1CCC[C@@H](Oc2ccc(/C(=C(/CC(F)(F)F)c3ccccc3)c3ccc4c(c3)c(F)nn4C3CCCCO3)cn2)C1]<br>(E)-N,N-Dimethyl-4-((3R)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-enamide 14a |

| Example No. | Structure and name of the compound | |
|---|---|---|
| 15a | 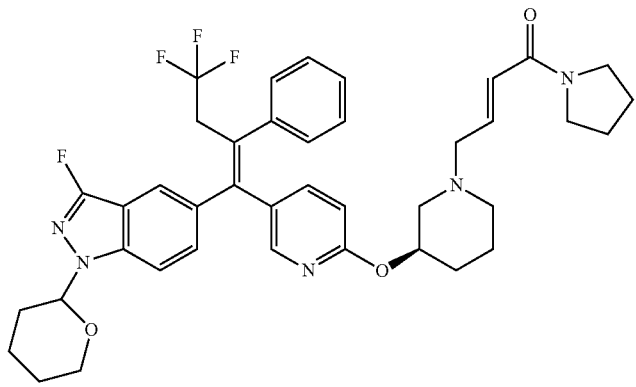 [SMILES: O=C(/C=C/CN1CCC[C@@H](Oc2ccc(/C(=C(/CC(F)(F)F)c3ccccc3)c3ccc4c(c3)c(F)nn4C3CCCCO3)cn2)C1)N1CCCC1]<br>(E)-1-(Pyrrolidin-1-yl)-4-((3R)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-en-1-one 15a | 15a |
| 16b | 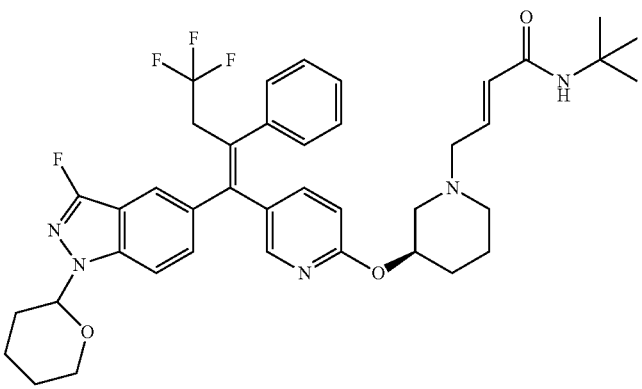 [SMILES: CC(C)(C)NC(=O)/C=C/CN1CCC[C@@H](Oc2ccc(/C(=C(/CC(F)(F)F)c3ccccc3)c3ccc4c(c3)c(F)nn4C3CCCCO3)cn2)C1]<br>(E)-N-(Tert-butyl)-4-((3R)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-enamide 16b | 16b |
| 17b | 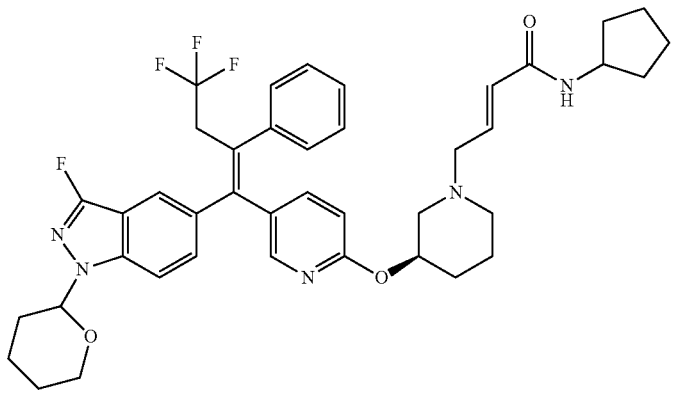 [SMILES: O=C(/C=C/CN1CCC[C@@H](Oc2ccc(/C(=C(/CC(F)(F)F)c3ccccc3)c3ccc4c(c3)c(F)nn4C3CCCCO3)cn2)C1)NC1CCCC1]<br>(E)-N-Cyclopentyl-4-((3R)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-enamide 17b | 17b |

| Example No. | Structure and name of the compound |
|---|---|
| 18a | 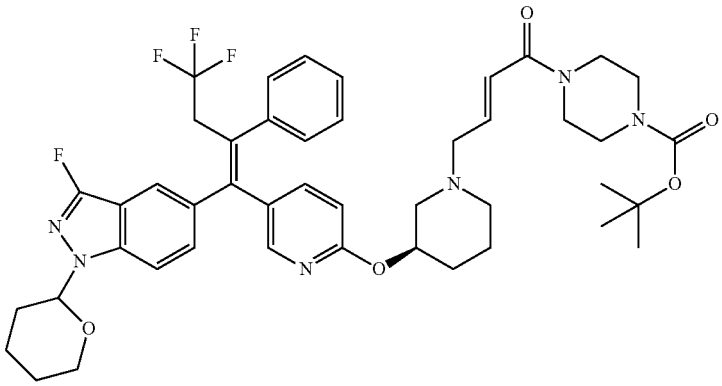 [SMILES: CC(C)(C)OC(=O)N1CCN(C(=O)/C=C/CN2CCC[C@@H](Oc3ccc(/C(=C(/CC(F)(F)F)c4ccccc4)c4ccc5c(c4)c(F)nn5C4CCCCO4)cn3)C2)CC1]

Tert-butyl 4-((E)-4-((3R)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-enoyl)piperazine-1-carboxylate 18a |
| 19d | 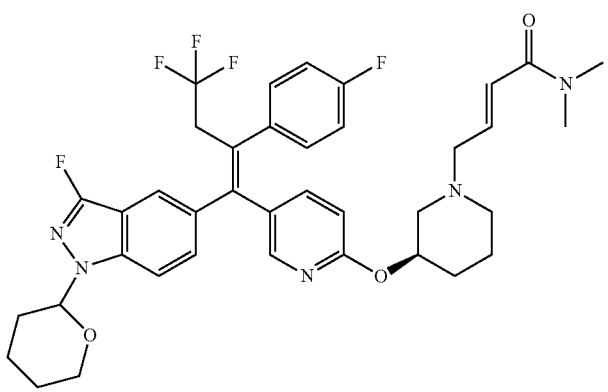 [SMILES: CN(C)C(=O)/C=C/CN1CCC[C@@H](Oc2ccc(/C(=C(/CC(F)(F)F)c3ccc(F)cc3)c3ccc4c(c3)c(F)nn4C3CCCCO3)cn2)C1]

(E)-N,N-Dimethyl-4-((3R)-3-((5-((Z)-4,4,4-trifluoro-1-(3-fluoro-1-(tetrahydro-2H-pyran-2-yl)-1H-indazol-5-yl)-2-(4-fluorophenyl)but-1-en-1-yl)pyridin-2-yl)oxy)piperidin-1-yl)but-2-enamide 19d |
| 20b | 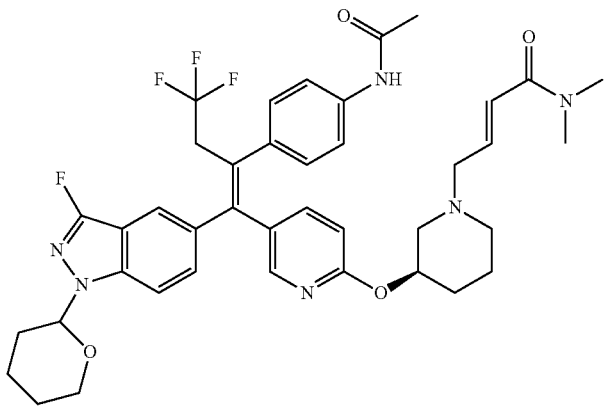 [SMILES: CC(=O)Nc1ccc(/C(CC(F)(F)F)=C(\c2ccc(O[C@@H]3CCCN(C/C=C/C(=O)N(C)C)C3)nc2)c2ccc3c(c2)c(F)nn3C2CCCCO2)cc1]

(E)-4-((3R)-3-((5-((Z)-2-(4-Acetamidophenyl)-4,4,4-trifluoro-1-(3-fluoro-1-(tetrahydro-2H-pyran-2-yl)-1H-indazol-5-yl)but-1-en-1-yl)pyridin-2-yl)oxy)piperidin-1-yl)-N,N-dimethylbut-2-enamide 20b |

| Example No. | Structure and name of the compound |
|---|---|
| 21b | 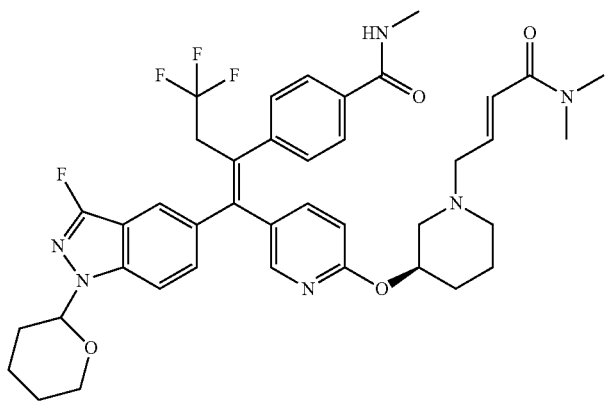 [SMILES: CNC(=O)c1ccc(/C(CC(F)(F)F)=C(\c2ccc(O[C@@H]3CCCN(C/C=C/C(=O)N(C)C)C3)nc2)c2ccc3c(c2)c(F)nn3C2CCCCO2)cc1]<br>4-((Z)-1-(6-(((R)-1-((E)-4-(Dimethylamino)-4-oxobut-2-en-1-yl)piperidin-3-yl)oxy)pyridin-3-yl)-4,4,4-trifluoro-1-(3-fluoro-1-(tetrahydro-2H-pyran-2-yl)-1H-indazol-5-yl)but-1-en-2-yl)-N-methylbenzamide 21b |
| 22b | 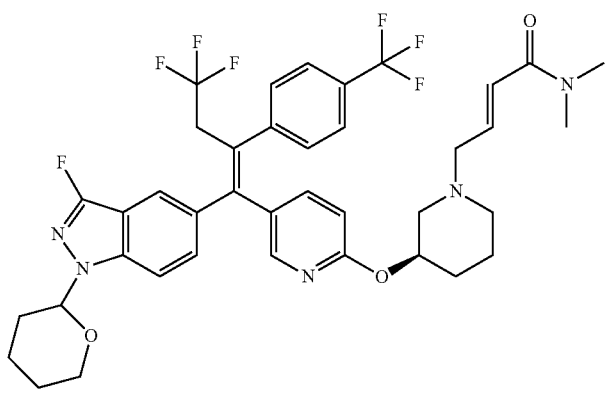 [SMILES: CN(C)C(=O)/C=C/CN1CCC[C@@H](Oc2ccc(/C(=C(/CC(F)(F)F)c3ccc(C(F)(F)F)cc3)c3ccc4c(c3)c(F)nn4C3CCCCO3)cn2)C1]<br>(E)-N,N-Dimethyl-4-((3R)-3-((5-((Z)-4,4,4-trifluoro-1-(3-fluoro-1-(tetrahydro-2H-pyran-2-yl)-1H-indazol-5-yl)-2-(4-(trifluoromethyl)phenyl)but-1-en-1-yl)pyridin-2-yl)oxy)piperidin-1-yl)but-2-enamide 22b |
| 23b | 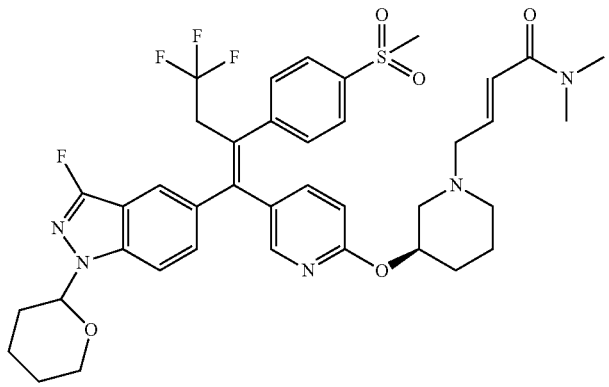 [SMILES: CN(C)C(=O)/C=C/CN1CCC[C@@H](Oc2ccc(/C(=C(/CC(F)(F)F)c3ccc(S(C)(=O)=O)cc3)c3ccc4c(c3)c(F)nn4C3CCCCO3)cn2)C1]<br>(E)-N,N-Dimethyl-4-((3R)-3-((5-((Z)-4,4,4-trifluoro-1-(3-fluoro-1-(tetrahydro-2H-pyran-2-yl)-1H-indazol-5-yl)-2-(4-(methylsulfonyl)phenyl)but-1-en-1-yl)pyridin-2-yl)oxy)piperidin-1-yl)but-2-enamide 23b |

| Example No. | Structure and name of the compound | |
|---|---|---|
| 24b | 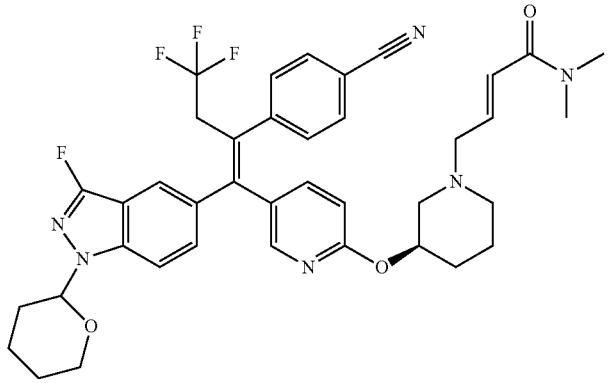 [SMILES: CN(C)C(=O)/C=C/CN1CCC[C@@H](Oc2ccc(/C(=C(/CC(F)(F)F)c3ccc(C#N)cc3)c3ccc4c(c3)c(F)nn4C3CCCCO3)cn2)C1]<br>(E)-4-((3R)-3-((5-((Z)-2-(4-Cyanophenyl)-4,4,4-trifluoro-1-(3-fluoro-1-(tetrahydro-2H-pyran-2-yl)-1H-indazol-5-yl)but-1-en-1-yl)pyridin-2-yl)oxy)piperidin-1-yl)-N,N-dimethylbut-2-enamide 24b | 24b |
| 25a | 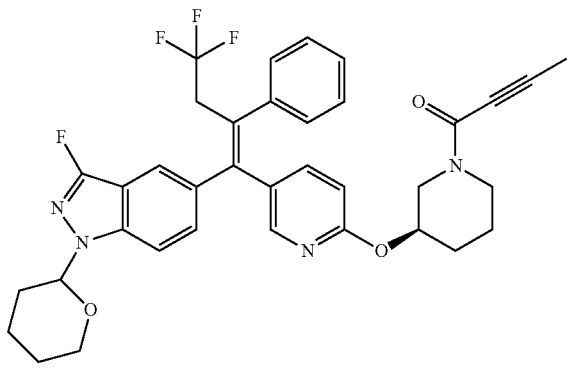 [SMILES: CC#CC(=O)N1CCC[C@@H](Oc2ccc(/C(=C(/CC(F)(F)F)c3ccccc3)c3ccc4c(c3)c(F)nn4C3CCCCO3)cn2)C1]<br>1-((3R)-3-((5-((Z)-4,4,4-Trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-yn-1-one 25a | 25a |
| 26b | 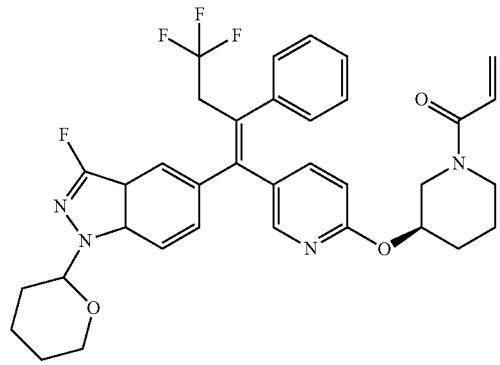 [SMILES: C=CC(=O)N1CCC[C@@H](Oc2ccc(/C(C3=CC4C(F)=NN(C5CCCCO5)C4C=C3)=C(/CC(F)(F)F)c3ccccc3)cn2)C1]<br>1-((3R)-3-((5-((Z)-4,4,4-Trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)prop-2-en-1-one 26b | 26b |

| Example No. | Structure and name of the compound | |
|---|---|---|
| 27e | 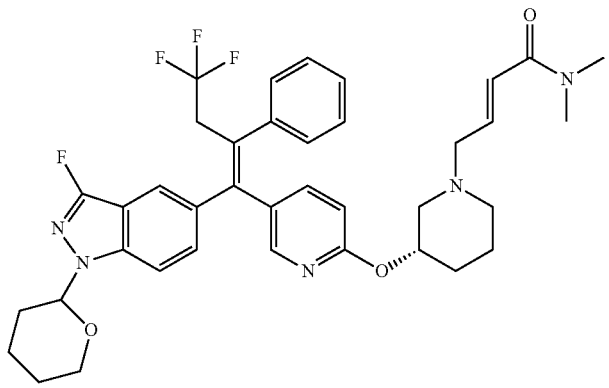 [SMILES: CN(C)C(=O)/C=C/CN1CCC[C@H](Oc2ccc(/C(=C(/CC(F)(F)F)c3ccccc3)c3ccc4c(c3)c(F)nn4C3CCCCO3)cn2)C1]<br>(E)-N,N-Dimethyl-4-((3S)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-enamide 27e | 27e |
| 28a | 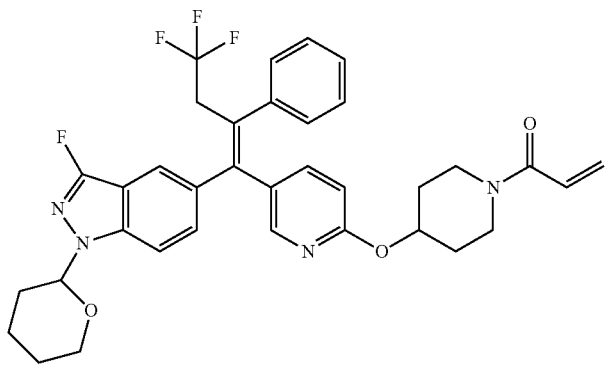 [SMILES: C=CC(=O)N1CCC(Oc2ccc(/C(=C(/CC(F)(F)F)c3ccccc3)c3ccc4c(c3)c(F)nn4C3CCCCO3)cn2)CC1]<br>(Z)-1-(4-((5-(4,4,4-Trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)prop-2-en-1-one 28a | 28a |
| 29e | 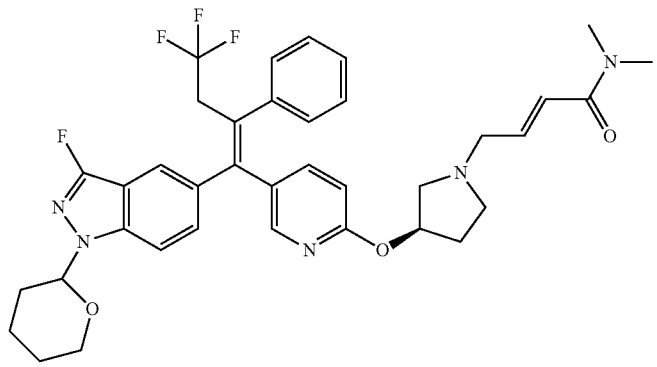 [SMILES: CN(C)C(=O)/C=C/CN1CC[C@@H](Oc2ccc(/C(=C(/CC(F)(F)F)c3ccccc3)c3ccc4c(c3)c(F)nn4C3CCCCO3)cn2)C1]<br>(E)-N,N-Dimethyl-4-((3R)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-enamide 29e | 29e |

| Example No. | Structure and name of the compound | |
|---|---|---|
| 30e | 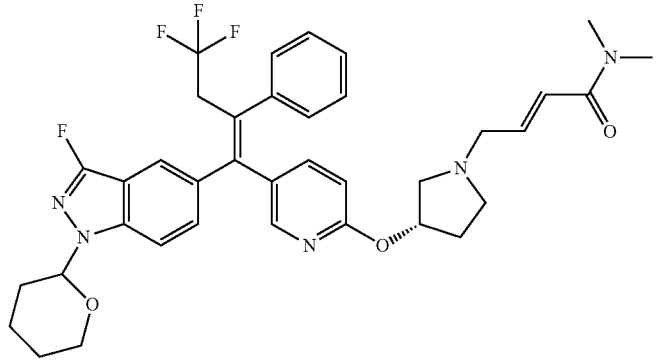 [SMILES: CN(C)C(=O)/C=C/CN1CC[C@H](Oc2ccc(/C(=C(/CC(F)(F)F)c3ccccc3)c3ccc4c(c3)c(F)nn4C3CCCCO3)cn2)C1]<br>(E)-N,N-Dimethyl-4-(((3S)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-enamide 30e | 30e |
| 33e | 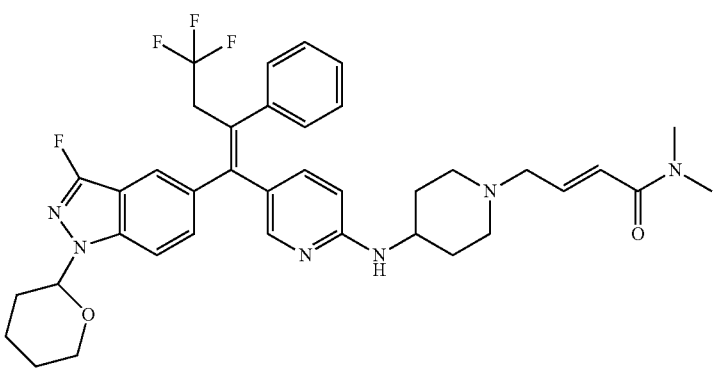<br>(E)-N,N-Dimethyl-4-(4-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)amino)piperidin-1-yl)but-2-enamide 33e | 33e |
| 34e | 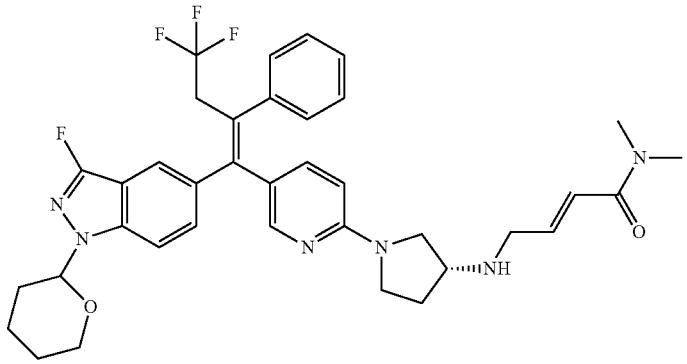 [SMILES: CN(C)C(=O)/C=C/CN[C@@H]1CCN(c2ccc(/C(=C(/CC(F)(F)F)c3ccccc3)c3ccc4c(c3)c(F)nn4C3CCCCO3)cn2)C1]<br>(E)-N,N-Dimethyl-4-(((3R)-1-(5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)pyrrolidin-3-yl)amino)but-2-enamide 34e | 34e |

| Example No. | Structure and name of the compound | |
|---|---|---|
| 35e | 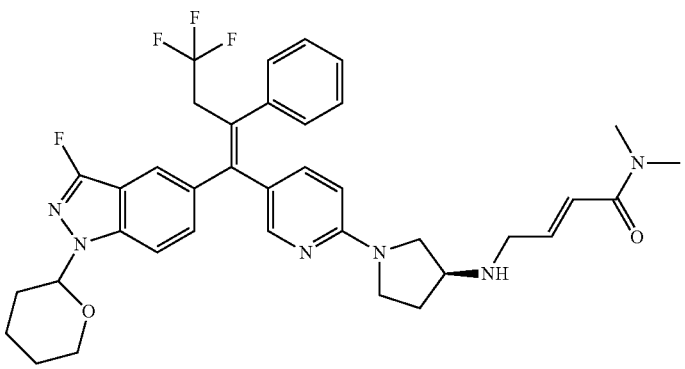 [SMILES: CN(C)C(=O)/C=C/CN[C@H]1CCN(c2ccc(/C(=C(/CC(F)(F)F)c3ccccc3)c3ccc4c(c3)c(F)nn4C3CCCCO3)cn2)C1]<br>(E)-N,N-Dimethyl-4-(((3S)-1-(5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)pyrrolidin-3-yl)amino)but-2-enamide 35e | 35e |
| 36e | 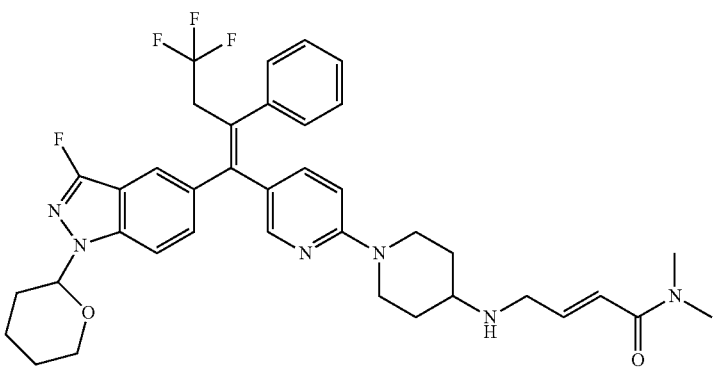 [SMILES: CN(C)C(=O)/C=C/CNC1CCN(c2ccc(/C(=C(/CC(F)(F)F)c3ccccc3)c3ccc4c(c3)c(F)nn4C3CCCCO3)cn2)CC1]<br>(E)-N,N-Dimethyl-4-((1-(5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)piperidin-4-yl)amino)but-2-enamide 36e | 36e |
| 37f | 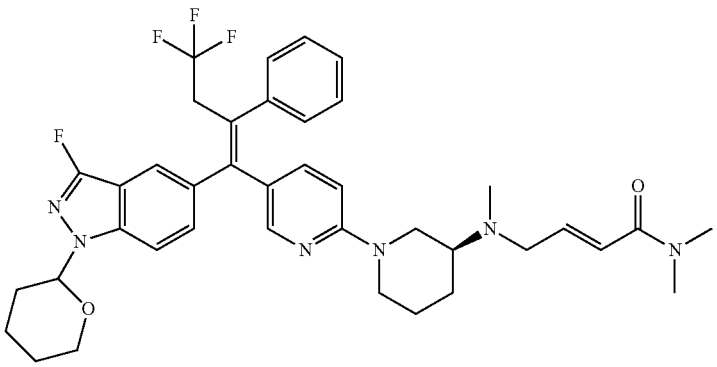 [SMILES: CN(C)C(=O)/C=C/CN(C)[C@H]1CCCN(c2ccc(/C(=C(/CC(F)(F)F)c3ccccc3)c3ccc4c(c3)c(F)nn4C3CCCCO3)cn2)C1]<br>(E)-N,N-Dimethyl-4-(methyl((3S)-1-(5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)piperidin-3-yl)amino)but-2-enamide 37f | 37f |

| Example No. | Structure and name of the compound | |
|---|---|---|
| 38c | 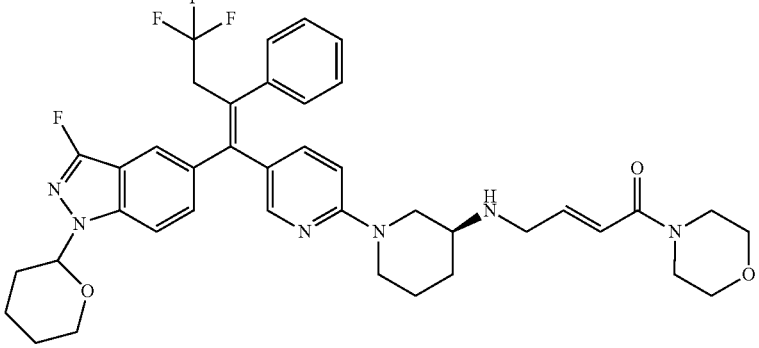<br>(E)-1-Morpholino-4-(((3S)-1-(5-((Z)-4,4,4-trifluoro-1-(3-fluoro-1-(tetrtahydro-2H-pyran-2-yl)-1H-indazol-5-yl)-2-phenylbut-1-en-1-yl)pyridin-2-yl)piperidin-3-yl)amino)but-2-en-1-one 38c | 38c |
| 39a | 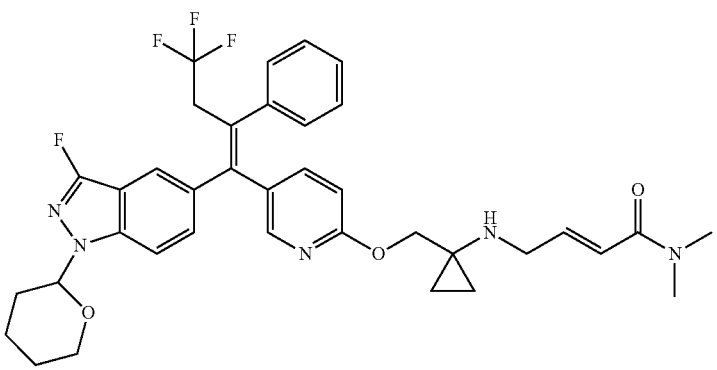 [SMILES: CN(C)C(=O)/C=C/CNC1(COc2ccc(/C(=C(/CC(F)(F)F)c3ccccc3)c3ccc4c(c3)c(F)nn4C3CCCCO3)cn2)CC1]<br>(E)-N,N-Dimethyl-4-((1-(5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-enamide 39a | 39a |
| 40b | 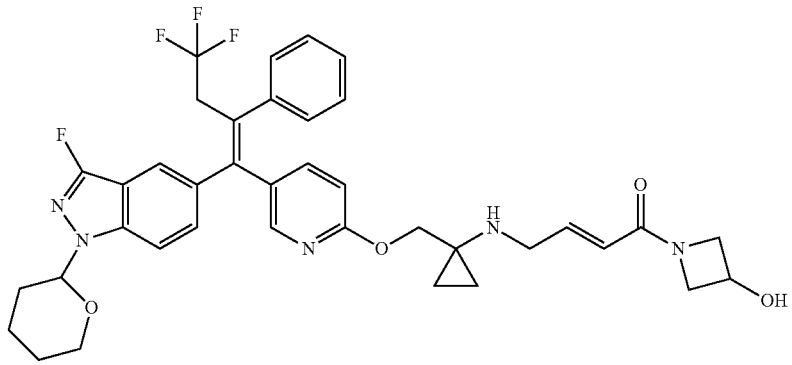 [SMILES: O=C(/C=C/CNC1(COc2ccc(/C(=C(/CC(F)(F)F)c3ccccc3)c3ccc4c(c3)c(F)nn4C3CCCCO3)cn2)CC1)N1CC(O)C1]<br>(E)-1-(3-Hydroxyazetidin-1-yl)-4-((1-(((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-en-1-one 40b | 40b |

| Example No. | Structure and name of the compound | |
|---|---|---|
| 41b | 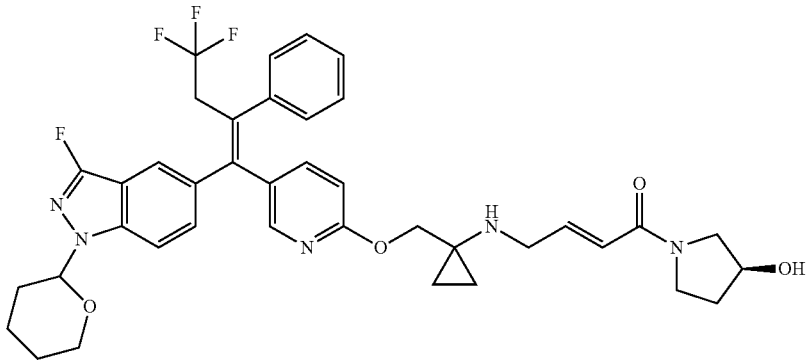 [SMILES: O=C(/C=C/CNC1(COc2ccc(/C(=C(/CC(F)(F)F)c3ccccc3)c3ccc4c(c3)c(F)nn4C3CCCCO3)cn2)CC1)N1CC[C@H](O)C1]<br>(E)-1-((S)-3-Hydroxypyrrolidin-1-yl)-4-((1-(((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-en-1-one 41b | 41b |
| 42b | 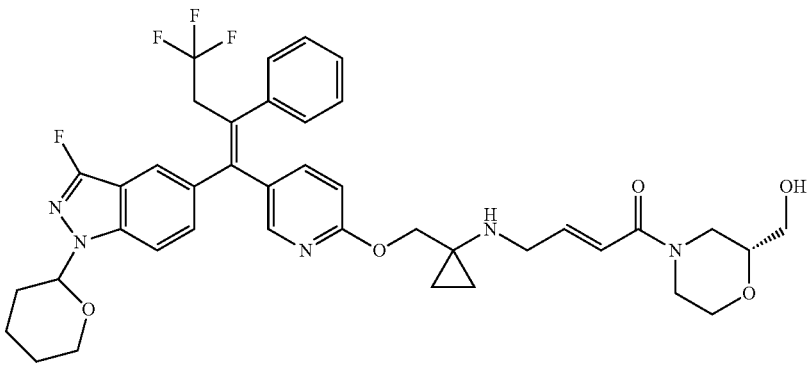 [SMILES: O=C(/C=C/CNC1(COc2ccc(/C(=C(/CC(F)(F)F)c3ccccc3)c3ccc4c(c3)c(F)nn4C3CCCCO3)cn2)CC1)N1CCO[C@@H](CO)C1]<br>(E)-1-((R)-3-(Hydroxymethyl)morpholino)-4-((1-(((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-en-1-one 42b | 42b | or a tautomer, mesomer, racemate, enantiomer, diastereomer thereof, or mixture thereof, a pharmaceutically acceptable salt thereof.

In another aspect, the present disclosure provides a method for preparing the compound of formula (I) or the tautomer, mesomer, racemate, enantiomer, diastereomer thereof, or mixture thereof, or the pharmaceutically acceptable salt thereof, comprising a step of:

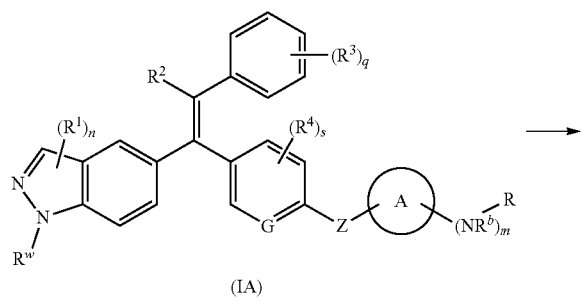

(IA)

-continued

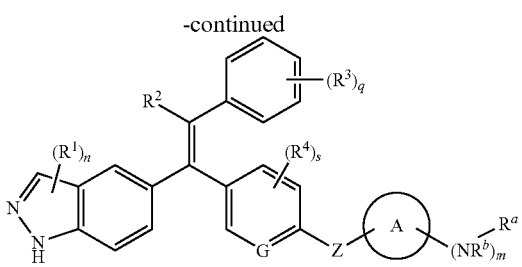

(I)

subjecting the compound of formula (IA) or the tautomer, mesomer, racemate, enantiomer, diastereomer thereof, or mixture thereof, or the pharmaceutically acceptable salt thereof to a deprotection reaction under an acidic condition to obtain the compound of formula (I) or the tautomer, mesomer, racemate, enantiomer, diastereomer thereof, or mixture thereof, or the pharmaceutically acceptable salt thereof;

wherein:

$R^w$ is an amino protecting group, and preferably tetrahydropyranyl or tert-butoxycarbonyl;

R is as defined in formula (IA);

ring A, G, Z, $R^1$, $R^2$, $R^3$, $R^4$, $R^a$, $R^b$, n, m, s and q are as defined in formula (I).

In another aspect, the present disclosure provides a method for preparing the compound of formula (II) or the tautomer, mesomer, racemate, enantiomer, diastereomer thereof, or mixture thereof, or the pharmaceutically acceptable salt thereof, comprising a step of:

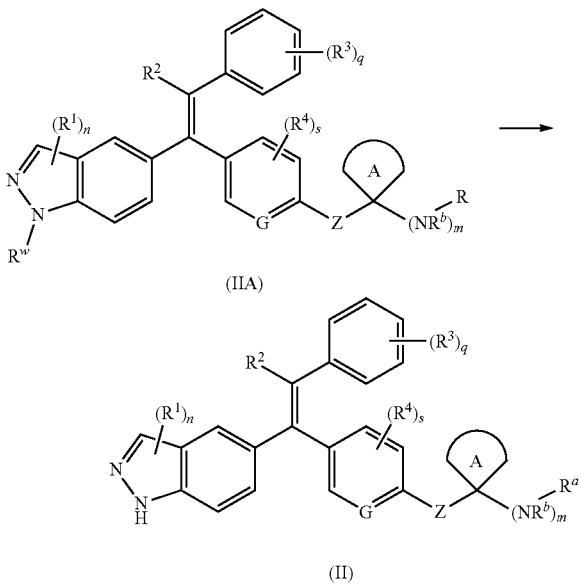

(IIA)

(II)

subjecting the compound of formula (IIA) or the tautomer, mesomer, racemate, enantiomer, diastereomer thereof, or mixture thereof, or the pharmaceutically acceptable salt thereof to a deprotection reaction under an acidic condition to obtain the compound of formula (II) or the tautomer, mesomer, racemate, enantiomer, diastereomer thereof, or mixture thereof, or the pharmaceutically acceptable salt thereof;

wherein:

$R^w$ is an amino protecting group, and preferably tetrahydropyranyl or tert-butoxycarbonyl;

R is as defined in formula (IIA);

ring A, G, Z, $R^1$, $R^2$, $R^3$, $R^4$, $R^a$, $R^b$, n, m, s and q are as defined in formula (II).

In another aspect, the present disclosure provides a method for preparing the compound of formula (III) or the tautomer, mesomer, racemate, enantiomer, diastereomer thereof, or mixture thereof, or the pharmaceutically acceptable salt thereof, comprising a step of:

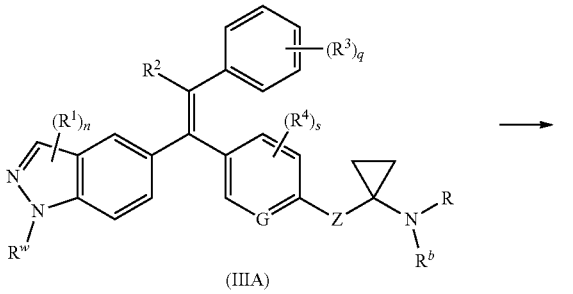

(IIIA)

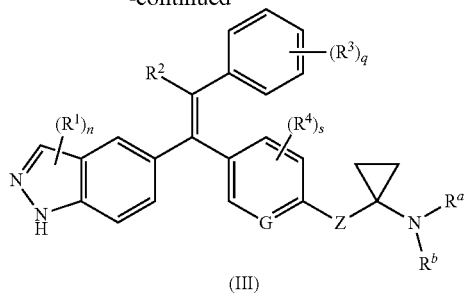

(III)

subjecting the compound of formula (IIIA) or the tautomer, mesomer, racemate, enantiomer, diastereomer thereof, or mixture thereof, or the pharmaceutically acceptable salt thereof to a deprotection reaction under an acidic condition to obtain the compound of formula (III) or the tautomer, mesomer, racemate, enantiomer, diastereomer thereof, or mixture thereof, or the pharmaceutically acceptable salt thereof;

wherein:

$R^w$ is an amino protecting group, and preferably tetrahydropyranyl or tert-butoxycarbonyl;

R is as defined in formula (IIIA);

G, Z, $R^1$, $R^2$, $R^3$, $R^4$, $R^a$, $R^b$, n, s and q are as defined in formula (III).

In another aspect, the present disclosure provides a method for preparing the compound of formula (IV) or the tautomer, mesomer, racemate, enantiomer, diastereomer thereof, or mixture thereof, or the pharmaceutically acceptable salt thereof, comprising a step of:

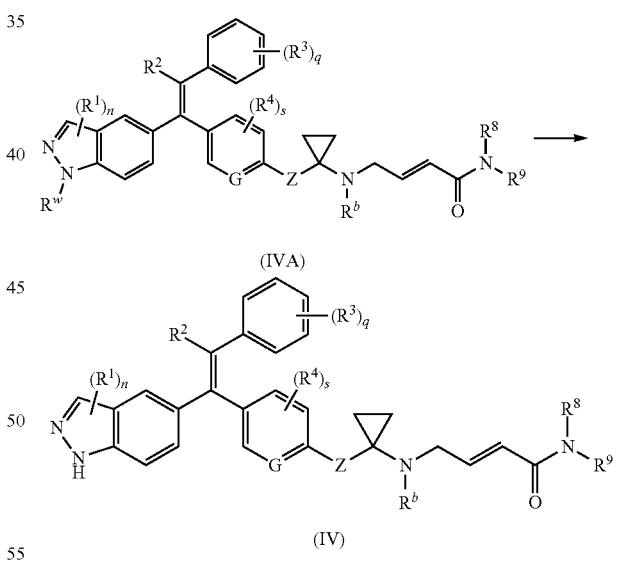

(IVA)

(IV)

subjecting the compound of formula (IVA) or the tautomer, mesomer, racemate, enantiomer, diastereomer thereof, or mixture thereof, or the pharmaceutically acceptable salt thereof to a deprotection reaction under an acidic condition to obtain the compound of formula (IV) or the tautomer, mesomer, racemate, enantiomer, diastereomer thereof, or mixture thereof, or the pharmaceutically acceptable salt thereof;

wherein:

$R^w$ is an amino protecting group, and preferably tetrahydropyranyl or tert-butoxycarbonyl;

G, Z, $R^1$, $R^2$, $R^3$, $R^4$, $R^8$, $R^9$, $R^b$, n, s and q are as defined in formula (IV).

In another aspect, the present disclosure relates to a pharmaceutical composition comprising a therapeutically effective amount of the compound of formula (I) to (IV) as defined above or the tautomer, mesomer, racemate, enantiomer, diastereomer thereof, or mixture thereof, or the pharmaceutically acceptable salt thereof, and one or more pharmaceutically acceptable carriers, diluents or excipients. The present disclosure also relates to a method for preparing the pharmaceutical composition as defined above, comprising a step of mixing the compound of formula (I) to (IV), or the tautomer, mesomer, racemate, enantiomer, diastereomer thereof, or mixture thereof, or the pharmaceutically acceptable salt thereof with the pharmaceutically acceptable carriers, diluents or excipients.

The present disclosure further relates to a use of the compound of formula (I) to (IV), or the tautomer, mesomer, racemate, enantiomer, diastereomer thereof, or mixture thereof, or the pharmaceutically acceptable salt thereof, or the pharmaceutical composition comprising the same in the preparation of an estrogen receptor modulator.

The present disclosure further relates to a use of the compound of formula (I) to (IV), or the tautomer, mesomer, racemate, enantiomer, diastereomer thereof, or mixture thereof, or the pharmaceutically acceptable salt thereof, or the pharmaceutical composition comprising the same in the preparation of a medicament for preventing and/or treating estrogen receptor-mediated or estrogen receptor-dependent disease or disorder, wherein the estrogen receptor-mediated or estrogen receptor-dependent disease or disorder is preferably cancer, more preferably breast cancer, ovarian cancer, endometrial cancer, prostate cancer or uterine cancer, and further preferably breast cancer.

The present disclosure further relates to the compound of formula (I) to (IV), or the tautomer, mesomer, racemate, enantiomer, diastereomer thereof, or mixture thereof, or the pharmaceutically acceptable salt thereof, for use as a medicament.

The present disclosure further relates to the compound of formula (I) to (IV), or the tautomer, mesomer, racemate, enantiomer, diastereomer thereof, or mixture thereof, or the pharmaceutically acceptable salt thereof, for use as a medicament for treating estrogen receptor-mediated or estrogen receptor-dependent disease or disorder, wherein the estrogen receptor-mediated or estrogen receptor-dependent disease or disorder is preferably cancer, more preferably breast cancer, ovarian cancer, endometrial cancer, prostate cancer or uterine cancer, and further preferably breast cancer.

The present disclosure further relates to a method for treating estrogen receptor-mediated or estrogen receptor-dependent disease or disorder, comprising a step of administering to a patient in need thereof a therapeutically effective amount of the compound of formula (I) to (IV) or the tautomer, mesomer, racemate, enantiomer, diastereomer thereof, or mixture thereof, or the pharmaceutically acceptable salt thereof of the present disclosure. This method shows outstanding efficacy and less side effects. The estrogen receptor-mediated or estrogen receptor-dependent disease or disorder is preferably cancer, more preferably breast cancer, ovarian cancer, endometrial cancer, prostate cancer or uterine cancer, and further preferably breast cancer.

The active compound can be formulated into a form suitable for administration by any appropriate route, and the active compound is preferably in the form of a unit dose, or in a form in which the patient can self-administer in a single dose. The form of the unit dose of the compound or composition of the present invention can be tablet, capsule, cachet, bottled portion, powder, granule, lozenge, suppository, regenerating powder or liquid preparation.

The dosage of the compound or composition used in the treatment method of the present invention will generally vary according to the severity of the disease, the weight of the patient, and the relative efficacy of the compound. However, as a general guide, a suitable unit dose can be 0.1 to 1000 mg.

In addition to the active ingredients, the pharmaceutical composition of the present invention can further comprise one or more auxiliaries including filler (diluent), binder, wetting agent, disintegrant, excipient and the like. Depending on the administration mode, the composition can comprise 0.1 to 99% by weight of the active compound.

The pharmaceutical composition containing the active ingredient can be in a form suitable for oral administration, for example, a tablet, troche, lozenge, aqueous or oily suspension, dispersible powder or granule, emulsion, hard or soft capsule, syrup or elixir. An oral composition can be prepared according to any known method in the art for the preparation of pharmaceutical composition. Such a composition can contain one or more ingredient(s) selected from the group consisting of sweeteners, flavoring agents, colorants and preservatives, in order to provide a pleasing and palatable pharmaceutical formulation. The tablet contains the active ingredient in admixture with nontoxic, pharmaceutically acceptable excipients suitable for the manufacture of tablets. These excipients can be inert excipients, granulating agents, disintegrants and lubricants. The tablet can be uncoated or coated by means of a known technique to mask drug taste or delay the disintegration and absorption of the active ingredient in the gastrointestinal tract, thereby providing a sustained release over a long period of time. For example, water soluble taste masking materials can be used. An oral formulation can also be provided as soft gelatin capsules in which the active ingredient is mixed with an inert solid diluent, or the active ingredient is mixed with a water-soluble carrier.

An aqueous suspension comprises an active ingredient in admixture with excipients suitable for the manufacture of an aqueous suspension. Such excipients are suspending agents, dispersants or wetting agents. The active ingredient of the aqueous suspension can be dispersible powders or granules. The active ingredient is mixed with one or more dispersant (s), wetting agent(s) or suspending agent(s) by adding water. The aqueous suspension can also comprise one or more preservative(s), one or more colorant(s), one or more flavoring agent(s), and one or more sweetener(s).

An oil suspension can be formulated by suspending the active ingredient in a vegetable oil or mineral oil. The oil suspension can comprise a thickener. The aforementioned sweeteners and flavoring agents can be added to provide a palatable formulation. These compositions can be preserved by adding an antioxidant.

The dispersible powders or granules suitable for the preparation of an aqueous suspension can provide the active ingredient in admixture with the dispersants or wetting agents, suspending agent or one or more preservatives by adding water. Suitable dispersants or wetting agents and suspending agents are exemplified by those already mentioned above. Additional excipients, such as sweeteners, flavoring agents and colorants, can also be added. These compositions can be preserved by adding an antioxidant, such as ascorbic acid.

The pharmaceutical composition of the present disclosure can also be in the form of an oil-in-water emulsion. The oil phase can be a vegetable oil, or a mineral oil, or a mixture thereof. Suitable emulsifying agents can be naturally occurring phospholipids. A sweetening agent can be used. Such formulations can also contain a demulcent, a preservative, a coloring agent and an antioxidant.

The pharmaceutical composition of the present disclosure can be in the form of a sterile injectable aqueous solution. Acceptable vehicles or solvents that can be used are water, Ringer's solution or isotonic sodium chloride solution. The sterile injectable formulation can be a sterile injectable oil-in-water micro-emulsion in which the active ingredient is dissolved in an oil phase. The injectable solution or microemulsion can be introduced into a patient's bloodstream by local bolus injection. Alternatively, the solution and microemulsion are preferably administered in a manner that maintains a constant circulating concentration of the compound of the present disclosure. In order to maintain this constant concentration, a continuous intravenous delivery device can be used. An example of such a device is Deltec CADD-PLUS.™ 5400 intravenous injection pump.

The pharmaceutical composition of the present disclosure can be in the form of a sterile injectable aqueous or oily suspension for intramuscular and subcutaneous administration. Such a suspension can be formulated with suitable dispersants or wetting agents and suspending agents as described above according to known techniques. The sterile injectable formulation can also be a sterile injectable solution or suspension prepared in a nontoxic parenterally acceptable diluent or solvent. Moreover, sterile fixed oils can easily be used as a solvent or suspending medium. In addition, fatty acids can also be used to prepare injections.

The compound of the present disclosure can be administered in the form of a suppository for rectal administration. These pharmaceutical compositions can be prepared by mixing the drug with a suitable non-irritating excipient that is solid at ordinary temperatures, but liquid in the rectum, thereby melting in the rectum to release the drug.

It is well known to those skilled in the art that the dosage of a drug depends on a variety of factors including, but not limited to the following factors: activity of a specific compound, age of the patient, weight of the patient, general health of the patient, behavior of the patient, diet of the patient, administration time, administration route, excretion rate, drug combination and the like. In addition, the optimal treatment, such as treatment mode, daily dose of the compound of formula (I) or the type of pharmaceutically acceptable salt thereof can be verified according to traditional therapeutic regimens.

Definitions

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 12 carbon atoms, and more preferably an alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferably, the alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "alkylene" refers to a saturated linear or branched aliphatic hydrocarbon group having two residues derived from the removal of two hydrogen atoms from the same carbon atom or two different carbon atoms of the parent alkane. It is a linear or branched alkylene having 1 to 20 carbon atoms, preferably 1 to 12 carbon atoms, and more preferably 1 to 6 carbon atoms. Non-limiting examples of alkylene include, but are not limited to, methylene (—CH$_2$—), 1,1-ethylene (—CH(CH$_3$)—), 1,2-ethylene (—CH$_2$CH$_2$—), 1,1-propylene (—CH(CH$_2$CH$_3$)—), 1,2-propylene (—CH$_2$CH(CH$_3$)—), 1,3-propylene (—CH$_2$CH$_2$CH$_2$—), 1,4-butylene (—CH$_2$CH$_2$CH$_2$CH$_2$—) and the like. The alkylene can be substituted or unsubstituted. When substituted, the substituent group(s) can be substituted at any available connection point. The substituent group(s) is preferably one or more groups independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio and oxo.

The term "alkenyl" refers to an alkyl containing carbon-carbon double bond(s) in the molecule, wherein the definition of the alkyl is as described above. The alkenyl can be substituted or unsubstituted. When substituted, the substituent group(s) is preferably one or more groups independently selected from the group consisting of hydrogen atom, alkyl, alkoxy, halogen, haloalkyl, hydroxy, hydroxyalkyl, cyano, amino, nitro, cycloalkyl, heterocyclyl, aryl and heteroaryl.

The term "alkynyl" refers to an alkyl containing carbon-carbon triple bond(s) in the molecule, wherein the definition of the alkyl is as described above. The alkynyl can be substituted or unsubstituted. When substituted, the substituent group(s) is preferably one or more groups independently selected from the group consisting of hydrogen atom, alkyl, alkoxy, halogen, haloalkyl, hydroxy, hydroxyalkyl, cyano, amino, nitro, cycloalkyl, heterocyclyl, aryl and heteroaryl.

The term "alkoxy" refers to an —O-(alkyl) or an —O-(unsubstituted cycloalkyl) group, wherein the alkyl is as defined above. Non-limiting examples of alkoxy include methoxy, ethoxy, propoxy, butoxy, cyclopropyloxy, cyclobutyloxy, cyclopentyloxy, cyclohexyloxy. The alkoxy can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "cycloalkyl" refers to a saturated or partially unsaturated monocyclic or polycyclic hydrocarbon substituent group having 3 to 20 carbon atoms, preferably 3 to 12 carbon atoms (for example 3, 4, 5, 6, 7, 8, 9, 10, 11, 12 carbon atoms), and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring.

The term "spiro cycloalkyl" refers to a 5 to 20 membered polycyclic group with individual rings connected through one shared carbon atom (called a spiro atom), wherein the rings can contain one or more double bonds, but none of the rings has a completely conjugated π-electron system. The spiro cycloalkyl is preferably a 6 to 14 membered spiro cycloalkyl (for example 6, 7, 8, 9, 10, 11, 12, 13, 14 membered spiro cycloalkyl), and more preferably a 7 to 10 membered spiro cycloalkyl. According to the number of the spiro atoms shared between the rings, the spiro cycloalkyl can be divided into a mono-spiro cycloalkyl, di-spiro cycloalkyl, or poly-spiro cycloalkyl, and the spiro cycloalkyl is preferably a mono-spiro cycloalkyl or di-spiro cycloalkyl, and more preferably a 4-membered/4-membered, 4-membered/5-membered, 4-membered/6-membered, 5-membered/5-membered, or 5-membered/6-membered mono-spiro cycloalkyl. Non-limiting examples of spiro cycloalkyl include:

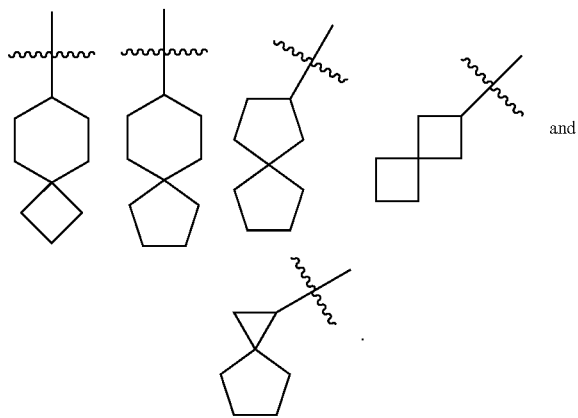

The term "fused cycloalkyl" refers to a 5 to 20 membered all-carbon polycyclic group, wherein each ring in the system shares an adjacent pair of carbon atoms with another ring, one or more rings can contain one or more double bonds, but none of the rings has a completely conjugated π-electron system. The fused cycloalkyl is preferably a 6 to 14 membered fused cycloalkyl, and more preferably a 7 to 10 membered fused cycloalkyl (for example 7, 8, 9 or 10 membered fused cycloalkyl). According to the number of membered rings, the fused cycloalkyl can be divided into a bicyclic, tricyclic, tetracyclic or polycyclic fused cycloalkyl, and the fused cycloalkyl is preferably a bicyclic or tricyclic fused cycloalkyl, and more preferably a 5-membered/5-membered, or 5-membered/6-membered bicyclic fused cycloalkyl. Non-limiting examples of fused cycloalkyl include:

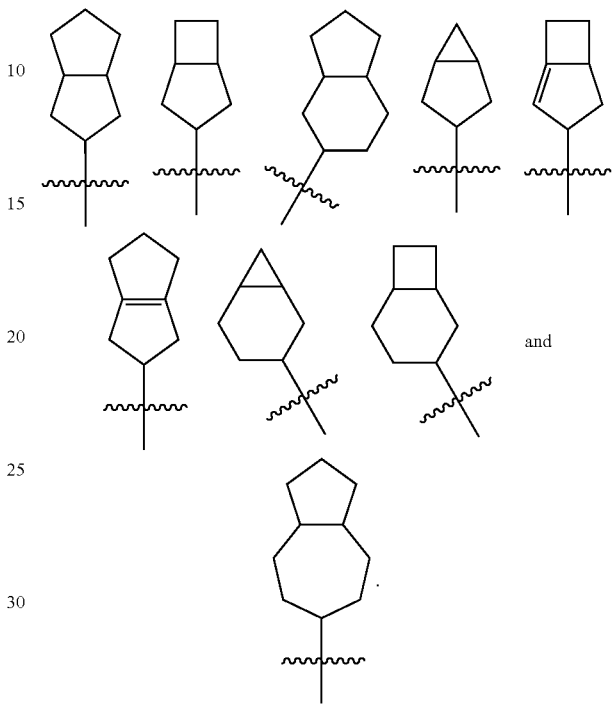

The term "bridged cycloalkyl" refers to a 5 to 20 membered all-carbon polycyclic group, wherein every two rings in the system share two disconnected carbon atoms, the rings can have one or more double bonds, but none of the rings has a completely conjugated π-electron system. The bridged cycloalkyl is preferably a 6 to 14 membered bridged cycloalkyl, and more preferably a 7 to 10 membered bridged cycloalkyl (for example 7, 8, 9 or 10 membered bridged cycloalkyl). According to the number of membered rings, the bridged cycloalkyl can be divided into a bicyclic, tricyclic, tetracyclic or polycyclic bridged cycloalkyl, and the bridged cycloalkyl is preferably a bicyclic, tricyclic or tetracyclic bridged cycloalkyl, and more preferably a bicyclic or tricyclic bridged cycloalkyl. Non-limiting examples of bridged cycloalkyl include:

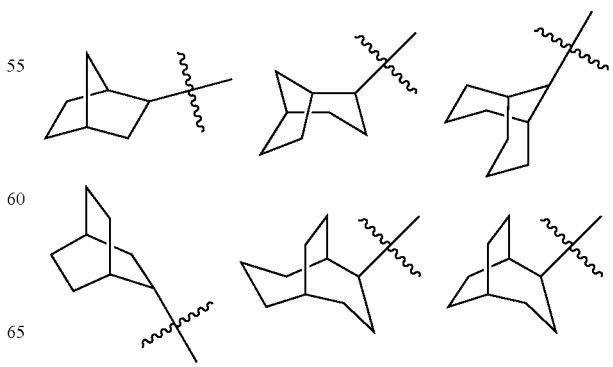

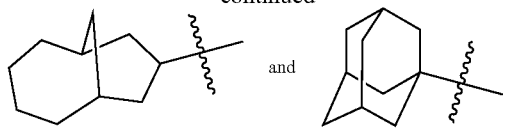 and .

The cycloalkyl (including cycloalkyl, spiro cycloalkyl, fused cycloalkyl and bridged cycloalkyl) ring can be fused to the ring of aryl, heteroaryl or heterocyclyl, wherein the ring bound to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "heterocyclyl" refers to a 3 to 20 membered saturated or partially unsaturated monocyclic or polycyclic hydrocarbon substituent group, wherein one or more ring atoms are heteroatoms selected from the group consisting of N, O, S, S(O) and S(O)$_2$, but excluding —O—O—, —O—S— or —S—S— in the ring, with the remaining ring atoms being carbon atoms. Preferably, the heterocyclyl has 3 to 12 ring atoms wherein 1 to 4 atoms (for example 1, 2, 3 or 4 atoms) are heteroatoms; more preferably, 3 to 6 ring atoms (for example 3, 4, 5 or 6 ring atoms). Non-limiting examples of monocyclic heterocyclyl include pyrrolidinyl, imidazolidinyl, tetrahydrofuranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl and the like, and preferably piperidinyl, pyrrolidinyl. Polycyclic heterocyclyl includes a heterocyclyl having a spiro ring, fused ring or bridged ring.

The term "spiro heterocyclyl" refers to a 5 to 20 membered polycyclic heterocyclyl group with individual rings connected through one shared atom (called a spiro atom), wherein one or more ring atoms are heteroatoms selected from the group consisting of N, O, S, S(O) and S(O)$_2$, with the remaining ring atoms being carbon atoms, where the rings can contain one or more double bonds, but none of the rings has a completely conjugated R-electron system. The spiro heterocyclyl is preferably a 6 to 14 membered spiro heterocyclyl, and more preferably a 7 to 10 membered spiro heterocyclyl (for example 7, 8, 9 or 10 membered spiro heterocyclyl). According to the number of the spiro atoms shared between the rings, the spiro heterocyclyl is divided into a mono-spiro heterocyclyl, di-spiro heterocyclyl, or poly-spiro heterocyclyl, and the spiro heterocyclyl is preferably a mono-spiro heterocyclyl or di-spiro heterocyclyl, and more preferably a 4-membered/4-membered, 4-membered/5-membered, 4-membered/6-membered, 5-membered/5-membered, or 5-membered/6-membered mono-spiro heterocyclyl. Non-limiting examples of spiro heterocyclyl include:

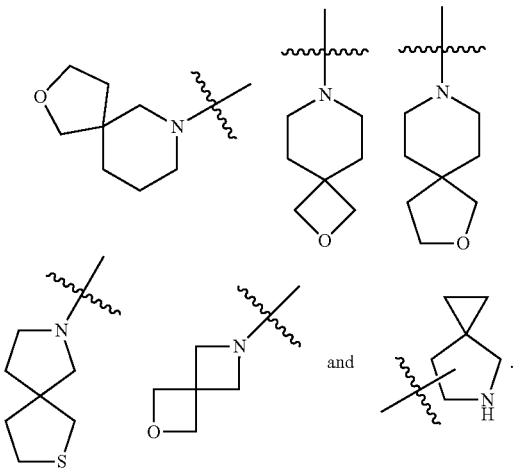

The term "fused heterocyclyl" refers to a 5 to 20 membered polycyclic heterocyclyl group, wherein each ring in the system shares an adjacent pair of atoms with another ring, wherein one or more rings can contain one or more double bonds, but none of the rings has a completely conjugated π-electron system, and wherein one or more ring atoms are heteroatoms selected from the group consisting of N, O, S, S(O) and S(O)$_2$, with the remaining ring atoms being carbon atoms. The fused heterocyclyl is preferably a 6 to 14 membered fused heterocyclyl, and more preferably a 7 to 10 membered fused heterocyclyl (for example 7, 8, 9 or 10 membered fused heterocyclyl). According to the number of membered rings, the fused heterocyclyl can be divided into a bicyclic, tricyclic, tetracyclic or polycyclic fused heterocyclyl, and the fused heterocyclyl is preferably a bicyclic or tricyclic fused heterocyclyl, and more preferably a 5-membered/5-membered or 5-membered/6-membered bicyclic fused heterocyclyl. Non-limiting examples of fused heterocyclyl include:

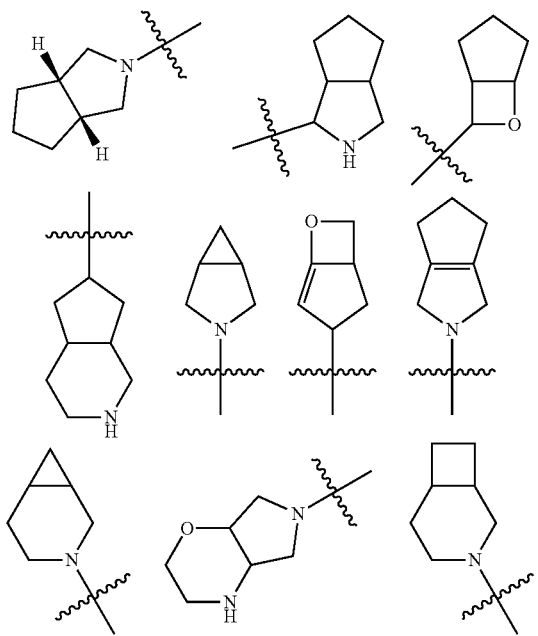

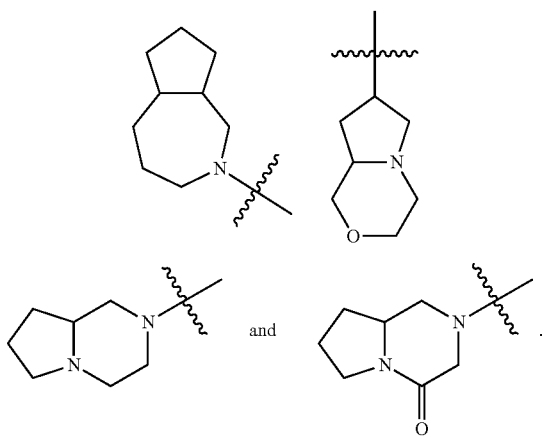

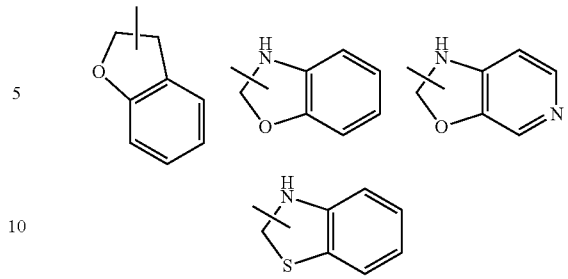

and the like.

The heterocyclyl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "bridged heterocyclyl" refers to a 5 to 14 membered polycyclic heterocyclyl group, wherein every two rings in the system share two disconnected atoms, wherein the rings can have one or more double bonds, but none of the rings has a completely conjugated π-electron system, and wherein one or more ring atoms are heteroatoms selected from the group consisting of N, O, S, S(O) and S(O)$_2$, with the remaining ring atoms being carbon atoms. The bridged heterocyclyl is preferably a 6 to 14 membered bridged heterocyclyl, and more preferably a 7 to 10 membered bridged heterocyclyl (for example 7, 8, 9 or 10 membered bridged heterocyclyl). According to the number of membered rings, the bridged heterocyclyl can be divided into a bicyclic, tricyclic, tetracyclic or polycyclic bridged heterocyclyl, and the bridged heterocyclyl is preferably a bicyclic, tricyclic or tetracyclic bridged heterocyclyl, and more preferably a bicyclic or tricyclic bridged heterocyclyl. Non-limiting examples of bridged heterocyclyl include:

The term "aryl" refers to a 6 to 14 membered all-carbon monocyclic ring or polycyclic fused ring (i.e. each ring in the system shares an adjacent pair of carbon atoms with another ring in the system) having a conjugated π-electron system, preferably a 6 to 10 membered aryl, for example, phenyl and naphthyl. The aryl ring can be fused to the ring of heteroaryl, heterocyclyl or cycloalkyl, wherein the ring bound to the parent structure is aryl ring, and non-limiting examples thereof include:

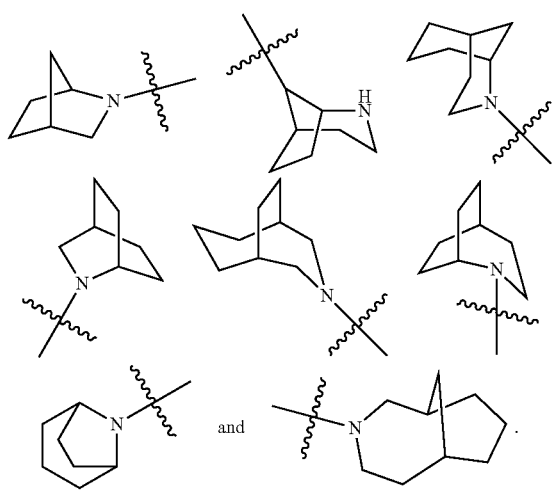

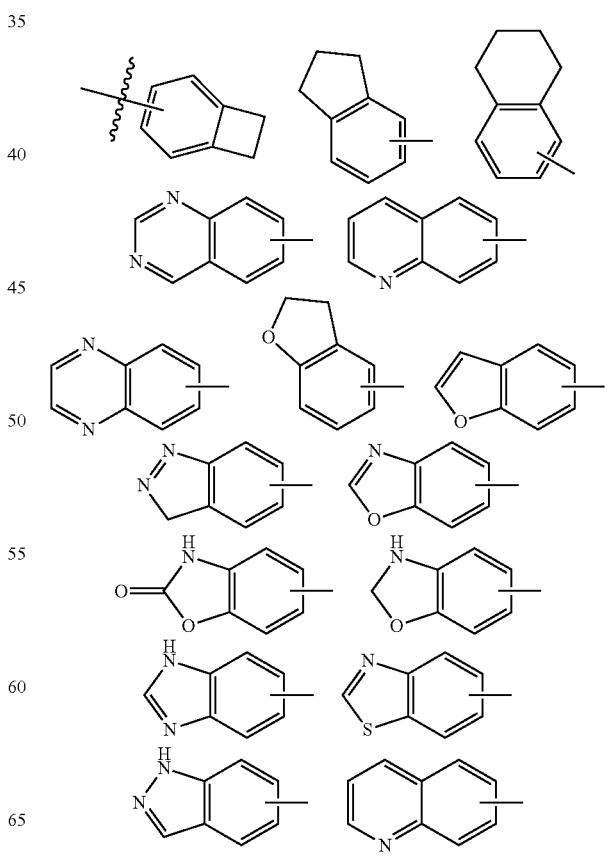

The heterocyclyl (including heterocyclyl, spiro heterocyclyl, fused heterocyclyl and bridged heterocyclyl) ring can be fused to the ring of aryl, heteroaryl or cycloalkyl, wherein the ring bound to the parent structure is heterocyclyl, and non-limiting examples thereof include:

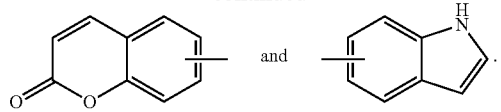

and

The aryl can be substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl, and preferably phenyl.

The term "heteroaryl" refers to a 5 to 14 membered heteroaromatic system having 1 to 4 heteroatoms selected from the group consisting of O, S and N. The heteroaryl is preferably a 5 to 10 membered heteroaryl (for example 5, 6, 7, 8, 9 or 10 membered heteroaryl), more preferably a 5 or 6 membered heteroaryl, for example, imidazolyl, furyl, thienyl, thiazolyl, pyrazolyl, oxazolyl, pyrrolyl, tetrazolyl, pyridyl, pyrimidinyl, thiadiazolyl, pyrazinyl and the like, preferably imidazolyl, pyrazolyl, pyrimidinyl or thiazolyl, and more preferably pyrazolyl or thiazolyl. The heteroaryl ring can be fused to the ring of aryl, heterocyclyl or cycloalkyl, wherein the ring bound to the parent structure is heteroaryl ring, and non-limiting examples thereof include:

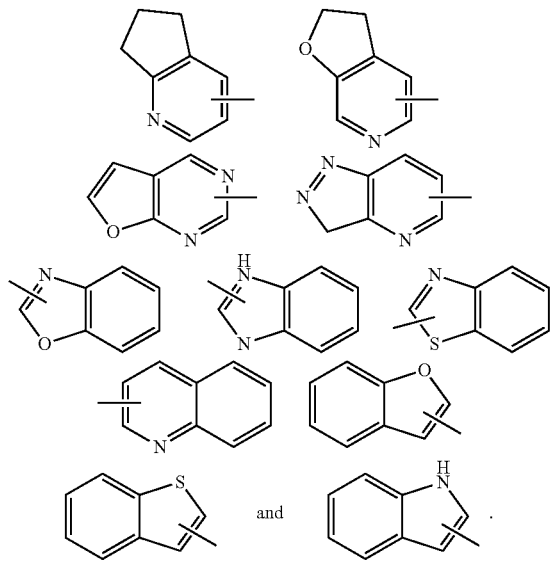

and

The heteroaryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "hydroxyalkyl" refers to an alkyl group substituted by hydroxy(s), wherein the alkyl is as defined above.

The term "haloalkyl" refers to an alkyl group substituted by halogen(s), wherein the alkyl is as defined above.

The term "deuterated alkyl" refers to an alkyl group substituted by deuterium atom(s), wherein the alkyl is as defined above.

The term "hydroxy" refers to an —OH group.
The term "halogen" refers to fluorine, chlorine, bromine or iodine.
The term "amino" refers to a —NH$_2$ group.
The term "cyano" refers to a —CN group.
The term "nitro" refers to a —NO$_2$ group.
The term "carboxy" refers to a —C(O)OH group.
The term "formyl" refers to a —CHO group.
The term "alkoxycarbonyl" refers to a —C(O)O(alkyl) or —C(O)O(cycloalkyl) group, wherein the alkyl and cycloalkyl are as defined above.
The term "acyl halide" refers to a compound containing a —C(O)-halogen group.

"Optional" or "optionally" means that the event or circumstance described subsequently can, but need not, occur, and such a description includes the situation in which the event or circumstance does or does not occur. For example, "the heterocyclyl optionally substituted by alkyl" means that an alkyl group can be, but need not be, present, and such a description includes the situation of the heterocyclyl being substituted by alkyl and the heterocyclyl being not substituted by alkyl.

"Substituted" refers to one or more hydrogen atoms in a group, preferably up to 5, and more preferably 1 to 3 hydrogen atoms, independently substituted by corresponding number of substituents. It goes without saying that the substituents only exist in their possible chemical position. The person skilled in the art is able to determine whether the substitution is possible or impossible by experiments or theory without excessive effort. For example, the combination of amino or hydroxy having free hydrogen and carbon atoms having unsaturated bonds (such as olefinic) may be unstable.

The term "pharmaceutical composition" refers to a mixture of one or more of the compounds described herein or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to show biological activity.

A "pharmaceutically acceptable salt" refers to a salt of the compound of the present disclosure, which is safe and effective in mammals and has the desired biological activity.

Different expressions "X is selected from the group consisting of A, B, or C", "X is selected from the group consisting of A, B and C", "X is A, B or C", "X is A, B and C" and the like all have the same meaning. They mean that X can be any one or more of A, B and C.

The compound of the present disclosure can also comprise isotopic derivatives thereof. The term "isotopic derivatives" refers to compounds that differ in structure only in the presence of one or more isotopically enriched atoms. For example, a compound having the structure of the present disclosure with replacing hydrogen with "deuterium" or "tritium", or replacing fluorine with an $^{18}$F-fluorine labeling ($^{18}$F isotope), or replacing carbon with $^{11}$C—, $^{13}$C—, or $^{14}$C-enriched carbon ($^{11}$C—, $^{13}$C—, or $^{14}$C-carbon labeling; $^{11}$C—, $^{13}$C—, or $^{14}$C-isotope) is within the scope of the present disclosure. Such compounds can be used, for example, as analytical tools or probes in biological assays, or as tracers for in vivo diagnostic imaging of disease, or as tracers for pharmacodynamics, pharmacokinetics or receptor studies. Deuterated compounds can generally retain activity comparable to undeuterated compounds, and when deuterated at certain specific sites, better metabolic stability can be achieved, resulting in certain therapeutic advantages (such as increased half-life in vivo or reduced required dose).

For drugs or pharmacologically active agents, the term "therapeutically effective amount" refers to a sufficient amount of a drug or medicament that is non-toxic but capable of achieving the desired effect. The determination of the effective amount varies from person to person, depending on the age and general condition of the recipient, and also on the specific active substance. The appropriate effective amount in a case can be determined by those skilled in the art based on routine experiments.

The present disclosure provides an estrogen receptor antagonist having a novel structure of formula (I). It is found that the compound having this kind of structure shows excellent in vitro activity. Compared with the prior art, this amide compound with α,β unsaturated bond can inactivate the estrogen receptor by specifically binding to the cysteine in the ligand binding domain of the estrogen receptor.

Synthesis Method of the Compound of the Present Disclosure

In order to achieve the object of the present disclosure, the present disclosure applies the following technical solutions:

Scheme I

A method for preparing the compound of formula (I) or the tautomer, mesomer, racemate, enantiomer, diastereomer thereof, or mixture thereof, or the pharmaceutically acceptable salt thereof according to the present disclosure, comprising the following step of:

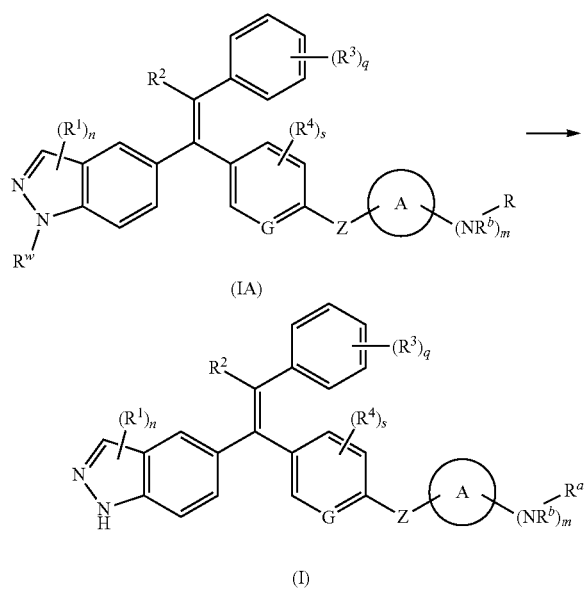

subjecting the compound of formula (IA) or the tautomer, mesomer, racemate, enantiomer, diastereomer thereof, or mixture thereof, or the pharmaceutically acceptable salt thereof to a deprotection reaction under an acidic condition to obtain the compound of formula (I) or the tautomer, mesomer, racemate, enantiomer, diastereomer thereof, or mixture thereof, or the pharmaceutically acceptable salt thereof;

wherein:

$R^w$ is an amino protecting group; R is as defined in formula (IA);

ring A, G, Z, $R^1$, $R^2$, $R^3$, $R^4$, $R^a$, $R^b$, n, m, s and q are as defined in formula (I).

Scheme II

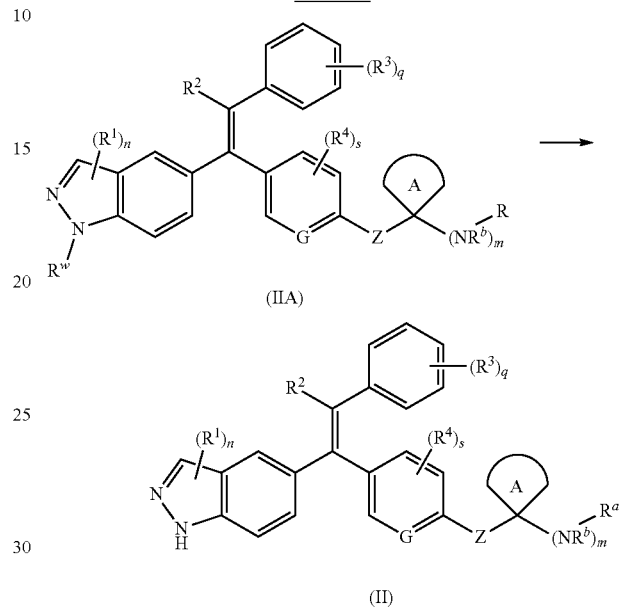

subjecting the compound of formula (IIA) or the tautomer, mesomer, racemate, enantiomer, diastereomer thereof, or mixture thereof, or the pharmaceutically acceptable salt thereof to a deprotection reaction under an acidic condition to obtain the compound of formula (II) or the tautomer, mesomer, racemate, enantiomer, diastereomer thereof, or mixture thereof, or the pharmaceutically acceptable salt thereof;

wherein:

$R^w$ is an amino protecting group;

R is as defined in formula (IIA);

ring A, G, Z, $R^1$, $R^2$, $R^3$, $R^4$, $R^a$, $R^b$, n, m, s and q are as defined in formula (II).

Scheme III

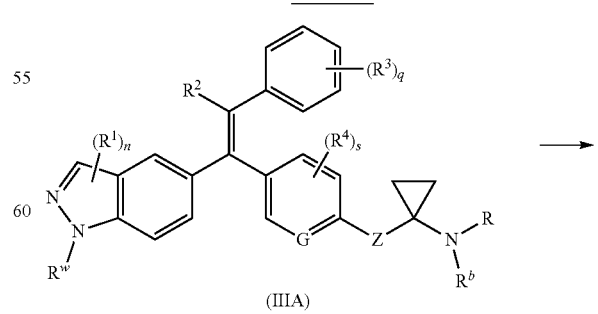

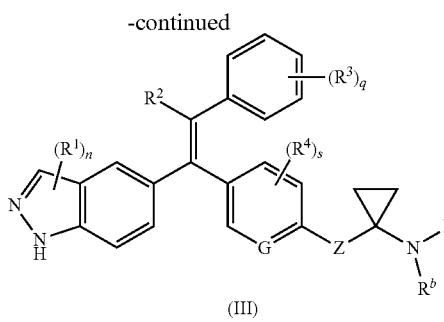

(III)

subjecting the compound of formula (IIIA) or the tautomer, mesomer, racemate, enantiomer, diastereomer thereof, or mixture thereof, or the pharmaceutically acceptable salt thereof to a deprotection reaction under an acidic condition to obtain the compound of formula (III) or the tautomer, mesomer, racemate, enantiomer, diastereomer thereof, or mixture thereof, or the pharmaceutically acceptable salt thereof;

wherein:

$R^w$ is an amino protecting group;

R is as defined in formula (IIIA);

G, Z, $R^1$, $R^2$, $R^3$, $R^4$, $R^a$, $R^b$, n, s and q are as defined in formula (III).

Scheme IV

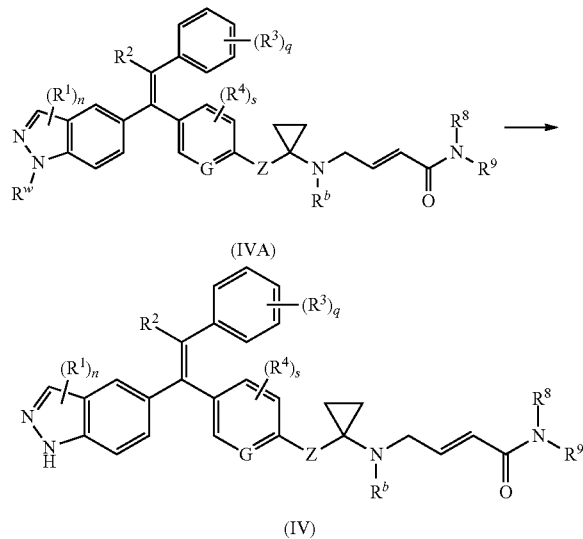

(IVA)

(IV)

subjecting the compound of formula (IVA) or the tautomer, mesomer, racemate, enantiomer, diastereomer thereof, or mixture thereof, or the pharmaceutically acceptable salt thereof to a deprotection reaction under an acidic condition to obtain the compound of formula (IV) or the tautomer, mesomer, racemate, enantiomer, diastereomer thereof, or mixture thereof, or the pharmaceutically acceptable salt thereof;

wherein:

$R^w$ is an amino protecting group;

G, Z, $R^1$, $R^2$, $R^3$, $R^4$, $R^8$, $R^9$, $R^b$, n, s and q are as defined in formula (IV).

The reagent that provides an acidic condition in the above schemes includes, but is not limited to, pyridine hydrobromide, trifluoroacetic acid, formic acid, acetic acid, hydrochloric acid, sulfuric acid and methanesulfonic acid, and preferably hydrochloric acid.

The amino protecting group is selected from the group consisting of tetrahydropyranyl, tert-butoxycarbonyl, acetyl, benzyl, allyl and p-methoxybenzyl, and preferably tetrahydropyranyl.

The above reactions are preferably carried out in a solvent. The solvent used includes, but is not limited to, acetic acid, methanol, ethanol, toluene, tetrahydrofuran, dichloromethane, dimethyl sulfoxide, 1,4-dioxane, water, N,N-dimethylformamide and mixtures thereof.

DETAILED DESCRIPTION

The present disclosure will be further described with reference to the following examples, but the examples should not be considered as limiting the scope of the present disclosure.

EXAMPLES

The structures of the compounds were identified by nuclear magnetic resonance (NMR) and/or mass spectrometry (MS). NMR shifts (δ) were given in $10^{-6}$ (ppm). NMR was determined by a Bruker AVANCE-400 machine. The solvents for determination were deuterated-dimethyl sulfoxide (DMSO-$d_6$), deuterated-chloroform (CDCl$_3$) and deuterated-methanol (CD$_3$OD), and the internal standard is tetramethylsilane (TMS).

MS was determined by an Agilent 1200/1290 DAD-6110/6120 Quadrupole M S liquid chromatograph/mass spectrometer (manufacturer: Agilent, MS model: 6110/6120 Quadrupole MS), waters ACQuity UPLC-QD/SQD (manufacturer: waters, MS model: waters ACQuity Qda Detector/waters SQ Detector), THERMO Ultimate 3000-Q Exactive (manufacturer: THERMO, MS model: THERMO Q Exactive).

High Performance Liquid Chromatography (HPLC) was determined on an Agilent HPLC 1200DAD, Agilent HPLC 1200VWD and Waters HPLC e2695-2489 high pressure liquid chromatograph.

Chiral HPLC was determined on an Agilent 1260 DAD high performance liquid chromatograph.

High Performance Liquid Preparative Chromatography was carried out on Waters 2545-2767, Waters 2767-SQ Detecor2, Shimadzu LC-20AP and Gilson GX-281 preparative chromatographs.

Chiral preparative HPLC was carried out on a Shimadzu LC-20AP preparative chromatograph.

CombiFlash rapid preparation instrument used was Combiflash Rf200 (TELEDYNE ISCO).

Yantai Huanghai HSGF254 or Qingdao GF254 silica gel plate was used as the thin-layer silica gel chromatography (TLC) plate. The dimension of the silica gel plate used in TLC was 0.15 mm to 0.2 mm, and the dimension of the silica gel plate used in product purification was 0.4 mm to 0.5 mm.

Yantai Huanghai 200 to 300 mesh silica gel was generally used as a carrier for silica gel column chromatography.

The average kinase inhibition rates and IC$_{50}$ values were determined by a NovoStar microplate reader (BMG Co., Germany).

The known starting materials of the present disclosure can be prepared by the known methods in the art, or can be purchased from ABCR GmbH & Co. KG, Acros Organics, Aldrich Chemical Company, Accela ChemBio Inc., Dari Chemical Company etc.

Unless otherwise stated, the reactions were carried out under argon atmosphere or nitrogen atmosphere.

"Argon atmosphere" or "nitrogen atmosphere" means that a reaction flask is equipped with an argon or nitrogen balloon (about 1 L).

"Hydrogen atmosphere" means that a reaction flask is equipped with a hydrogen balloon (about 1 L).

Pressurized hydrogenation reaction was performed on a Parr 3916EKX hydrogenation instrument and a Qinglan QL-500 hydrogen generator or HC2-SS hydrogenation instrument.

In hydrogenation reactions, the reaction system was generally vacuumed and filled with hydrogen, and the above operation was repeated three times.

CEM Discover-S 908860 type microwave reactor was used in microwave reactions.

Unless otherwise stated, the solution refers to an aqueous solution.

Unless otherwise stated, the reaction temperature is room temperature from 20° C. to 30° C.

The reaction process in the examples was monitored by thin layer chromatography (TLC). The developing solvent used in the reactions, the eluent system in column chromatography and the developing solvent system in thin layer chromatography for purification of the compounds included: A: dichloromethane/methanol system, B: n-hexane/ethyl acetate system, and C: petroleum ether/ethyl acetate system. The ratio of the volume of the solvent was adjusted according to the polarity of the compounds, and a small quantity of alkaline reagent such as triethylamine or acidic reagent such as acetic acid could also be added for adjustment.

Example 1

(E)-1-Morpholino-4-((1-(((5-((Z)-4,4,4-trifluoro-1-(3-fluoro-1H-indazol-5-yl)-2-phenylbut-1-en-1-yl) pyridin-2-yl)oxy)methyl)cyclopropyl)amino)but-2-en-1-one 1

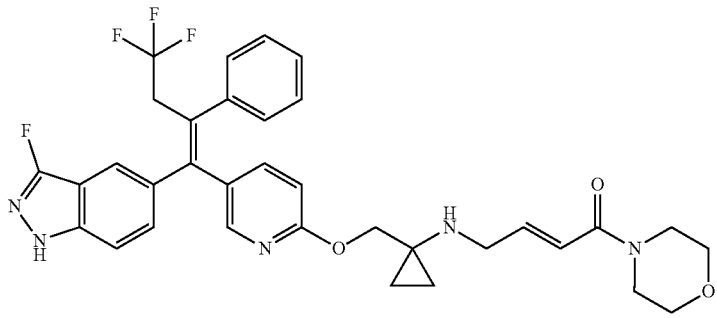

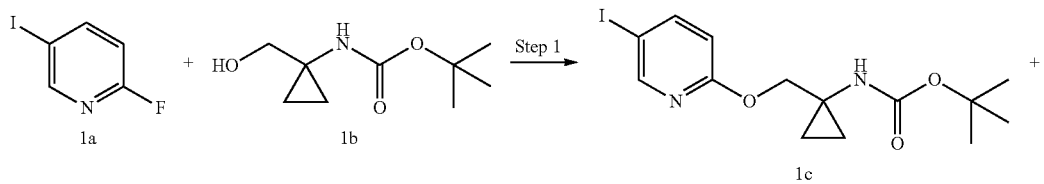

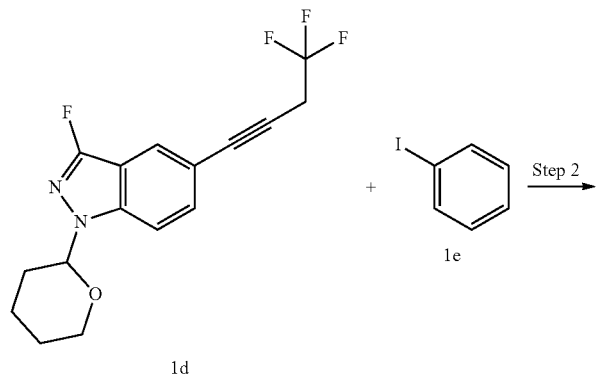

-continued
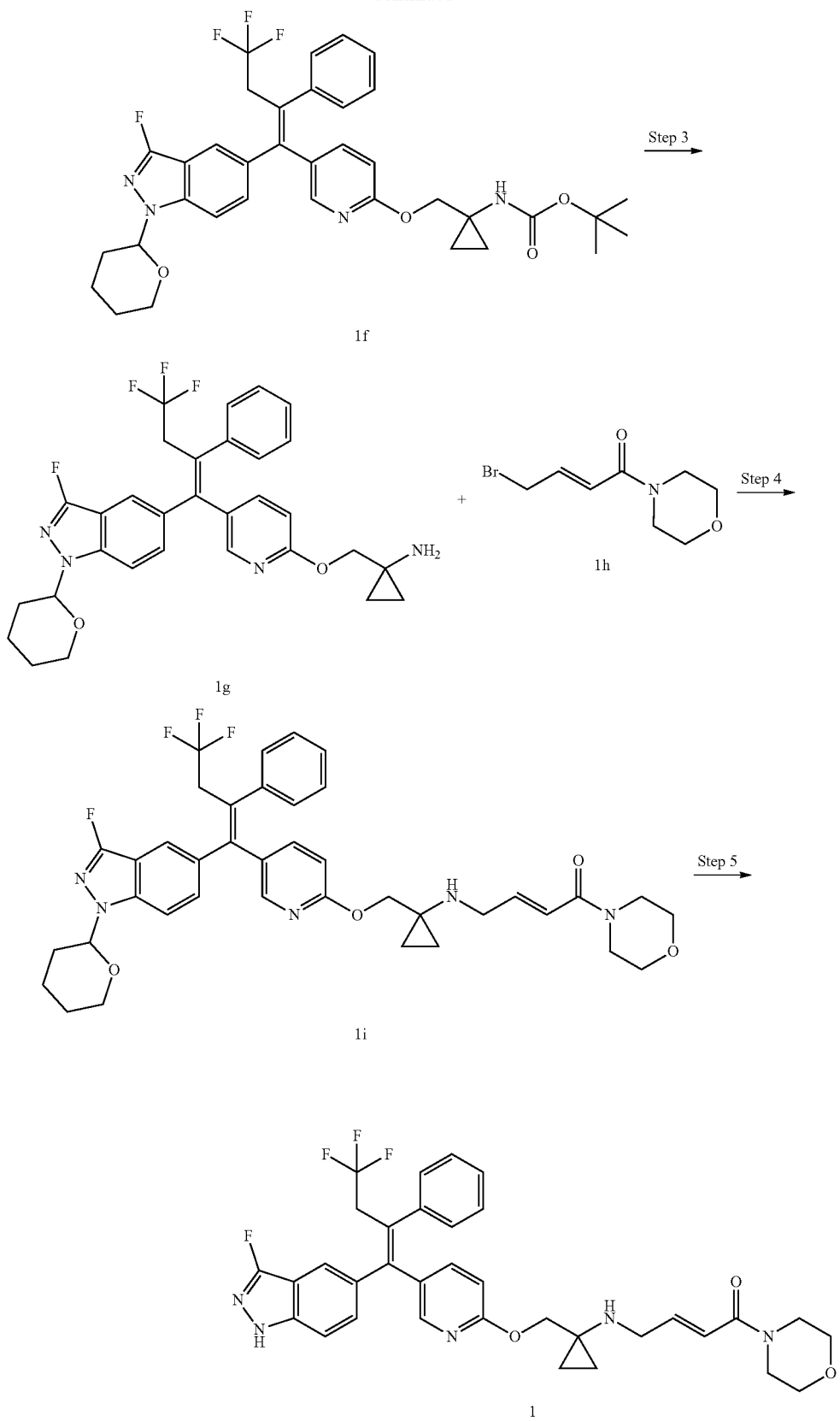

Step 1

Tert-butyl (1-(((5-iodopyridin-2-yl)oxy)methyl)cyclopropyl)carbamate 1c

Sodium hydride (0.4 g, 10.7 mmol) was dissolved in N,N-dimethylformamide (20 mL), followed by the addition of tert-butyl (1-(hydroxymethyl)cyclopropyl)carbamate 1b (1.0 g, 5.3 mmol, prepared according to the method disclosed in "*Journal of Organic Chemistry*, 2002, 67(11), 3965-3968") at room temperature. After completion of the addition, 2-fluoro-5-iodopyridine 1a (1.8 g, 8.0 mmol) was added slowly. The reaction was stirred at room temperature for 2 hours. The reaction solution was concentrated under reduced pressure, and the resulting residues were purified by thin layer chromatography with developing system B to obtain the title product 1c (2.4 g, yield: 86%).

MS m/z (ESI): 391.0 [M+1].

Step 2

Tert-butyl (Z)-(1-(((5-(4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)carbamate 1f 3-Fluoro-1-(tetrahydro-2H-pyran-2-yl)-5-(4,4,4-trifluorobut-1-yn-1-yl)-1H-indazole 1d (1.8 g, 5.5 mmol, prepared according to the method disclosed in Example 3 on page 84 of the description of the patent application WO2018098305) was dissolved in methyltetrahydrofuran (40 mL), followed by the addition of bis(pinacolato)diboron (1.7 g, 6.6 mmol) and tetrakis(triphenylphosphine) platinum (137 mg, 0.1 mmol). The reaction solution was purged with argon three times, warmed up to 85° C. and stirred for 3 hours. The reaction solution was cooled to room temperature, followed by the addition of compound 1c (2.0 g, 5.2 mmol), bis(triphenylphosphine)palladium dichloride (741 mg, 1.1 mmol), cesium carbonate (3.6 g, 11.0 mmol) and water (1 mL). The reaction solution was stirred at room temperature overnight. Iodobenzene 1e (1.2 g, 6.1 mmol) and potassium hydroxide (1.5 g, 27.6 mmol) were added. The reaction solution was purged with argon three times, warmed up to 85° C., stirred for 2 hours, and cooled to room temperature. The reaction solution was concentrated under reduced pressure, and the resulting residues were purified by thin layer chromatography with developing system B to obtain the title product 1f (3.0 g, yield: 88%).

MS m/z (ESI): 667.2 [M+1].

Step 3

(Z)-1-(((5-(4,4,4-Trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropan-1-amine 1g Compound 1f (1.8 g, 2.7 mmol) was dissolved in dichloromethane (15 mL), followed by the addition of trifluoroacetic acid (3 mL). The reaction was stirred at room temperature for 5 hours. The reaction solution was concentrated under reduced pressure, adjusted to about pH 8 with saturated sodium bicarbonate solution (100 mL), dried over anhydrous sodium sulfate and filtered. The filtrate was concentrated under reduced pressure to obtain the crude title product 1g (1.4 g, yield: 89%), which was used directly in the next step without purification.

Step 4

(E)-1-Morpholino-4-((1-(((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-en-1-one 1i Compound 1g (1.7 g, 2.8 mmol) was dissolved in N,N-dimethylformamide (20 mL), followed by the addition of diisopropylethylamine (1.1 g, 8.5 mmol) at room temperature. (E)-4-Bromo-1-morpholinobut-2-en-1-one 1h (0.7 g, 2.8 mmol, prepared according to the method disclosed in Example 15 on page 65 of the description of the patent application US2016347717) was added, and the reaction solution was stirred for 2 hours. The reaction was stopped, and the reaction solution was cooled. Saturated sodium bicarbonate solution (15 mL) was added, and the solution was extracted with ethyl acetate (50 mL×2). The organic phases were combined, washed with saturated sodium chloride solution (50 mL×4), dried over anhydrous sodium sulfate and filtered. The filtrate was concentrated under reduced pressure, and the resulting residues were purified by thin layer chromatography with developing system A to obtain the title product 1i (1.3 g, yield: 65%).

MS m/z (ESI): 720.2 [M+1].

Step 5

(E)-1-Morpholino-4-((1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)but-2-en-1-one 1

Compound 1i (2.0 g, 2.8 mmol) was dissolved in methanol (5 mL), followed by the addition of hydrochloric acid (12N, 10 mL). The reaction solution was stirred for 3 hours. The reaction was stopped, and the reaction solution was cooled and concentrated. Saturated sodium bicarbonate solution (15 mL) was added, and the solution was extracted with dichloromethane (50 mL×4). The organic phases were combined, washed with water (30 mL×3) and saturated sodium chloride solution (50 mL) successively, dried over anhydrous sodium sulfate and filtered. The filtrate was concentrated under reduced pressure, and the resulting residues were purified by thin layer chromatography with developing system A to obtain the title product 1 (1.3 g, yield: 73%).

MS m/z (ESI): 636.2 [M+1].

$^1$H NMR (400 MHz, CD$_3$OD) 7.65 (d, 2H), 7.49 (d, 1H), 7.30-7.22 (m, 7H), 6.82-6.76 (m, 1H), 6.60-6.52 (m, 2H), 4.15 (s, 2H), 3.62-3.39 (m, 12H), 0.76-0.64 (m, 4H).

Example 2
(E)-1-(Pyrrolidin-1-yl)-4-((1-(((5-((Z)-4,4-trifluoro-1-(3-fluoro-1H-indazol-5-yl)-2-phenylbut-1-en-1-yl)pyridin-2-yl)oxy)methyl)cyclopropyl)amino)but-2-en-1-one 2
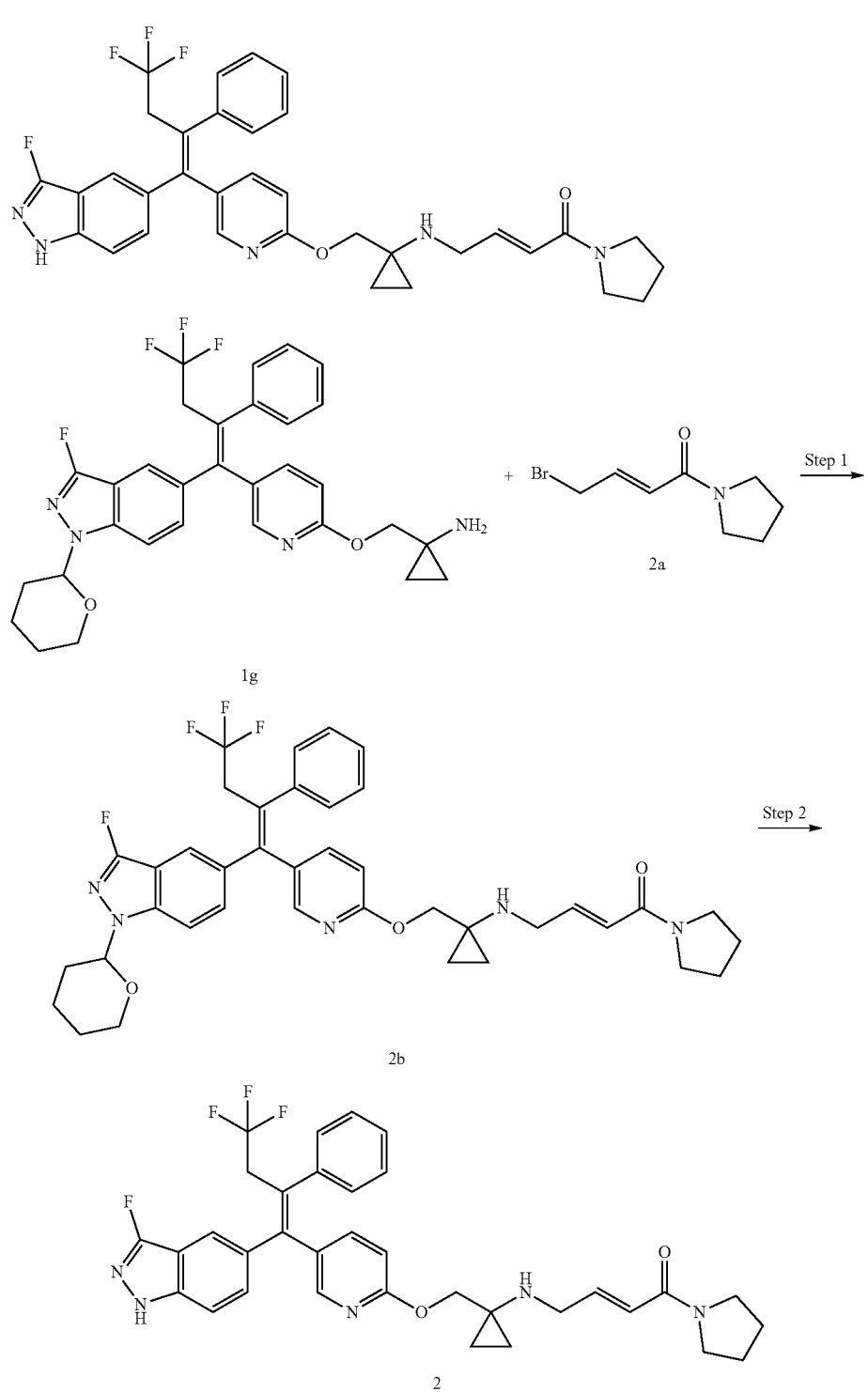

Step 1

(E)-1-(Pyrrolidin-1-yl)-4-((1-(((5-((Z)-4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-en-1-one 2b In accordance with the synthetic route in Example 1, the starting material 1h in Step 4 was replaced with (E)-4-bromo-1-(pyrrolidin-1-yl)but-2-en-1-one 2a (prepared according to the method disclosed in Example 11 on page 58 of the description of the patent application US2016347717), to give the title compound 2b (51 mg, yield: 69%).

MS m/z (ESI): 704.3 [M+1].

Step 2

(E)-1-(Pyrrolidin-1-yl)-4-((1-(((5-((Z)-4,4-trifluoro-1-(3-fluoro-1H-indazol-5-yl)-2-phenylbut-1-en-1-yl)pyridin-2-yl)oxy)methyl)cyclopropyl)amino)but-2-en-1-one 2

In accordance with the synthetic route in Example 1, the starting material 1i in Step 5 was replaced with compound 2b, to give the title compound 2 (20 mg, yield: 65%).

MS m/z (ESI): 620.3 [M+1].

$^1$H NMR (400 MHz, CD$_3$OD) 7.65 (d, 2H), 7.50 (d, 1H), 7.31-7.21 (m, 7H), 6.84-6.80 (m, 1H), 6.59 (d, 1H), 6.38 (d, 1H), 4.16 (s, 2H), 3.61-3.39 (m, 8H), 0.92-0.60 (m, 4H), 0.72-0.64 (m, 4H).

Example 3

(E)-1-(Piperidin-1-yl)-4-((1-(((5-((Z)-4,4-trifluoro-1-(3-fluoro-1H-indazol-5-yl)-2-phenylbut-1-en-1-yl)pyridin-2-yl)oxy)methyl)cyclopropyl)amino)but-2-en-1-one 3

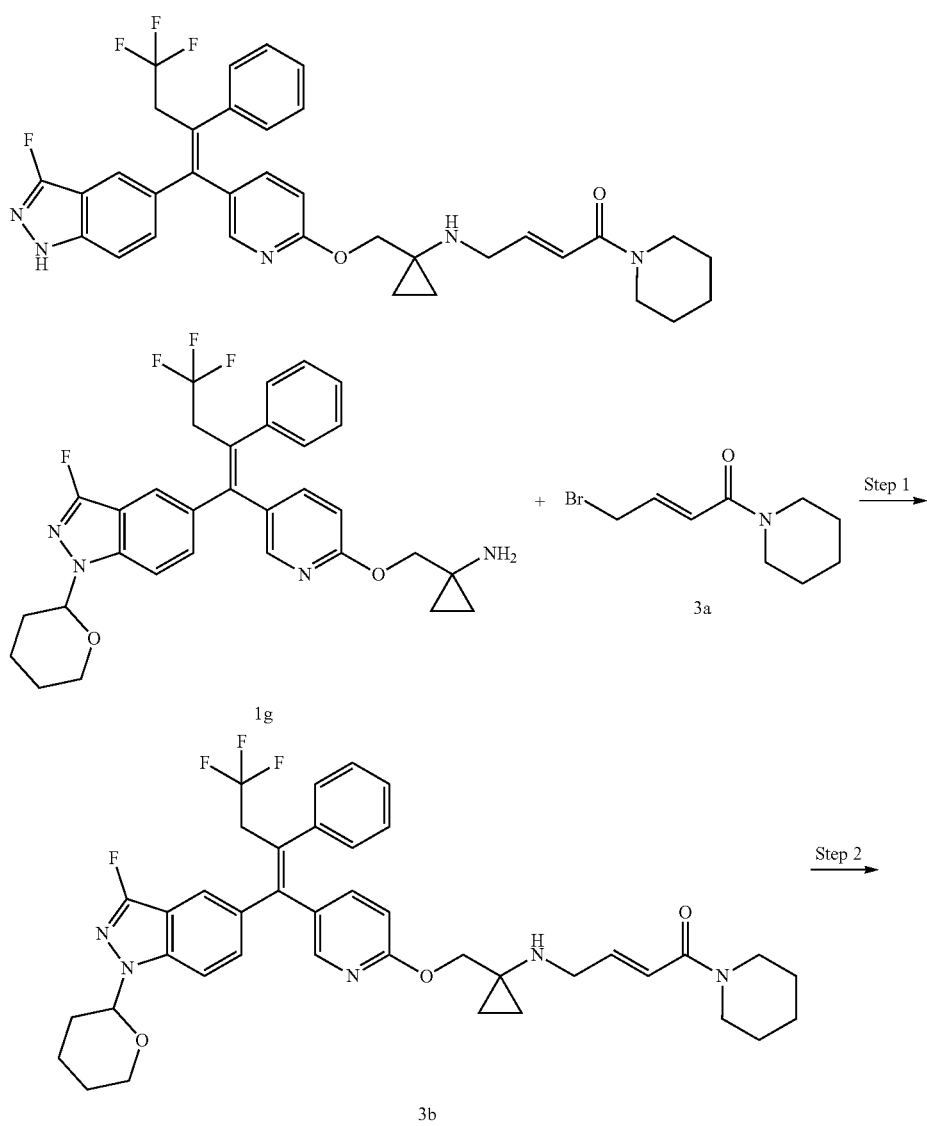

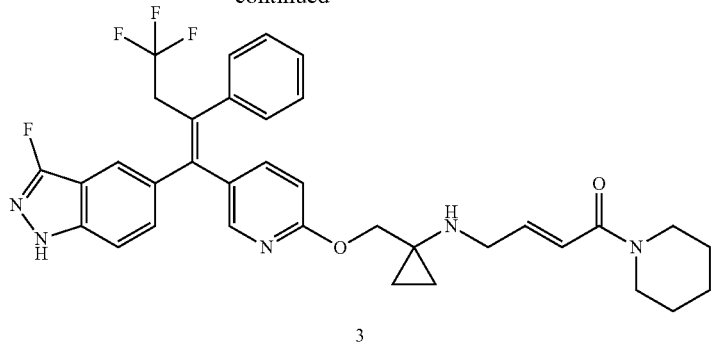

3

Step 1

(E)-1-(Piperidin-1-yl)-4-((1-(((5-((Z)-4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-en-1-one 3b In accordance with the synthetic route in Example 1, the starting material 1 h in Step 4 was replaced with (E)-4-bromo-1-(piperidin-1-yl)but-2-en-1-one 3a (prepared according to the method disclosed in Example 12 on page 58 of the description of the patent application US2016347717), to give the title compound 3b (40 mg, yield: 74%).
MS m/z (ESI): 718.4 [M+1].

Step 2

(E)-1-(Piperidin-1-yl)-4-((1-(((5-((Z)-4,4-trifluoro-1-(3-fluoro-1H-indazol-5-yl)-2-phenylbut-1-en-1-yl)pyridin-2-yl)oxy)methyl)cyclopropyl)amino)but-2-en-1-one 3

In accordance with the synthetic route in Example 1, the starting material 1i in Step 5 was replaced with compound 3b, to give the title compound 3 (15 mg, yield: 61%).
MS m/z (ESI): 634.3 [M+1].
$^1$H NMR (400 MHz, CD$_3$OD) 7.65 (d, 2H), 7.50 (d, 1H), 7.30-7.21 (m, 7H), 6.74-6.70 (m, 1H), 6.60-6.55 (m, 2H), 5.36-5.35 (m, 1H), 4.36 (s, 2H), 3.56-3.53 (m, 5H), 3.46-3.39 (m, 2H), 2.05 (s, 1H), 1.67-1.54 (m, 3H), 0.92-0.68 (m, 6H).

Example 4

(E)-1-(Piperazin-1-yl)-4-((1-(((5-((Z)-4,4-trifluoro-1-(3-fluoro-1H-indazol-5-yl)-2-phenylbut-1-en-1-yl)pyridin-2-yl)oxy)methyl)cyclopropyl)amino)but-2-en-1-one 4

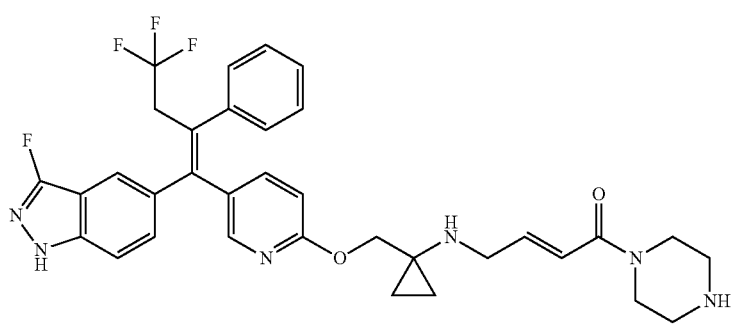

4

-continued
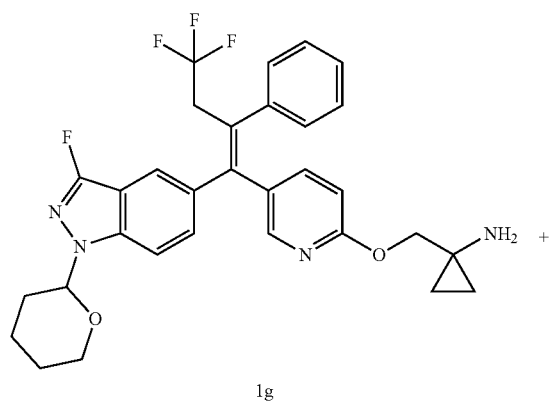
1g
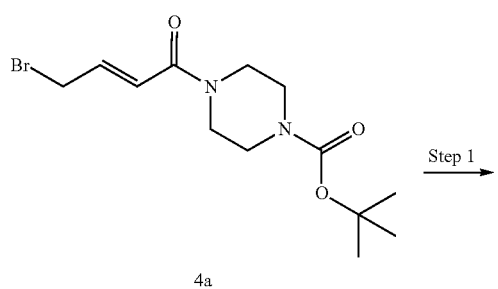
4a
Step 1 →
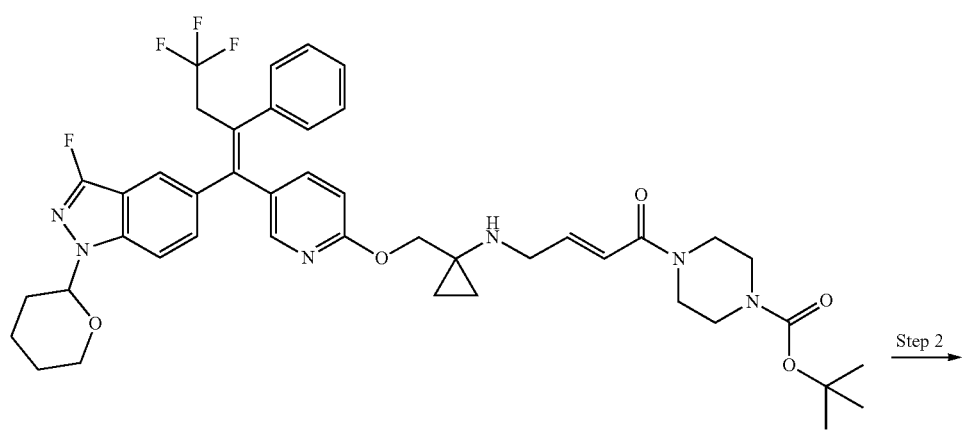
4b
Step 2 →
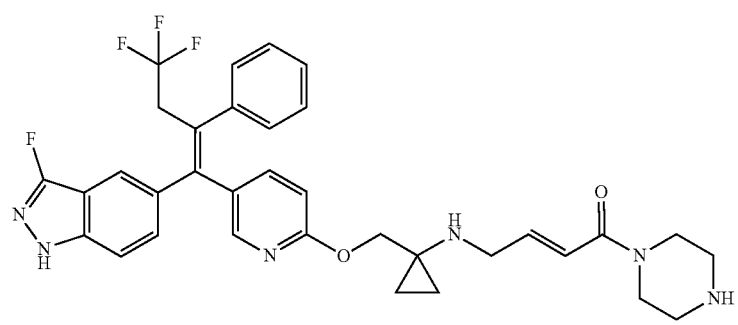
4

Step 1

Tert-butyl 4-((E)-4-((1-(((5-((Z)-4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-enoyl)piperazine-1-carboxylate 4b In accordance with the synthetic route in Example 1, the starting material 1 h in Step 4 was replaced with tert-butyl (E)-4-(4-bromobut-2-enoyl)piperazine-1-carboxylate 4a (prepared according to the method disclosed in Example 32 on page 129 of the description of the patent application WO2014160200), to give the title compound 4b (61 mg, yield: 72%).

MS m/z (ESI): 819.4 [M+1].

Step 2

(E)-1-(Piperazin-1-yl)-4-((1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)but-2-en-1-one 4

In accordance with the synthetic route in Example 1, the starting material 1i in Step 5 was replaced with compound 4b, to give the title compound 4 (20 mg, yield: 41%).

MS m/z (ESI): 635.3 [M+1].

$^1$H NMR (400 MHz, CD$_3$OD) 7.65 (d, 2H), 7.50 (d, 1H), 7.30-7.20 (m, 7H), 6.82-6.77 (m, 1H), 6.59-6.53 (m, 2H), 4.15 (s, 2H), 3.69-3.67 (m, 4H), 3.53-3.41 (m, 4H), 2.96-2.94 (m, 4H), 0.72-0.62 (m, 4H).

Example 5

(E)-N,N-Dimethyl-4-(methyl(1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)but-2-enamide 5

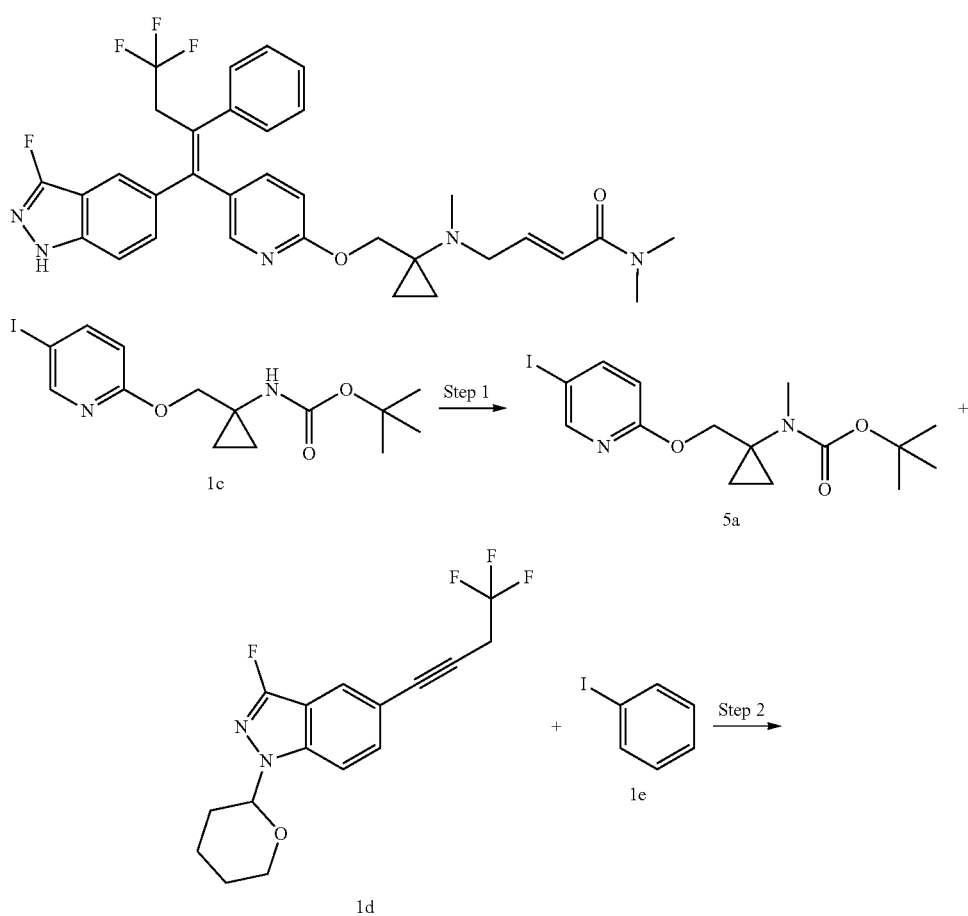

-continued
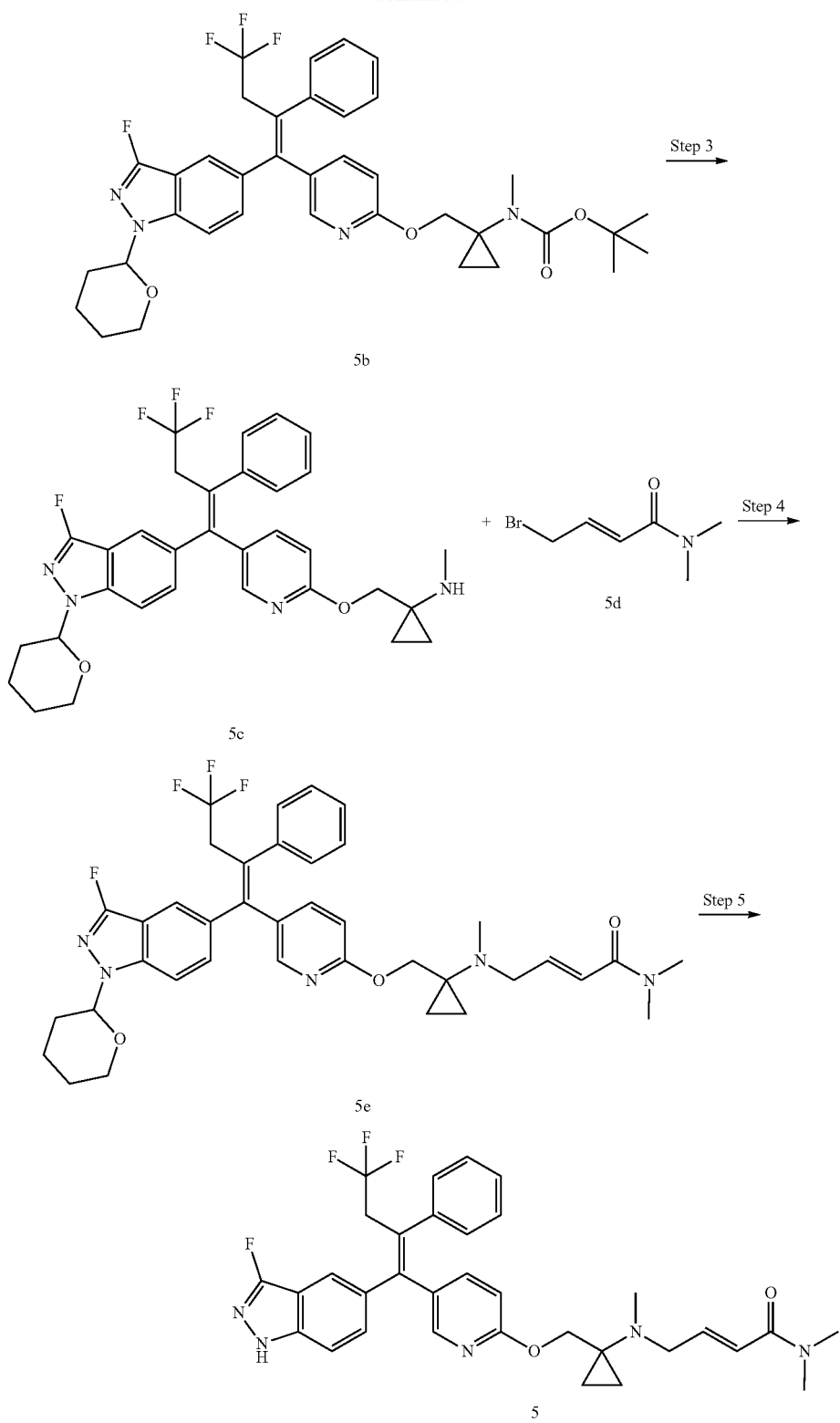

Step 1

Tert-butyl (1-(((5-iodopyridin-2-yl)oxy)methyl)cyclopropyl)(methyl)carbamate 5a

Compound 1c (0.5 g, 1.3 mmol) was dissolved in N,N-dimethylformamide (25 mL), followed by the addition of sodium hydride (0.1 g, 2.6 mmol) at room temperature. After completion of the addition, iodomethane (0.3 g, 1.9 mmol) was slowly added. The reaction was stirred at room temperature for 2 hours. The reaction solution was concentrated under reduced pressure, and the resulting residues were purified by thin layer chromatography with developing system B to obtain the title product 5a (0.5 g, yield: 87%).
MS m/z (ESI): 405.1 [M+1].

Step 2

Tert-butyl (Z)-methyl(1-(((5-(4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)carbamate 5b In accordance with the synthetic route in Example 1, the starting material 1c in Step 2 was replaced with compound 5a, to give the title compound 5b (89 mg, yield: 85%) was prepared.
MS m/z (ESI): 681.3 [M+1].

Step 3

(Z)—N-Methyl-1-(((5-(4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropan-1-amine 5c In accordance with the synthetic route in Example 1, the starting material 1f in Step 3 was replaced with compound 5b, to give the title compound 5c (60 mg, yield: 70%) was prepared.

Step 4

(E)-N,N-Dimethyl-4-(methyl(1-(((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-enamide 5e In accordance with the synthetic route in Example 1, the starting material 1 h in Step 4 was replaced with (E)-4-bromo-N,N-dimethylbut-2-enamide 5d (prepared according to the method disclosed in Example 1 on page 39 of the description of the patent application US2016347717), and the starting material 1g was replaced with 5c, to give the title compound 5e (60 mg, yield: 50%).

Step 5

(E)-N,N-Dimethyl-4-(methyl(1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)but-2-enamide 5

In accordance with the synthetic route in Example 1, the starting material 1i in Step 5 was replaced with compound 5e, to give the title compound 5 (15 mg, yield: 28%).
MS m/z (ESI): 608.2 [M+1].
$^1$H NMR (400 MHz, CDCl$_3$) 9.59 (s, 1H), 7.65 (d, 2H), 7.33 (d, 1H), 7.28-7.23 (m, 6H), 7.10 (d, 1H), 6.79-6.75 (m, 1H), 6.46 (d, 1H), 6.35 (d, 1H), 4.22 (s, 2H), 3.48 (d, 2H), 3.38-3.35 (m, 2H), 3.05 (d, 6H), 2.38 (s, 3H), 0.73-0.63 (m, 4H).

Example 6

(E)-4-(Ethyl(1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)-N,N-dimethylbut-2-enamide 6

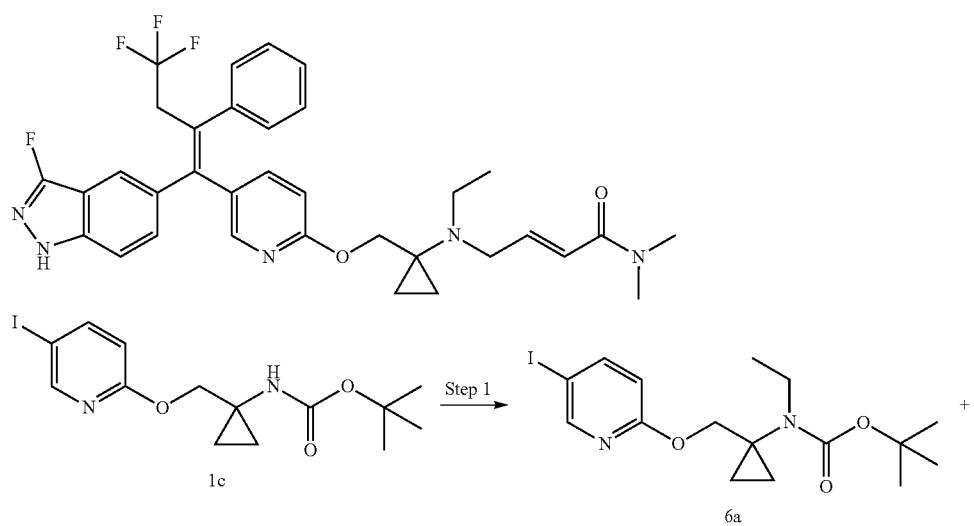

-continued
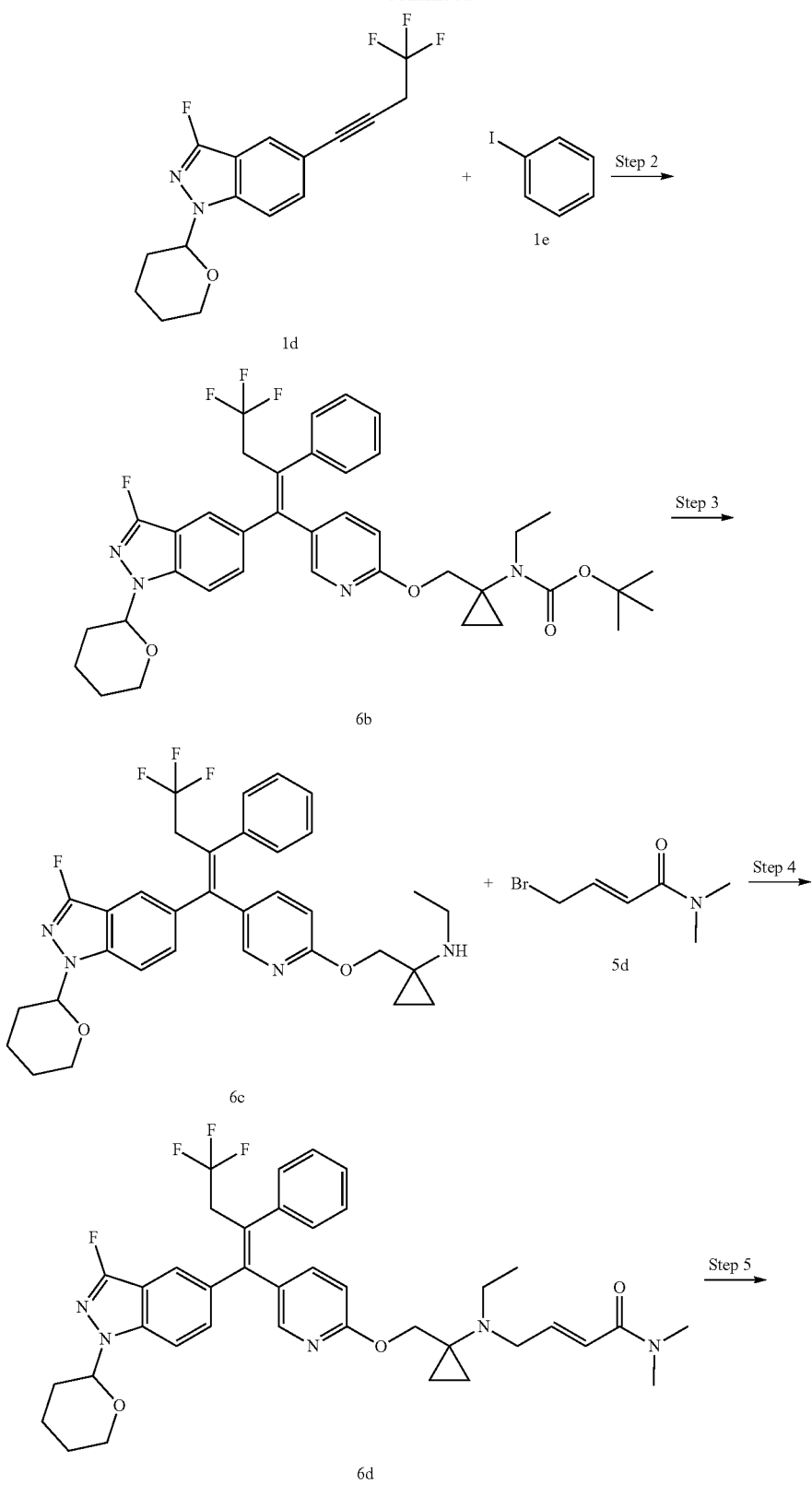

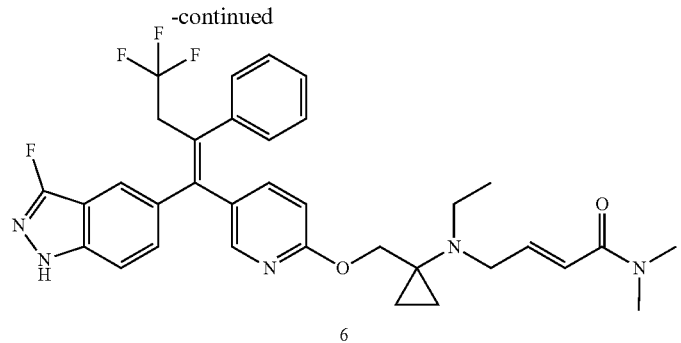

Step 1

Tert-butyl ethyl(1-(((5-iodopyridin-2-yl)oxy)methyl)cyclopropyl)carbamate 6a In accordance with the synthetic route in Example 5, the reagent iodomethane in Step 1 was replaced with iodoethane, to give the title compound 6a (58 mg, yield: 88%).

Step 2

Tert-butyl (Z)-ethyl(1-(((5-(4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)carbamate 6b In accordance with the synthetic route in Example 1, the starting material 1c in Step 2 was replaced with compound 6a, to give the title compound 6b (85 mg, yield: 80%).

Step 3

(Z)—N-Ethyl-1-(((5-(4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropan-1-amine 6c In accordance with the synthetic route in Example 1, the starting material 1f in Step 3 was replaced with compound 6b, to give the title compound 6c (65 mg, yield: 76%).

Step 4

(E)-4-(Ethyl(1-(((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)-N,N-dimethylbut-2-enamide 6d In accordance with the synthetic route in Example 5, the starting material 5c in Step 4 was replaced with compound 6c, to give the title compound 6d (70 mg, yield: 59%).
MS m/z (ESI): 706.3 [M+1].

Step 5

(E)-4-(Ethyl(1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)-N,N-dimethylbut-2-enamide 6

In accordance with the synthetic route in Example 1, the starting material 1i in Step 5 was replaced with compound 6d, to give the title compound 6 (15 mg, yield: 28%).
MS m/z (ESI): 622.3 [M+1].
$^1$H NMR (400 MHz, CDCl$_3$) 9.74 (s, 1H), 7.66 (d, 2H), 7.31 (d, 1H), 7.28-7.25 (m, 6H), 7.21 (d, 1H), 6.86-6.82 (m, 1H), 6.46-6.36 (m, 2H), 4.19 (s, 2H), 3.53 (d, 2H), 3.35-3.30 (m, 2H), 3.06 (d, 6H), 2.73-2.70 (m, 2H), 1.05-1.02 (m, 3H), 0.73-0.61 (m, 4H).

Example 7

(E)-N,N-Dimethyl-4-((1-(((5-((Z)-4,4,4-trifluoro-1-(3-fluoro-1H-indazol-5-yl)-2-phenylbut-1-en-1-yl)pyridin-2-yl)oxy)methyl)cyclopentyl)amino)but-2-enamide 7

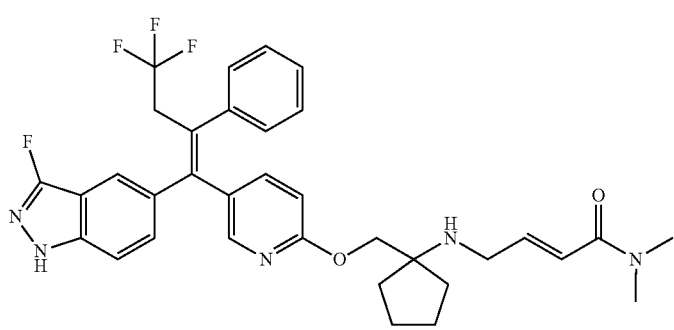

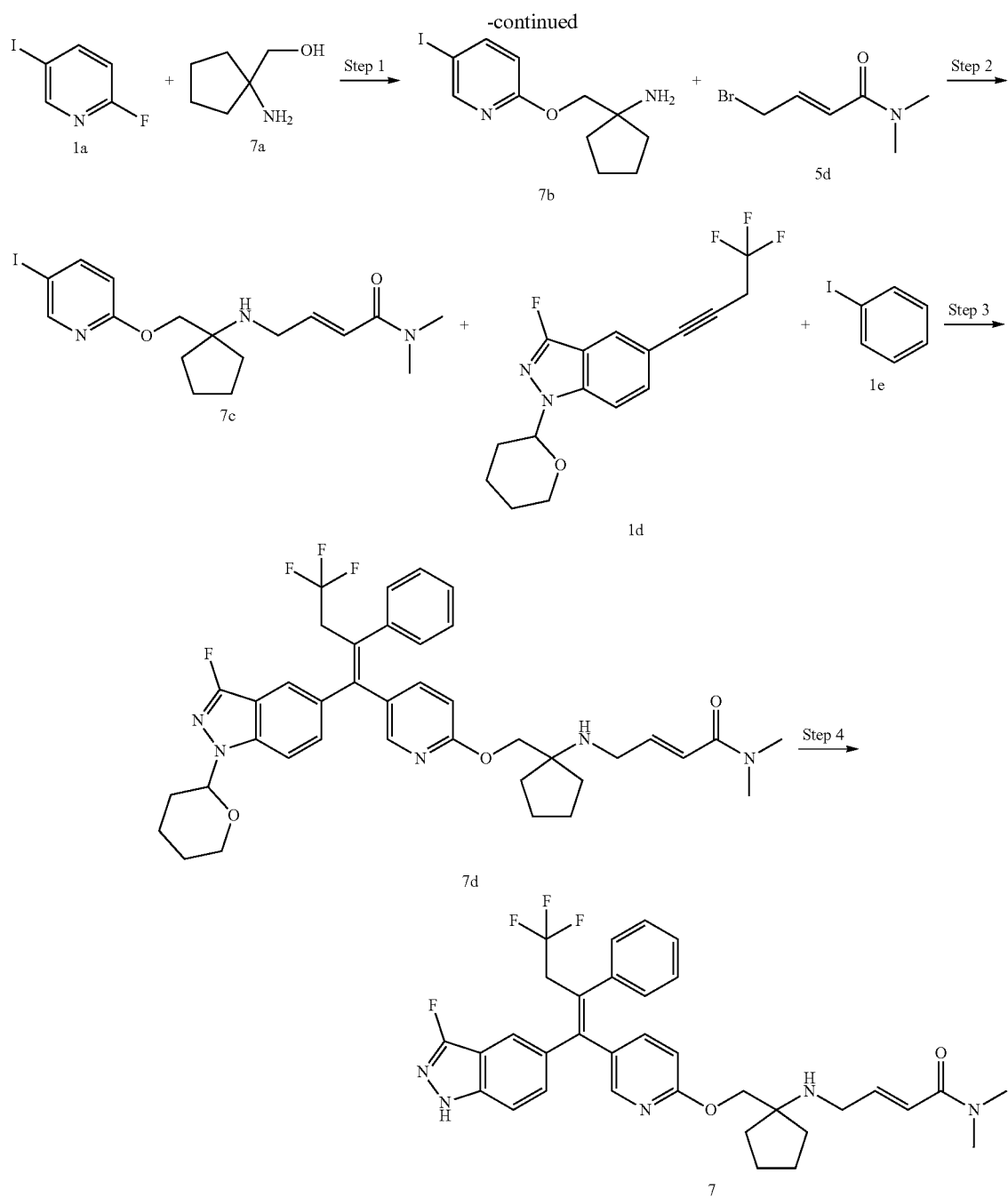

Step 1

1-(((5-Iodopyridin-2-yl)oxy)methyl)cyclopentan-1-amine 7b

Potassium tert-butoxide (0.4 g, 3.5 mmol) was dissolved in tetrahydrofuran (10 mL), followed by the addition of (1-aminocyclopentyl)methanol 7a (0.4 g, 3.5 mmol, prepared according to the method disclosed in "*Journal of the American Chemical Society*, 2004, 126(46), 15195-15201") at room temperature. After completion of the addition, compound 1a (0.8 g, 3.5 mmol) was added slowly. The reaction was stirred at room temperature for 2 hours. The reaction solution was concentrated under reduced pressure, and the resulting residues were purified by thin layer chromatography with developing system B to obtain the title product 7b (0.7 g, yield: 66%).

MS m/z (ESI): 319.1 [M+1].

Step 2

(E)-4-((1-(((5-Iodopyridin-2-yl)oxy)methyl)cyclopentyl)amino)-N,N-dimethylbut-2-enamide 7c Compound 7b (100 mg, 0.3 mmol) was dissolved in N,N-dimethylformamide (10 mL), followed by the successive addition of diisopropylethylamine (41 mg, 0.3 mmol) and compound 5d (60 g, 0.3 mmol) at room temperature.

The reaction solution was stirred for 2 hours. The reaction was stopped, and the reaction solution was cooled. Saturated sodium bicarbonate solution (15 mL) was added, and the solution was extracted with ethyl acetate (50 mL×2). The organic phases were combined, washed with saturated sodium chloride solution (50 mL×4), dried over anhydrous sodium sulfate and filtered. The filtrate was concentrated under reduced pressure, and the resulting residues were purified by thin layer chromatography with developing system A to obtain the title product 7c (86 mg, yield: 67%).

Step 3

(E)-N,N-Dimethyl-4-((1-(((5-((Z)-4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopentyl)amino)but-2-enamide 7d Compound 1d (50 mg, 0.2 mmol) was dissolved in methyltetrahydrofuran (20 mL), followed by the addition of bis(pinacolato)diboron (47 mg, 0.2 mmol) and tetrakis(triphenylphosphine) platinum (10 mg, 0.01 mmol). The reaction solution was purged with argon three times, warmed up to 85° C. and stirred for 3 hours. The reaction solution was cooled to room temperature, followed by the addition of compound 7c (66 mg, 0.2 mmol), bis(triphenylphosphine) palladium dichloride (11 mg, 0.02 mmol), cesium carbonate (150 mg, 0.5 mmol) and water (0.2 mL). The reaction solution was stirred at room temperature overnight. Compound 1e (63 mg, 0.3 mmol) and potassium hydroxide (26 mg, 0.5 mmol) were added. The reaction solution was purged with argon three times, warmed up to 85° C., stirred for 2 hours, and cooled to room temperature. The reaction solution was concentrated under reduced pressure, and the resulting residues were purified by thin layer chromatography with developing system B to obtain the title product 7d (84 mg, yield: 78%).

Step 4

(E)-N,N-Dimethyl-4-((1-(((5-((Z)-4,4,4-trifluoro-1-(3-fluoro-1H-indazol-5-yl)-2-phenylbut-1-en-1-yl)pyridin-2-yl)oxy)methyl)cyclopentyl)amino)but-2-enamide 7

Compound 7d (30 mg, 0.04 mmol) was dissolved in methanol (1 mL), followed by the addition of hydrochloric acid (12N, 2 mL). The reaction solution was stirred for 3 hours. The reaction was stopped, and the reaction solution was cooled and concentrated. Saturated sodium bicarbonate solution (15 mL) was added, and the solution was extracted with dichloromethane (10 mL×4). The organic phases were combined, washed with water (10 mL×3) and saturated sodium chloride solution (10 mL) successively, dried over anhydrous sodium sulfate and filtered. The filtrate was concentrated under reduced pressure, and the resulting residues were purified by thin layer chromatography with developing system A to obtain the title product 7 (10 mg, yield: 41%).

MS m/z (ESI): 622.3 [M+1].

$^1$H NMR (400 MHz, CDCl$_3$) 7.61-7.45 (m, 3H), 7.29-7.01 (m, 7H), 6.54-6.42 (m, 3H), 3.95 (s, 2H), 3.42-3.39 (m, 1H), 3.17-3.14 (m, 1H), 2.91 (s, 1H), 2.77 (s, 1H), 2.62 (s, 3H), 2.26 (s, 3H), 1.63-1.52 (m, 4H), 1.49-1.38 (m, 4H).

Example 8

(E)-N,N-Dimethyl-4-((1-(((5-((Z)-4,4,4-trifluoro-1-(3-fluoro-1H-indazol-5-yl)-2-phenylbut-1-en-1-yl)pyridin-2-yl)oxy)methyl)cyclohexyl)amino)but-2-enamide 8

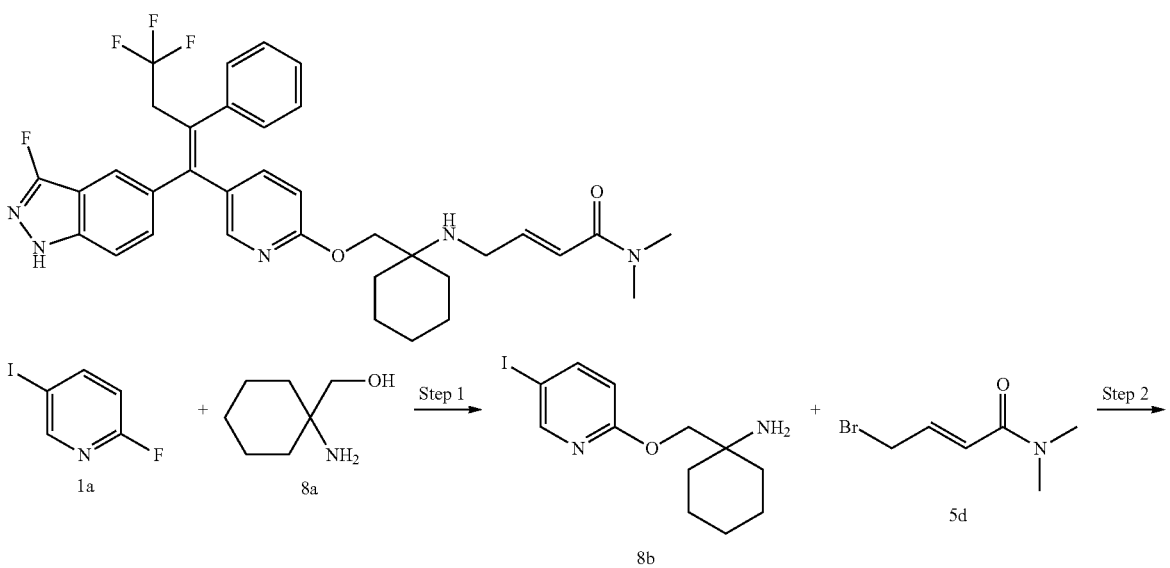

-continued
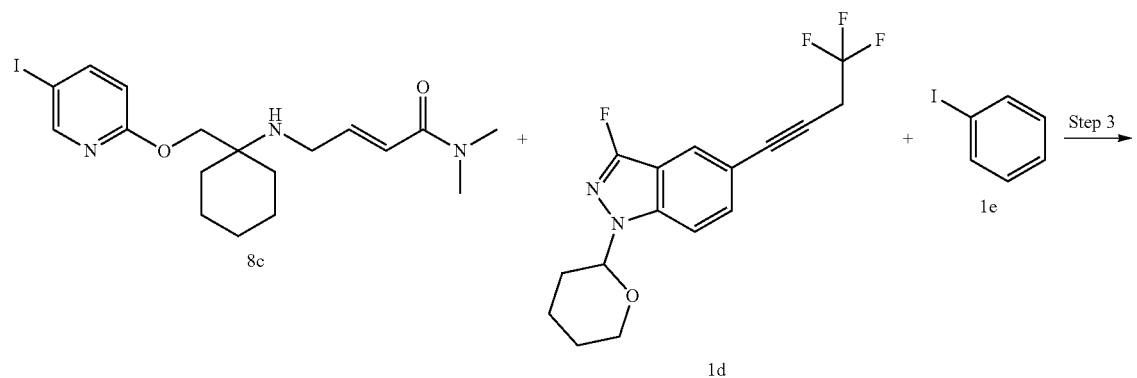
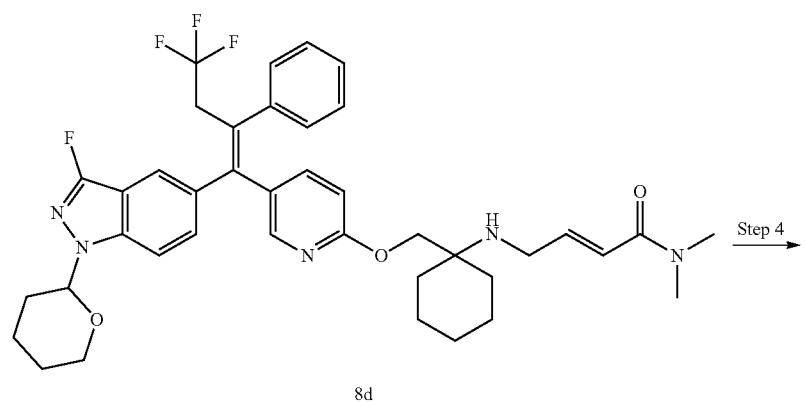
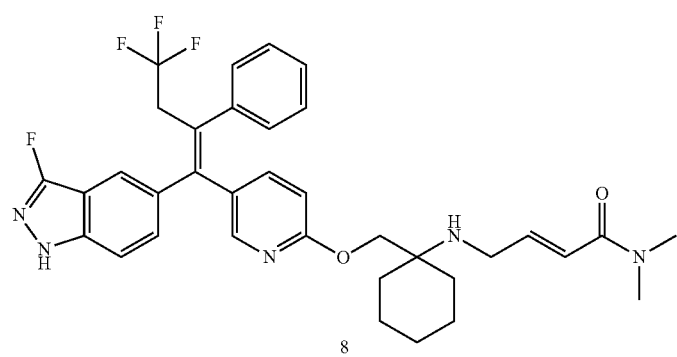

Step 1

1-(((5-Iodopyridin-2-yl)oxy)methyl)cyclohexan-1-amine 8b

In accordance with the synthetic route in Example 7, the starting material 7a in Step 1 was replaced with (1-aminocyclohexyl)methanol 8a (prepared according to the method disclosed in "*Journal of Medicinal Chemistry,* 2004, 47(18), 4613-4626"), to give the title compound 8b (650 mg, yield: 68%).

MS m/z (ESI): 333.1 [M+1].

Step 2

(E)-4-((1-(((5-Iodopyridin-2-yl)oxy)methyl)cyclohexyl)amino)-N,N-dimethylbut-2-enamide 8c In accordance with the synthetic route in Example 7, the starting material 7b in Step 2 was replaced with compound 8b, to give the title compound 8c (500 mg, yield: 58%).

MS m/z (ESI): 444.2 [M+1].

Step 3

(E)-N,N-Dimethyl-4-((1-(((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclohexyl)amino)but-2-enamide 8d In accordance with the synthetic route in Example 7, the starting material 7c in Step 3 was replaced with compound 8c, to give the title compound 8d (250 mg, yield: 94%).

MS m/z (ESI): 720.4 [M+1].

Step 4

(E)-N,N-Dimethyl-4-((1-(((5-((Z)-4,4,4-trifluoro-1-(3-fluoro-1H-indazol-5-yl)-2-phenylbut-1-en-1-yl)pyridin-2-yl)oxy)methyl)cyclohexyl)amino)but-2-enamide 8

In accordance with the synthetic route in Example 7, the starting material 7d in Step 4 was replaced with compound 8d, to give the title compound 8 (80 mg, yield: 36%).

MS m/z (ESI): 636.2 [M+1].
$^1$H NMR (400 MHz, CD$_3$OD) 7.72 (d, 1H), 7.65 (s, 1H), 7.49 (dd, 1H), 7.33 (dd, 2H), 7.31-7.24 (m, 5H), 6.80 (d, 1H), 6.68-6.65 (m, 2H), 4.53 (s, 2H), 3.85 (d, 2H), 3.46-3.38 (m, 2H), 3.08 (s, 3H), 2.98 (s, 3H), 2.06 (d, 2H), 1.75-1.64 (m, 3H), 1.64-1.47 (m, 4H), 1.31 (m, 1H).

Example 9

(E)-N,N-Dimethyl-4-(4-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide 9

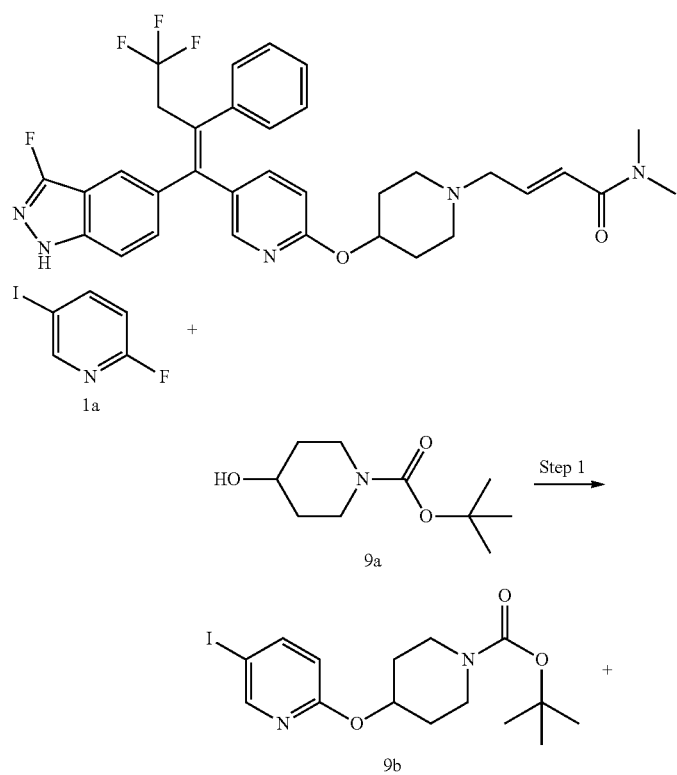

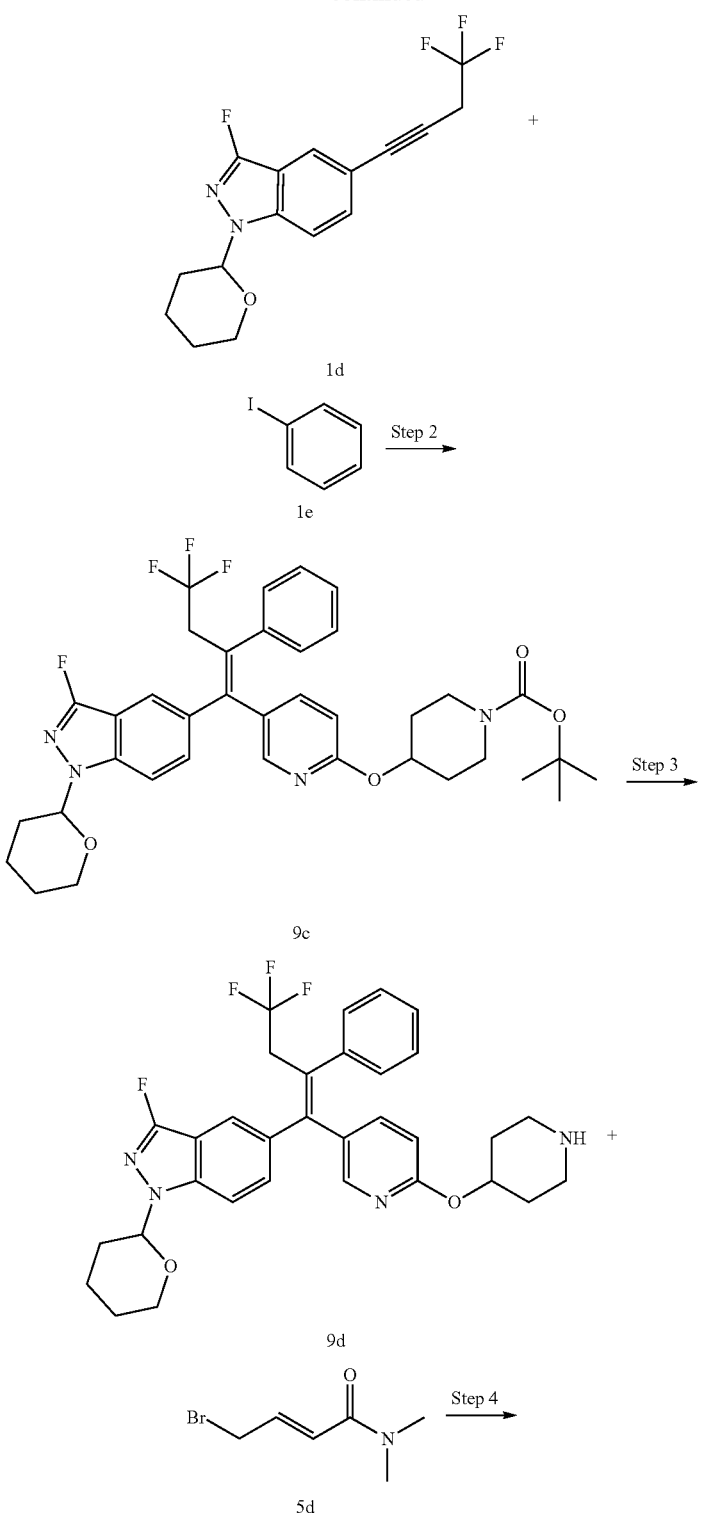

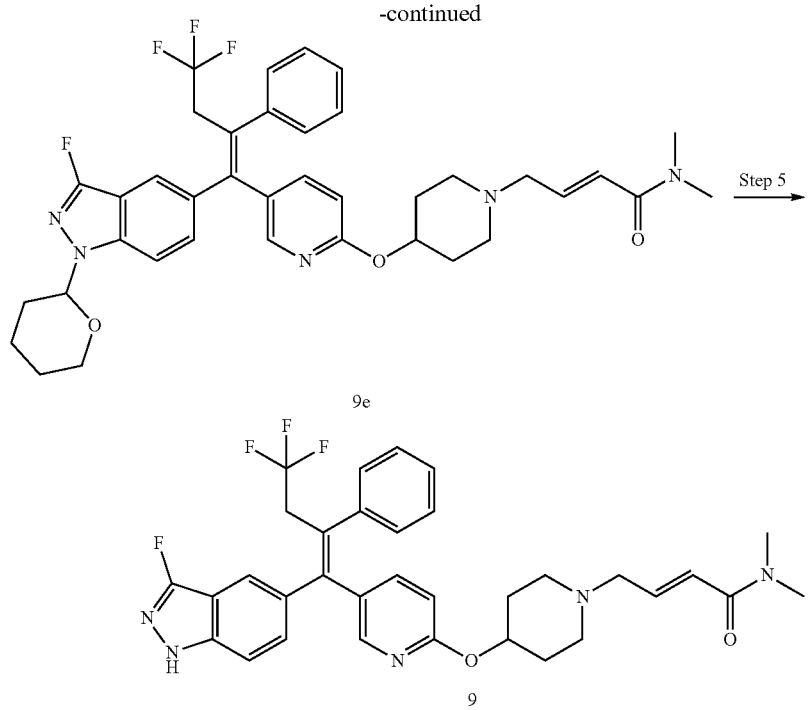

9e

9

Step 1

Tert-butyl 4-((5-iodopyridin-2-yl)oxy)piperidine-1-carboxylate 9b

Sodium hydride (0.6 g, 14.9 mmol) was dissolved in N,N-dimethylformamide (30 mL), followed by the addition of tert-butyl 4-hydroxypiperidine-1-carboxylate 9a (1.0 g, 5.0 mmol, prepared according to the method disclosed in "*Journal of the American Chemical Society*, 2018, 140(1), 155-158") at room temperature. After completion of the addition, compound 1a (2.2 g, 9.9 mmol) was added slowly. The reaction was stirred at room temperature for 2 hours. The reaction solution was concentrated under reduced pressure, and the resulting residues were purified by thin layer chromatography with developing system B to obtain the title product 9b (0.6 g, yield: 30%).

Step 2

Tert-butyl (Z)-4-((5-(4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidine-1-carboxylate 9c Compound 1d (150 mg, 0.5 mmol) was dissolved in methyltetrahydrofuran (15 mL), followed by the addition of bis(pinacolato)diboron (140 mg, 0.6 mmol) and tetrakis(triphenylphosphine) platinum (28 mg, 0.02 mmol). The reaction solution was purged with argon three times, warmed up to 85° C. and stirred for 3 hours. The reaction solution was cooled to room temperature, followed by the addition of compound 9b (167 mg, 0.4 mmol), bis(triphenylphosphine)palladium dichloride (31 mg, 0.05 mmol), cesium carbonate (300 mg, 0.9 mmol) and water (1 mL). The reaction solution was stirred at room temperature overnight. Compound 1e (187 mg, 0.9 mmol) and potassium hydroxide (129 mg, 2.3 mmol) were added. The reaction solution was purged with argon three times, warmed up to 85° C., stirred for 2 hours, and cooled to room temperature. The reaction solution was concentrated under reduced pressure, and the resulting residues were purified by thin layer chromatography with developing system B to obtain the title product 9c (210 mg, yield: 67%).

MS m/z (ESI): 681.3 [M+1].

Step 3

(Z)-3-Fluoro-1-(tetrahydro-2H-pyran-2-yl)-5-(4,4,4-trifluoro-2-phenyl-1-(6-(piperidin-4-yloxy)pyridin-3-yl)but-1-en-1-yl)-1H-indazole 9d Compound 9c (120 mg, 0.2 mmol) was dissolved in dichloromethane (5 mL), followed by the addition of trifluoroacetic acid (1 mL). The reaction was stirred at room temperature for 5 hours. The reaction solution was concentrated under reduced pressure, adjusted to about pH 8 with saturated sodium bicarbonate solution (10 mL), dried over anhydrous sodium sulfate and filtered. The filtrate was concentrated under reduced pressure to obtain the crude title product 9d (100 mg, yield: 98%), which was used directly in the next step without purification.

Step 4

(E)-N,N-Dimethyl-4-(4-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-enamide 9e Compound 9d (100 mg, 0.2 mmol) was dissolved in N,N-dimethylformamide (5 mL), followed by the successive addition of diisopropylethylamine (67 mg, 0.5 mmol) and compound 5d (31 mg, 0.2 mmol) at room temperature. The reaction solution was stirred for 2 hours. The reaction was stopped, and the reaction solution was cooled. Saturated sodium bicarbonate solution (15 mL) was added, and the solution was extracted with ethyl acetate (20 mL×2). The organic phases were combined, washed with saturated sodium chloride solution (20 mL×4), dried over anhydrous sodium sulfate and filtered. The filtrate was concentrated under reduced pressure, and the resulting residues were purified by thin layer chromatography with developing system A to obtain the title product 9e (85 mg, yield: 71%).

Step 5

(E)-N,N-Dimethyl-4-(4-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide 9

Compound 9e (80 mg, 0.1 mmol) was dissolved in methanol (5 mL), followed by the addition of hydrochloric acid (12N, 3 mL). The reaction solution was stirred for 3 hours. The reaction was stopped, and the reaction solution was cooled and concentrated. Saturated sodium bicarbonate solution (15 mL) was added, and the solution was extracted with dichloromethane (10 mL×4). The organic phases were combined, washed with water (10 mL×3) and saturated sodium chloride solution (10 mL) successively, dried over anhydrous sodium sulfate and filtered. The filtrate was concentrated under reduced pressure, and the resulting residues were purified by thin layer chromatography with developing system A to obtain the title product 9 (25 mg, yield: 36%).

MS m/z (ESI): 608.4 [M+1].

$^1$H NMR (400 MHz, CDCl$_3$) 9.91 (br, 1H), 7.68 (d, 2H), 7.45 (d, 1H), 7.33 (s, 1H), 7.24-7.15 (m, 5H), 6.82 (s, 2H), 6.47 (d, 1H), 5.31 (s, 1H), 3.86 (s, 2H), 3.49 (s, 2H), 3.80-3.31 (m, 2H), 3.15-3.12 (s, 3H), 3.11 (s, 3H), 3.05 (s, 3H), 2.26-2.18 (m, 4H).

Example 10

(Z)-1-(4-((5-(4,4,4-Trifluoro-1-(3-fluoro-1H-indazol-5-yl)-2-phenylbut-1-en-1-yl)pyridin-2-yl)oxy)piperidin-1-yl)but-2-yn-1-one 10

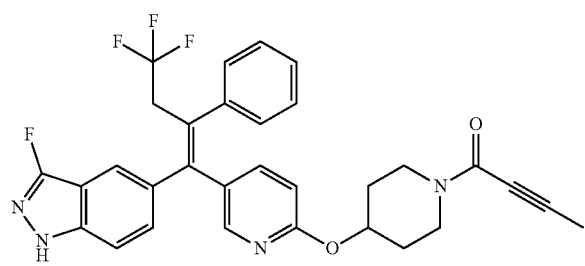

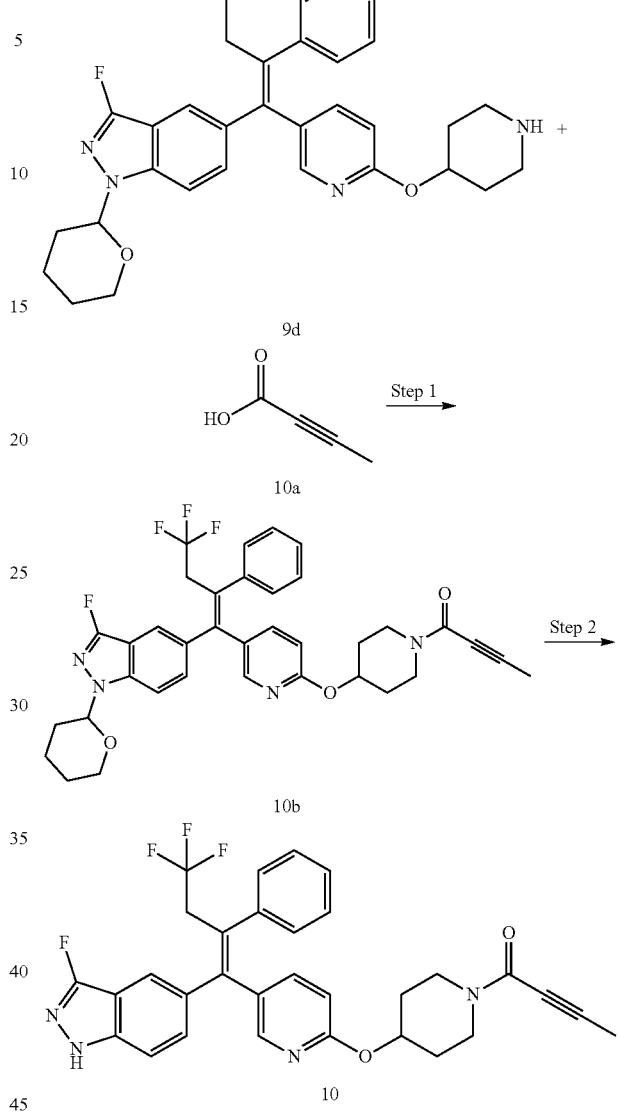

Step 1

(Z)-1-(4-((5-(4,4,4-Trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-yn-1-one 10b Compound 9d (60 mg, 0.1 mmol) was dissolved in N,N-dimethylformamide (3 mL), followed by the addition of triethylamine (52 mg, 0.5 mmol), but-2-ynoic acid 10a (17 mg, 0.2 mmol), 1-(3-dimethylaminopropyl)-3-ethylcarbodiimide hydrochloride (30 mg, 0.2 mmol) and 1-hydroxybenzotriazole (24 mg, 0.2 mmol) at room temperature. The reaction solution was stirred for 12 hours. The reaction solution was cooled. Saturated sodium bicarbonate solution (15 mL) was added, and the solution was extracted with ethyl acetate (20 mL×2). The organic phases were combined, washed with saturated sodium chloride solution (20 mL×4), dried over anhydrous sodium sulfate and filtered.

The filtrate was concentrated under reduced pressure, and the resulting residues were purified by thin layer chromatography with developing system A to obtain the title product 10b (45 mg, yield: 67%).

Step 2

(Z)-1-(4-((5-(4,4,4-Trifluoro-1-(3-fluoro-1H-indazol-5-yl)-2-phenylbut-1-en-1-yl)pyridin-2-yl)oxy)piperidin-1-yl)but-2-yn-1-one 10

Compound 10b (45 mg, 0.07 mmol) was dissolved in methanol (5 mL), followed by the addition of hydrochloric acid (12N, 3 mL). The reaction solution was stirred for 3 hours. The reaction solution was cooled and concentrated. Saturated sodium bicarbonate solution (15 mL) was added, and the solution was extracted with dichloromethane (10 mL×4). The organic phases were combined, washed with water (10 mL×3) and saturated sodium chloride solution (10 mL) successively, dried over anhydrous sodium sulfate and filtered. The filtrate was concentrated under reduced pressure, and the resulting residues were purified by thin layer chromatography with developing system A to obtain the title product 10 (15 mg, yield: 38%).

MS m/z (ESI): 563.3 [M+1].

$^1$H NMR (400 MHz, CDCl$_3$) 9.67 (br, 1H), 7.65 (d, 2H), 7.45 (d, 1H), 7.34 (m, 1H), 7.21-7.17 (m, 4H), 6.50 (d, 1H), 5.11 (s, 1H), 3.94-3.92 (m, 1H), 3.80-3.71 (m, 4H), 3.37-3.29 (m, 2H), 2.02 (s, 3H), 1.94-1.75 (m, 4H).

Example 11

(E)-N-Methyl-4-((R)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide 11

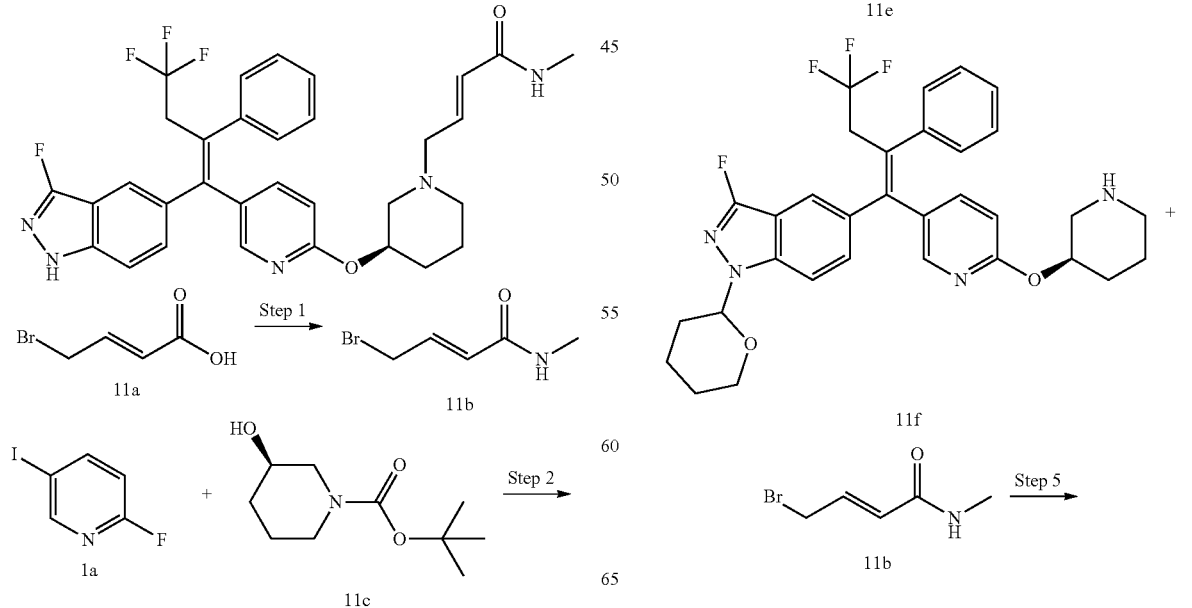

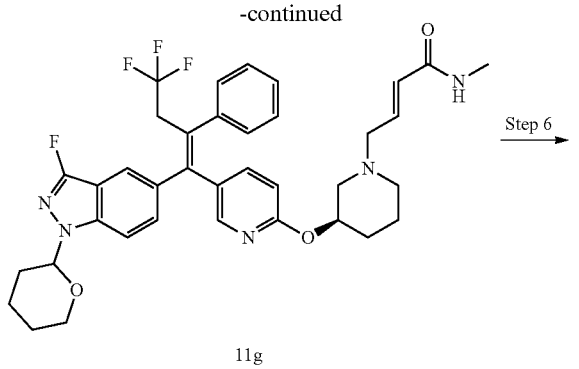

11g

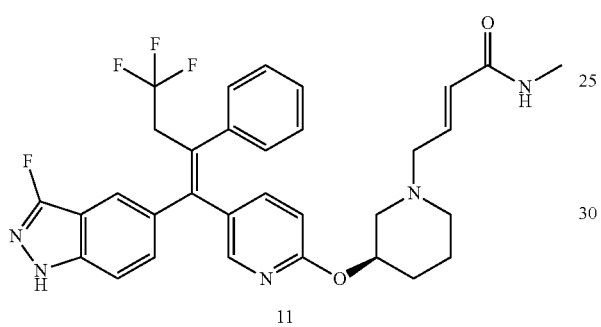

11

Step 1

(E)-4-Bromo-N-methylbut-2-enamide 11b (E)-4-Bromobut-2-enoic acid 11a (0.5 g, 3.0 mmol) was dissolved in dichloromethane (5 mL), followed by the addition of triethylamine (0.3 g, 3.3 mmol), methylamine (0.1 g, 3.3 mmol), 1-(3-dimethylaminopropyl)-3-ethylcarbodiimide hydrochloride (0.6 g, 3.3 mmol) and 1-hydroxybenzotriazole (0.4 g, 3.3 mmol) at room temperature. The reaction solution was stirred for 12 hours. The reaction solution was cooled. Saturated sodium bicarbonate solution (15 mL) was added, and the solution was extracted with ethyl acetate (20 mL×2). The organic phases were combined, washed with saturated sodium chloride solution (20 mL×4), dried over anhydrous sodium sulfate and filtered. The filtrate was concentrated under reduced pressure, and the resulting residues were purified by thin layer chromatography with developing system A to obtain the title product 11b (0.4 g, yield: 77%).

Step 2

Tert-butyl(R)-3-((5-iodopyridin-2-yl)oxy)piperidine-1-carboxylate 11d

In accordance with the synthetic route in Example 1, the starting material 1b in Step 1 was replaced with tert-butyl (R)-3-hydroxypiperidine-1-carboxylate 11c (prepared according to the method disclosed in "Tetrahedron, 2011, 67(7), 1485-1500"), to give the title compound 11d (653 mg, yield: 91%).

Step 3

Tert-butyl (3R)-3-((5-(((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidine-1-carboxylate 11e In accordance with the synthetic route in Example 1, the starting material 1c in Step 2 was replaced with compound 11d, to give the title compound 11e (200 mg, yield: 64%).

MS m/z (ESI): 680.9 [M+1].

Step 4

3-Fluoro-1-(tetrahydro-2H-pyran-2-yl)-5-((Z)-4,4,4-trifluoro-2-phenyl-1-(6-(((R)-piperidin-3-yl) oxy) pyridin-3-yl)but-1-en-1-yl)-1H-indazole 11f In accordance with the synthetic route in Example 1, the starting material 1f in Step 3 was replaced with compound 11e, to give the title compound 11f (170 mg, yield: 100%).

Step 5

(E)-N-Methyl-4-((3R)-3-((5-(((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-enamide 11g In accordance with the synthetic route in Example 1, the starting material 1g in Step 4 was replaced with compound 11f, and the starting material 1h was replaced with 11b, to give the title compound 11g (50 mg, yield: 86%).

Step 6

(E)-N-Methyl-4-((R)-3-((5-(((Z)-4,4,4-trifluoro-1-(3-fluoro-1H-indazol-5-yl)-2-phenylbut-1-en-1-yl)pyridin-2-yl)oxy)piperidin-1-yl)but-2-enamide 11

In accordance with the synthetic route in Example 1, the starting material 1i in Step 5 was replaced with compound 11g, to give the title compound 11 (20 mg, yield: 45%).

MS m/z (ESI): 594.2 [M+1].

$^1$H NMR (400 MHz, CD$_3$OD) 7.65 (d, 2H), 7.49 (d, 1H), 7.31-7.19 (m, 6H), 6.68-6.62 (m, 2H), 6.30 (d, 1H), 5.39 (s, 1H), 3.88 (s, 2H), 3.67 (s, 1H), 3.48-3.38 (m, 3H), 3.26-3.13 (m, 2H), 3.01 (s, 1H), 2.80 (s, 3H), 2.06 (s, 2H), 1.86-1.73 (m, 2H).

Example 12

(E)-1-Morpholino-4-((R)-3-((5-((Z)-4,4-trifluoro-1-(3-fluoro-1H-indazol-5-yl)-2-phenylbut-1-en-1-yl)pyridin-2-yl)oxy)piperidin-1-yl)but-2-en-1-one 12

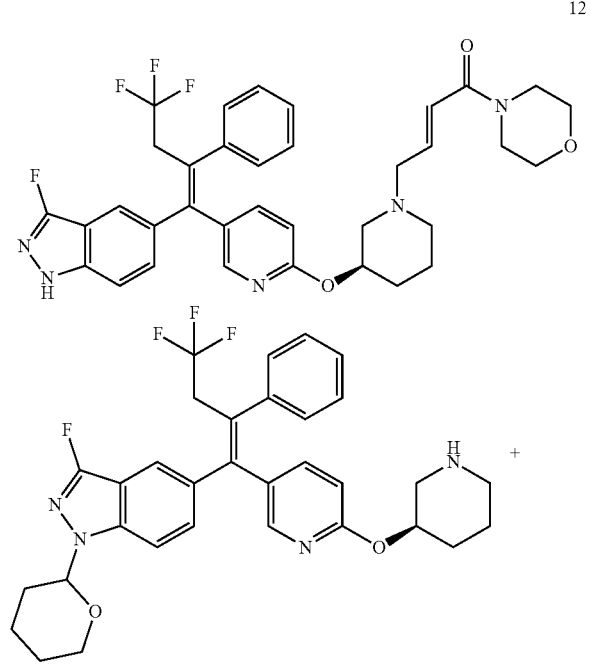

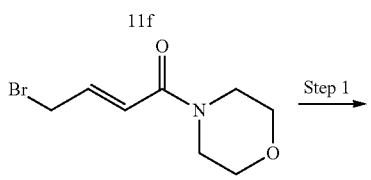

Step 1

(E)-1-Morpholino-4-((3R)-3-((5-((Z)-4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-en-1-one 12a In accordance with the synthetic route in Example 1, the starting material 1g in Step 4 was replaced with compound 11f, to give the title compound 12a (50 mg, yield: 79%).

Step 2

(E)-1-Morpholino-4-((R)-3-((5-((Z)-4,4-trifluoro-1-(3-fluoro-1H-indazol-5-yl)-2-phenylbut-1-en-1-yl)pyridin-2-yl)oxy)piperidin-1-yl)but-2-en-1-one 12

In accordance with the synthetic route in Example 1, the starting material 1i in Step 5 was replaced with compound 12a, to give the title compound 12 (20 mg, yield: 42%).

MS m/z (ESI): 650.3 [M+1].

$^1$H NMR (400 MHz, CDCl$_3$) 10.10 (s, 1H), 7.67-7.62 (m, 3H), 7.50 (d, 1H), 7.27-7.11 (m, 6H), 6.79 (s, 2H), 6.48 (s, 1H), 5.38 (s, 1H), 3.93 (s, 2H), 3.70 (s, 7H), 3.55 (s, 2H), 3.38-3.31 (m, 3H), 3.09-2.82 (m, 2H), 1.85-1.65 (m, 4H).

Example 13

(E)-N-(Tetrahydro-2H-pyran-4-yl)-4-((R)-3-((5-((Z)-4,4-trifluoro-1-(3-fluoro-1H-indazol-5-yl)-2-phenylbut-1-en-1-yl)pyridin-2-yl)oxy)piperidin-1-yl)but-2-enamide 13

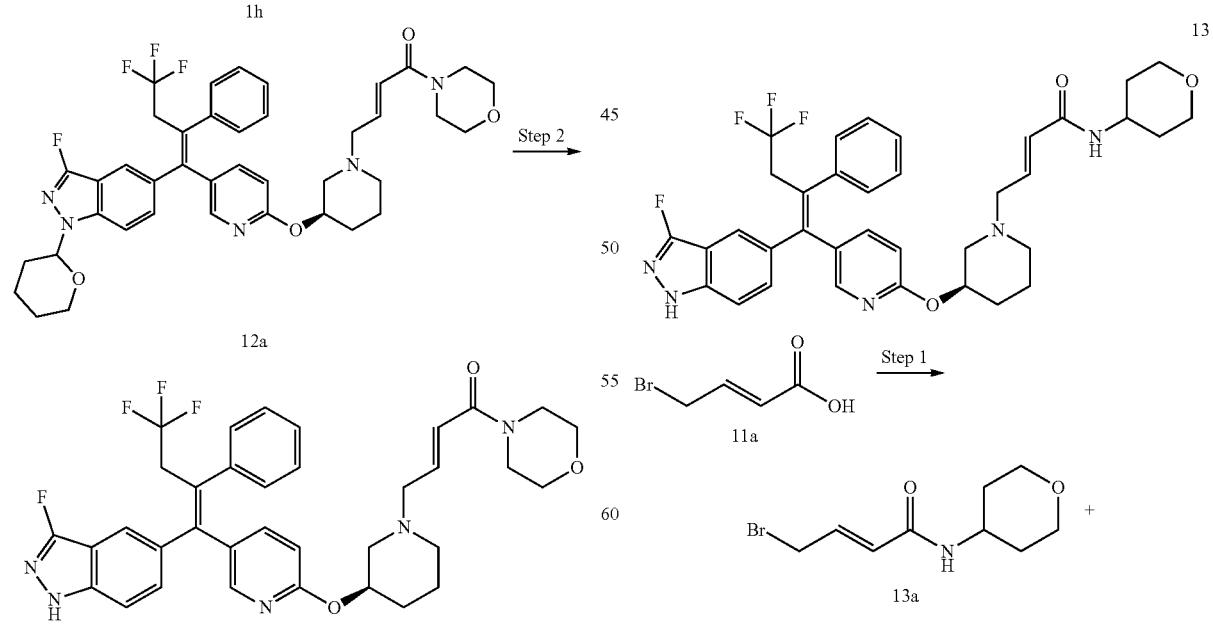

121

-continued

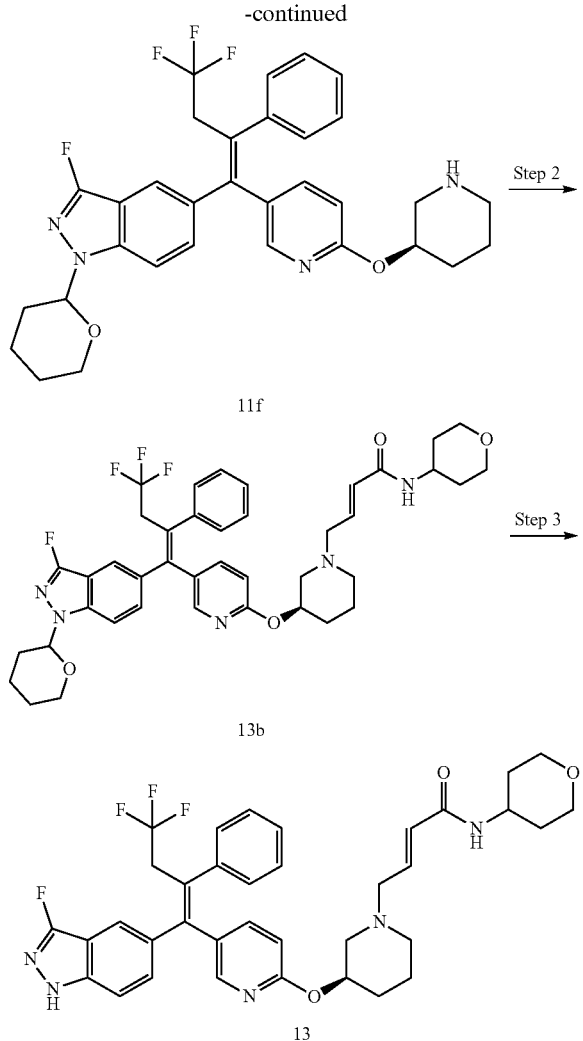

Step 1

(E)-4-Bromo-N-(tetrahydro-2H-pyran-4-yl)but-2-enamide 13a (E)-4-Bromobut-2-enoic acid 11a (1.0 g, 6.1 mmol) was dissolved in dichloromethane (10 mL), followed by the addition of triethylamine (1.8 g, 18.2 mmol), tetrahydropyran-4-amine (0.6 g, 6.1 mmol), 1-(3-dimethylaminopropyl)-3-ethylcarbodiimide hydrochloride (1.3 g, 6.7 mmol) and 1-hydroxybenzotriazole (0.9 g, 6.7 mmol) at room temperature. The reaction solution was stirred for 12 hours. The reaction solution was cooled. Saturated sodium bicarbonate solution (15 mL) was added, and the solution was extracted with ethyl acetate (20 mL×2). The organic phases were combined, washed with saturated sodium chloride solution (20 mL×4), dried over anhydrous sodium sulfate and filtered. The filtrate was concentrated under reduced pressure, and the resulting residues were purified by thin layer chromatography with developing system A to obtain the title product 13a (1.2 g, yield: 79%).

122

Step 2

(E)-N-(Tetrahydro-2H-pyran-4-yl)-4-((3R)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-enamide 13b In accordance with the synthetic route in Example 1, the starting material 1g in Step 4 was replaced with compound 11f, and the starting material 1h was replaced with 13a, to give the title compound 13b (41 mg, yield: 81%).

Step 3

(E)-N-(Tetrahydro-2H-pyran-4-yl)-4-((R)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide 13

In accordance with the synthetic route in Example 1, the starting material 1i in Step 5 was replaced with compound 13b, to give the title compound 13 (20 mg, yield: 32%).
MS m/z (ESI): 664.3 [M+1].
$^1$H NMR (400 MHz, DMSO-$d_6$) 12.68 (s, 1H), 7.92-7.90 (d, 1H), 7.60-7.59 (m, 1H), 7.52-7.50 (m, 1H), 7.23-7.14 (m, 6H), 6.50-6.43 (m, 2H), 5.97-5.93 (d, 1H), 4.86-4.79 (m, 1H), 3.79-3.74 (m, 3H), 3.47-3.38 (m, 2H), 3.33-3.32 (m, 1H), 3.00-2.98 (m, 2H), 2.80-2.78 (m, 1H), 2.55-2.50 (m, 1H), 2.00-1.24 (m, 12H).

Example 14

(E)-N,N-Dimethyl-4-((R)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide 14

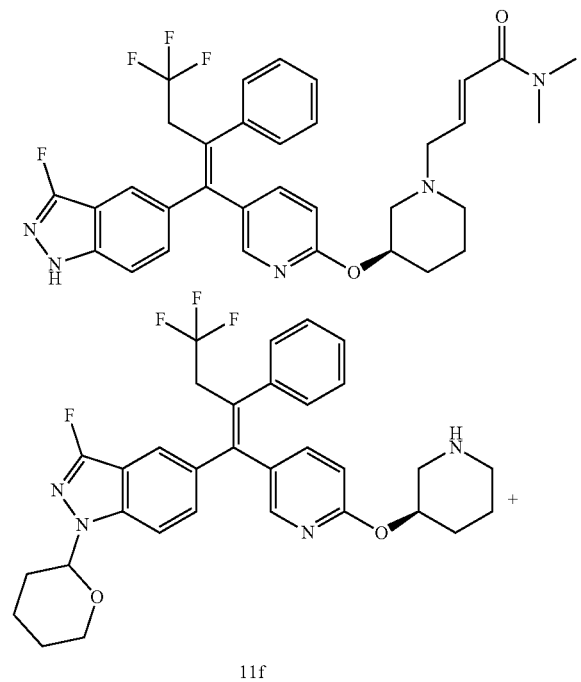

124

Example 15

(E)-1-(Pyrrolidin-1-yl)-4-((R)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-en-1-one 15

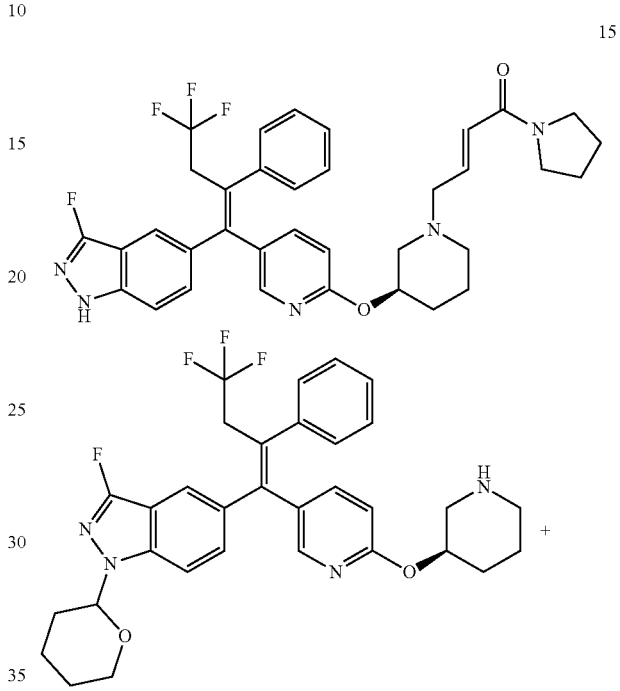

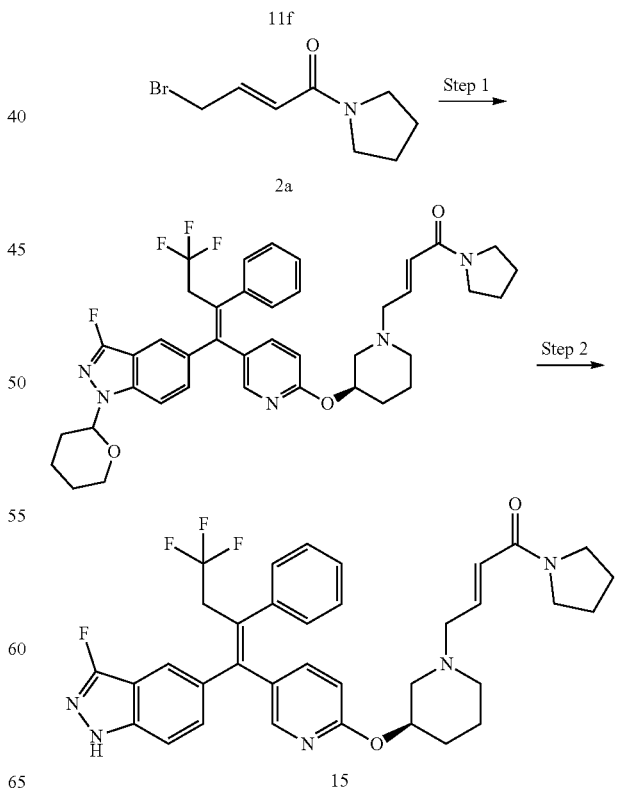

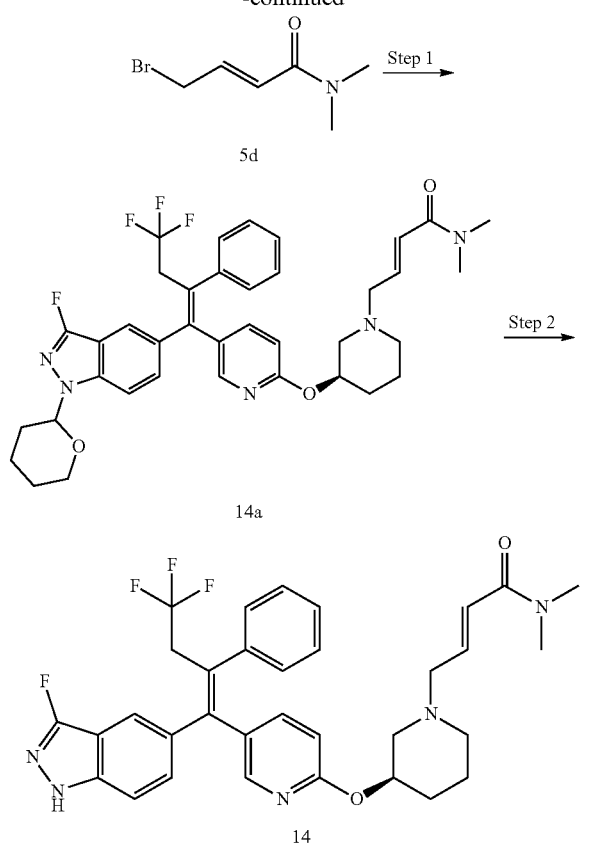

Step 1

(E)-N,N-Dimethyl-4-((3R)-3-((5-((Z)-4,4,4-trifluoro-1-(3-fluoro-1H-(tetrahydro-2H-pyran-2-yl)-1H-indazol-5-yl)-2-phenylbut-1-en-1-yl)pyridin-2-yl)oxy)piperidin-1-yl)but-2-enamide 14a In accordance with the synthetic route in Example 1, the starting material 11g in Step 4 was replaced with compound 11f, and the starting material 1 h was replaced with 5d, to give the title compound 14a (80 mg, yield: 79%).

Step 2

(E)-N,N-Dimethyl-4-((R)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide 14

In accordance with the synthetic route in Example 1, the starting material 1i in Step 5 was replaced with compound 14a, to give the title compound 14 (10 mg, yield: 27%).

MS m/z (ESI): 608.3 [M+1].

$^1$H NMR (400 MHz, CDCl$_3$) 9.77-7.75 (br, 1H), 7.68-7.62 (m, 2H), 7.46-7.43 (m, 1H), 7.36-7.30 (m, 2H), 7.27-7.18 (d, 5H), 6.87-6.76 (m, 2H), 6.80-6.48 (m, 1H), 5.42-5.28 (m, 1H), 3.97-3.67 (m, 5H), 3.38-3.31 (m, 2H), 3.12-3.07 (m, 6H), 2.31-1.69 (m, 4H).

Step 1

(E)-1-(Pyrrolidin-1-yl)-4-((3R)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-en-1-one 15a In accordance with the synthetic route in Example 1, the starting material 1g in Step 4 was replaced with compound 11f, and starting material 1h was replaced with 2a, to give the title compound 15a (49 mg, yield: 72%).

Step 1

(E)-1-(Pyrrolidin-1-yl)-4-((R)-3-((5-((Z)-4,4,4-trifluoro-1-(3-fluoro-1H-indazol-5-yl)-2-phenylbut-1-en-1- yl)pyridin-2-yl)oxy)piperidin-1-yl)but-2-en-1-one 15a In accordance with the synthetic route in Example 1, the starting material 1i in Step 5 was replaced with compound 15a, to give the title compound 15 (20 mg, yield: 47%).

MS m/z (ESI): 634.3 [M+1].

¹H NMR (400 MHz, CD$_3$OD) 7.63 (d, 2H), 7.49 (dd, 1H), 7.29-7.19 (m, 7H), 6.79-6.74 (m, 1H), 6.49-6.43 (m, 2H), 5.02-4.98 (m, 1H), 3.56-3.54 (m, 2H), 3.47-3.44 (m, 4H), 3.25 (d, 2H), 2.92 (d, 1H), 2.65-2.64 (m, 1H), 2.37-2.35 (m, 2H), 1.94-1.85 (m, 6H), 1.64-1.52 (m, 2H).

Example 16

(E)-N-(Tert-butyl)-4-((R)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide 16

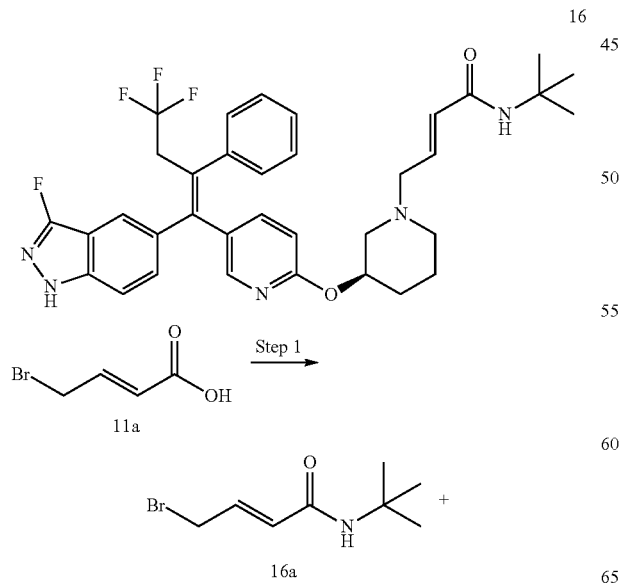

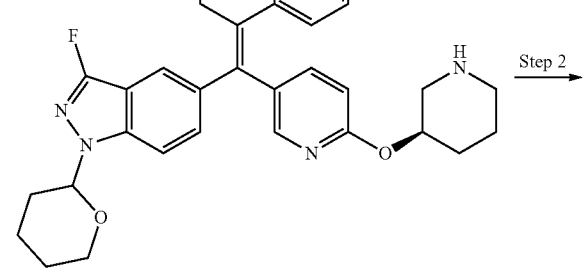

11f

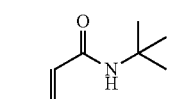

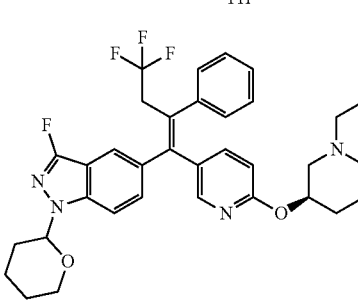

16b

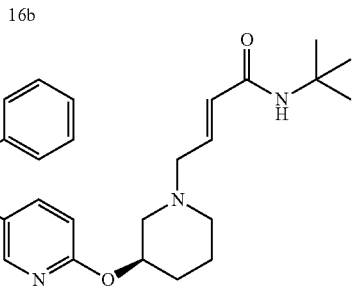

16

Step 1

(E)-4-Bromo-N-(tert-butyl)but-2-enamide 16a

Compound 11a (0.5 g, 3.0 mmol) was dissolved in dichloromethane (10 mL), followed by the addition of triethylamine (0.4 g, 3.6 mmol), tert-butylamine (0.2 g, 3.0 mmol), 1-(3-dimethylaminopropyl)-3-ethylcarbodiimide hydrochloride (0.7 g, 3.6 mmol) and 1-hydroxybenzotriazole (0.5 g, 3.6 mmol) at room temperature. The reaction solution was stirred for 12 hours. The reaction solution was cooled. Saturated sodium bicarbonate solution (15 mL) was added, and the solution was extracted with ethyl acetate (20 mL×2). The organic phases were combined, washed with saturated sodium chloride solution (20 mL×4), dried over anhydrous sodium sulfate and filtered. The filtrate was concentrated under reduced pressure, and the resulting residues were purified by thin layer chromatography with developing system A to obtain the title product 16a (0.3 g, yield: 39%).

Step 2

(E)-N-(Tert-butyl)-4-((3R)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-enamide 16b In accordance with the synthetic route in Example 1, the starting material 1g in Step 4 was replaced with compound 11f, and the starting material 1 h was replaced with 16a, to give the title compound 16b (47 mg, yield: 83%).

Step 3

(E)-N-(Tert-butyl)-4-((R)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide 16

In accordance with the synthetic route in Example 1, the starting material 1i in Step 5 was replaced with compound 16b, to give the title compound 16 (23 mg, yield: 28%).

MS m/z (ESI): 636.5 [M+1].

$^1$H NMR (400 MHz, CD$_3$OD) 7.67 (d, 2H), 7.50 (dd, 1H), 7.32-7.22 (m, 7H), 6.64-6.55 (m, 2H), 6.33 (d, 1H), 5.40 (s, 1H), 3.88 (s, 2H), 3.69 (d, 1H), 3.52-3.41 (m, 3H), 3.24 (d, 1H), 3.02-2.99 (m, 1H), 2.10-2.07 (m, 2H), 1.87-1.75 (m, 2H), 1.36 (s, 9H).

Example 17

(E)-N-Cyclopentyl-4-((R)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide 17

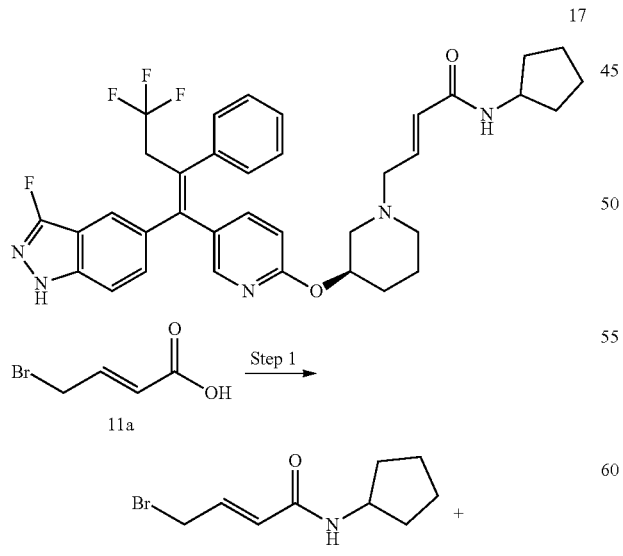

Step 1

(E)-4-Bromo-N-cyclopentylbut-2-enamide 17a

Compound 11a (0.5 g, 3.0 mmol) was dissolved in dichloromethane (10 mL), followed by the addition of triethylamine (0.4 g, 3.6 mmol), cyclopentylamine (0.3 g, 3.0 mmol), 1-(3-dimethylaminopropyl)-3-ethylcarbodiimide hydrochloride (0.7 g, 3.6 mmol) and 1-hydroxybenzotriazole (0.5 g, 3.6 mmol) at room temperature. The reaction solution was stirred for 12 hours. The reaction solution was cooled. Saturated sodium bicarbonate solution (15 mL) was added, and the solution was extracted with ethyl acetate (20 mL×2). The organic phases were combined, washed with saturated sodium chloride solution (20 mL×4), dried over anhydrous sodium sulfate and filtered. The filtrate was concentrated under reduced pressure, and the resulting residues were purified by thin layer chromatography with developing system A to obtain the title product 17a (0.3 g, yield: 49%).

Step 2

(E)-N-Cyclopentyl-4-((3R)-3-((5-((Z)-4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-enamide 17b In accordance with the synthetic route in Example 1, the starting material 1g in Step 4 was replaced with compound 11f, and the starting material 1 h was replaced with 17a, to give the title compound 17b (42 mg, yield: 73%).

Step 3

(E)-N-Cyclopentyl-4-((R)-3-((5-((Z)-4,4-trifluoro-1-(3-fluoro-1H-indazol-5-yl)-2-phenylbut-1-en-1-yl)pyridin-2-yl)oxy)piperidin-1-yl)but-2-enamide 17

In accordance with the synthetic route in Example 1, the starting material 1i in Step 5 was replaced with compound 17b, to give the title compound 17 (21 mg, yield: 38%).

MS m/z (ESI): 648.3 [M+1].

$^1$H NMR (400 MHz, DMSO-d$_6$) 12.75-12.68 (m, 1H) 7.88-7.86 (d, 1H), 7.61-7.59 (m, 2H), 7.53-7.50 (m, 1H), 7.23-7.15 (m, 6H), 6.47-6.41 (m, 2H), 5.96-5.93 (d, 1H), 4.85-4.79 (m, 1H), 4.02-3.97 (m, 1H), 3.47-3.39 (m, 2H), 2.99-2.98 (m, 2H), 2.80-2.79 (m, 1H), 2.56-2.50 (m, 2H), 2.30-2.25 (m, 1H), 1.99-1.27 (m, 12H).

Example 18

(E)-1-(Piperazin-1-yl)-4-((R)-3-((5-((Z)-4,4-trifluoro-1-(3-fluoro-1H-indazol-5-yl)-2-phenylbut-1-en-1-yl)pyridin-2-yl)oxy)piperidin-1-yl)but-2-en-1-one 18

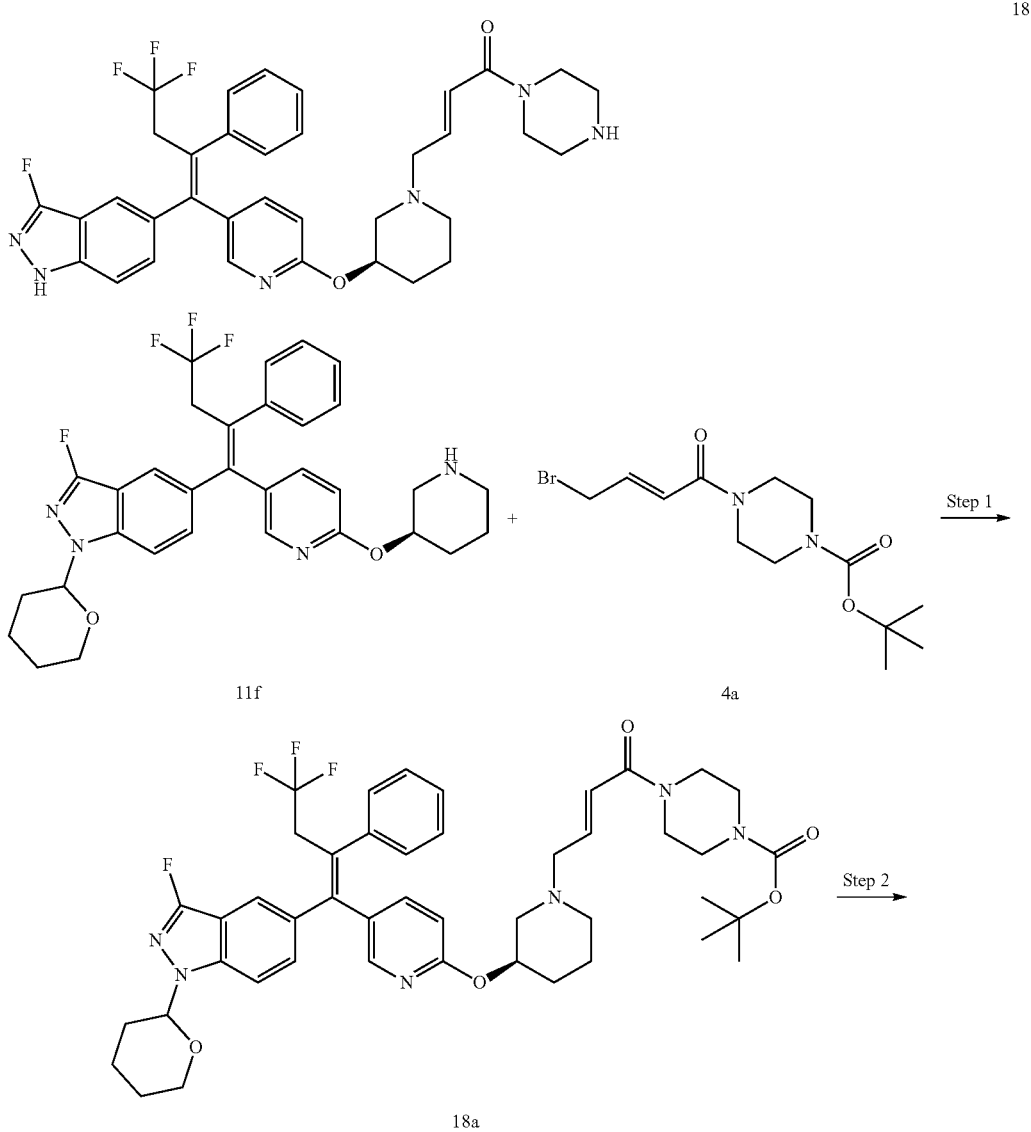

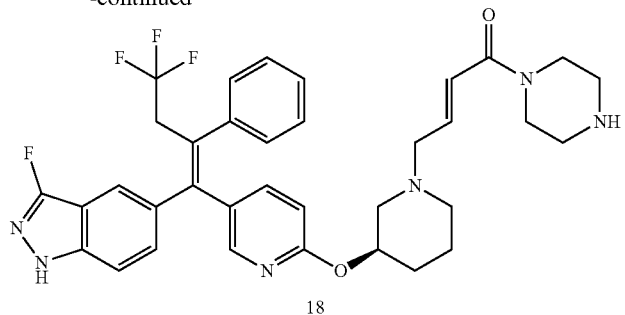

18

Step 1

Tert-butyl 4-((E)-4-((3R)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-enoyl)piperazine-1-carboxylate 18a In accordance with the synthetic route in Example 1, the starting material 1g in Step 4 was replaced with compound 11f, and the starting material 1h was replaced with compound 4a, to give the title compound 18a (51 mg, yield: 76%).

Step 2

(E)-1-(Piperazin-1-yl)-4-((R)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-en-1-one 18

In accordance with the synthetic route in Example 1, the starting material 1i in Step 5 was replaced with compound 18a, to give the title compound 18 (21 mg, yield: 31%).
MS m/z (ESI): 649.3 [M+1].
$^1$H NMR (400 MHz, CD$_3$OD) 7.67 (d, 2H), 7.50 (d, 1H), 7.34-7.20 (m, 6H), 6.92 (d, 1H), 6.78-6.61 (m, 2H), 5.36 (s, 1H), 3.94-3.88 (m, 5H), 3.50-3.39 (m, 6H), 3.28 (s, 2H), 2.23-1.88 (m, 5H), 1.34-1.30 (m, 3H).

Example 19

(E)-N,N-Dimethyl-4-((R)-3-((5-((Z)-4,4,4-trifluoro-1-(3-fluoro-1H-indazol-5-yl)-2-(4-fluorophenyl)but-1-en-1-yl)pyridin-2-yl)oxy)piperidin-1-yl)but-2-enamide 19

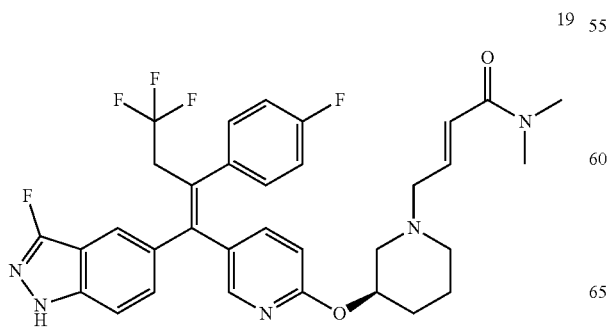

19

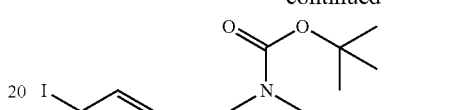

11d

Step 1

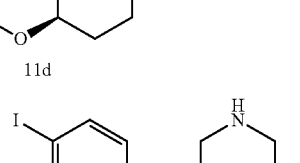

19a +

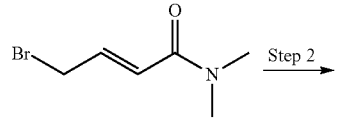

5d

Step 2

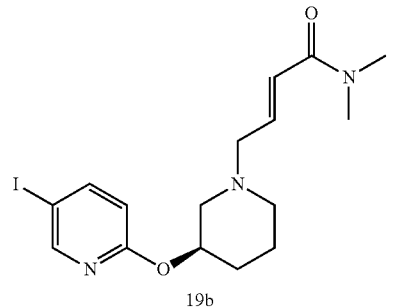

19b +

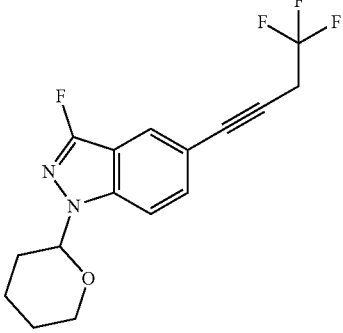

1d

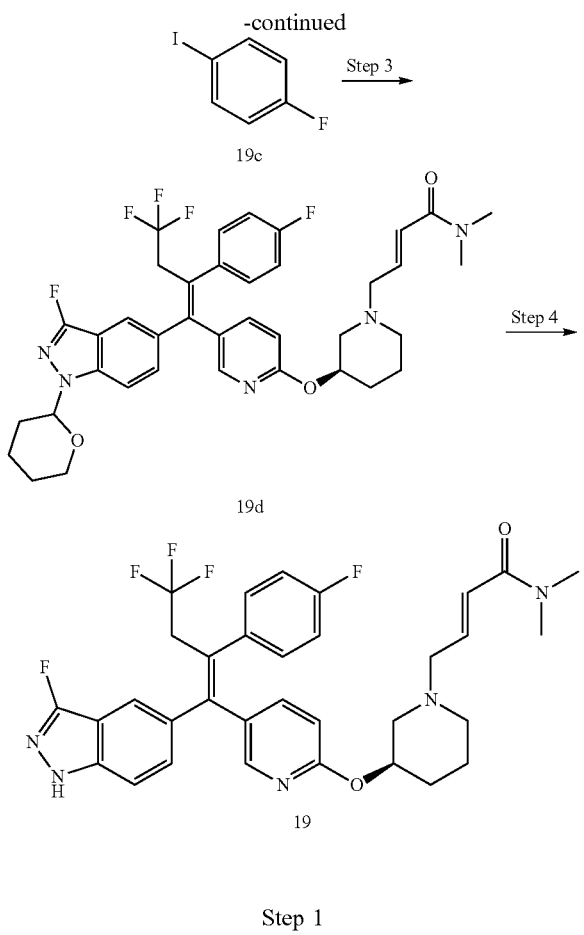

Step 1

(R)-5-Iodo-2-(piperidin-3-yloxy)pyridine 19a

Compound 11d (1.0 g, 2.5 mmol) was dissolved in dichloromethane (15 mL), followed by the addition of trifluoroacetic acid (3 mL). The reaction was stirred at room temperature for 5 hours. The reaction solution was concentrated under reduced pressure, adjusted to about pH 8 with saturated sodium bicarbonate solution (100 mL), dried over anhydrous sodium sulfate and filtered. The filtrate was concentrated under reduced pressure to obtain the crude title product 19a (0.8 g, yield: 1000%), which was used directly in the next step without purification.

Step 2

(R,E)-4-(3-((5-Iodopyridin-2-yl)oxy)piperidin-1-yl)-N,N-dimethylbut-2-enamide 19b Compound 19a (752 mg, 2.5 mmol) was dissolved in N,N-dimethylformamide (20 mL), followed by the successive addition of diisopropylethylamine (1.6 g, 12.4 mmol) and compound 5d (470 mg, 2.5 mmol) at room temperature. The reaction solution was stirred for 2 hours. The reaction solution was cooled. Saturated sodium bicarbonate solution (15 mL) was added, and the solution was extracted with ethyl acetate (50 mL×2). The organic phases were combined, washed with saturated sodium chloride solution (50 mL×4), dried over anhydrous sodium sulfate and filtered. The filtrate was concentrated under reduced pressure, and the resulting residues were purified by thin layer chromatography with developing system A to obtain the title product 19b (0.7 g, yield: 68%).

MS m/z (ESI):416.1 [M+1].

Step 3

(E)-N,N-Dimethyl-4-((3R)-3-((5-((Z)-4,4,4-trifluoro-1-(3-fluoro-1-(tetrahydro-2H-pyran-2-yl)-1H-indazol-5-yl)-2-(4-fluorophenyl)but-1-en-1-yl)pyridin-2-yl)oxy)piperidin-1-yl)but-2-enamide 19d Compound 1d (50 mg, 0.2 mmol) was dissolved in methyltetrahydrofuran (10 mL), followed by the addition of bis(pinacolato)diboron (47 mg, 0.2 mmol) and tetrakis(triphenylphosphine) platinum (4 mg, 0.003 mmol). The reaction solution was purged with argon three times, warmed up to 85° C. and stirred for 3 hours. The reaction solution was cooled to room temperature, followed by the addition of compound 19b (57 mg, 0.1 mmol), bis(triphenylphosphine) palladium dichloride (20 mg, 0.03 mmol), cesium carbonate (128 mg, 0.4 mmol) and water (0.5 mL). The reaction solution was stirred at room temperature overnight. 4-Fluoroiodobenzene 19c (68 mg, 0.3 mmol) and potassium hydroxide (43 mg, 0.8 mmol) were added. The reaction solution was purged with argon three times, warmed up to 85° C., stirred for 2 hours, and cooled to room temperature. The reaction solution was concentrated under reduced pressure, and the resulting residues were purified by thin layer chromatography with developing system B to obtain the title product 19d (50 mg, yield: 46%).

MS m/z (ESI): 710.3 [M+1].

Step 4

(E)-N,N-Dimethyl-4-((R)-3-((5-((Z)-4,4,4-trifluoro-1-(3-fluoro-1H-indazol-5-yl)-2-(4-fluorophen yl)but-1-en-1-yl)pyridin-2-yl)oxy)piperidin-1-yl)but-2-enamide 19

Compound 19d (50 mg, 0.07 mmol) was dissolved in methanol (2 mL), followed by the addition of hydrochloric acid (12N, 1 mL). The reaction solution was stirred for 3 hours. The reaction solution was cooled and concentrated. Saturated sodium bicarbonate solution (15 mL) was added, and the solution was extracted with dichloromethane (10 mL×4). The organic phases were combined, washed with water (10 mL×3) and saturated sodium chloride solution (10 mL) successively, dried over anhydrous sodium sulfate and filtered. The filtrate was concentrated under reduced pressure, and the resulting residues were purified by thin layer chromatography with developing system A to obtain the title product 19 (15 mg, yield: 34%).

MS m/z (ESI): 626.2 [M+1].

$^1$H NMR (400 MHz, CD$_3$OD) 7.70 (s, 1H), 7.65 (s, 1H), 7.52 (dd, 1H), 7.32-7.26 (m, 4H), 7.02-6.97 (t, 2H), 6.91-6.87 (m, 1H), 6.65-6.61 (d, 2H), 5.44 (s, 1H), 3.94 (s, 3H), 3.50-3.38 (m, 4H), 3.14 (s, 3H), 3.12-3.05 (m, 1H), 3.01 (s, 3H), 2.11-2.09 (m, 2H), 1.89-1.77 (m, 2H).

Example 20

(E)-4-((R)-3-((5-((Z)-2-(4-Acetamidophenyl)-4,4,4-trifluoro-1-(3-fluoro-1H-indazol-5-yl)but-1-en-1-yl)pyridin-2-yl)oxy)piperidin-1-yl)-N,N-dimethylbut-2-enamide 20

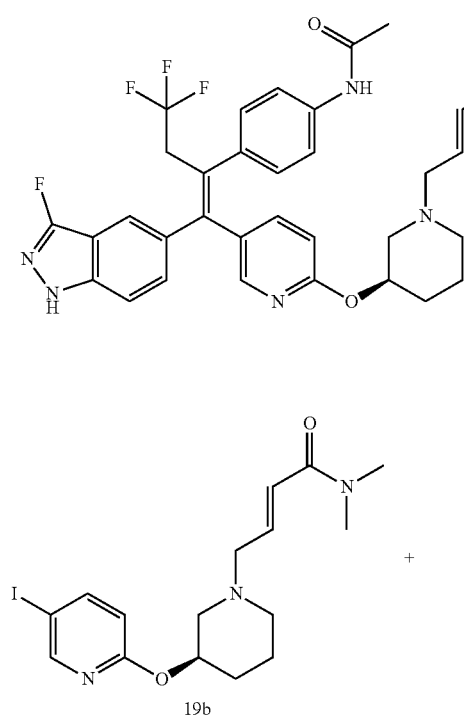

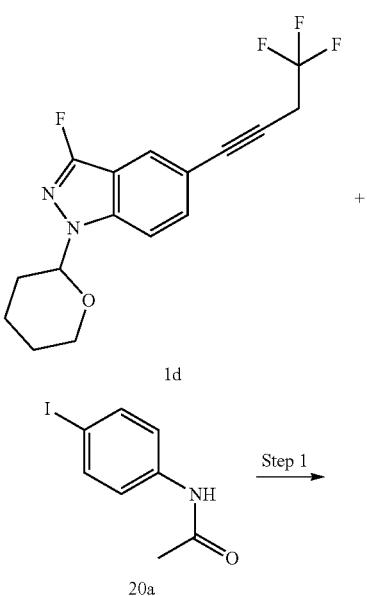

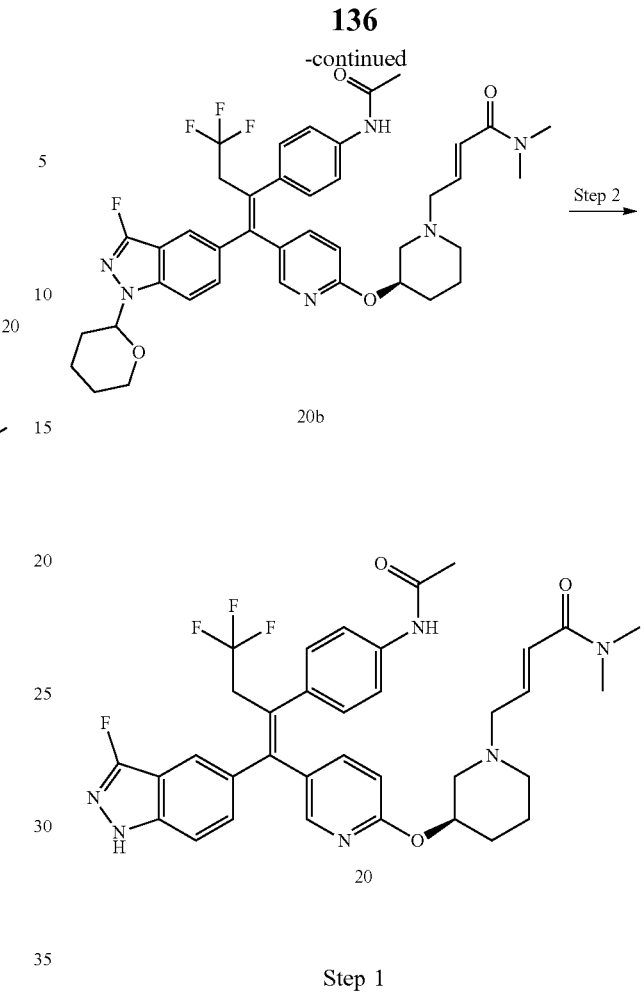

Step 1

(E)-4-((3R)-3-((5-((Z)-2-(4-Acetamidophenyl)-4,4,4-trifluoro-1-(3-fluoro-1-(tetrahydro-2H-pyran-2-yl)-1H-indazol-5-yl)but-1-en-1-yl)pyridin-2-yl)oxy)piperidin-1-yl)-N,N-dimethylbut-2-enamide 20b In accordance with the synthetic route in Example 19, the starting material 19c in Step 3 was replaced with N-(4-iodophenyl)acetamide 20a (prepared according to the method disclosed in "*Journal of Organic Chemistry*, 2018, 83(2), 930-938"), to give the title compound 20b (70 mg, yield: 61%).

Step 2

(E)-4-((R)-3-((5-((Z)-2-(4-Acetamidophenyl)-4,4,4-trifluoro-1-(3-fluoro-1H-indazol-5-yl)but-1-en-1-yl)pyridin-2-yl)oxy)piperidin-1-yl)-N,N-dimethylbut-2-enamide 20

In accordance with the synthetic route in Example 19, the starting material 19d in Step 4 was replaced with compound 20b, to give the title compound 20 (22 mg, yield: 41%).

MS m/z (ESI): 665.2 [M+1].

$^1$H NMR (400 MHz, CD$_3$OD) 7.67 (d, 2H), 7.48-7.44 (m, 3H), 7.28 (dd, 2H), 7.18 (d, 2H), 6.82 (d, 1H), 6.67-6.59 (m, 2H), 5.28 (s, 1H), 3.76 (s, 2H), 3.49-3.39 (m, 4H), 3.25 (d, 1H), 3.10 (s, 3H), 3.03 (d, 1H), 2.99 (s, 3H), 2.11 (s, 3H), 1.99-1.94 (m, 2H), 1.86-1.74 (m, 2H).

Example 21

4-((Z)-1-(6-(((R)-1-((E)-4-(Dimethylamino)-4-oxobut-2-en-1-yl)piperidin-3-yl)oxy)pyridin-3-yl)-4,4,4-trifluoro-1-(3-fluoro-1H-indazol-5-yl)but-1-en-2-yl)-N-methylbenzamide 21

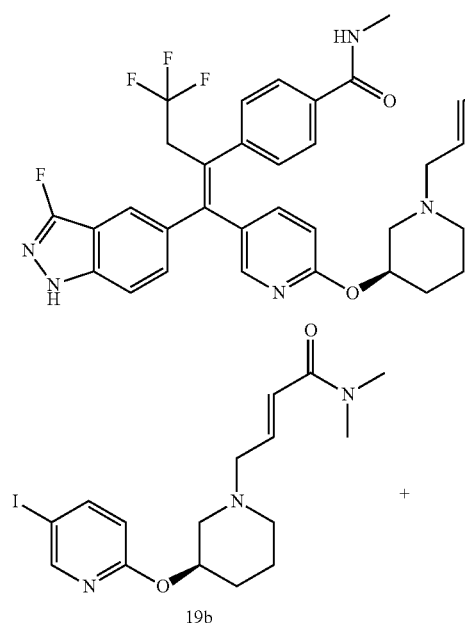

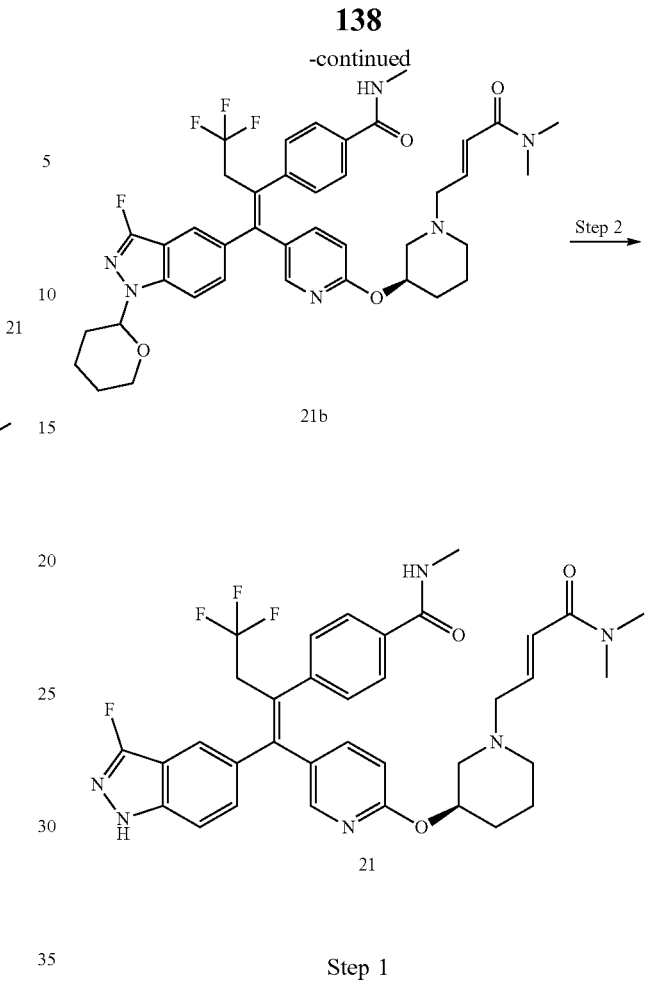

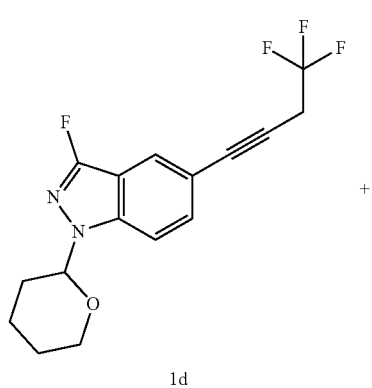

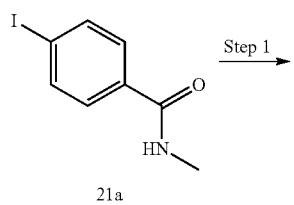

Step 1

4-((Z)-1-(6-(((R)-1-((E)-4-(Dimethylamino)-4-oxobut-2-en-1-yl)piperidin-3-yl)oxy)pyridin-3-yl)-4,4,4-trifluoro-1-(3-fluoro-1-(tetrahydro-2H-pyran-2-yl)-1H-indazol-5-yl)but-1-en-2-yl)-N-methylbenzamide 21b In accordance with the synthetic route in Example 19, the starting material 19c in Step 3 was replaced with 4-iodo-N-methylbenzamide 21a (prepared according to the method disclosed in "*Journal of the American Chemical Society*, 2013, 135(12), 4628-4631"), to give the title compound 21b (50 mg, yield: 44%).

Step 2

4-((Z)-1-(6-(((R)-1-((E)-4-(Dimethylamino)-4-oxobut-2-en-1-yl)piperidin-3-yl)oxy)pyridin-3-yl)-4,4,4-trifluoro-1-(3-fluoro-1H-indazol-5-yl)but-1-en-2-yl)-N-methylbenzamide 21

In accordance with the synthetic route in Example 19, the starting material 19d in Step 4 was replaced with compound 21b, to give the title compound 21 (10 mg, yield: 32%).

MS m/z (ESI): 665.3 [M+1].

$^1$H NMR (400 MHz, CD$_3$OD) 7.71-7.69 (m, 4H), 7.50 (d, 1H), 7.36-7.29 (m, 4H), 6.88 (d, 1H), 6.65-6.58 (m, 2H), 5.39 (s, 1H), 3.97-3.91 (m, 2H), 3.69 (d, 1H), 3.49-3.44 (m, 3H), 3.06 (s, 3H), 3.05-3.00 (m, 2H), 2.99 (s, 3H), 2.89 (s, 3H), 2.10-2.03 (m, 2H), 1.86-1.74 (m, 2H).

Example 22

(E)-N,N-Dimethyl-4-((R)-3-((5-((Z)-4,4,4-trifluoro-1-(3-fluoro-1H-indazol-5-yl)-2-(4-(trifluoromethyl)phenyl)but-1-en-1-yl)pyridin-2-yl)oxy)piperidin-1-yl)but-2-enamide 22

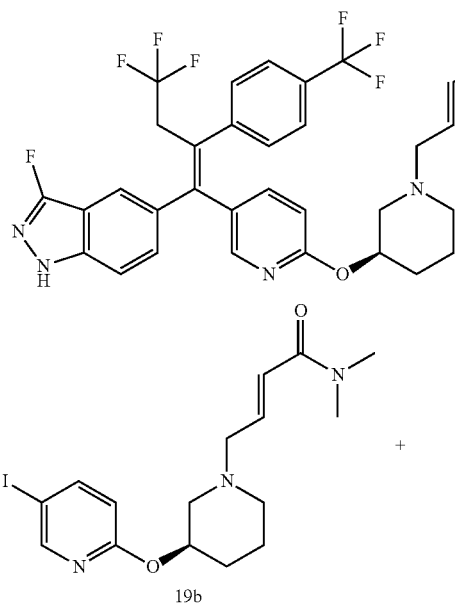

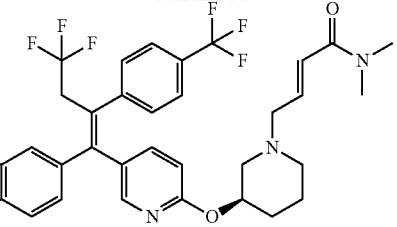

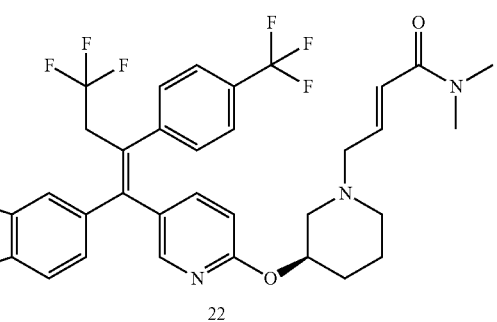

Step 1

(E)-N,N-Dimethyl-4-((3R)-3-((5-((Z)-4,4,4-trifluoro-1-(3-fluoro-1-(tetrahydro-2H-pyran-2-yl)-1H-indazol-5-yl)-2-(4-(trifluoromethyl)phenyl)but-1-en-1-yl)pyridin-2-yl)oxy)piperidin-1-yl)but-2-enamide 22b In accordance with the synthetic route in Example 19, the starting material 19c in Step 3 was replaced with 1-iodo-4-(trifluoromethyl)benzene 22a, to give the title compound 22b (80 mg, yield: 69%).

Step 2

(E)-N,N-Dimethyl-4-((R)-3-((5-((Z)-4,4,4-trifluoro-1-(3-fluoro-1H-indazol-5-yl)-2-(4-(trifluoromethyl)phenyl)but-1-en-1-yl)pyridin-2-yl)oxy)piperidin-1-yl)but-2-enamide 22

In accordance with the synthetic route in Example 19, the starting material 19d in Step 4 was replaced with compound 22b, to give the title compound 22 (20 mg, yield: 31%).

MS m/z (ESI): 676.2 [M+1].

$^1$H NMR (400 MHz, CD$_3$OD) 7.70 (dd, 2H), 7.57-7.55 (m, 3H), 7.47 (d, 2H), 7.32 (dd, 2H), 6.88 (d, 1H), 6.65-6.59 (m, 2H), 5.37 (s, 1H), 3.91 (d, 2H), 3.50 (q, 2H), 3.32 (s, 4H), 3.12 (s, 3H), 3.00 (s, 3H), 2.09-2.04 (m, 2H), 1.84 (d, 2H).

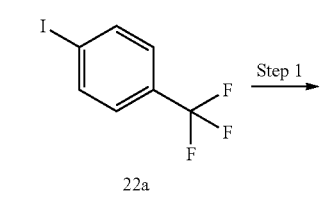

Example 23

(E)-N,N-Dimethyl-4-((R)-3-((5-((Z)-4,4-trifluoro-1-(3-fluoro-1H-indazol-5-yl)-2-(4-(methylsulfonyl)phenyl)but-1-en-1-yl)pyridin-2-yl)oxy)piperidin-1-yl)but-2-enamide 23

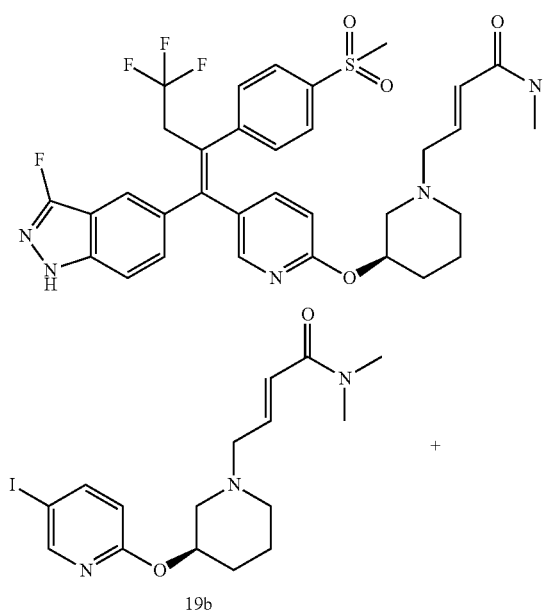

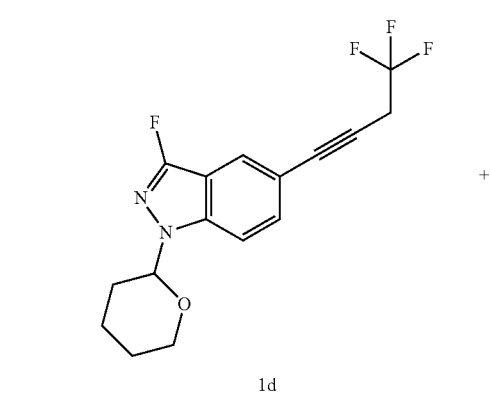

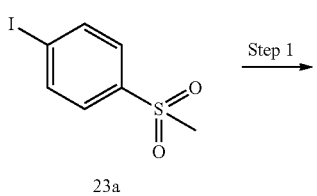

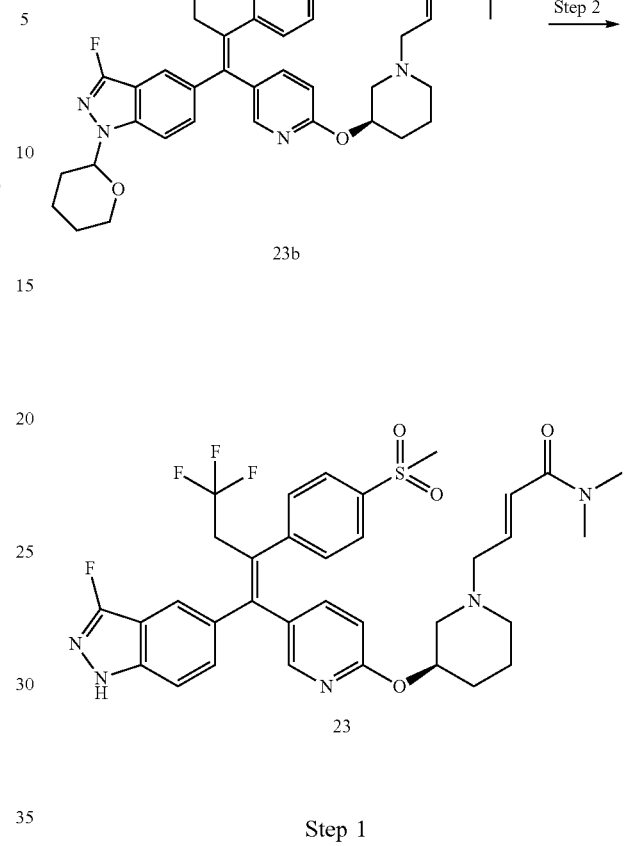

Step 1

(E)-N,N-Dimethyl-4-((3R)-3-((5-((Z)-4,4,4-trifluoro-1-(3-fluoro-1-(tetrahydro-2H-pyran-2-yl)-1H-indazol-5-yl)-2-(4-(methylsulfonyl)phenyl)but-1-en-1-yl)pyridin-2-yl)oxy)piperidin-1-yl)but-2-enamide 23b In accordance with the synthetic route in Example 19, the starting material 19c in Step 3 was replaced with 1-iodo-4-(methylsulfonyl)benzene 23a (prepared according to the method disclosed in "Organic Letters, 2014, 16(9), 2306-2309"), to give the title compound 23b (60 mg, yield: 51%).

Step 2

(E)-N,N-Dimethyl-4-((R)-3-((5-((Z)-4,4,4-trifluoro-1-(3-fluoro-1H-indazol-5-yl)-2-(4-(methylsulfonyl)phenyl)but-1-en-1-yl)pyridin-2-yl)oxy)piperidin-1-yl)but-2-enamide 23

In accordance with the synthetic route in Example 19, the starting material 19d in Step 4 was replaced with compound 23b, to give the title compound 23 (10 mg, yield: 28%).

MS m/z (ESI): 686.2 [M+1].

$^1$H NMR (400 MHz, CD$_3$OD) 7.83 (d, 2H), 7.67 (s, 2H), 7.53-7.50 (m, 3H), 7.30 (d, 2H), 6.89 (dd, 1H), 6.66-6.59 (m, 2H), 5.38 (s, 1H), 3.97-3.91 (m, 3H), 3.70-3.65 (m, 1H), 3.50 (q, 3H), 3.28 (d, 1H), 3.11 (s, 6H), 2.99 (s, 3H), 2.10-2.01 (m, 2H), 1.94-1.86 (m, 2H).

Example 24

(E)-4-((R)-3-((5-((Z)-2-(4-Cyanophenyl)-4,4,4-trifluoro-1-(3-fluoro-1H-indazol-5-yl)but-1-en-1-yl)pyridin-2-yl)oxy)piperidin-1-yl)-N,N-dimethylbut-2-enamide 24

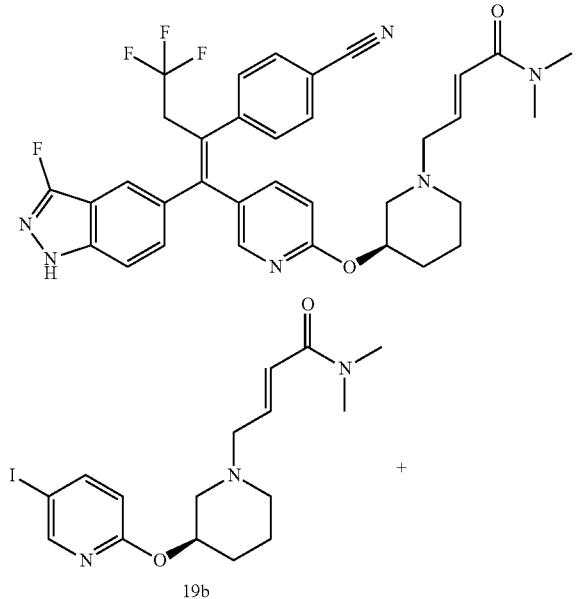

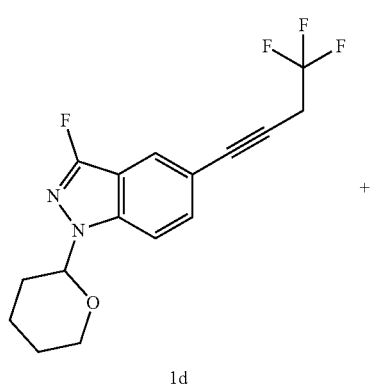

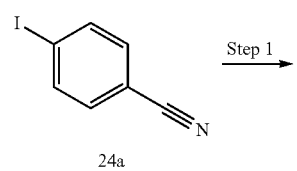

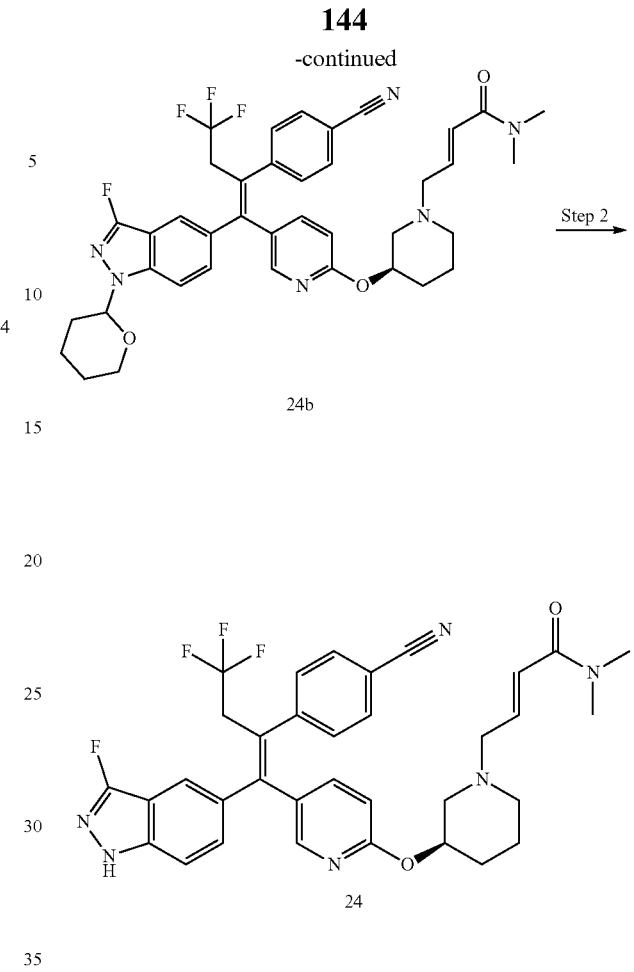

Step 1

(E)-4-((3R)-3-((5-((Z)-2-(4-Cyanophenyl)-4,4,4-trifluoro-1-(3-fluoro-1-(tetrahydro-2H-pyran-2-yl)-1H-indazol-5-yl)but-1-en-1-yl)pyridin-2-yl)oxy)piperidin-1-yl)-N,N-dimethylbut-2-enamide 24b In accordance with the synthetic route in Example 19, the starting material 19c in Step 3 was replaced with 4-iodobenzonitrile 24a, to give the title compound 24b (80 mg, yield: 73%).

Step 2

(E)-4-((R)-3-((5-((Z)-2-(4-Cyanophenyl)-4,4,4-trifluoro-1-(3-fluoro-1H-indazol-5-yl)but-1-en-1-yl)pyridin-2-yl)oxy)piperidin-1-yl)-N,N-dimethylbut-2-enamide 24

In accordance with the synthetic route in Example 19, the starting material 19d in Step 4 was replaced with compound 24b, to give the title compound 24 (20 mg, yield: 38%).

MS m/z (ESI): 633.2 [M+1].

$^1$H NMR (400 MHz, CD$_3$OD) 7.67-7.61 (m, 4H), 7.47 (d, 1H), 7.45 (d, 2H), 7.33 (d, 2H), 6.89 (d, 1H), 6.66-6.61 (m, 2H), 5.44 (s, 1H), 3.94-3.91 (m, 2H), 3.71 (d, 1H), 3.52-3.45 (m, 3H), 3.25 (d, 1H), 3.12 (s, 3H), 3.05 (d, 1H), 3.01 (s, 3H), 2.11-2.04 (m, 2H), 1.90-1.77 (m, 2H).

Example 25

(R,Z)-1-(3-((5-(4,4-Trifluoro-1-(3-fluoro-1H-indazol-5-yl)-2-phenylbut-1-en-1-yl)pyridin-2-yl) oxy)piperidin-1-yl)but-2-yn-1-one 25

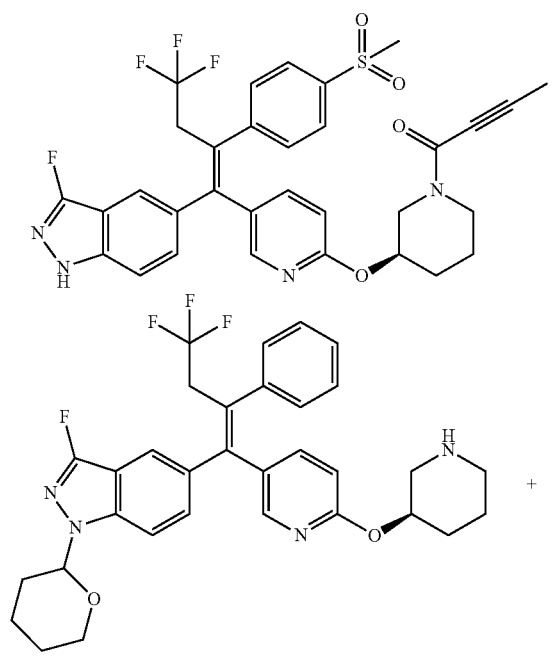

Step 1

1-((3R)-3-((5-((Z)-4,4-Trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-yn-1-one 25a In accordance with the synthetic route in Example 10, the starting material 9d in Step 1 was replaced with compound 25f, to give the title compound 25a (37 mg, yield: 83%).

Step 2

(R,Z)-1-(3-((5-(4,4,4-Trifluoro-1-(3-fluoro-1H-indazol-5-yl)-2-phenylbut-1-en-1-yl)pyridin-2-yl) oxy)piperidin-1-yl)but-2-yn-1-one 25

In accordance with the synthetic route in Example 10, the starting material 10b in Step 2 was replaced with compound 25a, to give the title compound 25 (4 mg, yield: 150%).

MS m/z (ESI): 563.2 [M+1].

$^1$H NMR (400 MHz, CDCl$_3$) 9.38 (s, 1H), 7.68-7.65 (m, 2H), 7.43-7.12 (m, 8H), 6.46-6.39 (m, 1H), 5.02 (d, 1H), 3.95-3.77 (m, 2H), 3.33-3.00 (m, 4H), 2.13-1.93 (m, 4H), 1.69 (d, 3H).

Example 26

(R,Z)-1-(3-((5-(4,4,4-Trifluoro-1-(3-fluoro-1H-indazol-5-yl)-2-phenylbut-1-en-1-yl)pyridin-2-yl) oxy)piperidin-1-yl)prop-2-en-1-one 26

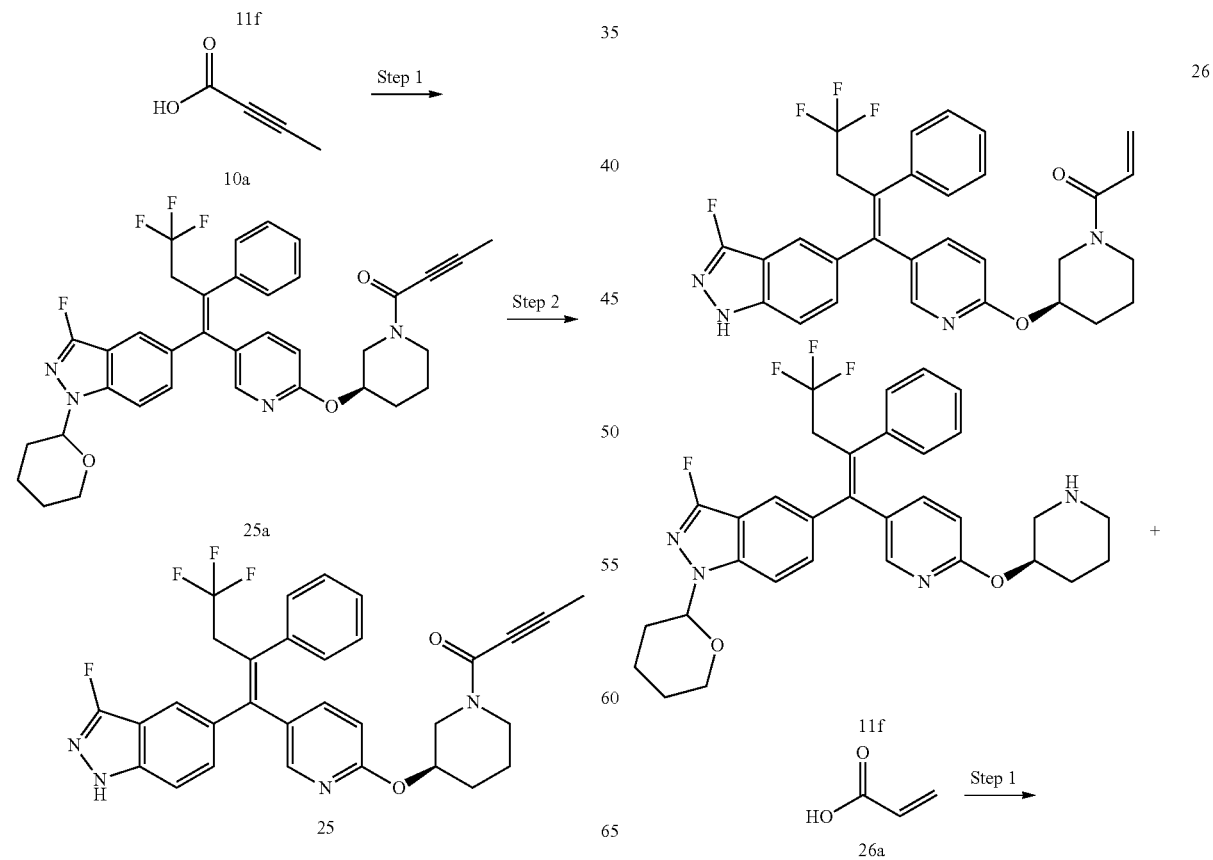

147 -continued

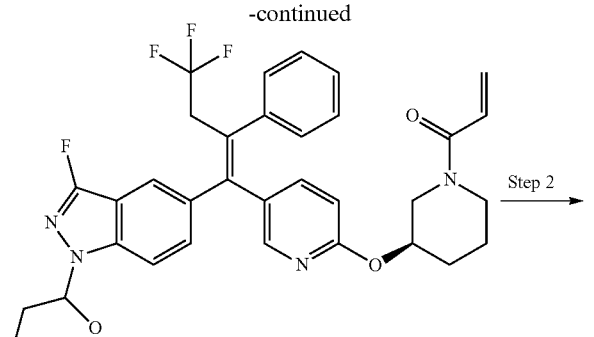

26b

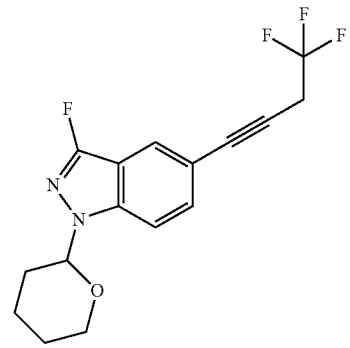

26

Step 1

1-((3R)-3-((5-((Z)-4,4-Trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)prop-2-en-1-one 26b In accordance with the synthetic route in Example 10, the starting material 9d in Step 1 was replaced with compound 11f, and the starting material 10a was replaced with acrylic acid 26a, to give the title compound 26b (30 mg, yield: 73%). Step 2 (R,Z)-1-(3-((5-(4,4,4-Trifluoro-1-(3-fluoro-1H-indazol-5-yl)-2-phenylbut-1-en-1-yl)pyridin-2-yl) oxy)piperidin-1-yl)prop-2-en-1-one 26

In accordance with the synthetic route in Example 10, the starting material 10b in Step 2 was replaced with compound 26b, to give the title compound 26 (3 mg, yield: 12%).

MS m/z (ESI): 551.2 [M+1].

$^1$H NMR (400 MHz, CDCl$_3$) 9.31 (s, 1H), 7.68 (d, 2H), 7.43 (d, 2H), 7.29-7.27 (m, 5H), 7.20-7.09 (m, 1H), 6.40 (d, 1H), 6.39-6.20 (m, 1H), 5.49-5.37 (m, 2H), 4.95 (s, 1H), 3.72 (s, 1H), 3.68 (d, 2H), 3.39 (d, 1H), 3.36-3.31 (m, 2H), 2.04-1.90 (m, 4H).

148

Example 27

(E)-N,N-Dimethyl-4-((S)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide 27

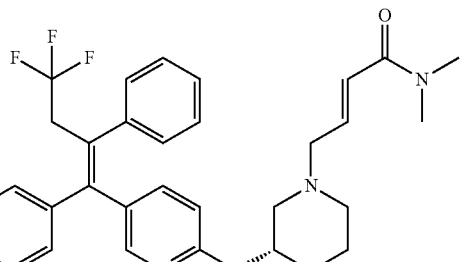

27

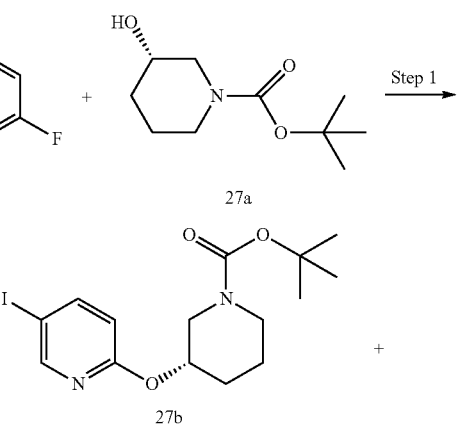

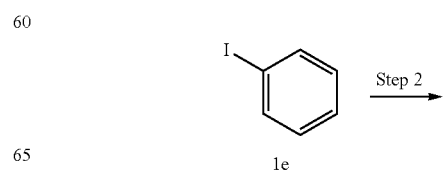

-continued

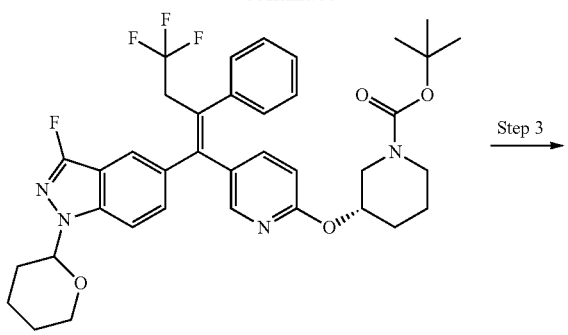

27c

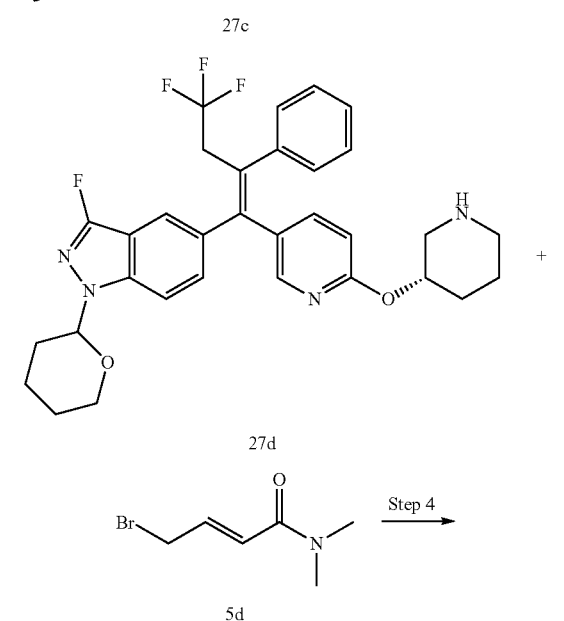

27d

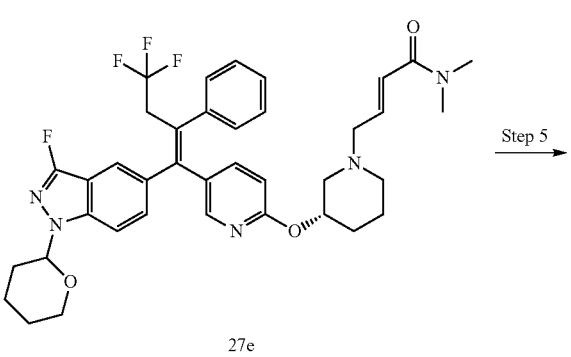

27e

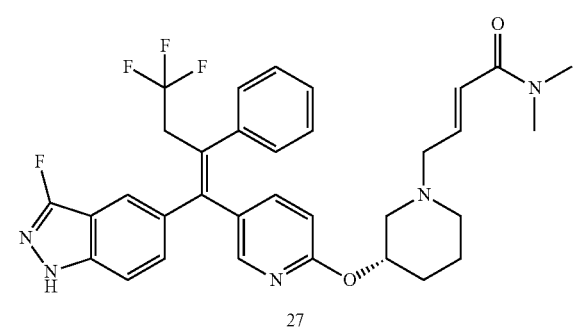 [SMILES: CN(C)C(=O)/C=C/CN1CCC[C@@H](Oc2ccc(/C(=C(/CC(F)(F)F)c3ccc(S(C)(=O)=O)cc3)c3ccc4[nH]nc(F)c4c3)cn2)C1]

27

Step 1

Tert-butyl(S)-3-((5-iodopyridin-2-yl)oxy)piperidine-1-carboxylate 27b

In accordance with the synthetic route in Example 1, the starting material 1b in Step 1 was replaced with tert-butyl (S)-3-hydroxypiperidine-1-carboxylate 27a (prepared according to the method disclosed in "Tetrahedron, 2007, 63(2), 331-336"), to give the title compound 27b (531 mg, yield: 92%).

Step 2

Tert-butyl (3S)-3-((5-((Z)-4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidine-1-carboxylate 27c In accordance with the synthetic route in Example 1, the starting material 1c in Step 2 was replaced with compound 27b, to give the title compound 27c (190 mg, yield: 76%). MS m/z (ESI): 680.9 [M+1].

Step 3

3-Fluoro-1-(tetrahydro-2H-pyran-2-yl)-5-((Z)-4,4,4-trifluoro-2-phenyl-1-(6-(((S)-piperidin-3-yl) oxy)pyridin-3-yl)but-1-en-1-yl)-1H-indazole 27d In accordance with the synthetic route in Example 1, the starting material 1f in Step 3 was replaced with compound 27c, to give the title compound 27d (85 mg, yield: 100%).

Step 4

(E)-N,N-Dimethyl-4-((3S)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)but-2-enamide 27e In accordance with the synthetic route in Example 1, the starting material 1g in Step 4 was replaced with compound 27d, and the starting material 1 h was replaced with compound 5d, to give the title compound 27e (65 mg, yield: 64%).

Step 5

(E)-N,N-Dimethyl-4-((S)-3-((5-((Z)-4,4,4-trifluoro-1-(3-fluoro-1H-indazol-5-yl)-2-phenylbut-1-en-1-yl)pyridin-2-yl)oxy)piperidin-1-yl)but-2-enamide 27

In accordance with the synthetic route in Example 1, the starting material 1i in Step 5 was replaced with compound 27e, to give the title compound 27 (15 mg, yield: 43%).
MS m/z (ESI): 607.9 [M+1].
$^1$H NMR (400 MHz, CDCl$_3$) 9.36 (s, 1H), 7.69-7.67 (m, 1H), 7.64-7.63 (d, 1H), 7.45-7.43 (m, 1H), 7.35-7.32 (d, 1H), 7.28-7.19 (m, 4H), 7.08-7.06 (d, 1H), 6.89-6.82 (m, 1H), 6.46-6.41 (m, 1H), 5.39-5.36 (m, 1H), 5.08-5.02 (br, 1H), 3.38-3.30 (m, 2H), 3.22-3.16 (m, 2H), 3.05 (s, 3H), 3.10 (s, 3H), 2.92-2.86 (m, 1H), 2.67-2.61 (m, 1H), 2.34-2.24 (m, 2H), 2.07-1.77 (m, 4H), 1.53-1.48 (m, 1H).

Example 28

(Z)-1-(4-((5-(4,4,4-Trifluoro-1-(3-fluoro-1H-indazol-5-yl)-2-phenylbut-1-en-1-yl)pyridin-2-yl)oxy)piperidin-1-yl)prop-2-en-1-one 28

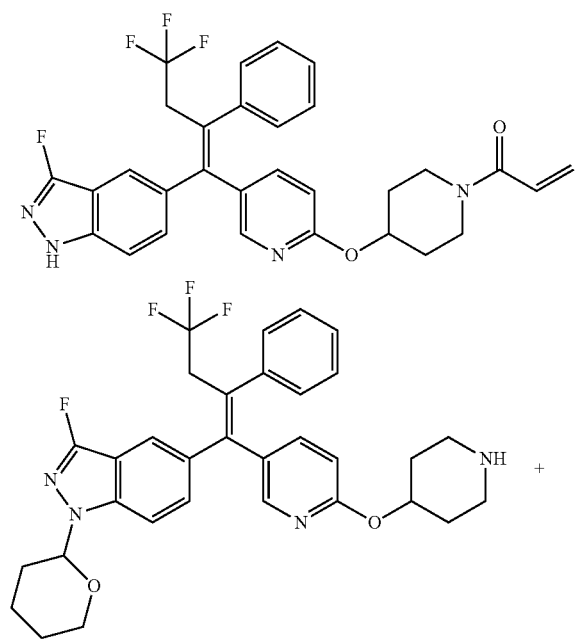

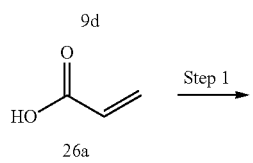

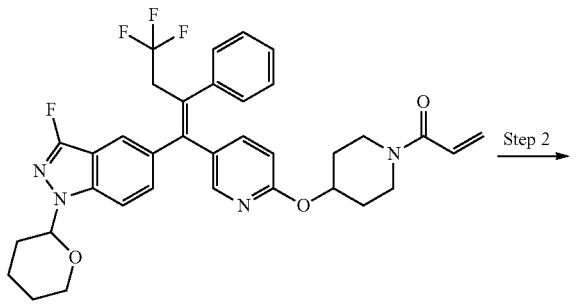

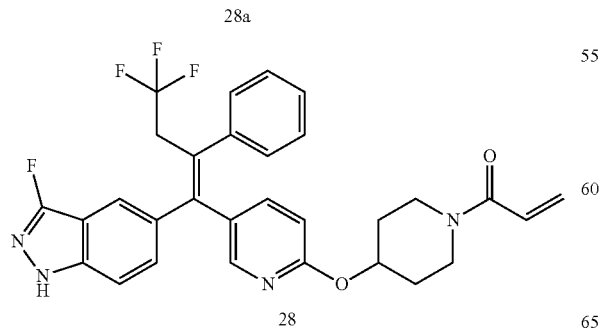

Step 1

(Z)-1-(4-((5-(4,4,4-Trifluoro-1-(3-fluoro-1-(tetrahydro-2H-pyran-2-yl)-1H-indazol-5-yl)-2-phenylbut-1-en-1-yl)pyridin-2-yl)oxy)piperidin-1-yl)prop-2-en-1-one 28a In accordance with the synthetic route in Example 10, the starting material 10a in Step 1 was replaced with compound 26a, to give the title compound 28a (50 mg, yield: 63%).

Step 2

(Z)-1-(4-((5-(4,4,4-Trifluoro-1-(3-fluoro-1H-indazol-5-yl)-2-phenylbut-1-en-1-yl)pyridin-2-yl)oxy)piperidin-1-yl)prop-2-en-1-one 28

In accordance with the synthetic route in Example 10, the starting material 10b in Step 2 was replaced with compound 28a, to give the title compound 28 (10 mg, yield: 23%).

MS m/z (ESI): 551.2 [M+1].

$^1$H NMR (400 MHz, CDCl$_3$) 9.47 (br, 1H), 7.60 (d, 2H), 7.35 (d, 1H), 7.28 (d, 1H), 7.26-7.19 (m, 5H), 6.59 (dd, 1H), 6.49 (d, 1H), 6.29 (d, 1H), 5.76 (d, 1H), 5.14 (m, 1H), 3.89-3.53 (m, 5H), 3.34 (t, 2H), 1.99-1.94 (m, 2H), 1.77-1.66 (m, 2H).

Example 29

(E)-N,N-Dimethyl-4-((R)-3-((5-((Z)-4,4,4-trifluoro-1-(3-fluoro-1H-indazol-5-yl)-2-phenylbut-1-en-1-yl)pyridin-2-yl)oxy)pyrrolidin-1-yl)but-2-enamide 29

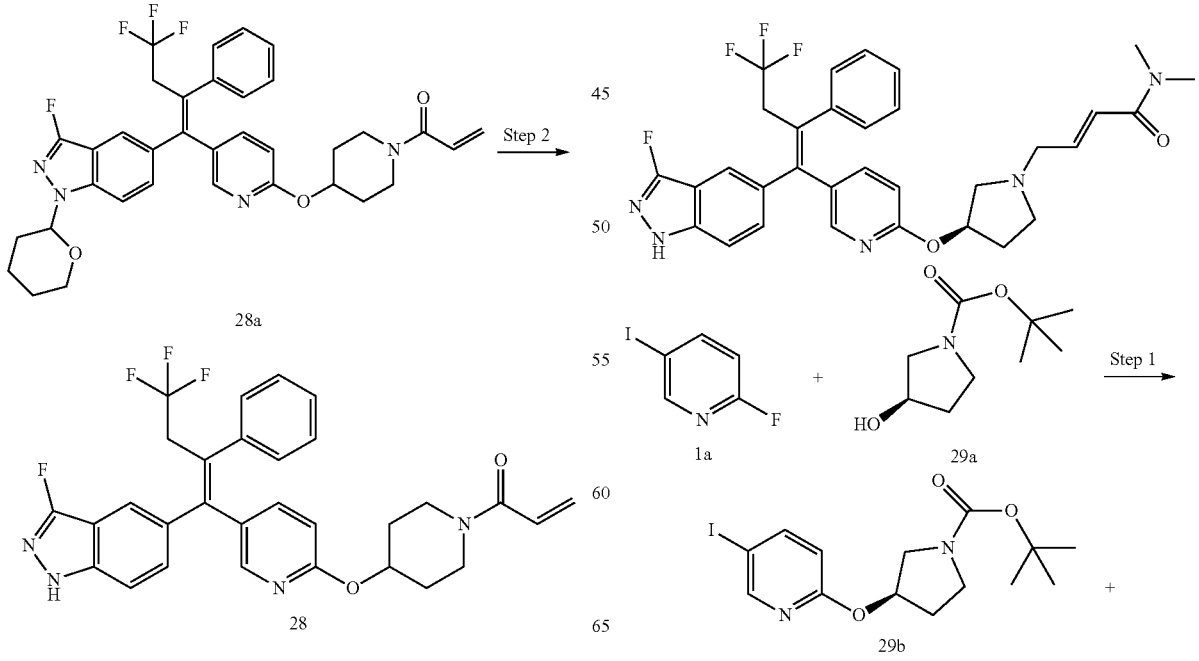

-continued

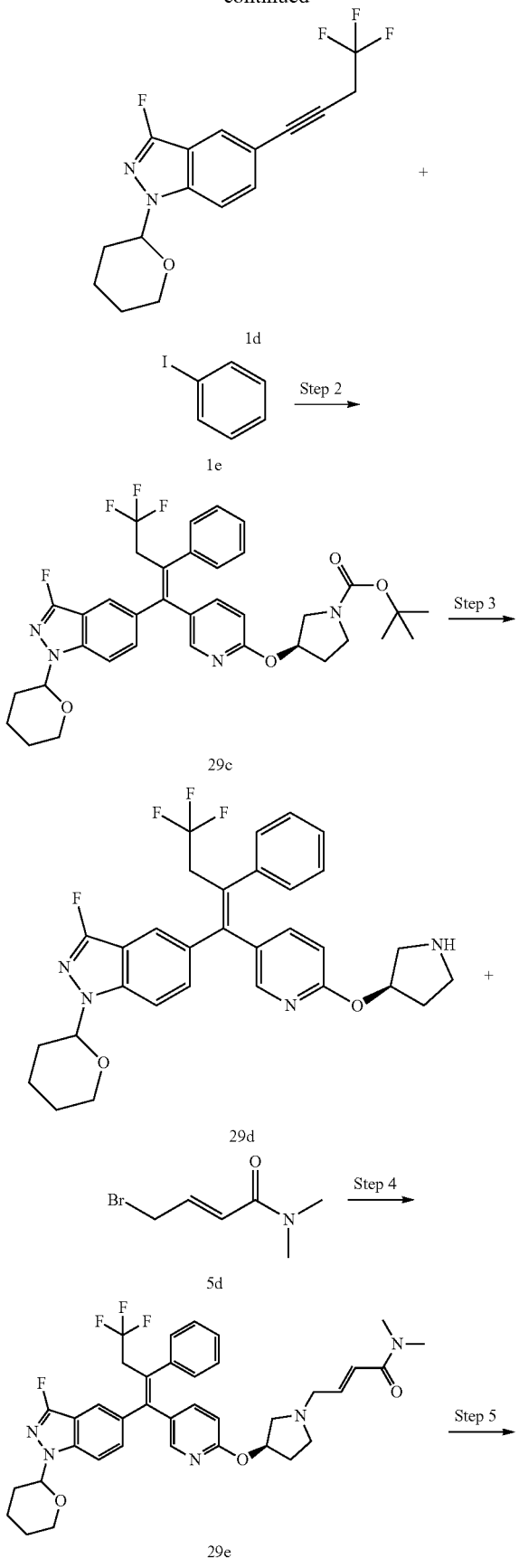

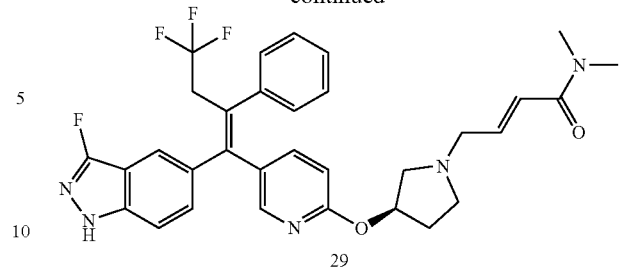

Step 1

Tert-butyl(R)-3-((5-iodopyridin-2-yl)oxy)pyrrolidine-1-carboxylate 29b

In accordance with the synthetic route in Example 1, the starting material 1b in Step 1 was replaced with tert-butyl (R)-3-hydroxypyrrolidine-1-carboxylate 29a, to give the title compound 29b (0.9 g, yield: 86%).

Step 2

Tert-butyl (3R)-3-((5-((Z)-4,4,4-trifluoro-1-(3-fluoro-1-(tetrahydro-2H-pyran-2-yl)-1H-indazol-5-yl)-2-phenyl-but-1-en-1-yl)pyridin-2-yl)oxy)pyrrolidine-1-carboxylate 29c In accordance with the synthetic route in Example 1, the starting material 1c in Step 2 was replaced with compound 29b, to give the title compound 29c (260 mg, yield: 37%).

Step 3

3-Fluoro-1-(tetrahydro-2H-pyran-2-yl)-5-((Z)-4,4,4-trifluoro-2-phenyl-1-(6-(((R)-pyrrolidin-3-yl)oxy)pyridin-3-yl)but-1-en-1-yl)-1H-indazole 29d In accordance with the synthetic route in Example 1, the starting material 1f in Step 3 was replaced with compound 29c, to give the title compound 29d (93 mg, yield: 99%).

Step 4

(E)-N,N-Dimethyl-4-((3R)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)pyrrolidin-1-yl)but-2-enamide 29e In accordance with the synthetic route in Example 1, the starting material 1g in Step 4 was replaced with compound 29d, and the starting material 1h was replaced with compound 5d, to give the title compound 29e (60 mg, yield: 54%).
MS m/z (ESI): 678.3 [M+1].

Step 5

(E)-N,N-Dimethyl-4-((R)-3-((5-((Z)-4,4,4-trifluoro-1-(3-fluoro-1H-indazol-5-yl)-2-phenylbut-1-en-1-yl)pyridin-2-yl)oxy)pyrrolidin-1-yl)but-2-enamide 29

In accordance with the synthetic route in Example 1, the starting material 1i in Step 5 was replaced with compound 29e, to give the title compound 29 (15 mg, yield: 29%).

MS m/z (ESI): 594.3 [M+1].
$^1$H NMR (400 MHz, CDCl$_3$) 12.72 (s, 1H), 7.70-7.65 (m, 2H), 7.60-7.50 (d, 1H), 7.25-7.20 (m, 5H), 7.19-7.15 (m, 2H), 6.55-6.45 (m, 3H), 5.17-5.10 (m, 1H), 3.50-3.35 (m, 2H), 3.15-3.10 (m, 2H), 2.95 (s, 3H), 2.83 (s, 3H), 2.70-2.60 (m, 2H), 2.50-2.45 (m, 1H), 2.35-2.25 (m, 1H), 2.15-2.05 (m, 1H), 1.70-1.60 (m, 1H).
Example 30
(E)-N,N-Dimethyl-4-((S)-3-((5-((Z)-4,4,4-trifluoro-1-(3-fluoro-1H-indazol-5-yl)-2-phenylbut-1-en-1-yl)pyridin-2-yl)oxy)pyrrolidin-1-yl)but-2-enamide 30
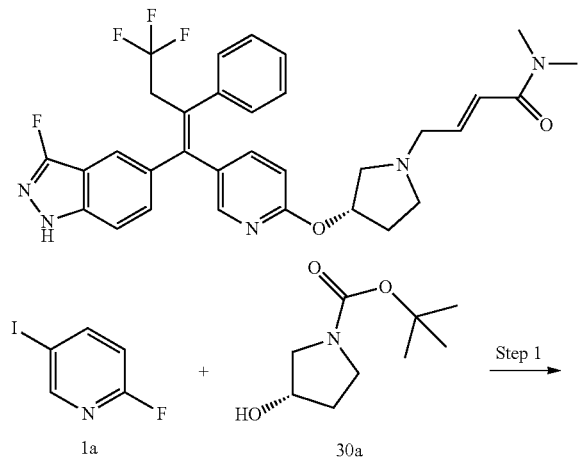
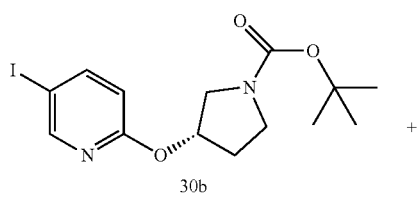
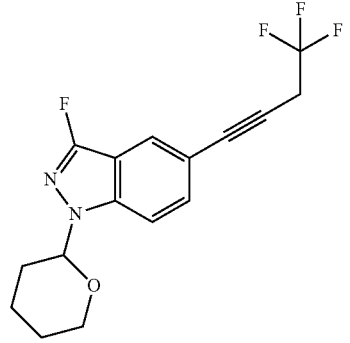
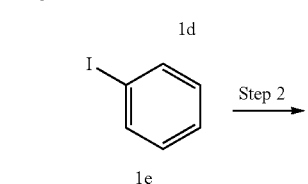
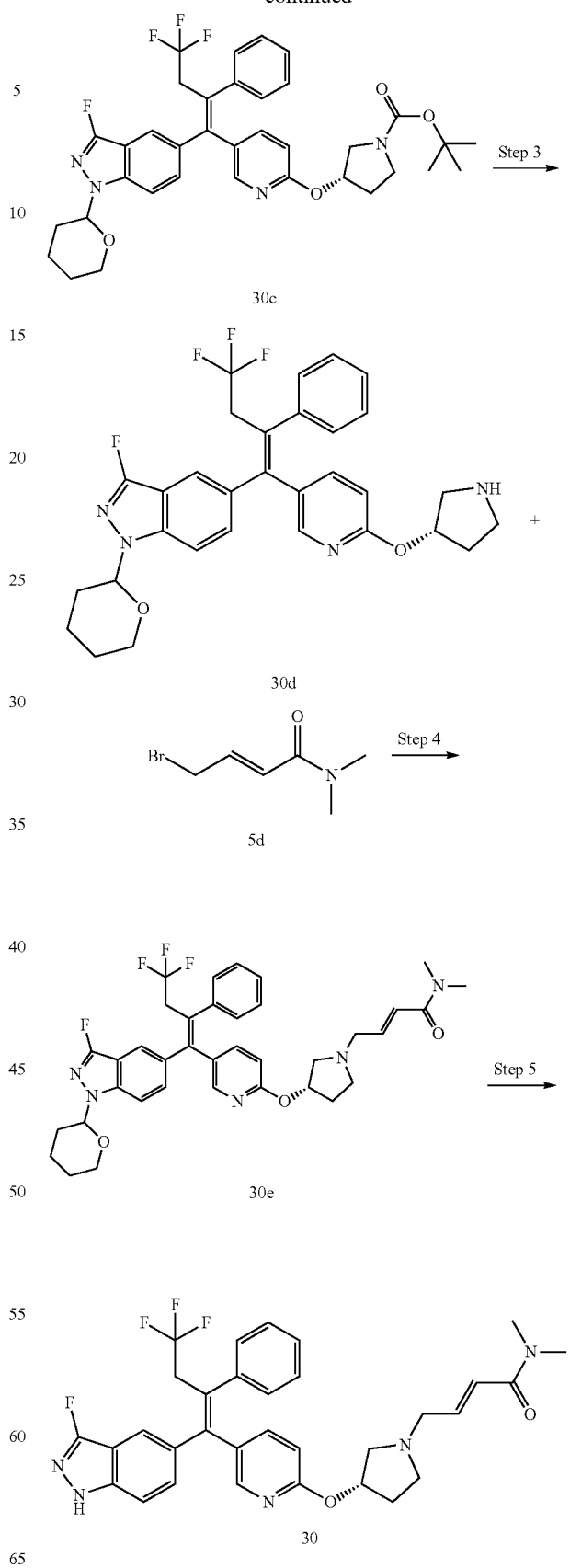

Step 1

Tert-butyl(S)-3-((5-iodopyridin-2-yl)oxy)pyrrolidine-1-carboxylate 30b

In accordance with the synthetic route in Example 1, the starting material 1b in Step 1 was replaced with tert-butyl (S)-3-hydroxypyrrolidine-1-carboxylate 30a, to give the title compound 30b (0.5 g, yield: 500%).

Step 2

Tert-butyl (3S)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)pyrrolidine-1-carboxylate 30c In accordance with the synthetic route in Example 1, the starting material 1c in Step 2 was replaced with compound 30b, to give the title compound 30c (260 mg, yield: 85%).

Step 3

3-Fluoro-1-(tetrahydro-2H-pyran-2-yl)-5-((Z)-4,4,4-trifluoro-2-phenyl-1-(6-(((S)-pyrrolidin-3-yl) oxy)pyridin-3-yl)but-1-en-1-yl)-1H-indazole 30d In accordance with the synthetic route in Example 1, the starting material 1f in Step 3 was replaced with compound 30c, to give the title compound 30d (100 mg, yield: 98%).

Step 4

(E)-N,N-Dimethyl-4-((3S)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)pyrrolidin-1-yl)but-2-enamide 30e In accordance with the synthetic route in Example 1, the starting material 1g in Step 4 was replaced with compound 30d, and the starting material 1 h was replaced with compound 5d, to give the title compound 30e (70 mg, yield: 62%).

MS m/z (ESI): 678.3 [M+1].

Step 5

(E)-N,N-Dimethyl-4-((S)-3-((5-((Z)-4,4,4-trifluoro-1-(3-fluoro-1H-indazol-5-yl)-2-phenylbut-1-en-1-yl)pyridin-2-yl)oxy)pyrrolidin-1-yl)but-2-enamide 30

In accordance with the synthetic route in Example 1, the starting material 1i in Step 5 was replaced with compound 30e, to give the title compound 30 (10 mg, yield: 23%).

MS m/z (ESI): 593.9 [M+1].

$^1$H NMR (400 MHz, CDCl$_3$) 9.58 (s, 1H), 7.67-7.65 (m, 2H), 7.46 (d, 1H), 7.34-7.30 (m, 2H), 7.27-7.16 (m, 4H), 6.87-6.77 (m, 2H), 6.59 (d, 1H), 5.53 (s, 1H), 4.14 (s, 1H), 3.93 (s, 3H), 3.39-3.31 (m, 2H), 3.29-3.03 (m, 7H), 2.41-2.28 (m, 4H).

Example 31

(E)-N,N-Dimethyl-4-((R)-3-((5-((Z)-4,4,4-trifluoro-1-(3-fluoro-1H-indazol-5-yl)-2-phenylbut-1-en-1-yl)pyridin-2-yl)amino)piperidin-1-yl)but-2-enamide 31

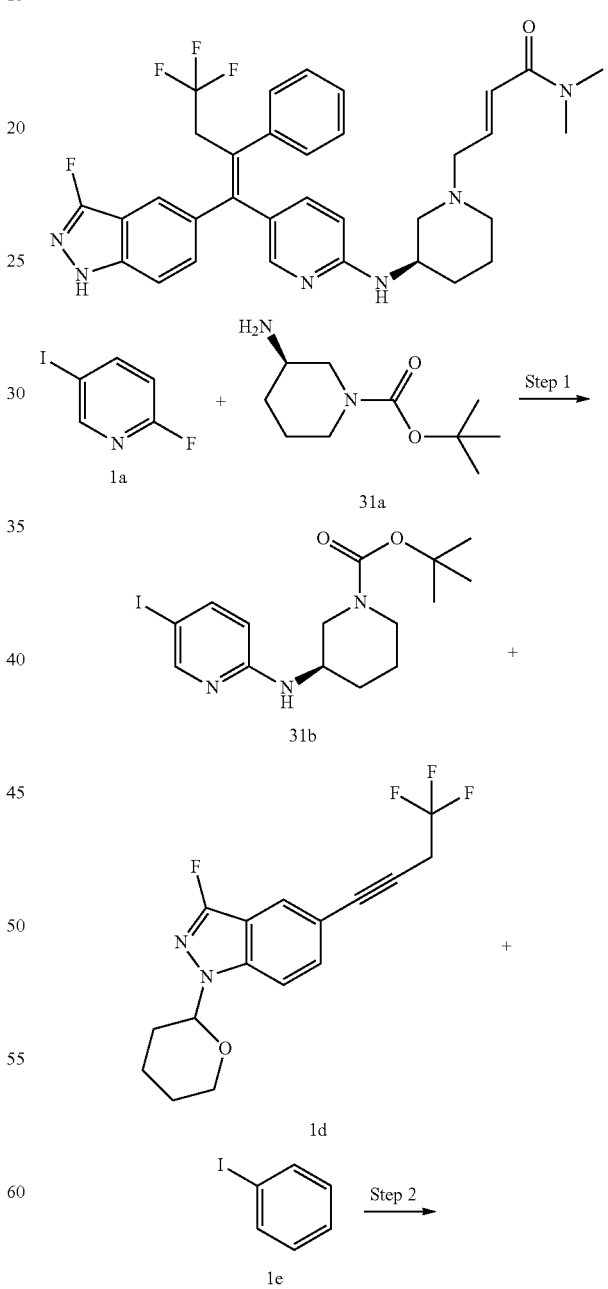

-continued

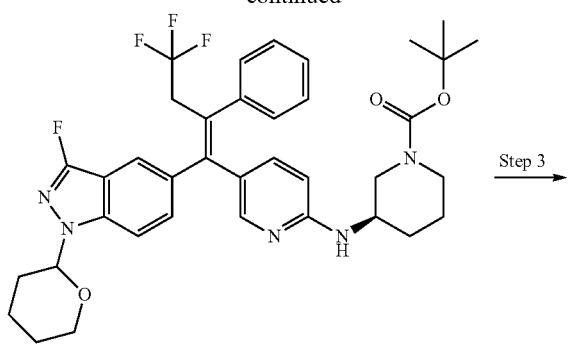

31c

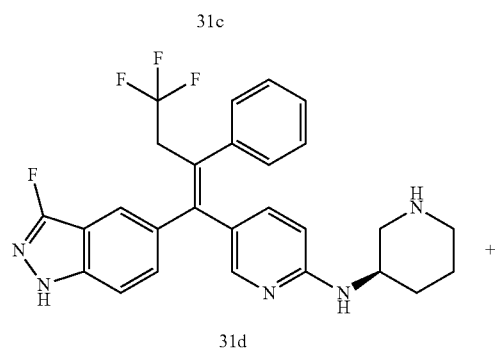

31d

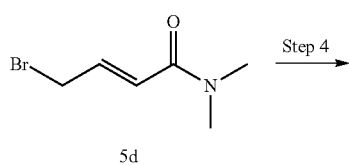

5d

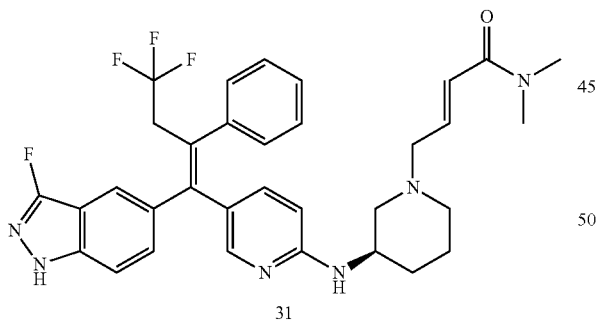

31

Step 1

Tert-butyl(R)-3-((5-iodopyridin-2-yl)amino)piperidine-1-carboxylate 31b

In accordance with the synthetic route in Example 1, the starting material 1b in Step 1 was replaced with tert-butyl (R)-3-aminopiperidine-1-carboxylate 31a, to give the title compound 31b (0.8 g, yield: 57%).

Step 2

Tert-butyl (3R)-3-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)amino)piperidine-1-carboxylate 31c In accordance with the synthetic route in Example 1, the starting material 1c in Step 2 was replaced with compound 31b, to give the title compound 31c (210 mg, yield: 75%).

Step 3

(R,Z)—N-(Piperidin-3-yl)-5-(4,4,4-trifluoro-1-(3-fluoro-1H-indazol-5-yl)-2-phenylbut-1-en-1-yl)pyridin-2-amine 31d In accordance with the synthetic route in Example 1, the starting material 1f in Step 3 was replaced with compound 31c, to give the title compound 31d (42 mg, yield: 92%).

Step 4

(E)-N,N-Dimethyl-4-((R)-3-((5-((Z)-4,4,4-trifluoro-1-(3-fluoro-1H-indazol-5-yl)-2-phenylbut-1-en-1-yl)pyridin-2-yl)amino)piperidin-1-yl)but-2-enamide 31

In accordance with the synthetic route in Example 1, the starting material 1g in Step 4 was replaced with compound 31d, and the starting material 1h was replaced with compound 5d, to give the title compound 31 (20 mg, yield: 39%). MS m/z (ESI): 607.3 [M+1].
$^1$H NMR (400 MHz, CDCl$_3$) 9.26 (s, 1H), 7.68 (s, 1H), 7.55-7.54 (m, 1H), 7.44-7.41 (m, 1H), 7.36-7.31 (m, 1H), 7.28-7.23 (m, 4H), 6.92-6.80 (m, 2H), 6.45-6.41 (m, 1H), 6.15-6.13 (m, 1H), 5.39-5.37 (m, 1H), 3.35-3.28 (m, 2H), 3.17-3.15 (m, 2H), 3.07 (s, 3H), 3.02 (s, 3H), 2.70-2.68 (m, 1H), 2.47-2.45 (m, 1H), 2.47-2.45 (m, 1H), 2.06-2.04 (m, 2H), 1.34-1.29 (m, 4H).

Example 32

(E)-1-Morpholino-4-((R)-3-((5-((Z)-4,4,4-trifluoro-1-(3-fluoro-1H-indazol-5-yl)-2-phenylbut-1-en-1-yl)pyridin-2-yl)amino)piperidin-1-yl)but-2-en-1-one 32

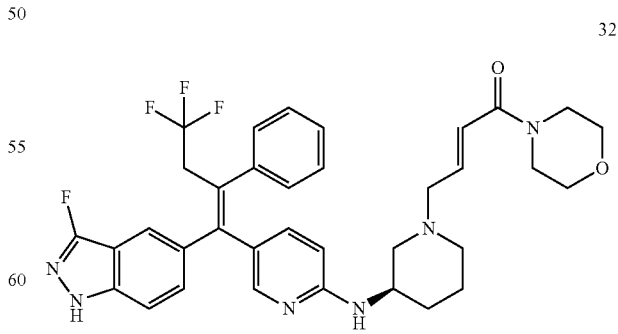

32

In accordance with the synthetic route in Example 31, the starting material 5d in Step 4 was replaced with compound 1h, to give the title compound 32 (8 mg, yield: 19%). MS m/z (ESI): 649.2 [M+1].

¹H NMR (400 MHz, CDCl₃) 9.25 (s, 1H), 7.68 (s, 1H), 7.56-7.52 (m, 1H), 7.45-7.40 (m, 1H), 7.36-7.32 (m, 1H), 7.28-7.21 (m, 4H), 6.94-6.82 (m, 2H), 6.44-6.37 (m, 1H), 6.15-6.07 (m, 1H), 5.39-5.35 (m, 1H), 3.76-3.46 (m, 8H), 3.36-3.26 (m, 2H), 3.17-3.05 (m, 2H), 2.99-2.92 (m, 1H), 2.65-2.03 (m, 7H), 0.95-0.87 (m, 1H).
Example 33
(E)-N,N-Dimethyl-4-(4-((5-((Z)-4,4,4-trifluoro-1-(3-fluoro-1H-indazol-5-yl)-2-phenylbut-1-en-1-yl)pyridin-2-yl)amino)piperidin-1-yl)but-2-enamide 33
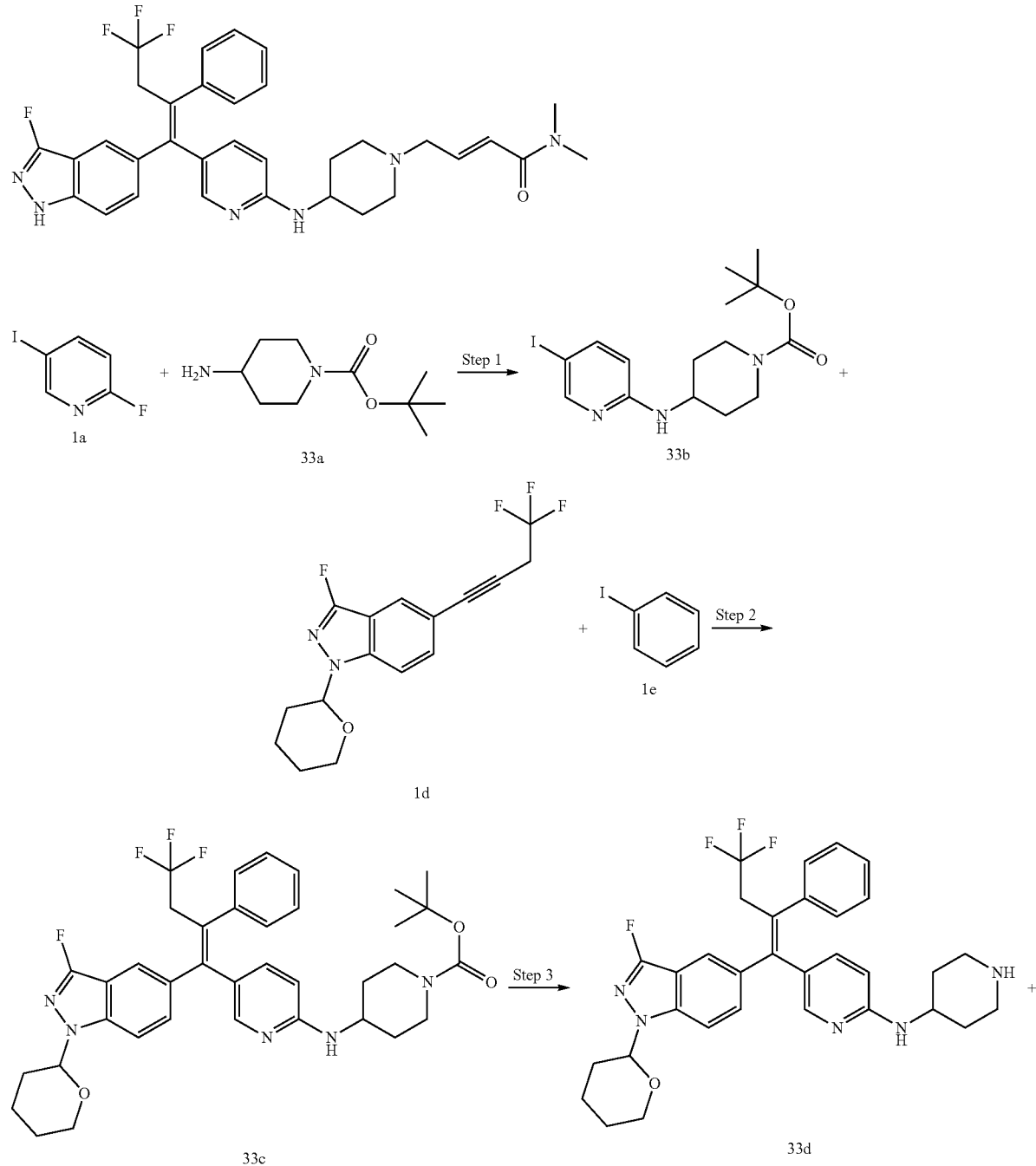

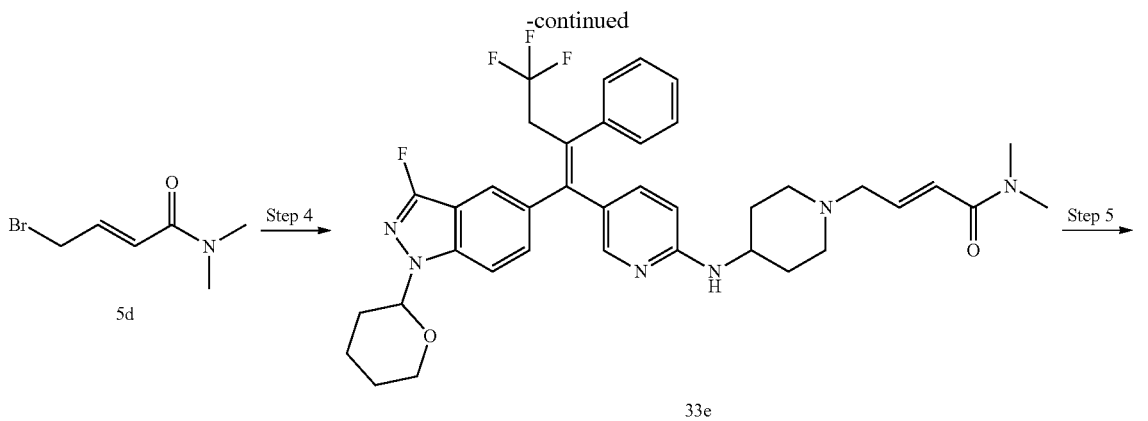

Step 1

Tert-butyl 4-((5-iodopyridin-2-yl)amino)piperidine-1-carboxylate 33b

In accordance with the synthetic route in Example 1, the starting material 1b in Step 1 was replaced with tert-butyl 4-aminopiperidine-1-carboxylate 33a, to give the title compound 33b (0.2 g, yield: 20%).

Step 2

Tert-butyl (Z)-4-((5-(4,4,4-trifluoro-1-(3-fluoro-1-(tetrahydro-2H-pyran-2-yl)-1H-indazol-5-yl)-2-phenylbut-1-en-1-yl)pyridin-2-yl)amino)piperidine-1-carboxylate 33c In accordance with the synthetic route in Example 1, the starting material 1c in Step 2 was replaced with compound 33b, to give the title compound 33c (80 mg, yield: 64%). MS m/z (ESI): 680.3 [M+1].

Step 3

(Z)—N-(Piperidin-4-yl)-5-(4,4,4-trifluoro-1-(3-fluoro-1-(tetrahydro-2H-pyran-2-yl)-1H-indazol-5-yl)-2-phenylbut-1-en-1-yl)pyridin-2-amine 33d In accordance with the synthetic route in Example 1, the starting material 1f in Step 3 was replaced with compound 33c, to give the title compound 33d (68 mg, yield: 100%).

Step 4

(E)-N,N-Dimethyl-4-(4-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)amino)piperidin-1-yl)but-2-enamide 33e In accordance with the synthetic route in Example 1, the starting material 1g in Step 4 was replaced with compound 33d, and the starting material 1h was replaced with compound 5d, to give the title compound 33e (70 mg, yield: 86%).

Step 5

(E)-N,N-Dimethyl-4-(4-((5-((Z)-4,4,4-trifluoro-1-(3-fluoro-1H-indazol-5-yl)-2-phenylbut-1-en-1-yl)pyridin-2-yl)amino)piperidin-1-yl)but-2-enamide 33

In accordance with the synthetic route in Example 1, the starting material 1i in Step 5 was replaced with compound 33e, to give the title compound 33 (15 mg, yield: 24%).
MS m/z (ESI): 607.7 [M+1].
$^1$H NMR (400 MHz, CDCl$_3$) 7.63 (s, 1H), 7.59 (s, 1H), 7.38-7.32 (m, 4H), 7.24 (d, 2H), 7.23-7.02 (m, 2H), 6.77 (s, 2H), 6.47 (d, 1H), 5.36 (s, 1H), 3.93 (s, 1H), 3.83 (s, 2H), 3.39-3.29 (m, 6H), 3.12 (s, 3H), 3.09 (s, 3H), 2.42 (m, 2H), 2.07 (s, 2H).

Example 34
(E)-N,N-Dimethyl-4-(((R)-1-(5-((Z)-4,4,4-trifluoro-1-(3-fluoro-1H-indazol-5-yl)-2-phenylbut-1-en-1-yl)pyridin-2-yl)pyrrolidin-3-yl)amino)but-2-enamide 34
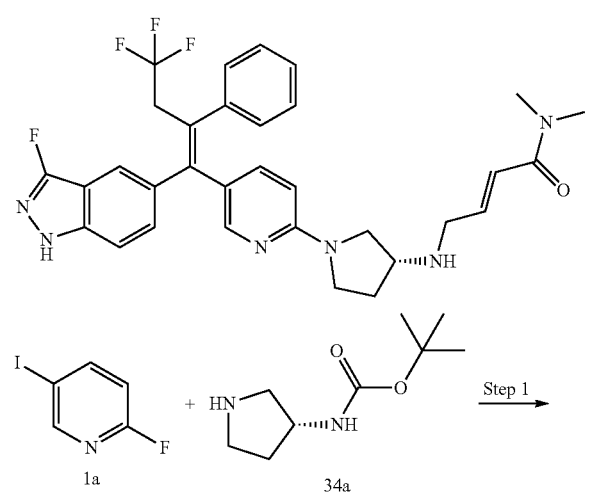
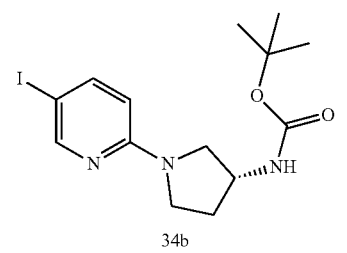
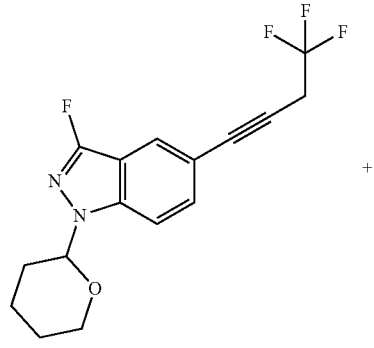
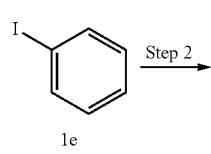
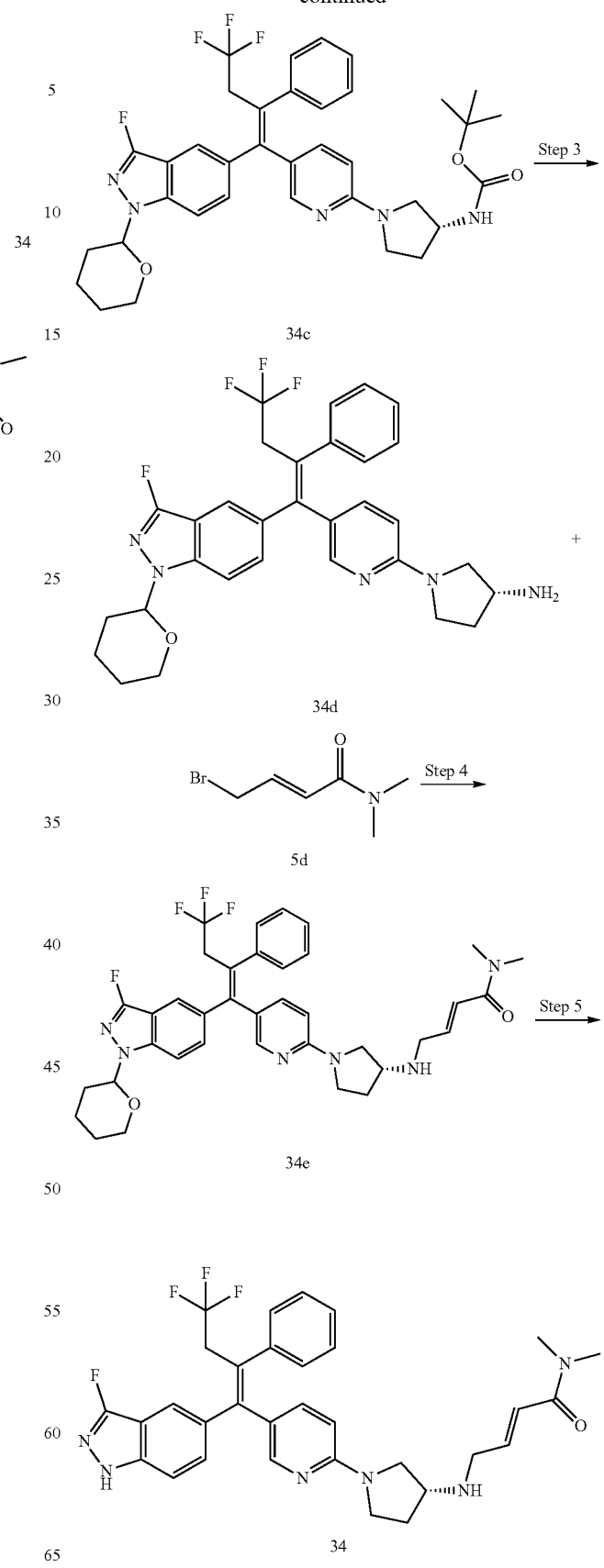

Step 1

Tert-butyl(R)-(1-(5-iodopyridin-2-yl)pyrrolidin-3-yl) carbamate 34b

In accordance with the synthetic route in Example 1, the starting material 1b in Step 1 was replaced with tert-butyl (R)-pyrrolidin-3-ylcarbamate 34a, to give the title compound 34b (0.8 g, yield: 70%).

Step 2

Tert-butyl ((3R)-1-(5-((Z)-4,4,4-trifluoro-1-(3-fluoro-1-(tetra-hydro-2H-pyran-2-yl)-1H-indazol-5-yl)-2-phenyl-but-1-en-1-yl)pyridin-2-yl)pyrrolidin-3-yl)carbamate 34c In accordance with the synthetic route in Example 1, the starting material 1c in Step 2 was replaced with compound 34b, to give the title compound 34c (85 mg, yield: 83%). MS m/z (ESI): 665.9 [M+1].

Step 3

(3R)-1-(5-((Z)-4,4,4-Trifluoro-1-(3-fluoro-1-(tetra-hydro-2H-pyran-2-yl)-1H-indazol-5-yl)-2-phenyl-but-1-en-1-yl)pyridin-2-yl)pyrrolidin-3-amine 34d In accordance with the synthetic route in Example 1, the starting material 1f in Step 3 was replaced with compound 34c, to give the title compound 34d (60 mg, yield: 82%).

Step 4

(E)-N,N-Dimethyl-4-(((3R)-1-(5-((Z)-4,4,4-trif-luoro-1-(3-fluoro-1-(tetrahydro-2H-pyran-2-yl)-1H-indazol-5-yl)-2-phenylbut-1-en-1-yl)pyridin-2-yl) pyrrolidin-3-yl)amino)but-2-enamide 34e In accordance with the synthetic route in Example 1, the starting material 1g in Step 4 was replaced with compound 34d, and the starting material 1 h was replaced with compound 5d, to give the title compound 34e (45 mg, yield: 63%).

Step 5

(E)-N,N-Dimethyl-4-(((R)-1-(5-((Z)-4,4,4-trifluoro-1-(3-fluoro-1H-indazol-5-yl)-2-phenylbut-1-en-1-yl) pyridin-2-yl)pyrrolidin-3-yl)amino)but-2-enamide 34

In accordance with the synthetic route in Example 1, the starting material 1i in Step 5 was replaced with compound 34e, to give the title compound 34 (9 mg, yield: 23%).
MS m/z (ESI): 592.9 [M+1].
$^1$H NMR (400 MHz, CDCl$_3$) 9.53 (s, 1H), 7.67 (s, 2H), 7.38 (d, 1H), 7.30-7.22 (m, 6H), 6.95-6.87 (m, 2H), 6.45 (d, 1H), 6.07 (d, 1H), 3.63-3.59 (m, 1H), 3.54-3.48 (m, 3H), 3.41-3.28 (m, 3H), 3.23-3.19 (m, 1H), 3.06 (d, 6H), 2.27-2.14 (m, 2H), 1.89-1.81 (m, 2H).

Example 35

(E)-N,N-Dimethyl-4-(((S)-1-(5-((Z)-4,4,4-trifluoro-1-(3-fluoro-1H-indazol-5-yl)-2-phenylbut-1-en-1-yl) pyridin-2-yl)pyrrolidin-3-yl)amino)but-2-enamide 35

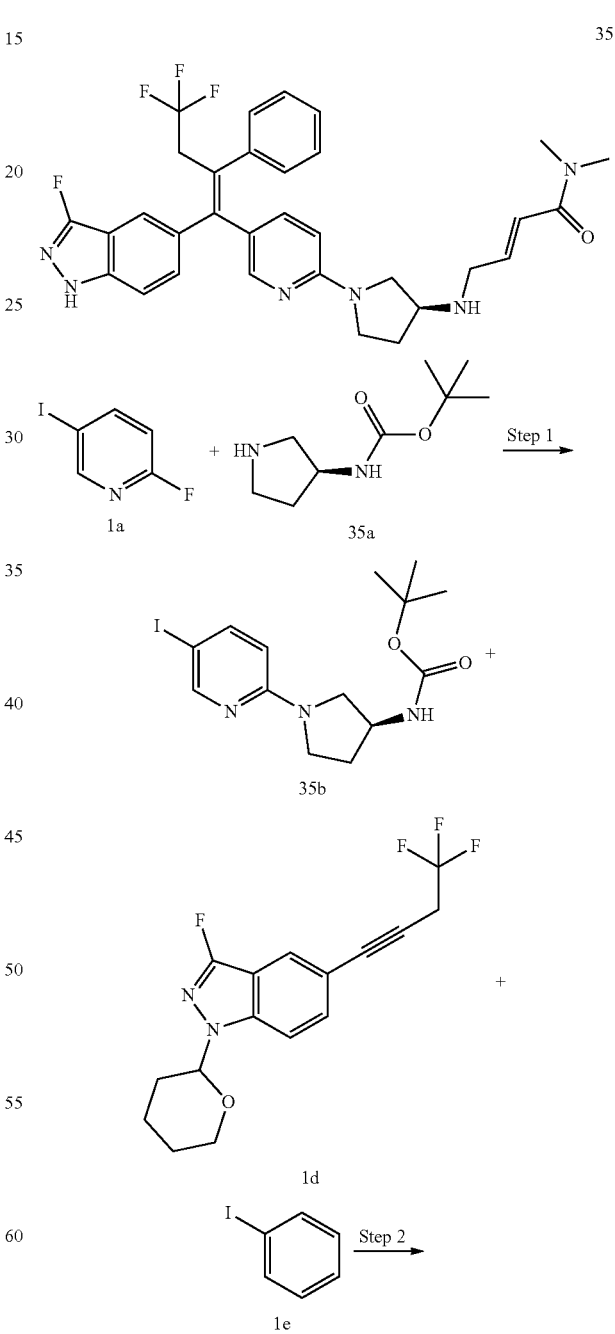

-continued

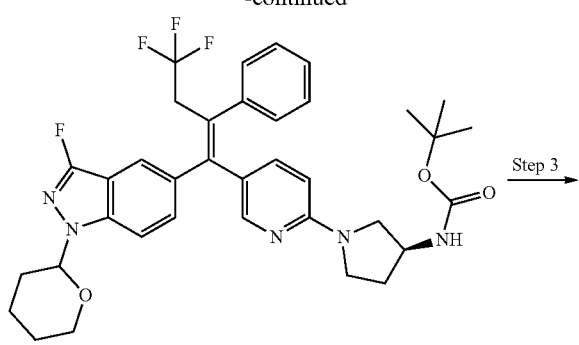

35c

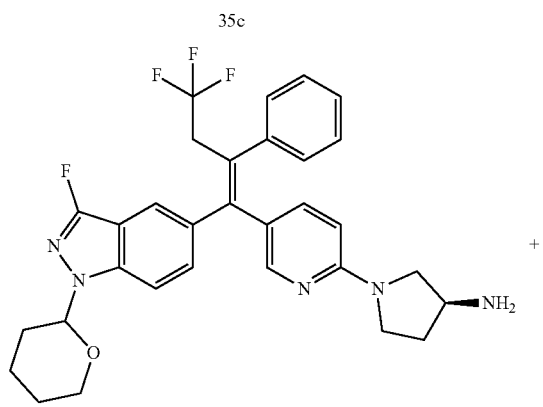

35d

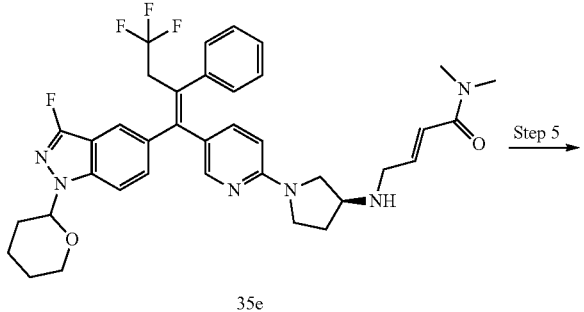

35e

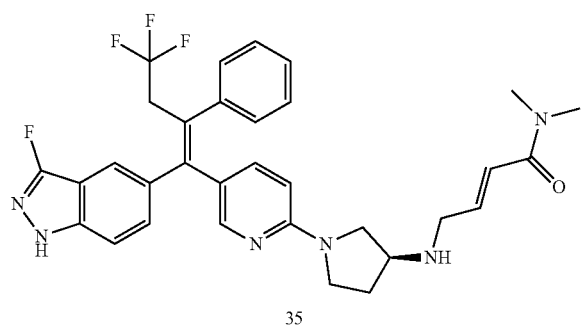

35

Step 1

Tert-butyl(S)-(1-(5-iodopyridin-2-yl)pyrrolidin-3-yl)carbamate 35b

In accordance with the synthetic route in Example 1, the starting material 1b in Step 1 was replaced with Tert-butyl (S)-pyrrolidin-3-ylcarbamate 35a, to give the title compound 35b (0.8 g, yield: 69%).

Step 2

Tert-butyl ((3S)-1-(5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)pyrrolidin-3-yl)carbamate 35c In accordance with the synthetic route in Example 1, the starting material 1c in Step 2 was replaced with compound 35b, to give the title compound 35c (86 mg, yield: 84%).
MS m/z (ESI): 666.3 [M+1].

Step 3

(3S)-1-(5-((Z)-4,4,4-Trifluoro-1-(3-fluoro-1-(tetrahydro-2H-pyran-2-yl)-1H-indazol-5-yl)-2-phenylbut-1-en-1-yl)pyridin-2-yl)pyrrolidin-3-amine 35d In accordance with the synthetic route in Example 1, the starting material 1f in Step 3 was replaced with compound 35c, to give the title compound 35d (55 mg, yield: 80%).

Step 4

(E)-N,N-Dimethyl-4-(((3S)-1-(5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)pyrrolidin-3-yl)amino)but-2-enamide 35e In accordance with the synthetic route in Example 1, the starting material 1g in Step 4 was replaced with compound 35d, and the starting material 1 h was replaced with compound 5d, to give the title compound 35e (40 mg, yield: 61%).

Step 5

(E)-N,N-Dimethyl-4-(((S)-1-(5-((Z)-4,4,4-trifluoro-1-(3-fluoro-1H-indazol-5-yl)-2-phenylbut-1-en-1-yl)pyridin-2-yl)pyrrolidin-3-yl)amino)but-2-enamide 35

In accordance with the synthetic route in Example 1, the starting material 1i in Step 5 was replaced with compound 35e, to give the title compound 35 (8 mg, yield: 23%).
MS m/z (ESI): 592.9 [M+1].
$^1$H NMR (400 MHz, CDCl$_3$) 9.47 (s, 1H), 7.67 (s, 2H), 7.39 (dd, 1H), 7.34 (dd, 1H), 7.28-7.22 (m, 5H), 6.96-6.87 (m, 2H), 6.45 (dd, 1H), 6.07 (dd, 1H), 3.63-3.59 (m, 1H), 3.54-3.46 (m, 3H), 3.41-3.28 (m, 3H), 3.22-3.19 (m, 1H), 3.07 (d, 6H), 2.20-2.15 (m, 2H), 1.88-1.81 (m, 2H).

Example 36
(E)-N,N-Dimethyl-4-((1-(5-((Z)-4,4,4-trifluoro-1-(3-fluoro-1H-indazol-5-yl)-2-phenylbut-1-en-1-yl)pyridin-2-yl)piperidin-4-yl)amino)but-2-enamide 36
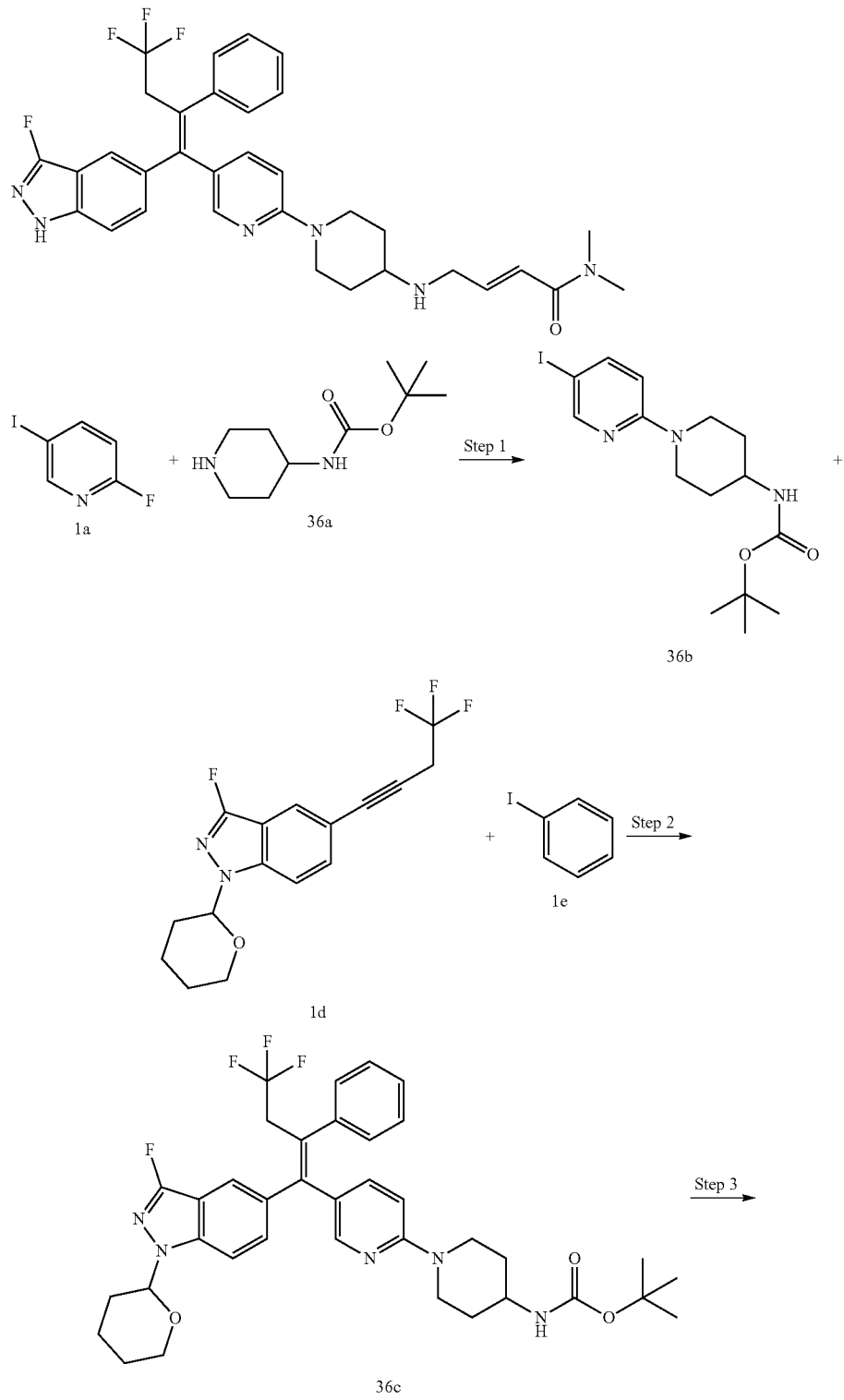

-continued
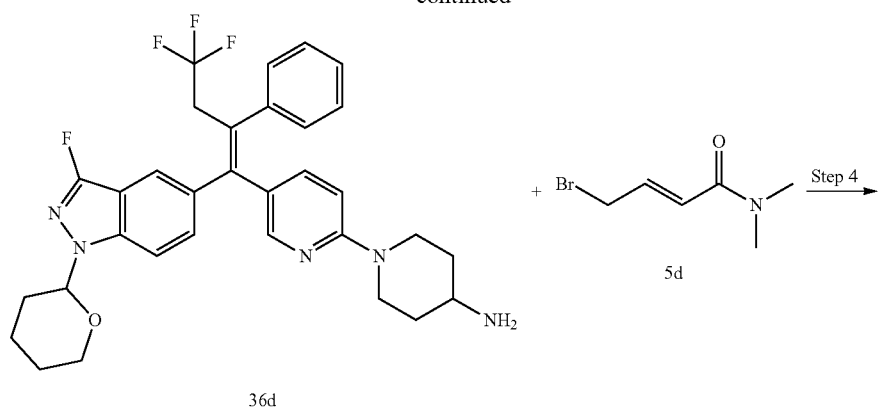
36d
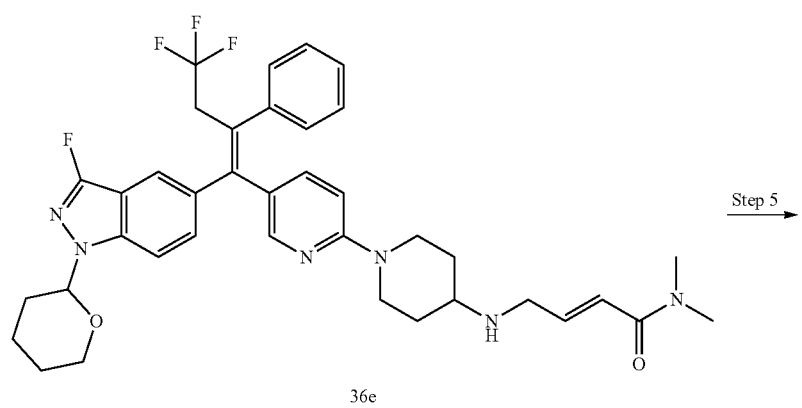
36e
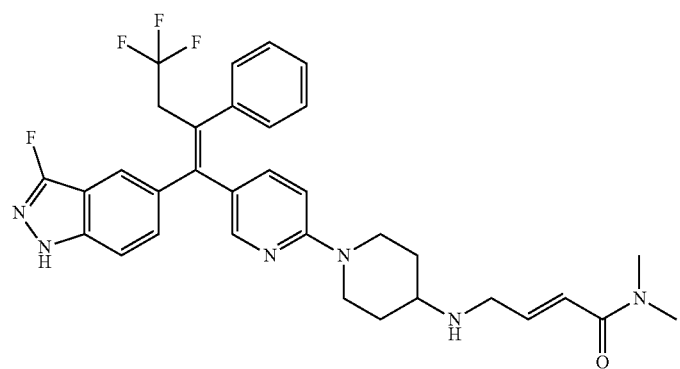
36

Tert-butyl (1-(5-iodopyridin-2-yl)piperidin-4-yl)carbamate 36b

In accordance with the synthetic route in Example 1, the starting material 1b in Step 1 was replaced with tert-butyl piperidin-4-ylcarbamate 36a, to give the title compound 36b (0.3 g, yield: 28%).

Step 2

Tert-butyl (Z)-(1-(5-(4,4,4-trifluoro-1-(3-fluoro-1-(tetrahydro-2H-pyran-2-yl)-1H-indazol-5-yl)-2-phenylbut-1-en-1-yl)pyridin-2-yl)piperidin-4-yl)carbamate 36c In accordance with the synthetic route in Example 1, the starting material 1c in Step 2 was replaced with compound 36b, to give the title compound 36c (120 mg, yield: 740%).
MS m/z (ESI): 679.9 [M+1].

Step 3

(Z)-1-(5-(4,4,4-Trifluoro-1-(3-fluoro-1-(tetrahydro-2H-pyran-2-yl)-1H-indazol-5-yl)-2-phenylbut-1-en-1-yl)pyridin-2-yl)piperidin-4-amine 36d In accordance with the synthetic route in Example 1, the starting material 1f in Step 3 was replaced with compound 36c, to give the title compound 36d (68 mg, yield: 100%).

Step 4

(E)-N,N-Dimethyl-4-((1-(5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)piperidin-4-yl)amino)but-2-enamide 36e In accordance with the synthetic route in Example 1, the starting material 1g in Step 4 was replaced with compound 36d, and the starting material 1 h was replaced with compound 5d, to give the title compound 36e (70 mg, yield: 86%).

Step 5

(E)-N,N-Dimethyl-4-((1-(5-((Z)-4,4,4-trifluoro-1-(3-fluoro-1H-indazol-5-yl)-2-phenylbut-1-en-1-yl)pyridin-2-yl)piperidin-4-yl)amino)but-2-enamide 36

In accordance with the synthetic route in Example 1, the starting material 1i in Step 5 was replaced with compound 36e, to give the title compound 36 (15 mg, yield: 24%).
MS m/z (ESI): 607.7 [M+1].
$^1$H NMR (400 MHz, CD$_3$OD) 7.70 (s, 1H), 7.56-7.53 (m, 1H), 7.48-7.42 (m, 1H), 7.35-7.32 (m, 1H), 7.30-7.26 (m, 6H), 7.00-6.98 (d, 1H), 6.92-6.89 (m, 1H), 6.72-6.64 (m, 1H), 4.25-4.21 (d, 2H), 3.92-3.90 (d, 2H), 3.57-3.39 (m, 4H), 3.17-3.11 (m, 4H), 3.01 (s, 3H), 2.24-2.22 (m, 2H), 1.67-1.67 (m, 2H).

Example 37

(E)-N,N-Dimethyl-4-(methyl((S)-1-(5-((Z)-4,4,4-trifluoro-1-(3-fluoro-1H-indazol-5-yl)-2-phenyl but-1-en-1-yl)pyridin-2-yl)piperidin-3-yl)amino)but-2-enamide 37

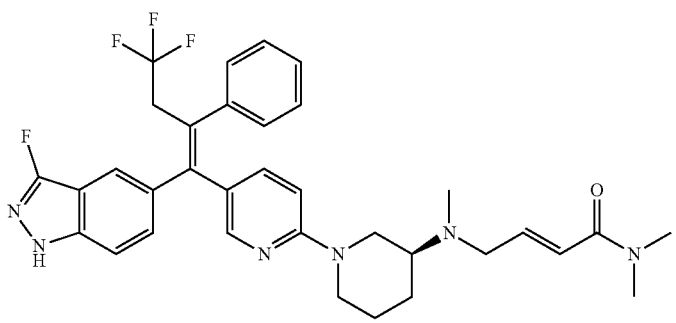

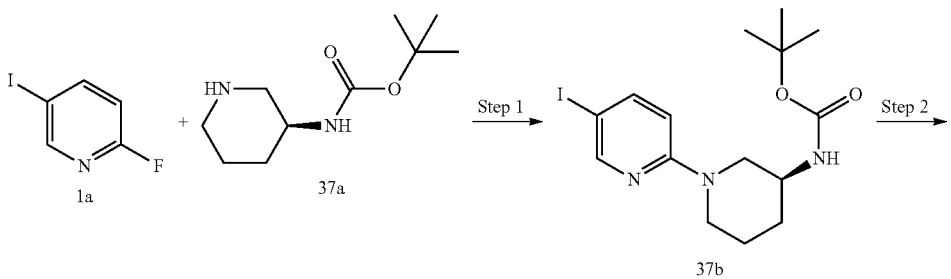

-continued
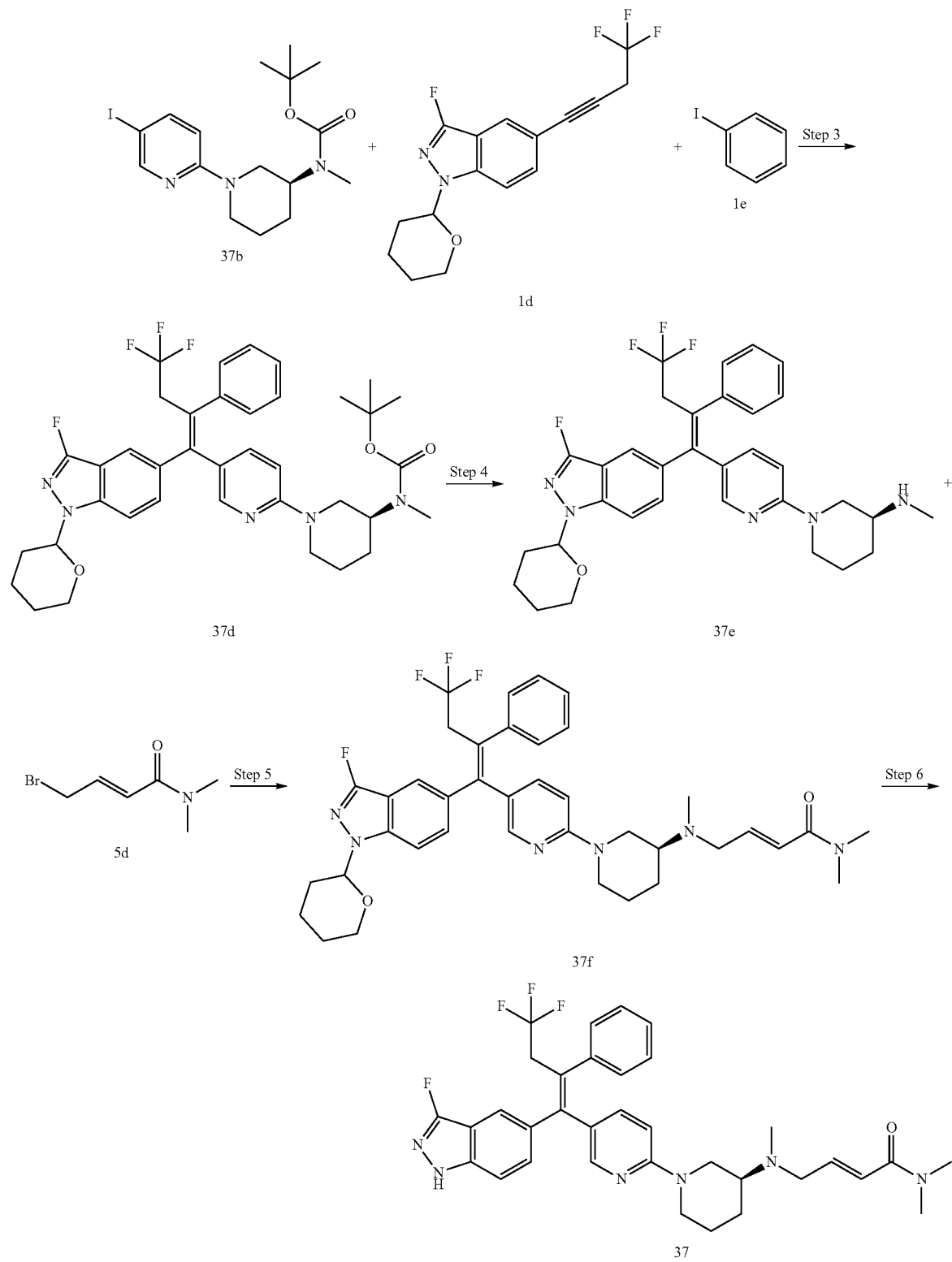

Step 1

Tert-butyl(S)-(1-(5-iodopyridin-2-yl)piperidin-3-yl) carbamate 37b

Potassium carbonate (1.5 g, 20.5 mmol) was dissolved in N,N-dimethylformamide (10 mL), followed by the addition of tert-butyl(S)-piperidin-3-ylcarbamate 37a (2.0 g, 10.0 mmol) at room temperature. After completion of the addition, compound 1a (2.2 g, 10.0 mmol) was slowly added. The reaction was heated to 100° C., and stirred for 4 hours. The reaction solution was concentrated under reduced pressure, and the resulting residues were purified by thin layer chromatography with developing system B to obtain the title product 37b (3.5 g, yield: 87%).

Step 2

Tert-butyl(S)-(1-(5-iodopyridin-2-yl)piperidin-3-yl) (methyl)carbamate 37c

Sodium hydride (12 mg, 0.5 mmol) was dissolved in N,N-dimethylformamide (10 mL), followed by the addition of compound 37b (100 mg, 0.2 mmol) at room temperature. After completion of the addition, iodomethane (28 mg, 0.2 mmol) was slowly added. The reaction was stirred at room temperature for 2 hours. The reaction solution was concentrated under reduced pressure, and the resulting residues were purified by thin layer chromatography with developing system B to obtain the title product 37c (95 mg, yield: 92%).
MS m/z (ESI): 418.1 [M+1].

Step 3

Tert-butyl methyl((3S)-1-(5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)piperidin-3-yl)carbamate 37d In accordance with the synthetic route in Example 1, the starting material 1c in Step 2 was replaced with compound 37c, to give the title compound 37d (150 mg, yield: 71%).
MS m/z (ESI): 694.4 [M+1].

Step 4

(3S)—N-Methyl-1-(5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)piperidin-3-amine 37e In accordance with the synthetic route in Example 1, the starting material 1f in Step 3 was replaced with compound 37d, to give the title compound 37e (80 mg, yield: 93%).

Step 5

(E)-N,N-Dimethyl-4-(methyl((3S)-1-(5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)piperidin-3-yl)amino)but-2-enamide 37f In accordance with the synthetic route in Example 1, the starting material 1g in Step 4 was replaced with compound 37e, and the starting material 1h was replaced with compound 5d, to give the title compound 37f (75 mg, yield: 79%).

Step 6

(E)-N,N-Dimethyl-4-(methyl((S)-1-(5-((Z)-4,4,4-trifluoro-1-(3-fluoro-1H-indazol-5-yl)-2-phenyl but-1-en-1-yl)pyridin-2-yl)piperidin-3-yl)amino)but-2-enamide 37

In accordance with the synthetic route in Example 1, the starting material 1i in Step 5 was replaced with compound 37f, to give the title compound 37 (22 mg, yield: 25%).
MS m/z (ESI): 621.2 [M+1].
$^1$H NMR (400 MHz, CDCl$_3$) 10.51 (s, 1H), 7.71 (s, 1H), 7.62 (s, 1H), 7.74-7.31 (m, 4H), 7.29-7.21 (m, 4H), 6.80 (s, 2H), 6.65 (dd, 1H), 4.71 (dd, 1H), 4.04 (d, 2H), 3.87 (d, 2H), 3.41 (d, 2H), 3.35-3.31 (m, 2H), 3.06 (d, 6H), 2.84 (s, 3H), 2.29 (d, 1H), 2.02-1.92 (m, 2H), 1.69 (d, 1H).

Example 38

(E)-1-Morpholino-4-(((S)-1-(5-((Z)-4,4,4-trifluoro-1-(3-fluoro-1H-indazol-5-yl)-2-phenylbut-1-en-1-yl) pyridin-2-yl)piperidin-3-yl)amino)but-2-en-1-one 38

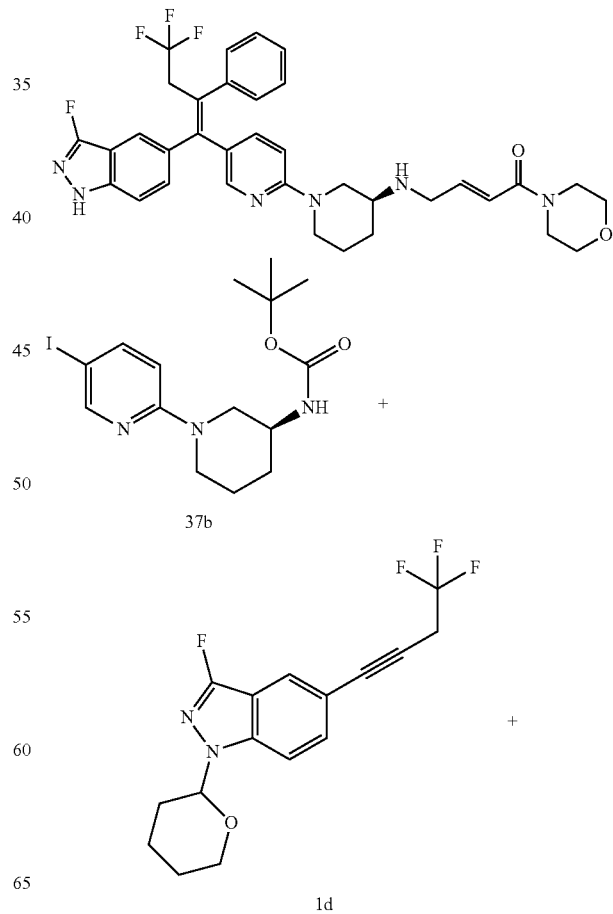

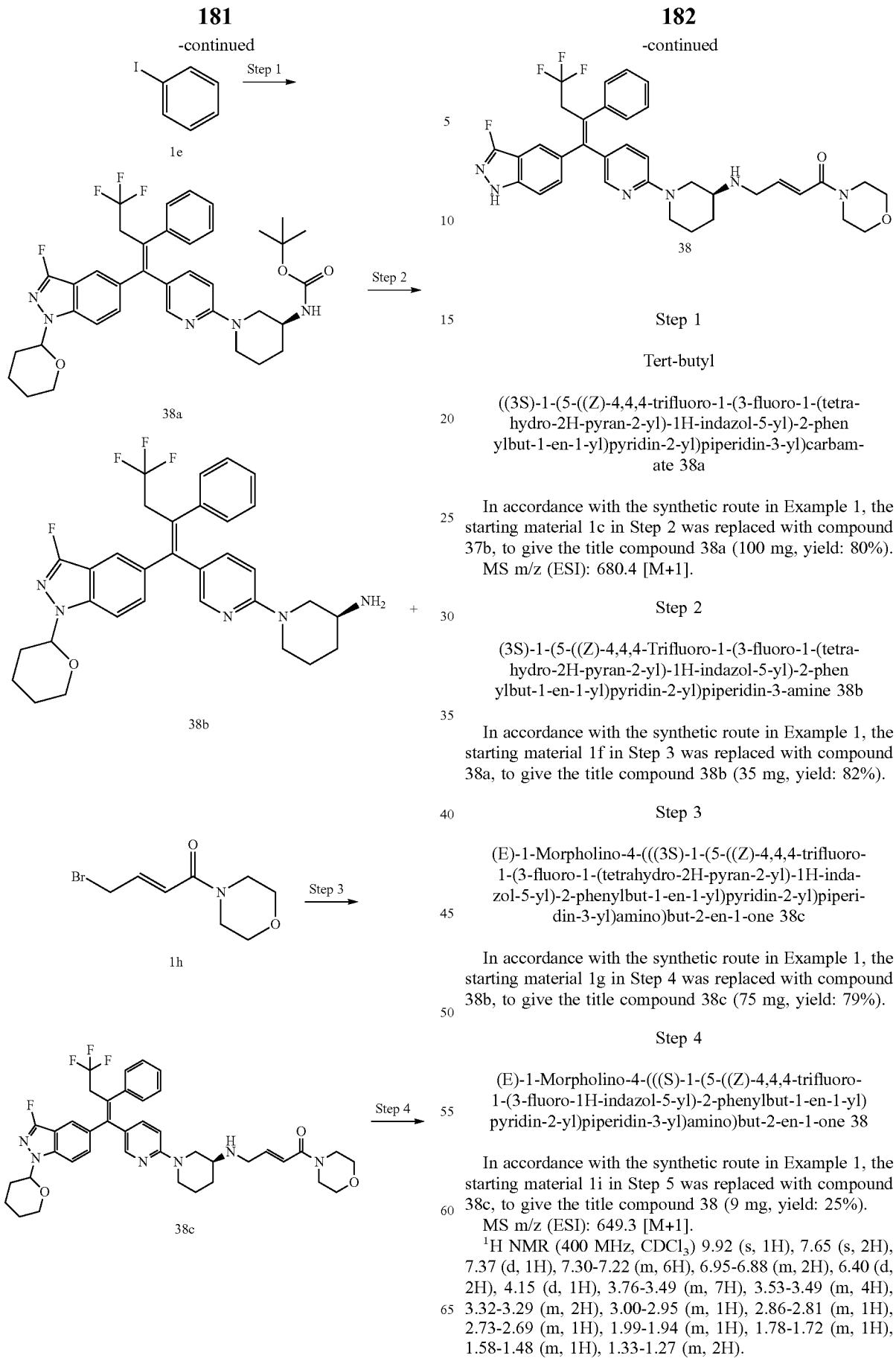

Step 1

Tert-butyl ((3S)-1-(5-((Z)-4,4-trifluoro-1-(3-fluoro-1-(tetrahydro-2H-pyran-2-yl)-1H-indazol-5-yl)-2-phenylbut-1-en-1-yl)pyridin-2-yl)piperidin-3-yl)carbamate 38a In accordance with the synthetic route in Example 1, the starting material 1c in Step 2 was replaced with compound 37b, to give the title compound 38a (100 mg, yield: 80%). MS m/z (ESI): 680.4 [M+1].

Step 2

(3S)-1-(5-((Z)-4,4,4-Trifluoro-1-(3-fluoro-1-(tetrahydro-2H-pyran-2-yl)-1H-indazol-5-yl)-2-phenylbut-1-en-1-yl)pyridin-2-yl)piperidin-3-amine 38b In accordance with the synthetic route in Example 1, the starting material 1f in Step 3 was replaced with compound 38a, to give the title compound 38b (35 mg, yield: 82%).

Step 3

(E)-1-Morpholino-4-(((3S)-1-(5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)piperidin-3-yl)amino)but-2-en-1-one 38c In accordance with the synthetic route in Example 1, the starting material 1g in Step 4 was replaced with compound 38b, to give the title compound 38c (75 mg, yield: 79%).

Step 4

(E)-1-Morpholino-4-(((S)-1-(5-((Z)-4,4,4-trifluoro-1-(3-fluoro-1H-indazol-5-yl)-2-phenylbut-1-en-1-yl)pyridin-2-yl)piperidin-3-yl)amino)but-2-en-1-one 38

In accordance with the synthetic route in Example 1, the starting material 1i in Step 5 was replaced with compound 38c, to give the title compound 38 (9 mg, yield: 25%).
MS m/z (ESI): 649.3 [M+1].
$^1$H NMR (400 MHz, CDCl$_3$) 9.92 (s, 1H), 7.65 (s, 2H), 7.37 (d, 1H), 7.30-7.22 (m, 6H), 6.95-6.88 (m, 2H), 6.40 (d, 2H), 4.15 (d, 1H), 3.76-3.49 (m, 7H), 3.53-3.49 (m, 4H), 3.32-3.29 (m, 2H), 3.00-2.95 (m, 1H), 2.86-2.81 (m, 1H), 2.73-2.69 (m, 1H), 1.99-1.94 (m, 1H), 1.78-1.72 (m, 1H), 1.58-1.48 (m, 1H), 1.33-1.27 (m, 2H).

Example 39

(E)-N,N-Dimethyl-4-((1-(((5-((Z)-4,4-trifluoro-1-(3-fluoro-1H-indazol-5-yl)-2-phenylbut-1-en-1-yl)pyridin-2-yl)oxy)methyl)cyclopropyl)amino)but-2-enamide 39

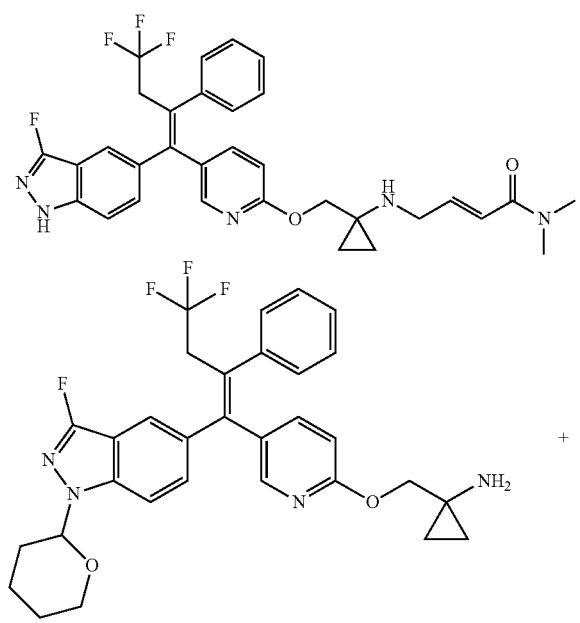

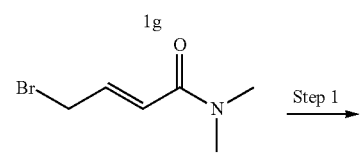

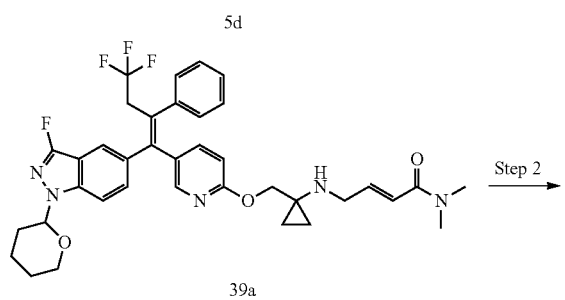

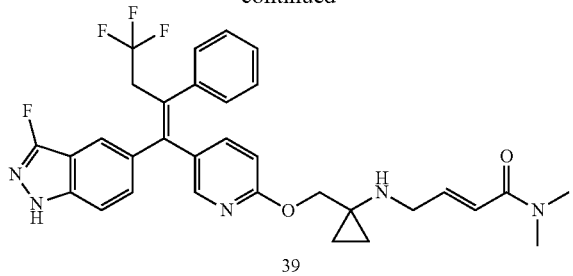

Step 1

(E)-N,N-Dimethyl-4-((1-(((5-((Z)-4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-enamide 39a In accordance with the synthetic route in Example 1, the starting material 1h in Step 4 was replaced with compound 5d, to give the title compound 39a (53 mg, yield: 65%).

Step 2

(E)-N,N-Dimethyl-4-((1-(((5-((Z)-4,4-trifluoro-1-(3-fluoro-1H-indazol-5-yl)-2-phenylbut-1-en-1-yl)pyridin-2-yl)oxy)methyl)cyclopropyl)amino)but-2-enamide 39

In accordance with the synthetic route in Example 1, the starting material 1i in Step 5 was replaced with compound 39a, to give the title compound 39 (24 mg, yield: 62%).

MS m/z (ESI): 593.9 [M+1].

$^1$H NMR (400 MHz, CD$_3$OD) 7.63 (d, 2H), 7.41-7.08 (m, 8H), 6.83-6.76 (m, 1H), 6.48-6.36 (m, 2H), 4.12 (s, 2H), 3.49-3.48 (m, 2H), 3.36-3.31 (m, 2H), 3.09 (s, 3H), 3.03 (s, 3H), 0.67-0.55 (m, 4H).

Example 40

(E)-1-(3-Hydroxy azetidin-1-yl)-4-((1-(((5-((Z)-4,4,4-trifluoro-1-(3-fluoro-1H-indazol-5-yl)-2-phenyl-but-1-en-1-yl)pyridin-2-yl)oxy)methyl)cyclopropyl)amino)but-2-en-1-one 40

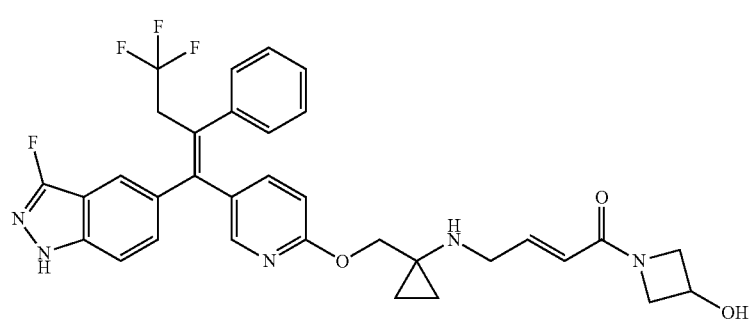

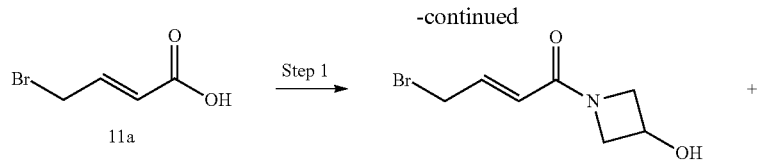

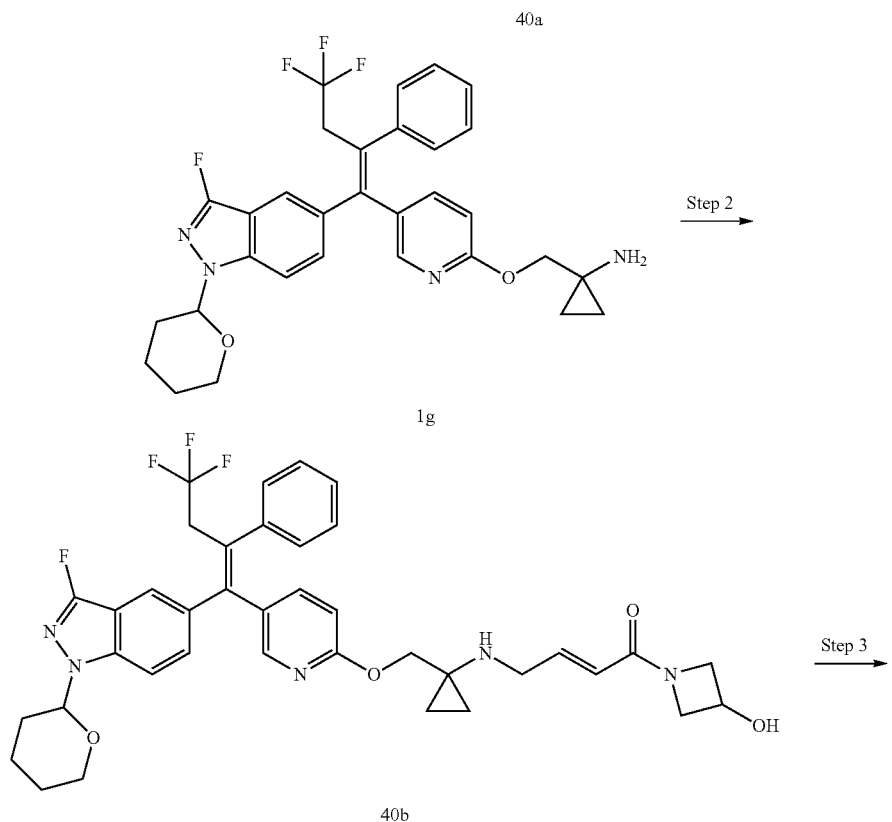

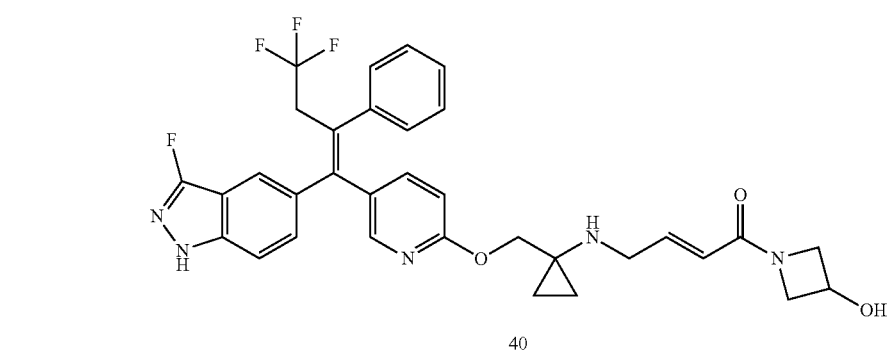

Step 1

(E)-4-Bromo-1-(3-hydroxyazetidin-1-yl)but-2-en-1-one 40a

Compound 11a (0.5 g, 3.0 mmol) was dissolved in dichloromethane (5 mL), followed by the addition of triethylamine (0.3 g, 3.3 mmol), 3-hydroxyazetidine (0.2 g, 3.3 mmol), 1-(3-dimethylaminopropyl)-3-ethylcarbodiimide hydrochloride (0.6 g, 3.3 mmol) and 1-hydroxybenzotriazole (0.4 g, 3.3 mmol) at room temperature. The reaction solution was stirred for 12 hours. The reaction solution was cooled. Saturated sodium bicarbonate solution (15 mL) was added, and the solution was extracted with ethyl acetate (20 mL×2). The organic phases were combined, washed with saturated sodium chloride solution (20 mL×4), dried over anhydrous sodium sulfate and filtered. The filtrate was concentrated under reduced pressure, and the resulting residues were purified by thin layer chromatography with developing system A to obtain the title product 40a (0.5 g, yield: 72%).

Step 2

(E)-1-(3-Hydroxyazetidin-1-yl)-4-((1-(((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-en-1-one 40b In accordance with the synthetic route in Example 1, the starting material 1h in Step 4 was replaced with compound 40a, to give the title compound 40b (43 mg, yield: 51%).

Step 3

(E)-1-(3-Hydroxyazetidin-1-yl)-4-((1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)but-2-en-1-one 40

In accordance with the synthetic route in Example 1, the starting material 1i in Step 5 was replaced with compound 40b, to give the title compound 40 (27 mg, yield: 67%).

MS m/z (ESI): 622.1 [M+1].

¹H NMR (400 MHz, CD₃OD) 7.71-7.66 (m, 2H), 7.53-7.51 (m, 1H), 7.35-7.21 (m, 8H), 6.71-6.65 (m, 2H), 4.63-4.48 (m, 2H), 4.43 (s, 2H), 4.29-4.25 (m, 1H), 4.05-4.00 (m, 3H), 3.85-3.81 (m, 1H), 3.48-3.33 (m, 2H), 1.17-1.11 (m, 4H).

Example 41

(E)-1-((S)-3-Hydroxypyrrolidin-1-yl)-4-((1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)but-2-en-1-one 41

41

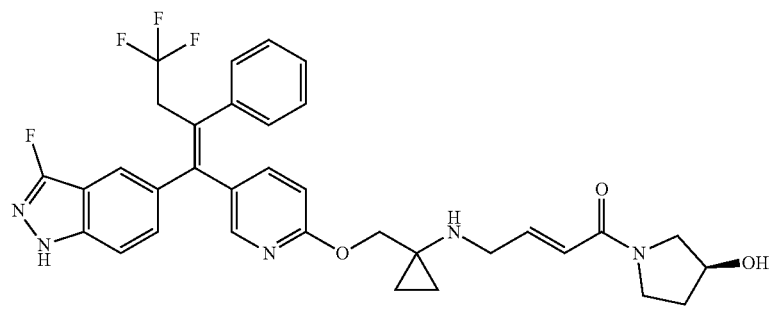

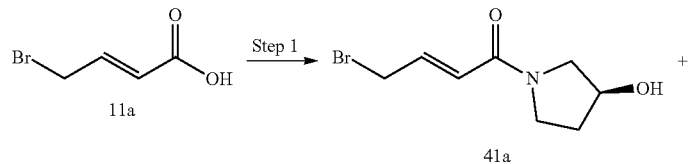

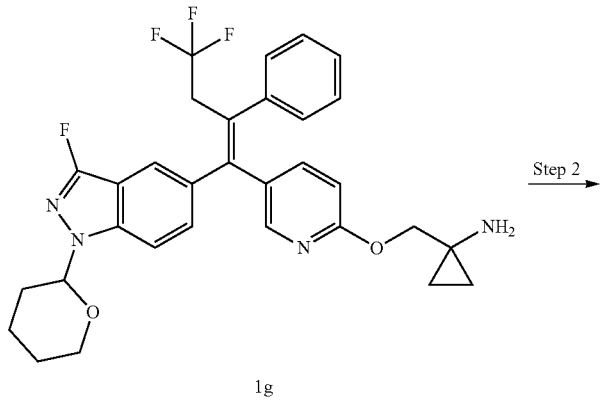

-continued

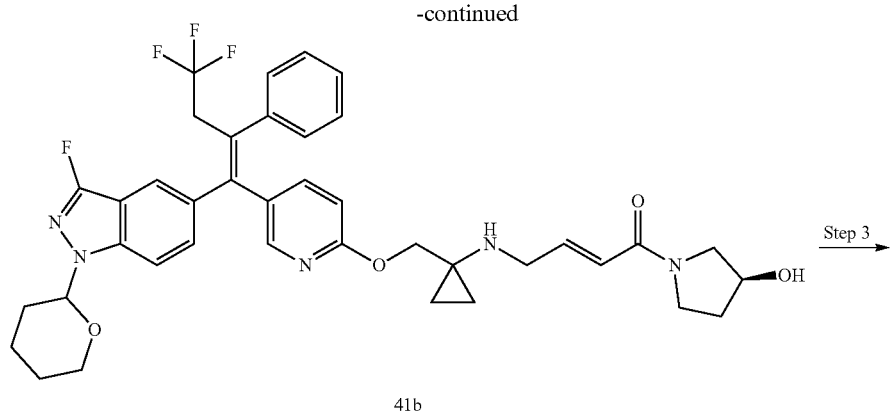

41b

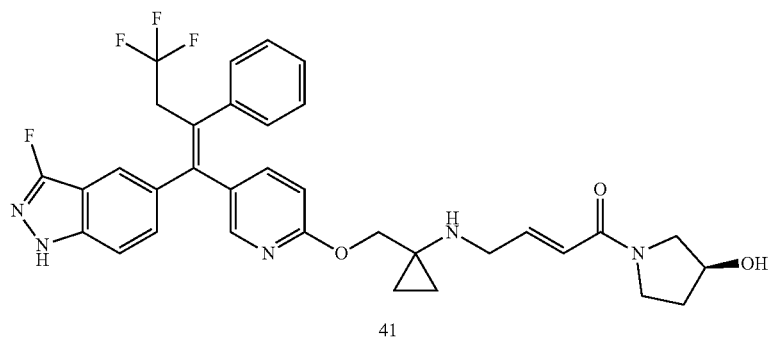

41

Step 1

(S,E)-4-Bromo-1-(3-hydroxypyrrolidin-1-yl)but-2-en-1-one 41a

Compound 11a (0.5 g, 3.0 mmol) was dissolved in dichloromethane (5 mL), followed by the addition of triethylamine (0.3 g, 3.3 mmol), (S)-3-hydroxypyrrolidine (0.2 g, 3.3 mmol), 1-(3-dimethylaminopropyl)-3-ethylcarbodiimide hydrochloride (0.6 g, 3.3 mmol) and 1-hydroxybenzotriazole (0.4 g, 3.3 mmol) at room temperature. The reaction solution was stirred for 12 hours. The reaction solution was cooled. Saturated sodium bicarbonate solution (15 mL) was added, and the solution was extracted with ethyl acetate (20 mL×2). The organic phases were combined, washed with saturated sodium chloride solution (20 mL×4), dried over anhydrous sodium sulfate and filtered. The filtrate was concentrated under reduced pressure, and the resulting residues were purified by thin layer chromatography with developing system A to obtain the title product 41a (0.5 g, yield: 73%).

Step 2

(E)-1-((S)-3-Hydroxypyrrolidin-1-yl)-4-((1-(((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-en-1-one 41b In accordance with the synthetic route in Example 1, the starting material 1h in Step 4 was replaced with compound 41a, to give the title compound 41b (41 mg, yield: 57%).

Step 3

(E)-1-((S)-3-Hydroxypyrrolidin-1-yl)-4-((1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)but-2-en-1-one 41

In accordance with the synthetic route in Example 1, the starting material 1i in Step 5 was replaced with compound 41b, to give the title compound 41 (37 mg, yield: 69%).

MS m/z (ESI): 636.2 [M+1].

$^1$H NMR (400 MHz, CD$_3$OD) 7.71-7.66 (m, 2H), 7.53-7.51 (m, 1H), 7.35-7.22 (m, 8H), 6.71-6.66 (m, 2H), 4.44 (s, 2H), 4.07-4.00 (m, 2H), 3.74-3.67 (m, 2H), 3.55-3.51 (m, 5H), 2.21-2.19 (m, 2H), 1.19-1.13 (m, 4H).

Example 42
(E)-1-((R)-2-(Hydroxymethyl)morpholino)-4-((1-(((5-((Z)-4,4,4-trifluoro-1-(3-fluoro-1H-indazol-5-yl)-2-phenylbut-1-en-1-yl)pyridin-2-yl)oxy)methyl)cyclopropyl)amino)but-2-en-1-one 42
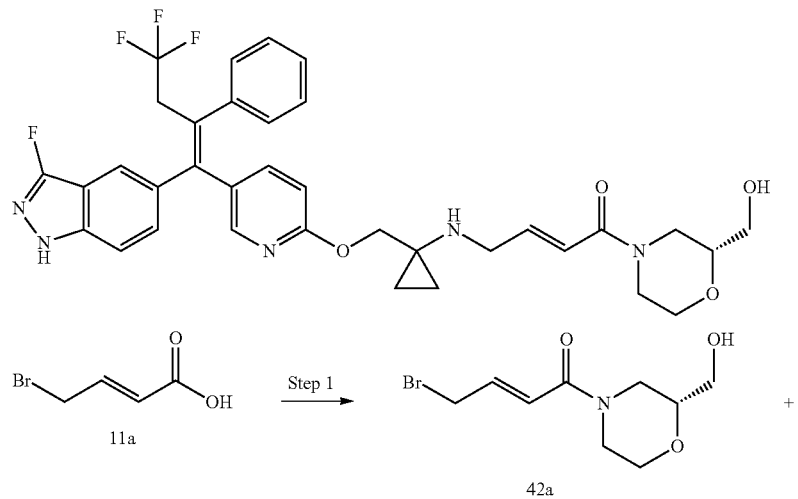
42
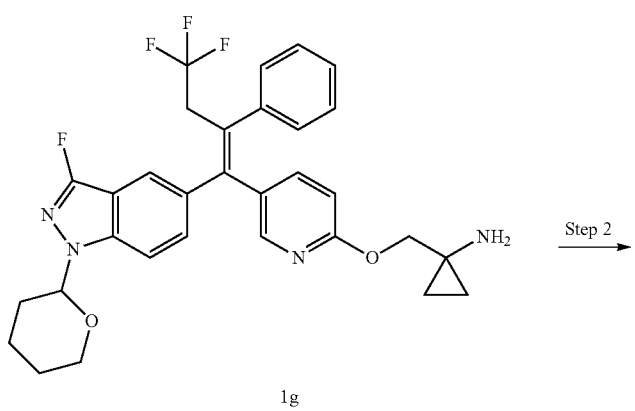
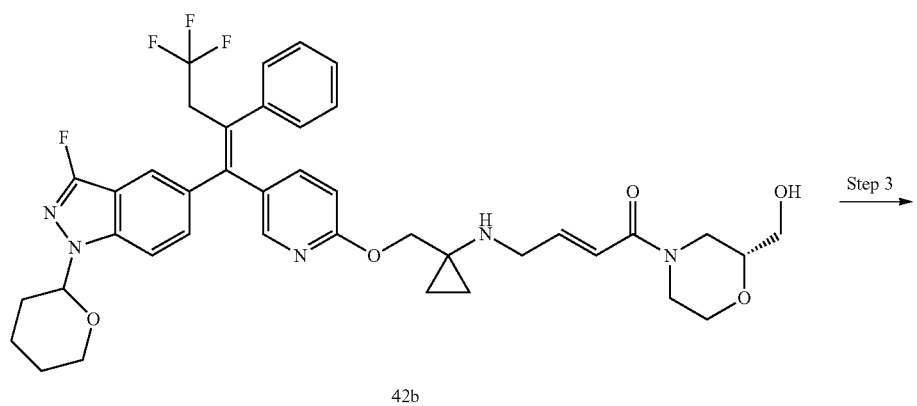

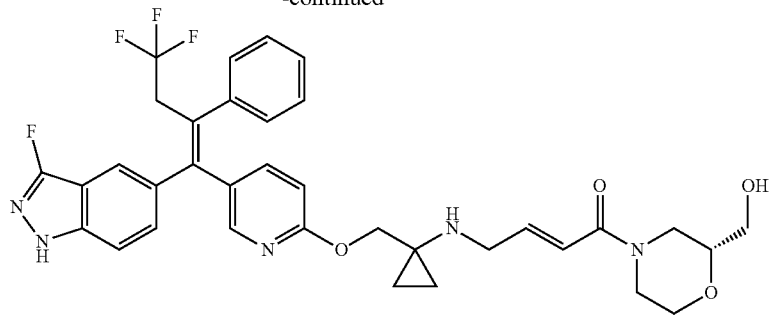

42

Step 1

(R,E)-4-Bromo-1-(2-(hydroxymethyl)morpholino)but-2-en-1-one 42a

Compound 11a (0.5 g, 3.0 mmol) was dissolved in dichloromethane (5 mL), followed by the addition of triethylamine (0.3 g, 3.3 mmol), (R)-morpholin-2-ylmethanol (0.4 g, 3.3 mmol), 1-(3-dimethylaminopropyl)-3-ethylcarbodiimide hydrochloride (0.6 g, 3.3 mmol) and 1-hydroxybenzotriazole (0.4 g, 3.3 mmol) at room temperature. The reaction solution was stirred for 12 hours. The reaction solution was cooled. Saturated sodium bicarbonate solution (15 mL) was added, and the solution was extracted with ethyl acetate (20 mL×2). The organic phases were combined, washed with saturated sodium chloride solution (20 mL×4), dried over anhydrous sodium sulfate and filtered. The filtrate was concentrated under reduced pressure, and the resulting residues were purified by thin layer chromatography with developing system A to obtain the title product 42a (0.5 g, yield: 63%).

Step 2

(E)-1-((R)-2-(Hydroxymethyl)morpholino)-4-((1-(((5-((Z)-4,4-trifluoro-1-(3-fluoro-1-(tetrahydro-2H-pyran-2-yl)-1H-indazol-5-yl)-2-phenylbut-1-en-1-yl)pyridin-2-yl)oxy)methyl)cyclopropyl)amino)but-2-en-1-one 42b In accordance with the synthetic route in Example 1, the starting material 1h in Step 4 was replaced with compound 42a, to give the title compound 42b (31 mg, yield: 47%).

Step 3

(E)-1-((R)-2-(Hydroxymethyl)morpholino)-4-((1-(((5-((Z)-4,4-trifluoro-1-(3-fluoro-1H-indazol-5-yl)-2-phenylbut-1-en-1-yl)pyridin-2-yl)oxy)methyl)cyclopropyl)amino)but-2-en-1-one 42

In accordance with the synthetic route in Example 1, the starting material 1i in Step 5 was replaced with compound 42b, to give the title compound 42 (27 mg, yield: 59%).
MS m/z (ESI): 666.1 [M+1].
¹H NMR (400 MHz, CD₃OD) 7.67-7.65 (m, 2H), 7.52-7.50 (m, 1H), 7.31-7.26 (m, 7H), 6.81-6.77 (m, 1H), 6.61-6.59 (m, 2H), 4.45-4.42 (m, 1H), 4.30 (s, 2H), 3.99-3.93 (m, 2H), 3.61-3.42 (m, 9H), 3.03-3.00 (m, 1H), 0.81-0.72 (m, 4H).

Example 43

(E)-1-Morpholino-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-en-1-one 43

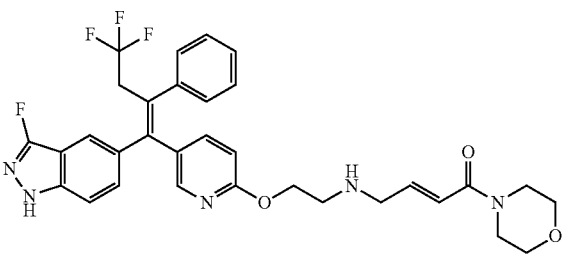

43

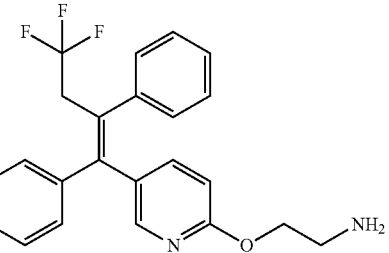

43a

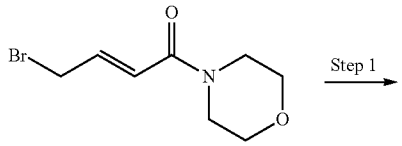

1h

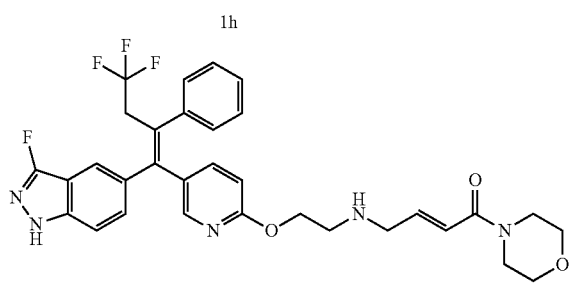

43

In accordance with the synthetic route in Example 1, the starting material 1g in Step 4 was replaced with 43a (prepared according to the method disclosed in Example 1 on page 77 of the description of the patent application WO2018098305), to give the title compound 43 (21 mg, yield: 42%).

MS m/z (ESI): 610.2 [M+1].

$^1$H NMR (400 MHz, CD$_3$OD) 7.69-7.67 (m, 2H), 7.53-7.50 (m, 1H), 7.32-7.20 (m, 7H), 6.80-6.59 (m, 3H), 4.36-4.34 (m, 2H), 3.66-3.58 (m, 10H), 3.48-3.40 (m, 3H), 3.13-3.10 (m, 2H).

Biological Assay

The present disclosure will be further described with reference to the following test examples, but the examples should not be considered as limiting the scope of the present disclosure.

Test Example 1. Inhibitory Effect of the Compounds of the Present Disclosure on the Activity of the Estrogen Receptor Reporter Gene 1. Experimental Purpose The purpose of the experiment is to determine the inhibitory effect of the compounds of the present disclosure on the activity of the estrogen receptor reporter gene, and evaluate the in vitro activity of the compounds according to IC$_{50}$.

2. Experimental Method

MCF7 cells MCF7/ERE-luc (ATCC, HTB-22) expressing the luciferase reporter gene ERE-luc (synthesized by GENEWIZ, Inc.) controlled by the estrogen receptor response element were cultured in MEM (GE Healthcare, SH30024.01) medium containing 10% fetal bovine serum and 500 g/ml G418. On the first day of the experiment, MCF7/ERE-luc cells were seeded in a 96-well plate with incomplete MEM medium containing 10% fetal bovine serum treated with activated charcoal (BioSun, BS-0004-500) at a density of 30,000 cells/well (100 μl of cell suspension per well), and the plate was incubated in a cell incubator at 37° C. and 5% CO$_2$ overnight. On the second day, 10 μl of β-estradiol (SIGMA, E2758-250MG) solution formulated with the above incomplete medium or test compound solution of different concentrations formulated with the above incomplete medium was added to each well, wherein the final concentration of β-estradiol was 0.1 nM, and the final concentrations of the compound were nine concentration points obtained by a 10-fold gradient dilution starting from 10 μM, a blank control containing 0.5% DMSO was set, and the plate was incubated in a cell incubator at 37° C. and 5% CO$_2$ for 20 hours. On the third day, the 96-well plate was taken out, and 100 μl of ONE-Glo™ Luciferase Assay system (Promega, E6110) was added to each well to determine the activity of luciferase. The plate was left to stand at room temperature for 3 minutes until the cells were fully lysed, and the luminescence signal values were measured using a multi-label microplate reader (PerkinElmer, VICTOR 3). The IC$_{50}$ values of the inhibitory activity of the compounds were calculated using Graphpad Prism software based on the concentrations and luminescence signal values of the compounds.

3. Experimental Results

The inhibitory effect of the compounds of the present disclosure on the activity of the estrogen receptor reporter gene was determined by the above test. A graph of the chemiluminescence signal values versus the logarithmic concentrations of the compound was made using Graghpad Prism. The resulting IC$_{50}$ values are shown in Table 1 below.

TABLE 1

IC$_{50}$ of inhibitory activity of the compounds of the present disclosure on the activity of the estrogen receptor reporter gene

| Example No. | IC$_{50}$ (nM) |
| --- | --- |
| 1 | 1 |
| 2 | 3 |
| 3 | 4 |
| 4 | 4 |
| 5 | 3 |
| 6 | 0.5 |
| 7 | 38 |
| 8 | 3 |
| 9 | 2 |
| 10 | 8 |
| 11 | 3 |
| 12 | 2 |
| 13 | 3 |
| 14 | 2 |
| 15 | 3 |
| 16 | 5 |
| 17 | 6 |
| 18 | 6 |
| 19 | 4 |
| 22 | 24 |
| 23 | 13 |
| 24 | 9 |
| 25 | 3 |
| 26 | 3 |
| 27 | 7 |
| 28 | 4 |
| 29 | 3 |
| 30 | 3 |
| 31 | 6 |
| 32 | 28 |
| 33 | 3 |
| 34 | 3 |
| 35 | 4 |
| 36 | 5 |
| 37 | 8 |
| 38 | 5 |
| 39 | 2 |
| 40 | 2 |
| 41 | 3 |
| 42 | 0.7 |

Conclusion: The compounds of the present disclosure have a significant inhibitory effect on the estrogen receptor reporter gene.

Test Example 2. Inhibitory Effect of the Compounds of the Present Disclosure on the Proliferation of MCF7 Cell 1. Experimental Purpose The purpose of the experiment is to determine the inhibitory activity of the compounds of the present disclosure on the proliferation of MCF7 cell, and evaluate the in vitro activity of the compounds according to IC$_{50}$.

2. Experimental Method

MCF7 cells (ATCC, HTB-22) were cultured in MEM (GE Healthcare, SH30024.01) complete medium containing 10% fetal bovine serum. On the first day of the experiment, MCF7 cells were seeded in a 96-well plate with the complete medium at a density of 3,000 cells/well (100 μl of cell suspension per well), and the plate was incubated in a cell incubator at 37° C. and 5% CO$_2$ overnight. On the second day, the medium in each well was replaced with 135 μl of MEM incomplete medium containing 2% fetal bovine serum. 15 μl of test compound solution of different concentrations formulated with the incomplete medium was added to each well, wherein the final concentrations of the compound were nine concentration points obtained by a 4-fold gradient dilution starting from 100 nM. A blank control containing 0.5% DMSO was set. The plate was incubated in a cell incubator at 37° C. and 5% $CO_2$ for 144 hours. On the eighth day, the 96-well plate was taken out, and 150 μl of CellTiter-Glo® Luminescent Cell Viability Assay (Promega, G7573) was added to each well. The plate was left to stand at room temperature for 10 minutes, and the luminescence signal values were measured using a multi-label microplate reader (PerkinElmer, VICTOR 3). The $IC_{50}$ values of the inhibitory activity of the compounds were calculated based on the concentrations and luminescence signal values of the compounds using Graphpad Prism software.

3. Data Analysis

A graph of the chemiluminescence signal values versus the logarithmic concentrations of the compound was made using Graghpad Prism to obtain the $IC_{50}$ values of the compound. The results are shown in Table 2.

TABLE 2

$IC_{50}$ of the inhibitory effect $IC_{50}$ of the compounds of the present disclosure on the proliferation of MCF7 cell

| Example No. | $IC_{50}$ (nM) | Maximum inhibition (%) |
|---|---|---|
| 1 | 0.5 | 100 |
| 2 | 0.6 | 112 |
| 3 | 2 | 101 |
| 4 | 1.5 | 113 |
| 5 | 0.1 | 96 |
| 6 | 0.15 | 94 |
| 7 | 2 | 102 |
| 8 | 0.1 | 113 |
| 9 | 0.1 | 110 |
| 10 | 0.3 | 104 |
| 11 | 0.5 | 110 |
| 12 | 0.4 | 108 |
| 13 | 0.6 | 88 |
| 14 | 0.8 | 108 |
| 15 | 0.2 | 107 |
| 16 | 0.8 | 102 |
| 17 | 0.6 | 96 |
| 18 | 1 | 100 |
| 19 | 0.4 | 97 |
| 21 | 45 | 90 |
| 22 | 4 | 103 |
| 23 | 1 | 97 |
| 24 | 1 | 98 |
| 25 | 0.5 | 109 |
| 26 | 0.3 | 103 |
| 27 | 0.3 | 86 |
| 28 | 0.1 | 90 |
| 29 | 0.4 | 93 |
| 30 | 0.2 | 93 |
| 31 | 0.7 | 97 |
| 32 | 5 | 100 |
| 33 | 0.3 | 105 |
| 34 | 0.2 | 103 |
| 35 | 1.1 | 105 |
| 36 | 0.5 | 104 |
| 37 | 0.8 | 98 |
| 38 | 0.8 | 96 |
| 39 | 0.2 | 113 |
| 40 | 0.1 | 115 |
| 41 | 0.1 | 115 |
| 42 | 0.03 | 105 |

Conclusion: The compounds of the present disclosure have a significant inhibitory effect on the proliferation of MCF7 cell.

Test Example 3. Inhibitory Effect of the Compounds of the Present Disclosure on the Proliferation of MCF7 Cell Expressing ERα Mutant 1. Experimental Purpose The purpose of the experiment is to determine the inhibitory activity of the compounds of the present disclosure on the proliferation of MCF7 cell expressing ERα mutant.

2. Experimental Method

Site-Directed Mutagenesis and Cell Line Construction

The mutants ERα Y537S and ERα D538G of human estrogen receptor α (ERαs) protein were obtained by site-directed mutagenesis using the cDNA of wild-type ESR1 gene (Accession No. NM000125) as a template according to double-primer PCR. The primer sequences used for mutagenesis are as follows (the nucleotides underlined are the sites of mutagenesis):

| No. | Primer name | Primer sequence |
|---|---|---|
| SEQ ID NO: 1 | Y537S-F | AAG AAC GTG GTG CCC CTC TCT GAC CTG CTG CTG GAG ATG |
| SEQ ID NO: 2 | Y537S-R | CAT CTC CAG CAG CAG GTC AGA GAG GGG CAC CAC GTT CTT |
| SEQ ID NO: 3 | D538G-F | AAC GTG GTG CCC CTC TAT GGC CTG CTG CTG GAG ATG CTG |
| SEQ ID NO: 4 | D538G-R | CAG CAT CTC CAG CAG CAG GCC ATA GAG GGG CAC CAC GTT |

The cDNA of mutant ESR1 was cloned into the target lentiviral vector pCDH-CMV-MCS-EF1-Puro (SBI, CD510B-1). The lentiviral plasmid with the mutant ESR1 gene sequence and the lentiviral packaging plasmids pVSV-G and pCMV-dR8.91 (SBI, LV500A-1) were transfected into HEK-293T cells (ATCC, CRL-3216) by Lipofectamine 3000 Transfection Reagent (ThermoFisher Scientific, Cat #L3000075). 48 hours after the transfection, the supernatant of the virus-containing DMEM high-glycemic medium (GE Healthcare, SH30243.01) containing 10% FBS was filtered, and ultracentrifuged to obtain the virus pellet. The virus pellet was resuspended in an appropriate amount of MEM medium (GE Healthcare, SH30024.01) containing 10% FBS, non-essential amino acids (SIGMA, M7145-100ML) and sodium pyruvate (SIGMA, S8636-100ML), and the resulting suspension was added to MCF7 cells (ATCC, HTB-22). Polybrene (SIGMA, H9268-5G) at a final concentration of 8 g/ml was added, and the cells were incubated overnight. Two days after the transfection, 1 g/ml puromycin (invitrogen, A11138-03) was added to the cell culture medium for resistance screening. After about two weeks, the MCF7 cell line capable of stably expressing ERαY537S and ERα D538G mutants was obtained.

Cell Proliferation Inhibition Test

MCF7 cells expressing ERα mutant were cultured in MEM (GE Healthcare, SH30024.01) complete medium containing 10% fetal bovine serum. On the first day of the experiment, the cells were seeded in a 96-well plate with the complete medium at a density of 3,000 cells/well (100 μl of cell suspension per well), and the plate was incubated in a cell incubator at 37° C. and 5% $CO_2$ overnight. On the second day, the medium in each well was replaced with 135 μl of MEM incomplete medium containing 2% fetal bovine serum. 15 μl of test compound solution of different concentrations formulated with the incomplete medium was added to each well, wherein the final concentrations of the compound were nine concentration points obtained by a 4-fold gradient dilution starting from 100 nM. A blank control containing 0.500 DMSO was set. The plate was incubated in a cell incubator at 37° C. and 500 $CO_2$ for 144 hours. On the eighth day, the 96-well plate was taken out, and 150 of CellTiter-Glo® Luminescent Cell Viability Assay (Promega, G7573) was added to each well. The plate was left to stand at room temperature for 10 minutes, and the luminescence signal values were measured using a multi-label microplate reader (PerkinElmer, VICTOR 3). The $IC_{50}$ values of the inhibitory activity of the compounds were calculated based on the concentrations and luminescence signal values of the compounds using Graphpad Prism software.

TABLE 3

$IC_{50}$ of inhibitory effect of the compounds of the present disclosure on the proliferation of MCF7 cell expressing ERα mutant

| | MCF7 D538G | | MCF7 ERαY537S | |
|---|---|---|---|---|
| Example No. | $IC_{50}$ (nM) | Maximum inhibition (%) | $IC_{50}$ (nM) | Maximum inhibition (%) |
| 1 | 2 | 100 | 3 | 100 |
| 2 | 2 | 104 | 3 | 107 |
| 3 | 9 | 96 | 9 | 93 |
| 4 | 10 | 105 | 11 | 101 |
| 5 | 0.2 | 98 | 0.3 | 107 |
| 6 | 0.5 | 98 | 1 | 102 |
| 7 | 12 | 84 | 12 | 88 |
| 8 | 1 | 103 | 2 | 107 |
| 9 | 0.8 | 108 | 2 | 94 |
| 10 | 4 | 104 | 7 | 86 |
| 11 | 1 | 100 | 2 | 107 |
| 12 | 1 | 96 | 2 | 104 |
| 13 | 3 | 107 | 5 | 104 |
| 14 | 3 | 107 | 6 | 97 |
| 15 | 1 | 105 | 2 | 102 |
| 16 | 2 | 110 | 4 | 88 |
| 17 | 3 | 104 | 3 | 102 |
| 18 | 5 | 104 | 8 | 92 |
| 19 | 2 | 97 | 2 | 106 |
| 22 | 15 | 93 | 15 | 97 |
| 23 | 7 | 101 | 5 | 94 |
| 24 | 8 | 94 | 8 | 102 |
| 25 | 1 | 112 | 1 | 107 |
| 26 | 1 | 111 | 2 | 104 |
| 29 | 3 | 93 | 2 | 93 |
| 31 | 2 | 101 | 3 | 105 |
| 32 | 11 | 95 | 19 | 84 |
| 33 | 1 | 106 | 2 | 105 |
| 34 | 1 | 101 | 1 | 105 |
| 35 | 3 | 104 | 6 | 97 |
| 36 | 2 | 99 | 3 | 100 |
| 37 | 2 | 101 | 3 | 86 |
| 38 | 2 | 108 | 4 | 102 |
| 39 | 0.6 | 105 | 1 | 112 |
| 40 | 0.2 | 106 | 0.5 | 112 |
| 41 | 0.2 | 106 | 0.6 | 111 |
| 42 | 0.1 | 105 | 0.2 | 107 |

Conclusion: The compounds of the present disclosure have a significant inhibitory effect on the proliferation of MCF7 cell expressing ERα mutant.

Test Example 4. Determination of the Inhibitory Activity of the Compounds of the Present Invention on $Na_v1.5$ The purpose of the experiment is to investigate the effect of the compounds on $Na_v1.5$ ion channel in an ex-vivo experiment. $Na_v1.5$ ion channel is stably expressed on HEK293 cell. After the $Na_v1.5$ current becomes stable, the $Na_v1.5$ currents before and after the administration of the compound are compared so as to obtain the effect of the compound on the $Na_v1.5$ ion channel.

1. Experimental Materials and Instruments
   1) Patch clamp amplifier: patch clamp PC-505B (WARNER instruments)
   2) Digital-to-analog converter: Digidata 1440A (Axon CNS)
   3) Micro-manipulator: MIP-225 (SUTTER instrument)
   4) Inverted microscope: TL4 (Olympus)
   5) Glass microelectrode puller: PC-10 (NARISHIGE)
   6) Microelectrode glass capillary: B 12024F (Wuhan Weitan Scientific Instrument Co., Ltd.)
   7) Dimethyl sulfoxide (DMSO): D2650 (Sigma-Aldrich)
2. Experimental Procedures
   2.1 Formulation of the Compounds
   Except for NaOH and KOH used for acid titration and base titration, all the agents used for formulating the extracellular fluid and intracellular fluid were purchased from Sigma (St. Louis, Mo.).
   Extracellular fluid: NaCl, 137 mM; KCl, 4 mM; $CaCl_2$), 1.8 mM; $MgCl_2$, 1 mM; HEPES, 10; glucose, 10 mM; pH 7.4 (NaOH titration).
   Intracellular fluid: aspartic acid, 140 mM; $MgCl_2$, 2 mM; EGTA, 11 mM; HEPES, 10 mM; pH 7.2 (CsOH titration).
   The test compound was dissolved in dimethyl sulfoxide (DMSO) at a stock concentration of 9 mM. The stock solution of the test compound was dissolved in the extracellular fluid on the day of the test and formulated into the required concentration.
   2.2 Test Process of the Manual Patch Clamp
   1) The compound was formulated into solutions with specified concentrations. The solutions were added to the pipelines respectively in order from high to low concentration, and the pipelines were marked.
   2) The cell was transferred to the perfusion tank, and perfused with the extracellular fluid. The intracellular fluid was stored in small batches in a −80° C. refrigerator, and melted on the day of the experiment. The electrode was pulled with PC-10 (Narishige, Japan). Recording was carried out with the whole-cell patch clamp, and the noise was filtered at one-fifth of the sampling frequency.
   3) All compounds were perfused with a perfusion system that uses its own gravity. Each concentration was tested in at least two cells. After the current stabilized (or after 5 minutes), the blocking effect of the compound was calculated by comparing the changes in the current before and after the administration of the compound.
   4) The perfusion tank was cleaned. The perfusion tank was rinsed with the drug solutions in order from high to low concentration, and the rinse duration for each concentration of drug solution was 20 seconds. The perfusion tank was finally rinsed with the extracellular fluid for 1 minute.
   2.3 Test Voltage Equation (Resting) and Results
   The cell was clamped at −80 mV. The cell was depolarized to Vhalf with a square wave lasting 8 milliseconds, hyperpolarized to −120 mV with a square wave lasting 20 milliseconds, and depolarized to −10 mV with a square wave lasting 20 milliseconds to obtain the $Na_v1.5$ current. This procedure was repeated every 15 seconds. The maximum current caused by the −10 mV square wave was measured. After the current became stable, the test compound was perfused. After the response became stable, the blocking intensity was calculated.

3. Data Analysis

The data was stored in the computer system for analysis. Data collection and analysis were carried out by pCLAMP 10 (Molecular Devices, Union City, CA). Stable current means that the absolute average value of the peak current of four consecutive scans exceeds 200 pA and the CV value is less than 10%, or the average value of the peak current of four consecutive scans is between 200 pA and 50 pA and the CV value is less than 30%. The average value of the last four current peaks after the current stabilized was used to calculate the effect of the compound at the concentration.

The inhibitory activity of the compounds of the present invention on $Na_v1.5$ was determined by the above test, and the resulting $IC_{50}$ values are shown in Table 4 below.

TABLE 4

$IC_{50}$ of the compounds of the present invention on inhibiting the $Na_v1.5$ channel activity

| Example No. | $IC_{50}$ (uM) |
| --- | --- |
| 1 | >10 |
| 39 | 8.2 |
| 40 | 11.5 |
| 41 | 5.3 |
| 43 | 2.7 |

Conclusion: The inhibitory effect of compounds 1 and 39 to 41 of the present invention on $Na_v1.5$ channel is weaker than that of the compound of Example 43. It can be seen that the risk of cardiotoxicity of these compounds is significantly lower than that of the compound of Example 43.

Pharmacokinetics Evaluation

Test Example 5. Pharmacokinetics Assay of the Compounds of the Examples of the Present Disclosure in BALB/C Nude Mice 1. Abstract BALB/C nude mice were used as test animals. The drug concentration in plasma at different time points was determined by LC/MS/MS method after intragastric administration of the compounds of the present disclosure to BALB/C nude mice. The pharmacokinetic behavior and characteristics of the compounds of the present disclosure was studied and evaluated in BALB/C nude mice.

2. Test Protocol 2.1 Test Compounds and Instruments

Compounds of Example 1, Example 14, Example 15 and Examples 39 to 42

LC/MS/MS instruments: LC/MS/MS API4000 triple quadrupole tandem mass spectrometer (No. 3, Applied Biosystems, USA), Shimadzu LC-30AD ultra high performance liquid chromatography system (Shimadzu, Japan). 2.2 Test Animals Sixty-three BALB/C nude mice (female, equally divided into seven groups, nine mice per group) were purchased from Jiesijie Laboratory Animal Co., LTD. (Certificate No.: SCXK (Shanghai)2013-0006).

2.3 Preparation of the Test Compound

For the compound of Example 14, an appropriate amount of the compound was weighed, followed by the addition of 5% of DMSO, 5% of tween 80 and 90% of normal saline by volume to obtain a colorless, clear and transparent solution (0.1 mg/mL).

For the compounds of Examples 1, 15 and 39 to 42, an appropriate amount of the compound was weighed, followed by the addition of 9% of PEG400, 0.5% of tween 80 and 90.5% of 0.5% CMC-Na by volume to obtain a colorless, clear and transparent solution (1.5 mg/mL).

2.4 Administration

After an overnight fast, the test compounds were intragastrically administered at an administration volume of 0.2 ml/10 g respectively. The administration dose of the compound of Example 14 was 2 mg/kg, and the administration dose of the compounds of Examples 1, 15 and 39 to 42 was 30 mg/kg.

3. Process

After an overnight fast, sixty-three female BALB/C nude mice were intragastrically administered the test compounds.

For the compounds of Examples 1 and 39, 0.1 ml of blood was taken at 0.25, 0.5, 1.0, 2.0, 4.0, 6.0, 8.0, 11.0 and 24.0 hours after the administration (from three animals per time point). The samples were stored in blood collection tubes treated with heparin (Sinopharm Chemical Reagent Co., Ltd.), and centrifuged for 10 minutes at 3500 rpm to separate the blood plasma. The blood plasma was stored at −20° C. The content of the test compound in the plasma of nude mouse after intragastrical administration of the test compound was determined. 25 µL of nude mouse plasma at each time point after the administration was taken, followed by the addition of 30 µL of the internal standard camptothecin solution (National Institutes for Food and Drug Control) (100 ng/mL) and 225 µL of acetonitrile. The resulting solution was vortex-mixed for 5 minutes, and centrifuged for 10 minutes (3700 to 4000 rpm). 0.1 to 0.5 µL of the supernatant was taken from the plasma samples for LC/MS/MS analysis.

For the compounds of Examples 14 and 15, 0.1 ml of blood was taken at 0.5, 1.0, 2.0, 4.0, 6.0, 8.0, 11.0 and 24.0 hours after the administration (from three animals per time point). The samples were stored in heparinized tubes, and centrifuged for 10 minutes at 3500 rpm to separate the blood plasma. The blood plasma was stored at −20° C. The content of the test compound in the plasma of nude mouse after intragastrical administration of the test compound was determined. 25 µL of nude mouse plasma at each time point after the administration was taken, followed by the addition of 30 µL of the internal standard camptothecin solution (100 ng/mL) and 200 µL of acetonitrile. The resulting solution was vortex-mixed for 5 minutes, and centrifuged for 10 minutes (3700 rpm). 0.25 to 1 µL of the supernatant was taken from the plasma samples for LC/MS/MS analysis.

For the compounds of Examples 40 to 42, 0.1 ml of blood was taken at 0.25, 0.5, 1.0, 2.0, 4.0, 6.0, 8.0, 11.0 and 24.0 hours after the administration (from three animals per time point). The samples were stored in tubes anticoagulated with EDTA-K2 (Shanghai Titan Scientific Co., Ltd.), and centrifuged for 1 minute at 10000 rpm and 4° C. The blood plasma was separated within one hour, and stored at −20° C. The process from blood collection to centrifugation was operated under an ice bath condition. The content of the test compound in the plasma of nude mouse after intragastrical administration of the test compound was determined. 25 µL of nude mouse plasma at each time point after the administration was taken, followed by the addition of 50 L of the internal standard camptothecin solution (100 ng/mL) and 200 µL of acetonitrile. The resulting solution was vortex-mixed for 5 minutes, and centrifuged for 10 minutes (3700 rpm). 1 L of the supernatant was taken from the plasma samples for LC/MS/MS analysis.

4. Results of Pharmacokinetic Parameters in BALB/C Nude Mice

The pharmacokinetic parameters of the compounds of the Examples of the present disclosure are shown in Table 5 below.

TABLE 5

Pharmacokinetic parameters of the compounds of the Examples of the present disclosure in BALB/C nude mice

| Example No. | Compound dose | Plasma concentration Cmax (ng/mL) | Area under curve AUC (ng/mL * h) | Half-life $t_{1/2}$ (h) | Residence time MRT (h) | Clearance rate CL/F (ml/min/kg) | Apparent volume of distribution Vz/F (ml/kg) | Bioavailability F(%) |
|---|---|---|---|---|---|---|---|---|
| 1 | 30 mg/kg | 4276 | 9849 | 1.99 | 1.6 | 50.8 | 8760 | — |
| 14 | 2 mg/kg | 87 | 205 | 1.01 | 1.9 | 163 | 14214 | 24.8 |
| 15 | 30 mg/kg | 4573 | 6564 | 0.89 | 1.41 | 76 | 5871 | — |
| 39 | 30 mg/kg | 6597 | 16486 | 0.94 | 1.57 | 30.3 | 2468 | — |
| 40 | 30 mg/kg | 3565 | 11867 | 1.26 | 2.3 | 42.1 | 4587 | — |
| 41 | 30 mg/kg | 2889 | 5019 | 1.67 | 2.26 | 99.6 | 14392 | — |
| 42 | 30 mg/kg | 2567 | 4512 | 1.2 | 1.56 | 111 | 11502 | — |

"—" refers to not determined.

Conclusion: The compounds of the present disclosure are well absorbed, and have a significant pharmacokinetic absorption effect.

Test Example 6. Biological Evaluation of the Covalent Modification of Estrogen Receptor ERα Wild-Type and ERα Y537S Mutant-Type 1. Experimental Purpose The purpose of the experiment is to determine the covalent modification effect of the compounds of the present disclosure on estrogen receptor ERα wild-type and ERα Y537S mutant-type.

2. Experimental Method

The ligand binding domain (LBD, aa296-554) of estrogen receptor ERα wild-type and ERα Y537S mutant-type was expressed in *E. coli* and purified. 2 μM ERα wild-type or ERα Y537S mutant-type protein and 10 μM compound were added to a buffer solution containing 50 mM Tris-HCl, pH7.5, 150 mM NaCl, 1 mM TCEP and 5% glycerol and mixed well. The solution was incubated at 4° C. for 24 hours, followed by high-resolution mass spectrometry (Agilent Technologies, Agilent Q-tof 6530) assay. Alternatively, 1 μM ERα wild-type or ERα Y537S mutant-type protein and 3 μM compound were added to a buffer solution containing 50 mM Tris-HCl, pH7.5, 150 mM NaCl, 1 mM TCEP and 5% glycerol and mixed well. The solution was incubated at 37° C. for 15 minutes, followed by high-resolution mass spectrometry assay. In the mass spectrometry assay results, the peak whose molecular weight is the sum of the molecular weight of the protein and compound is the product of covalent modification. The percentage of covalent modification is obtained by calculating the ratio of unbound protein to total protein. The results are shown in Table 6 below.

TABLE 6

Percentage of covalent modification of the estrogen receptor ERα wild-type and ERα Y537S mutant-type after 24 hours of covalent modification by the compounds of the present disclosure

| Example No. | Covalent modification effect on the estrogen receptor ERα wild-type (%) | Covalent modification effect on the estrogen receptor ERα Y537S mutant-type (%) |
|---|---|---|
| 1 | 97 | 97 |
| 2 | 87 | 90 |
| 8 | 96 | 97 |
| 12 | 85 | 83 |
| 14 | 93 | 94 |
| 15 | 95 | 96 |
| 18 | 98 | 99 |
| 19 | 94 | 97 |
| 22 | 95 | 100 |
| 23 | 95 | 99 |
| 24 | 90 | 99 |
| 31 | 80 | 83 |
| 32 | 94 | 95 |
| 38 | 95 | 96 |
| 39 | 97 | 98 |
| 40 | 96 | 98 |
| 41 | 93 | 95 |
| 42 | — | 97 |

Conclusion: The tested compounds have excellent covalent modification effect on the ERα wild-type or ERα Y537S mutant-type protein.

What is claimed is:

1. A compound of formula (I) or a tautomer, mesomer, racemate, enantiomer, diastereomer thereof, or mixture thereof, or a pharmaceutically acceptable salt thereof:

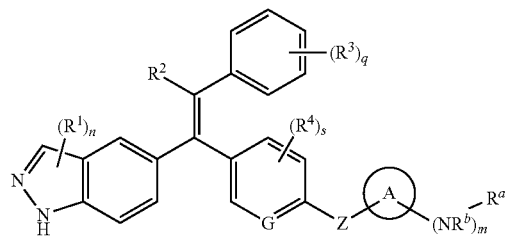

(I)

wherein:

G is CH or N;

Z is selected from the group consisting of a bond, $CR^5R^6$, —O—$(CH_2)_t$— and —$NR^7$—$(CH_2)_t$—;

ring A is selected from the group consisting of cycloalkyl and heterocyclyl;

$R^a$ is selected from the group consisting of —$CH_2CH$=$CHC(O)NR^8R^9$, —$C(O)CH$=$CR^{10}R^{11}$ and —$C(O)C$≡$CR^{12}$;

$R^b$ is selected from the group consisting of hydrogen atom and alkyl;

each $R^1$ is identical or different and each is independently selected from the group consisting of hydrogen atom, halogen, alkyl, haloalkyl, hydroxyalkyl, cycloalkyl, heterocyclyl, aryl and heteroaryl;

$R^2$ is selected from the group consisting of hydrogen atom, halogen, alkyl, haloalkyl, alkoxy, amino, cyano, nitro, carboxy, formyl, hydroxy, hydroxyalkyl, cycloalkyl, aryl and heteroaryl;

each $R^3$ is identical or different and each is independently selected from the group consisting of hydrogen atom, halogen, alkyl, haloalkyl, alkoxy, cyano, amino, nitro, carboxy, formyl, hydroxy, hydroxyalkyl, $NR^{13}C(O)R^{14}$, $C(O)NR^{13}R^{14}$, $SO_2R^{15}$, cycloalkyl, heterocyclyl, aryl and heteroaryl;

each $R^4$ is identical or different and each is independently selected from the group consisting of hydrogen atom, halogen, alkyl, haloalkyl, alkoxy, cyano, amino, nitro, carboxy, formyl, hydroxy, hydroxyalkyl, cycloalkyl, heterocyclyl, aryl and heteroaryl;

$R^5$ and $R^6$ are identical or different and are each independently selected from the group consisting of hydrogen atom, halogen, alkyl, haloalkyl, alkoxy, cyano, amino, nitro, carboxy, formyl, hydroxy, hydroxyalkyl, cycloalkyl, heterocyclyl, aryl and heteroaryl;

$R^7$ is selected from the group consisting of hydrogen atom, alkyl, haloalkyl, hydroxyalkyl, cycloalkyl, heterocyclyl, aryl and heteroaryl;

$R^8$ and $R^9$ are identical or different and are each independently selected from the group consisting of hydrogen atom, alkyl, haloalkyl, hydroxyalkyl, cycloalkyl, heterocyclyl, aryl and heteroaryl;

or, $R^8$ and $R^9$ together with the nitrogen atom to which they are attached form a heterocyclyl, wherein the heterocyclyl optionally contains in addition to one nitrogen atom, one to two identical or different heteroatoms selected from the group consisting of N, O and S, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

$R^{10}$ and $R^{11}$ are identical or different and are each independently selected from the group consisting of hydrogen atom, halogen, alkyl, haloalkyl, alkoxy, cyano, amino, nitro, carboxy, formyl, hydroxy, hydroxyalkyl, cycloalkyl, heterocyclyl, aryl and heteroaryl;

$R^{12}$ is selected from the group consisting of hydrogen atom, alkyl, haloalkyl, hydroxyalkyl, cycloalkyl, heterocyclyl, aryl and heteroaryl;

$R^{13}$ and $R^{14}$ are identical or different and are each independently selected from the group consisting of hydrogen atom, halogen, alkyl, haloalkyl, alkoxy, cyano, amino, nitro, carboxy, formyl, hydroxy, hydroxyalkyl, cycloalkyl, heterocyclyl, aryl and heteroaryl;

$R^{15}$ is selected from the group consisting of hydrogen atom, alkyl, haloalkyl, hydroxyalkyl, cycloalkyl, heterocyclyl, aryl and heteroaryl;

m is 0 or 1;

n is 0, 1, 2 or 3;

q is 0, 1, 2, 3, 4 or 5;

s is 0, 1, 2 or 3; and t is 0, 1, 2, 3, 4, 5 or 6.

2. The compound of formula (I) or the tautomer, mesomer, racemate, enantiomer, diastereomer thereof, or mixture thereof, or the pharmaceutically acceptable salt thereof according to claim 1, wherein ring A is selected from the group consisting of $C_3$-$C_6$ cycloalkyl and 3 to 6 membered heterocyclyl; the heterocyclyl contains one to three heteroatoms selected from the group consisting of N, O and S.

3. The compound of formula (I) or the tautomer, mesomer, racemate, enantiomer, diastereomer thereof, or mixture thereof, or the pharmaceutically acceptable salt thereof according to claim 1, being a compound of formula (II) or a tautomer, mesomer, racemate, enantiomer, diastereomer thereof, or mixture thereof, or a pharmaceutically acceptable salt thereof:

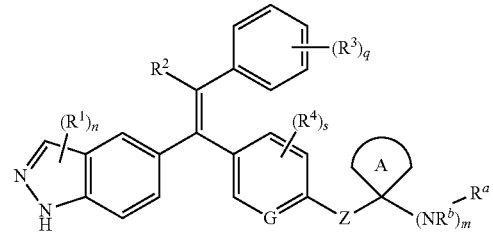

(II)

wherein ring A, G, Z, $R^1$, $R^2$, $R^3$, $R^4$, $R^a$, $R^b$, n, m, s and q are as defined in claim 1.

4. The compound of formula (I) or the tautomer, mesomer, racemate, enantiomer, diastereomer thereof, or mixture thereof, or the pharmaceutically acceptable salt thereof according to claim 1, being a compound of formula (III) or a tautomer, mesomer, racemate, enantiomer, diastereomer thereof, or mixture thereof, or a pharmaceutically acceptable salt thereof:

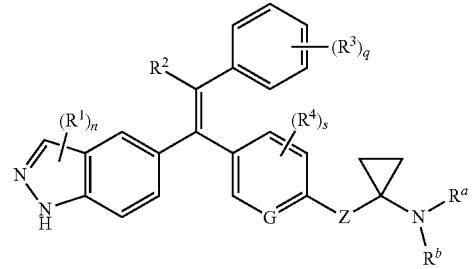

(III)

wherein: G, Z, $R^1$, $R^2$, $R^3$, $R^4$, $R^a$, $R^b$, n, s and q are as defined in claim 1.

5. The compound of formula (I) or the tautomer, mesomer, racemate, enantiomer, diastereomer thereof, or mixture thereof, or the pharmaceutically acceptable salt thereof according to claim 1, wherein G is an N atom.

6. The compound of formula (I) or the tautomer, mesomer, racemate, enantiomer, diastereomer thereof, or mixture thereof, or the pharmaceutically acceptable salt thereof according to claim 1, wherein $R^1$ is selected from the group consisting of halogen and hydrogen atom.

7. The compound of formula (I) or the tautomer, mesomer, racemate, enantiomer, diastereomer thereof, or mixture thereof, or the pharmaceutically acceptable salt thereof according to claim 1, wherein $R^2$ is a haloalkyl.

8. The compound of formula (I) or the tautomer, mesomer, racemate, enantiomer, diastereomer thereof, or mixture thereof, or the pharmaceutically acceptable salt thereof according to claim 1, wherein $R^3$ is selected from the group consisting of hydrogen atom, cyano, halogen, alkyl, haloalkyl, $NR^{13}C(O)R^{14}$, $C(O)NR^{13}R^{14}$ and $SO_2R^{15}$; $R^{13}$ and $R^{14}$ are identical or different and are each independently selected from the group consisting of hydrogen atom and alkyl; and $R^{15}$ is selected from the group consisting of hydrogen atom and alkyl.

9. The compound of formula (I) or the tautomer, mesomer, racemate, enantiomer, diastereomer thereof, or mixture thereof, or the pharmaceutically acceptable salt thereof according to claim 1, wherein each $R^4$ is identical or different and each is independently selected from the group consisting of hydrogen atom, halogen, alkyl and alkoxy.

10. The compound of formula (I) or the tautomer, mesomer, racemate, enantiomer, diastereomer thereof, or mixture thereof, or the pharmaceutically acceptable salt thereof according to claim 1, wherein Z is selected from the group consisting of a bond, —O—, —O—$CH_2$-and-NH—.

11. The compound of formula (I) or the tautomer, mesomer, racemate, enantiomer, diastereomer thereof, or mixture thereof, or the pharmaceutically acceptable salt thereof according to claim 1, wherein $R^a$ is selected from the group consisting of —$CH_2CH$=$CHC(O)NR^8R^9$, —C(O)CH=$CR^{10}R^{11}$ and —C(O)C=$CR^{12}$;

$R^8$ and $R^9$ are identical or different and are each independently selected from the group consisting of hydrogen atom, alkyl, cycloalkyl and heterocyclyl;

or, $R^8$ and Ro together with the nitrogen atom to which they are attached form a heterocyclyl, wherein the heterocyclyl optionally contains in addition to one nitrogen atom, one to two identical or different heteroatoms selected from the group consisting of N, O and S, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

$R^{10}$ and $R^{11}$ are identical or different and are each independently selected from the group consisting of hydrogen atom and alkyl;

$R^{12}$ is selected from the group consisting of hydrogen atom and alkyl.

12. The compound of formula (I) or the tautomer, mesomer, racemate, enantiomer, diastereomer thereof, or mixture thereof, or the pharmaceutically acceptable salt thereof according to claim 1, wherein $R^a$ is selected from the group consisting of —$CH_2CH$=$CHC(O)N(CH_3)_2$, —$CH_2CH$=$CHC(O)NH(CH_3)$, —$CH_2CH$=$CHC(O)NHC(CH_3)_3$, —C(O)CH=$CH_2$, —C(O)C≡$CCH_3$,

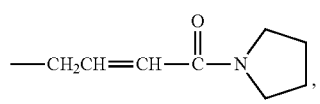,

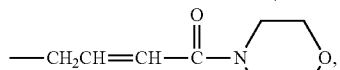,

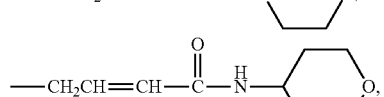,

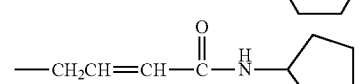,

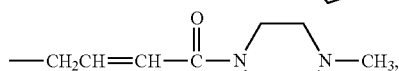,

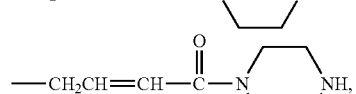,

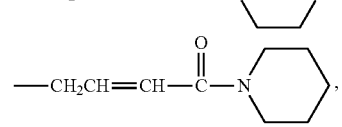,

-continued

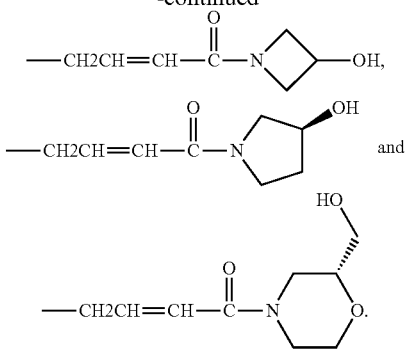

and

13. The compound of formula (I) or the tautomer, mesomer, racemate, enantiomer, diastereomer thereof, or mixture thereof, or the pharmaceutically acceptable salt thereof according to claim 1, selected from the group consisting of:

1

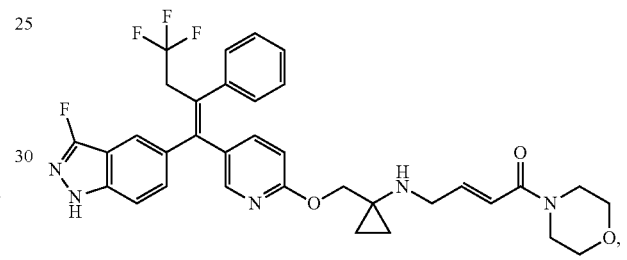

2

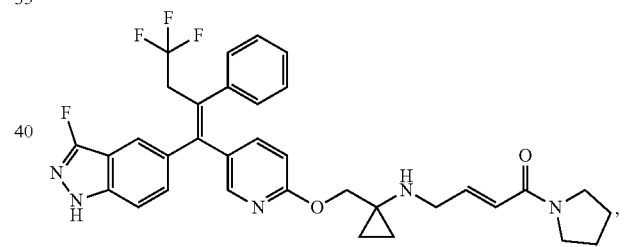

3

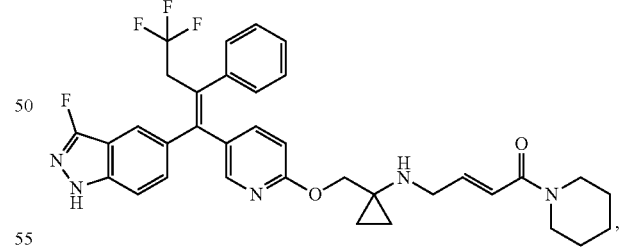

4

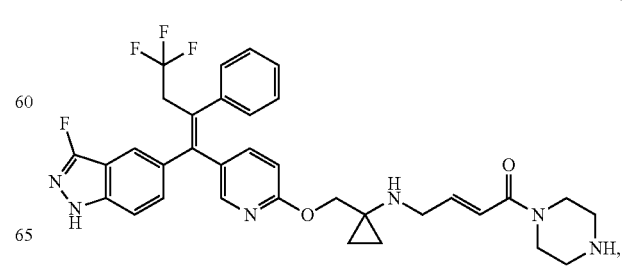

211
-continued
5
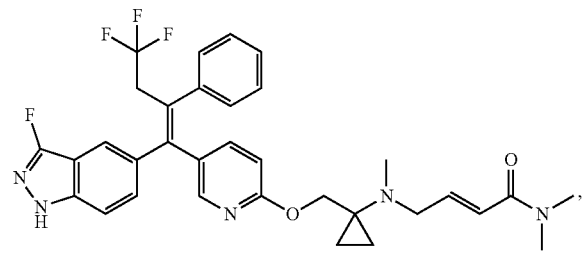
6
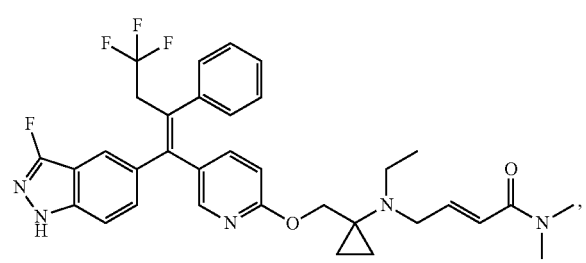
7
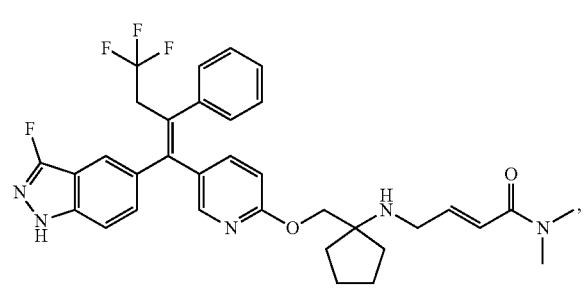
8
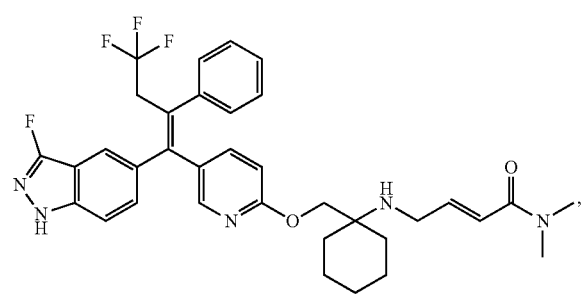
9
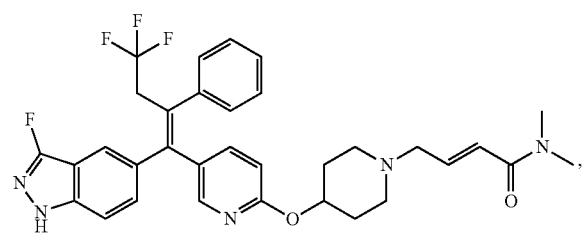
212
-continued
10
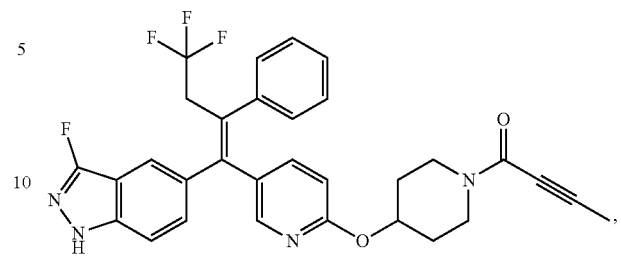
11
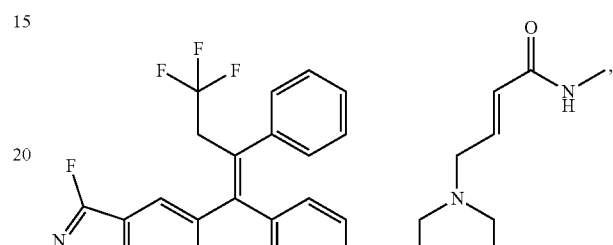
12
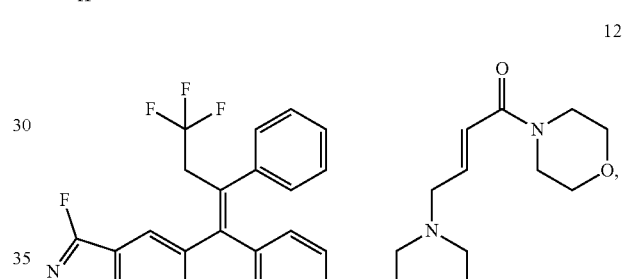
13
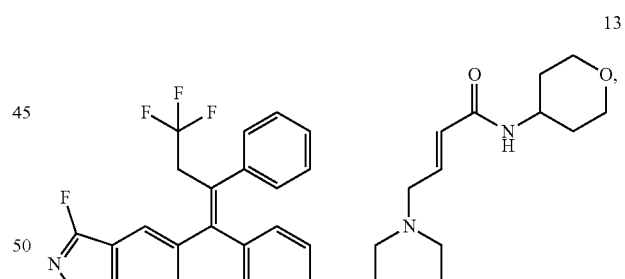
14
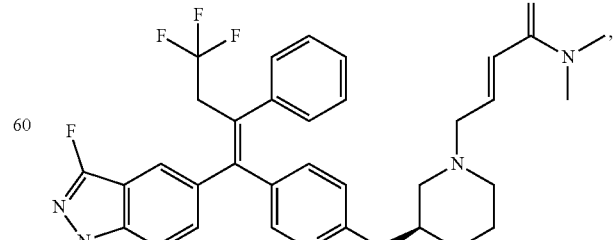

15
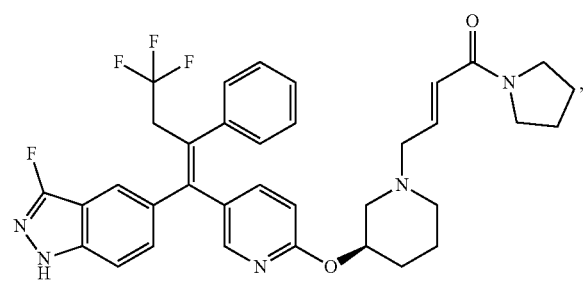
16
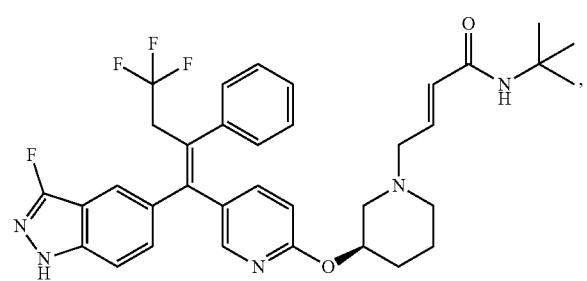
17
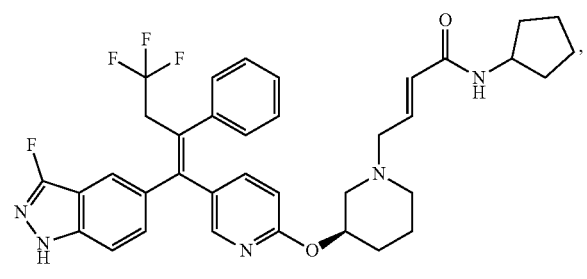
18
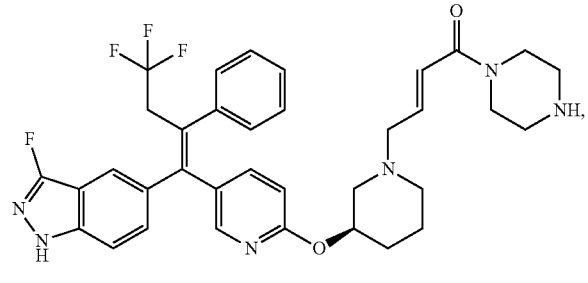
19
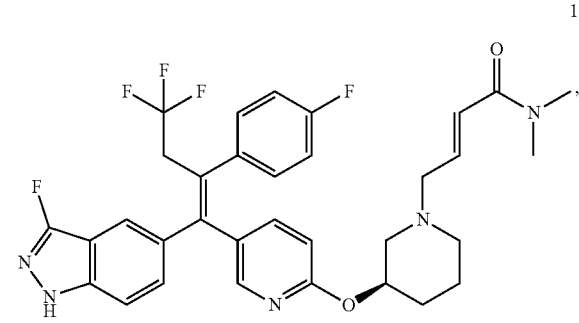
20
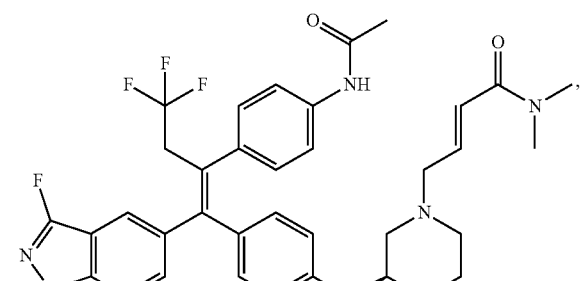
21
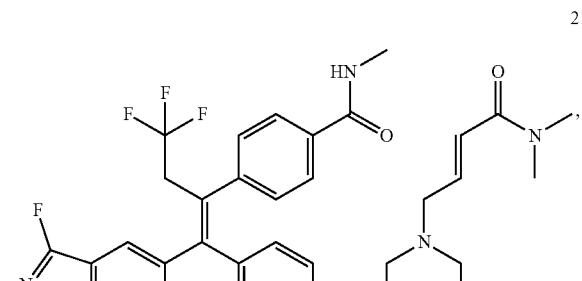
22
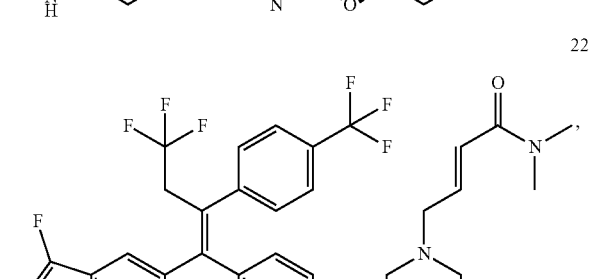
23
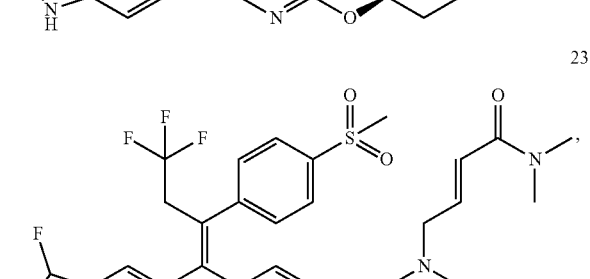
24
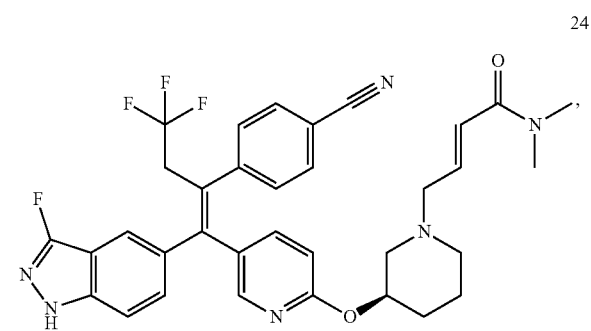

25
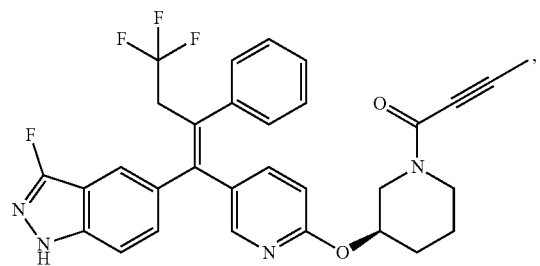
26
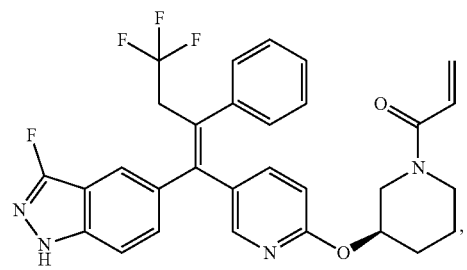
27
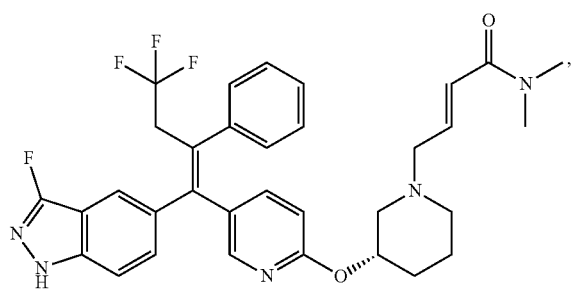
28
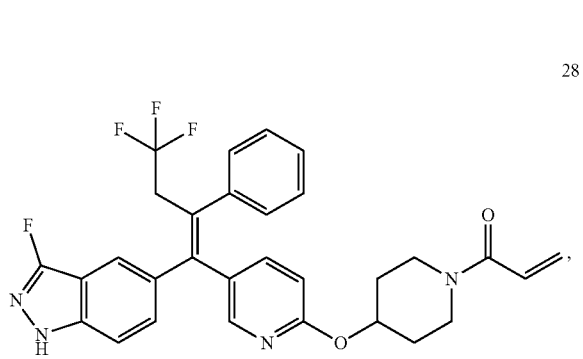
29
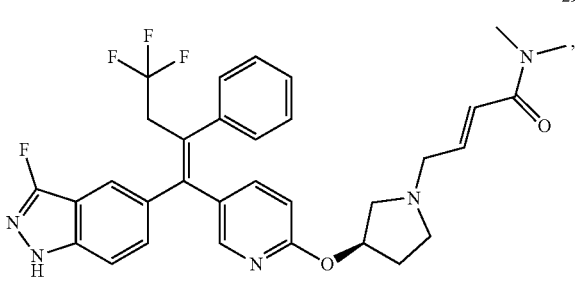
30
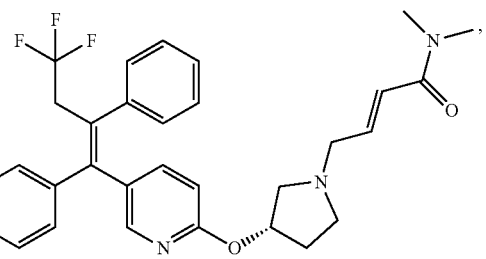
31
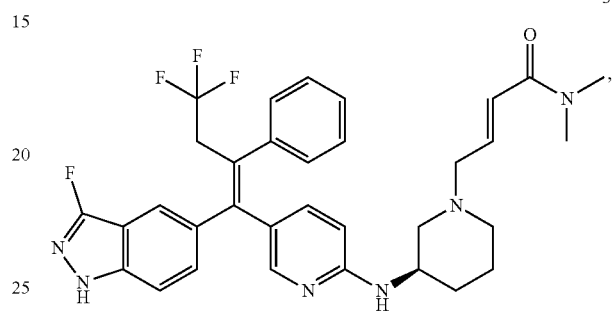
32
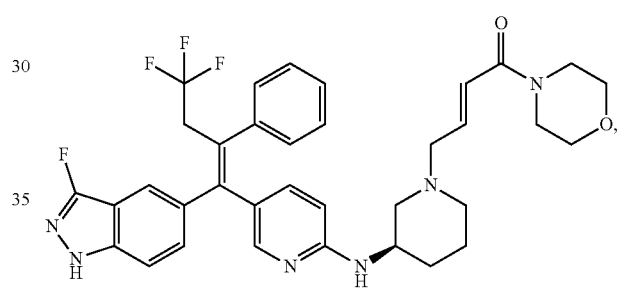
33
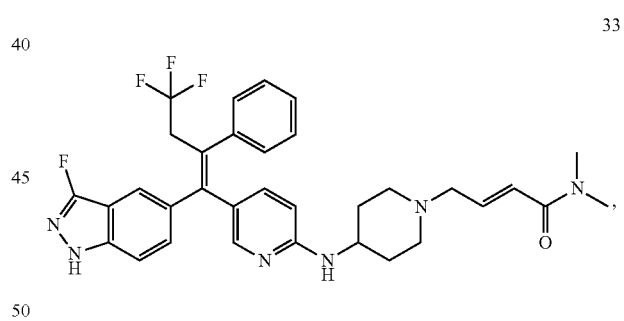
34
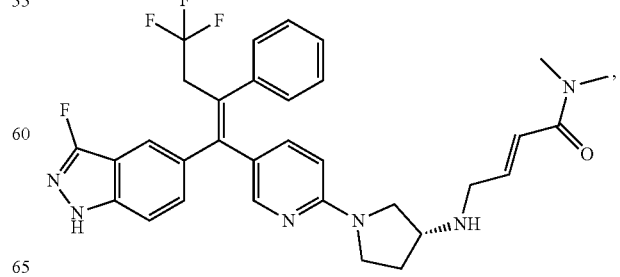

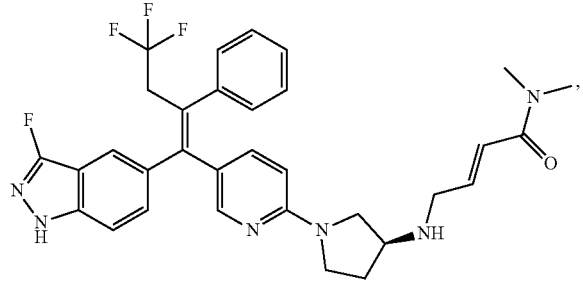

35

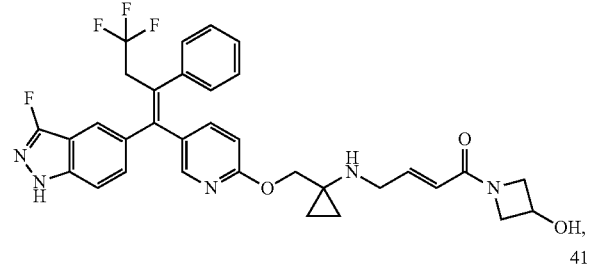

40

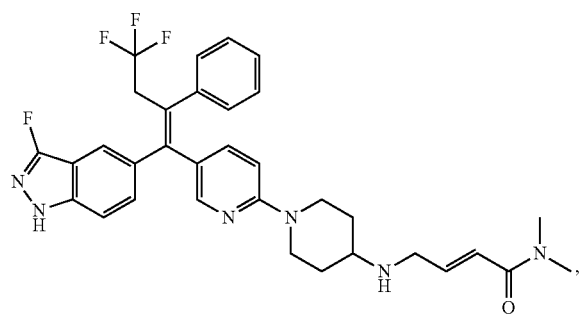

36

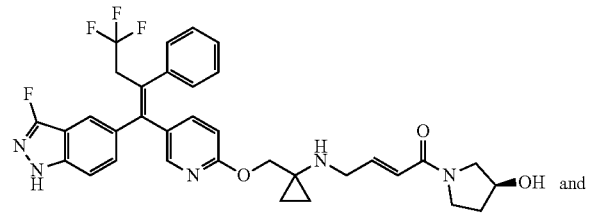

41

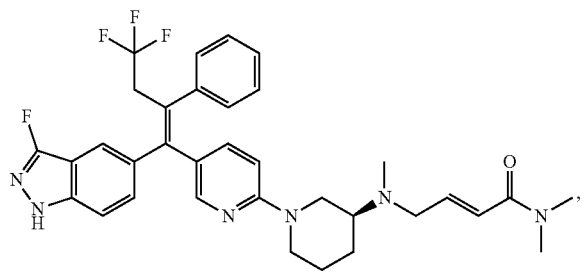

37

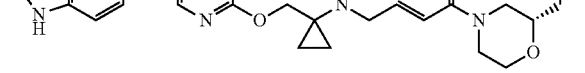

and

42

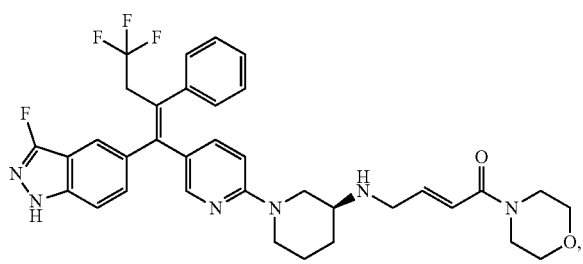

38

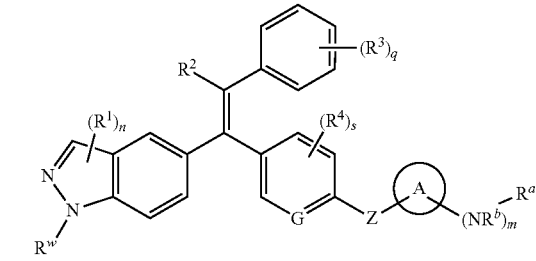

14. A compound of formula (IA) or a tautomer, mesomer, racemate, enantiomer, diastereomer thereof, or mixture thereof, or a pharmaceutically acceptable salt thereof:

(IA)

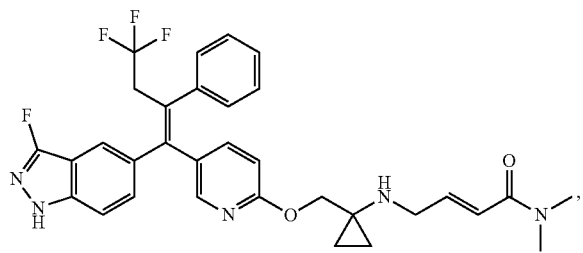

39 wherein:
$R^w$ is an amino protecting group;
R is selected from the group consisting of —CH$_2$CH=CHC(O)NR$^8$R$^9$, —C(O)CH=CR$^{10}$R$^{11}$ and —C(O)C≡CR$^{12}$;
$R^8$ and $R^9$ are identical or different and are each independently selected from the group consisting of hydrogen atom, alkyl, haloalkyl, hydroxyalkyl, cycloalkyl, heterocyclyl, aryl and heteroaryl;
or, $R^8$ and $R^9$ together with the nitrogen atom to which they are attached form a heterocyclyl, wherein the heterocyclyl optionally contains in addition to one nitrogen atom, one to two identical or different heteroatoms selected from the group consisting of N, O and S, and the heterocyclyl is optionally substituted by one or more substituents selected from the group consisting of alkyl, alkoxy, halogen, amino, cyano, nitro, hydroxy, hydroxyalkyl, —COOR$^{16}$, cycloalkyl, heterocyclyl, aryl and heteroaryl;

R$^{10}$ and R$^{11}$ are identical or different and are each independently selected from the group consisting of hydrogen atom, halogen, alkyl, haloalkyl, alkoxy, cyano, amino, nitro, carboxy, formyl, hydroxy, hydroxyalkyl, cycloalkyl, heterocyclyl, aryl and heteroaryl;

R$^{12}$ is selected from the group consisting of hydrogen atom, alkyl, haloalkyl, hydroxyalkyl, cycloalkyl, heterocyclyl, aryl and heteroaryl;

R$^{16}$ is selected from the group consisting of hydrogen atom, alkyl, haloalkyl and hydroxyalkyl;

Ring A is selected from the group consisting of cycloalkyl and heterocyclyl;

G is CH or N;

Z is selected from the group consisting of a bond, CR$^5$R$^6$, —O—(CH$_2$)$_t$— and —NR$^7$—(CH$_2$)$_t$—;

each R$^1$ is identical or different and each is independently selected from the group consisting of hydrogen atom, halogen, alkyl, haloalkyl, hydroxyalkyl, cycloalkyl, heterocyclyl, aryl and heteroaryl;

R$^2$ is selected from the group consisting of hydrogen atom, halogen, alkyl, haloalkyl, alkoxy, amino, cyano, nitro, carboxy, formyl, hydroxy, hydroxyalkyl, cycloalkyl, aryl and heteroaryl;

each R$^3$ is identical or different and each is independently selected from the group consisting of hydrogen atom, halogen, alkyl, haloalkyl, alkoxy, cyano, amino, nitro, carboxy, formyl, hydroxy, hydroxyalkyl, NR$^{13}$C(O)R$^{14}$, C(O)NR$^{13}$R$^{14}$, SO$_2$R$^{15}$, cycloalkyl, heterocyclyl, aryl and heteroaryl;

each R$^4$ is identical or different and each is independently selected from the group consisting of hydrogen atom, halogen, alkyl, haloalkyl, alkoxy, cyano, amino, nitro, carboxy, formyl, hydroxy, hydroxyalkyl, cycloalkyl, heterocyclyl, aryl and heteroaryl;

R$^b$ is selected from the group consisting of hydrogen atom and alkyl;

R$^5$ and R$^6$ are identical or different and are each independently selected from the group consisting of hydrogen atom, halogen, alkyl, haloalkyl, alkoxy, cyano, amino, nitro, carboxy, formyl, hydroxy, hydroxyalkyl, cycloalkyl, heterocyclyl, aryl and heteroaryl;

R$^7$ is selected from the group consisting of hydrogen atom, alkyl, haloalkyl, hydroxyalkyl, cycloalkyl, heterocyclyl, aryl and heteroaryl;

R$^{13}$ and R$^{14}$ are identical or different and are each independently selected from the group consisting of hydrogen atom, halogen, alkyl, haloalkyl, alkoxy, cyano, amino, nitro, carboxy, formyl, hydroxy, hydroxyalkyl, cycloalkyl, heterocyclyl, aryl and heteroaryl;

R$^{15}$ is selected from the group consisting of hydrogen atom, alkyl, haloalkyl, hydroxyalkyl, cycloalkyl, heterocyclyl, aryl and heteroaryl;

m is 0 or 1;

n is 0, 1, 2, or 3;

q is 0, 1, 2, 3, 4 or 5;

s is 0, 1, 2, or 3; and t is 0, 1, 2, 3, 4, 5 or 6.

15. The compound of formula (IA) or the tautomer, mesomer, racemate, enantiomer, diastereomer thereof, or mixture thereof, or the pharmaceutically acceptable salt thereof according to claim 14, selected from the group consisting of:

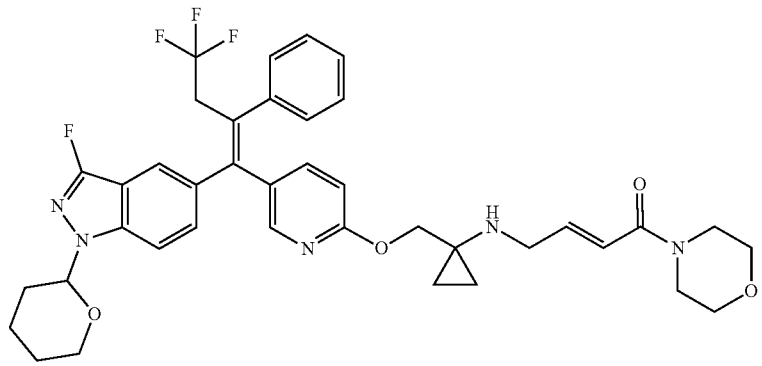

1i

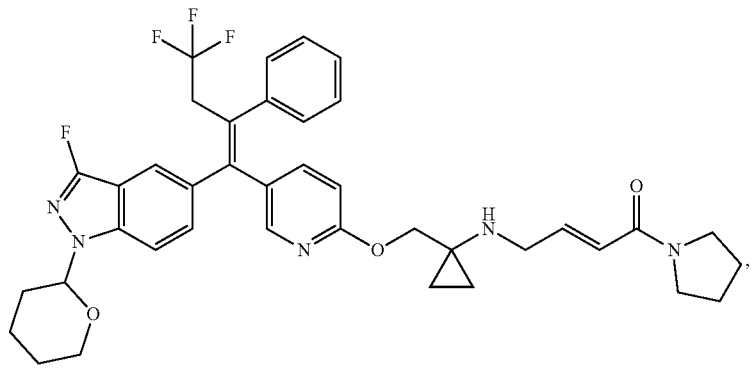

2b 221 222
-continued
3b
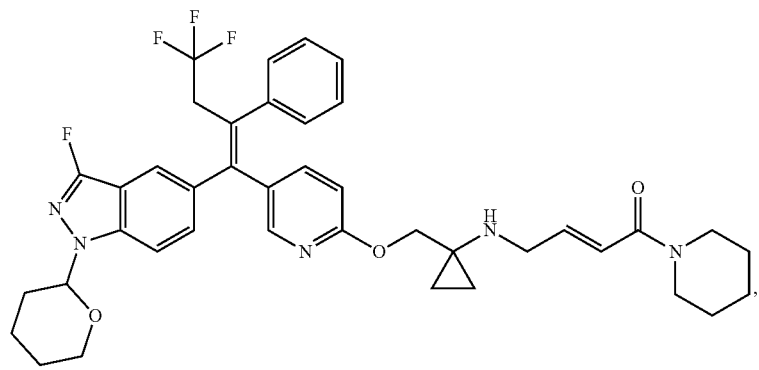
4b
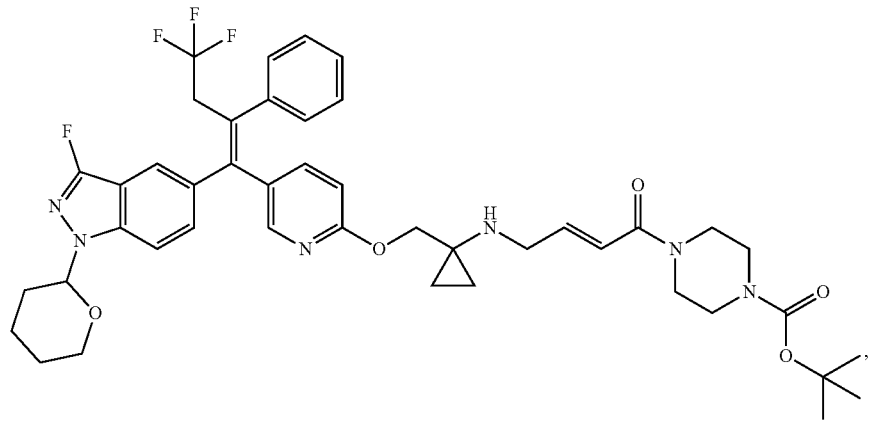
5e
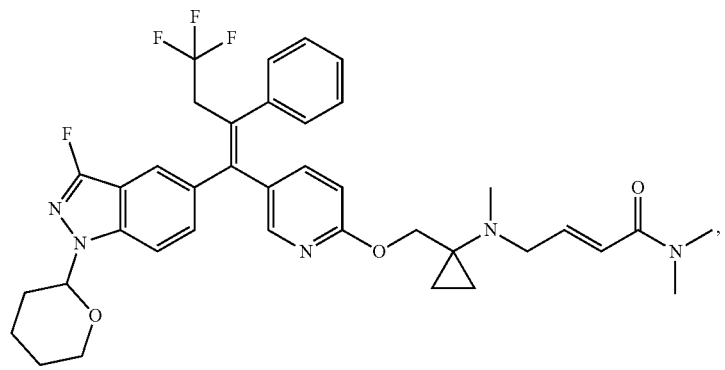
6d
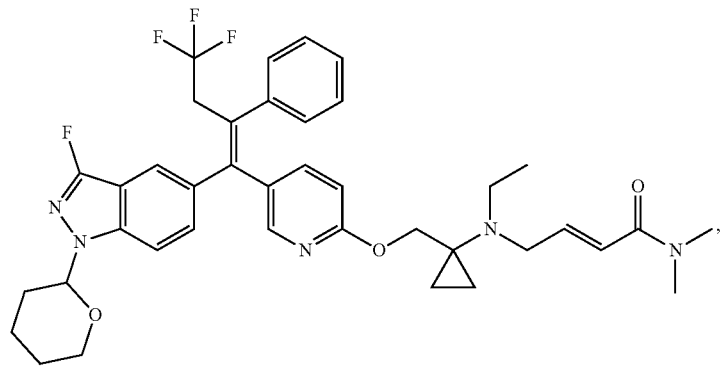

-continued
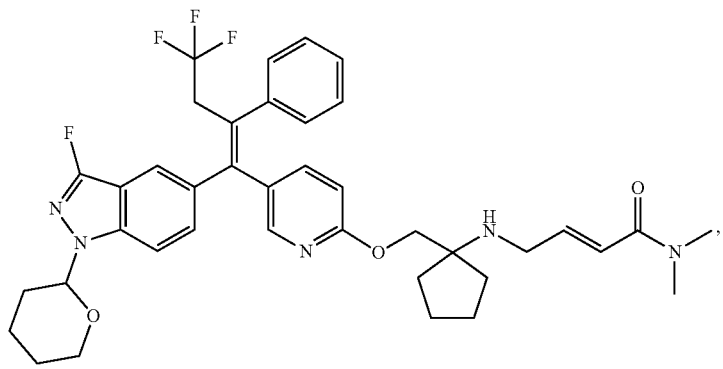
7d
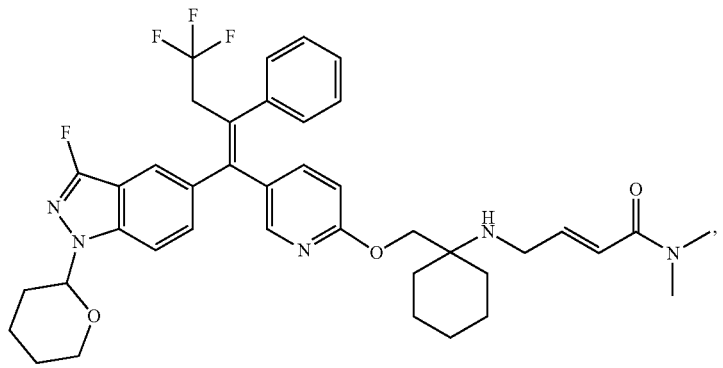
8d
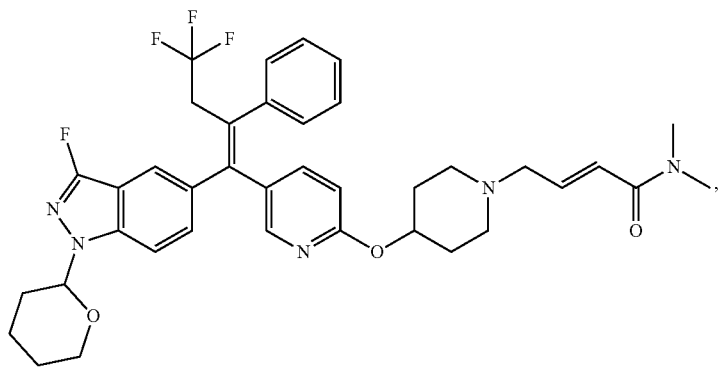
9e
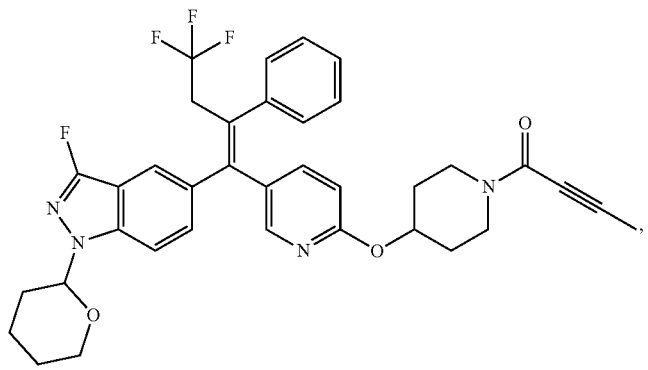
10b

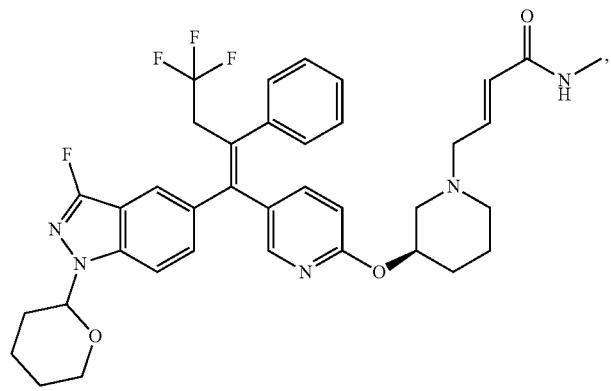
11g
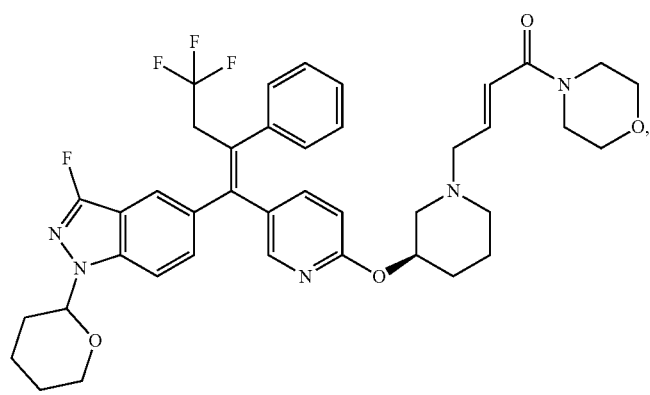
12a
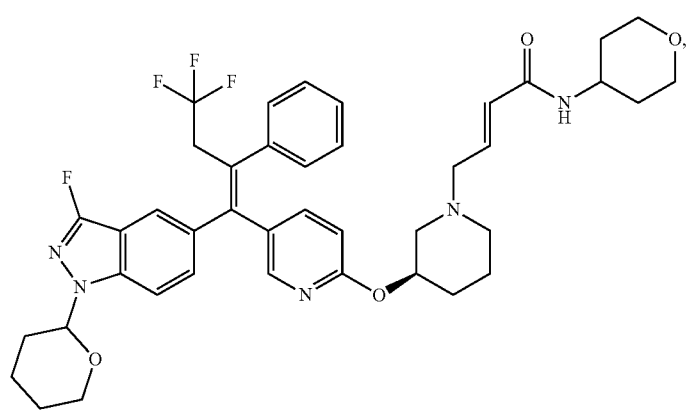
13b
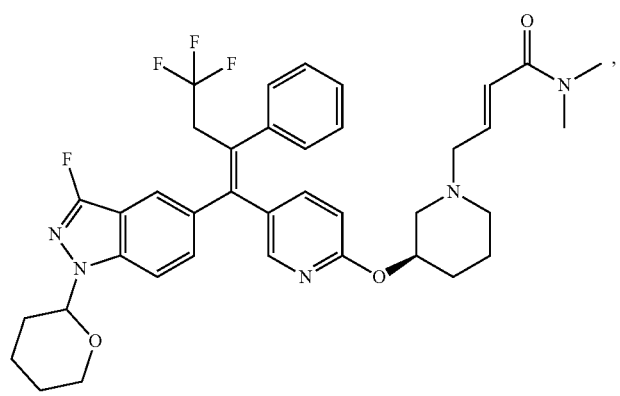
14a

-continued
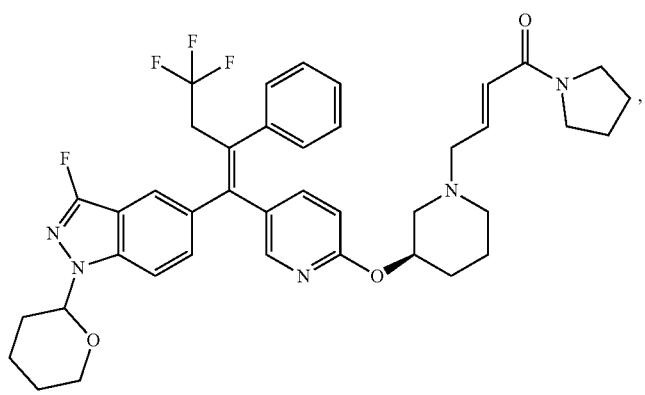
15a
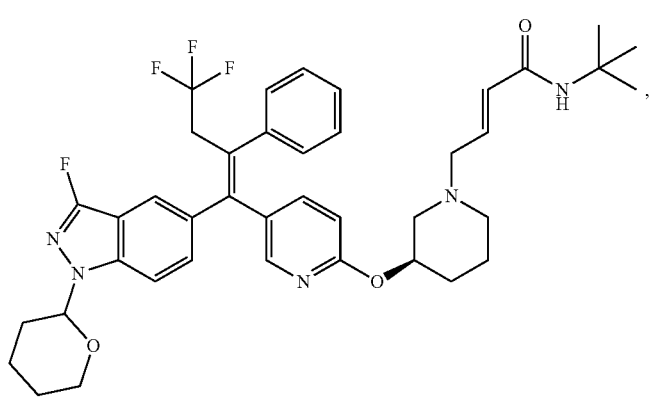
16b
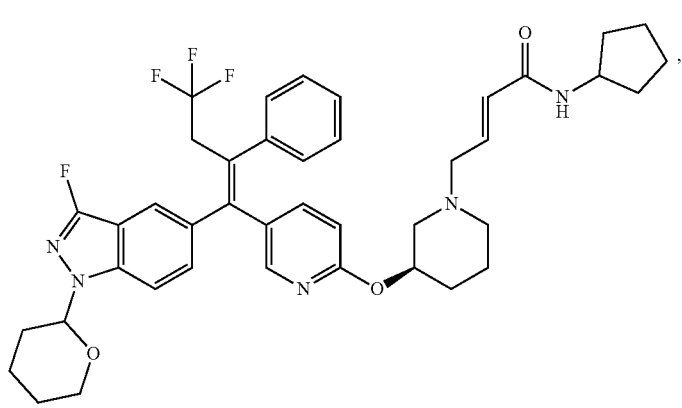
17b

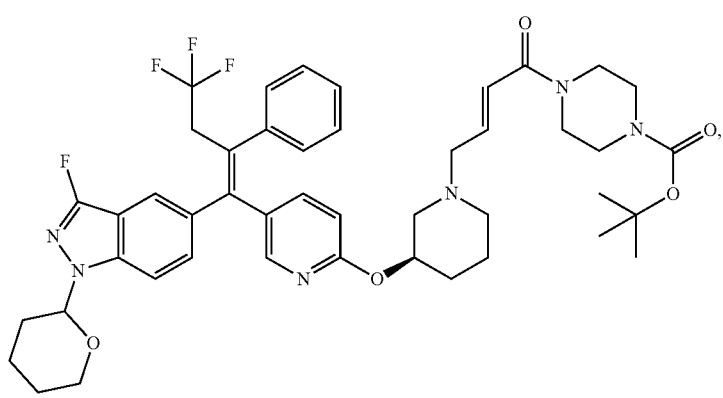
18a
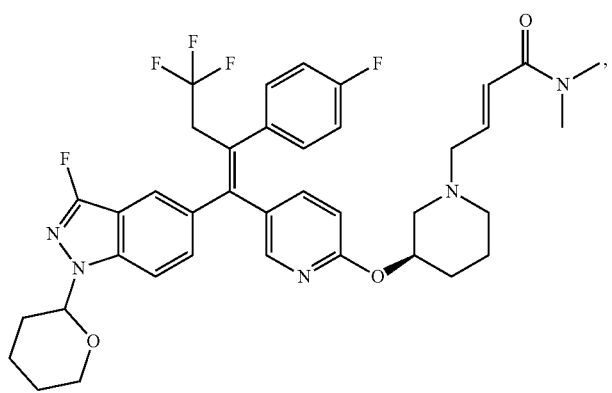
19d
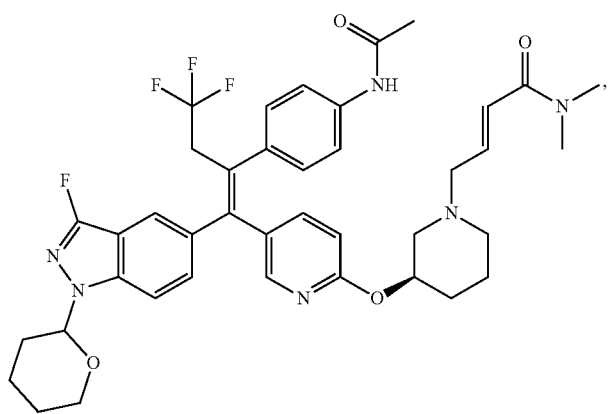
20b

21b
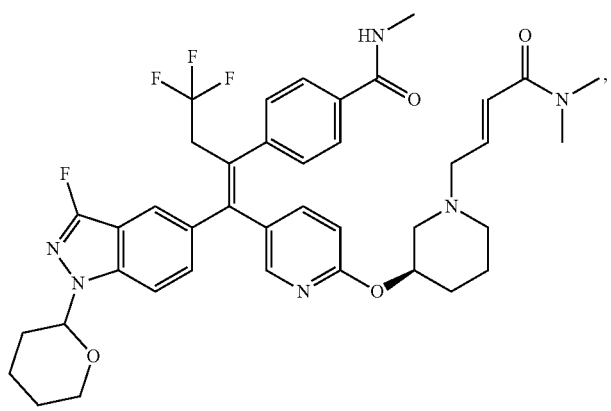
22b
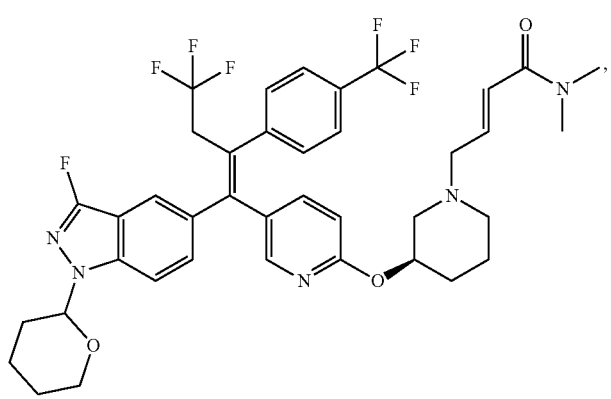
23b
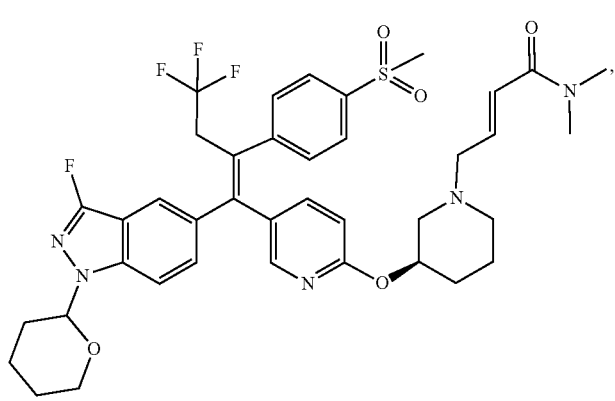
24b
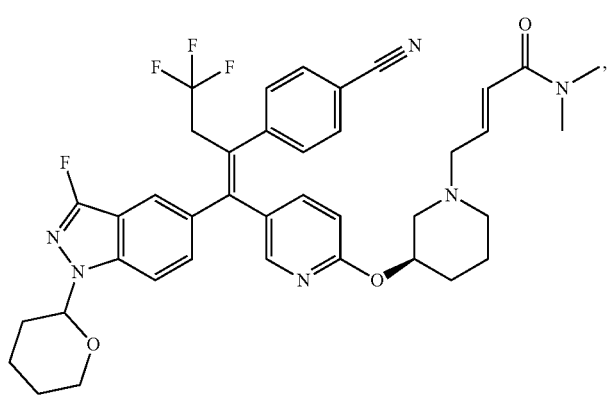

25a
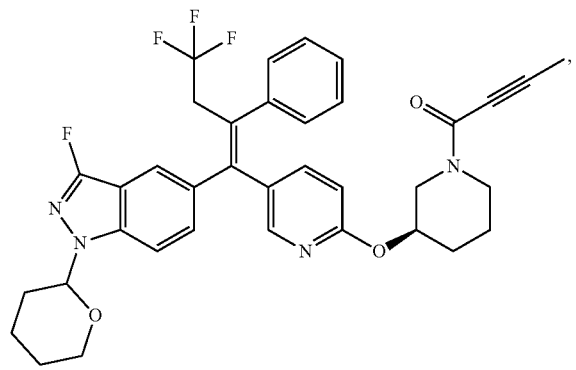
26b
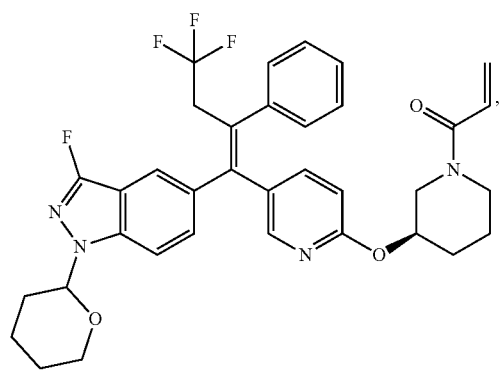
27e
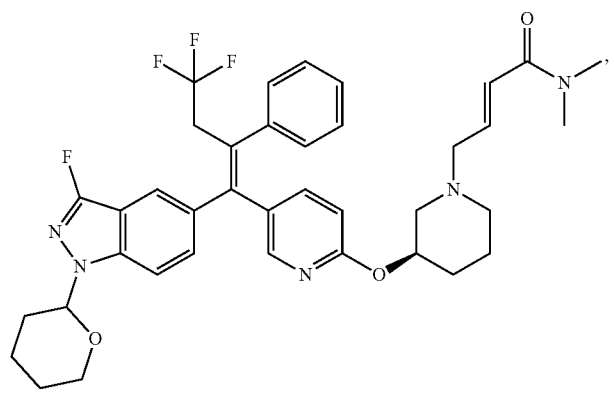
28a
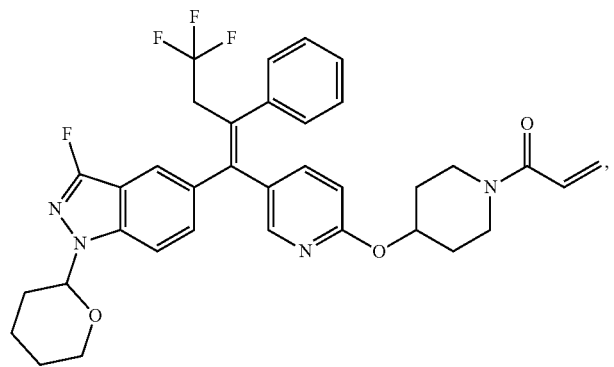

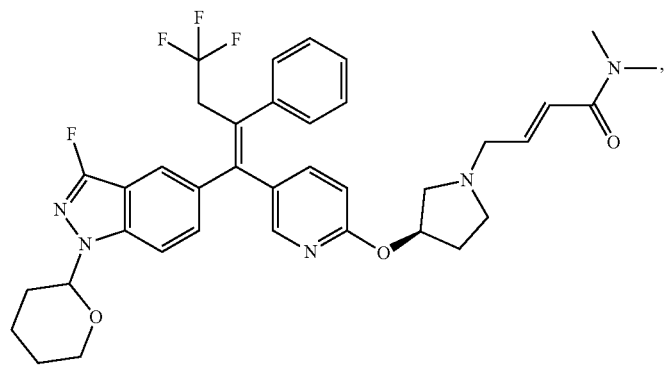
29e
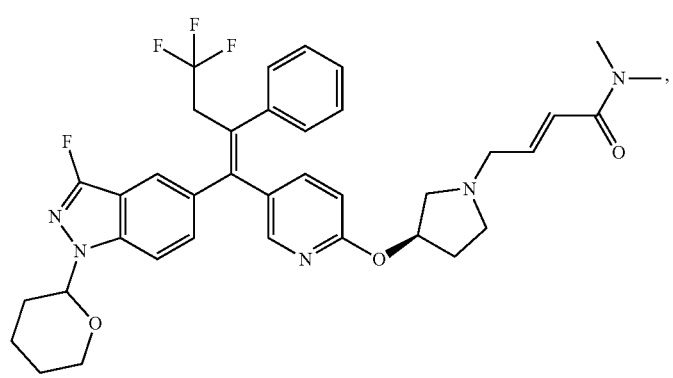
30e
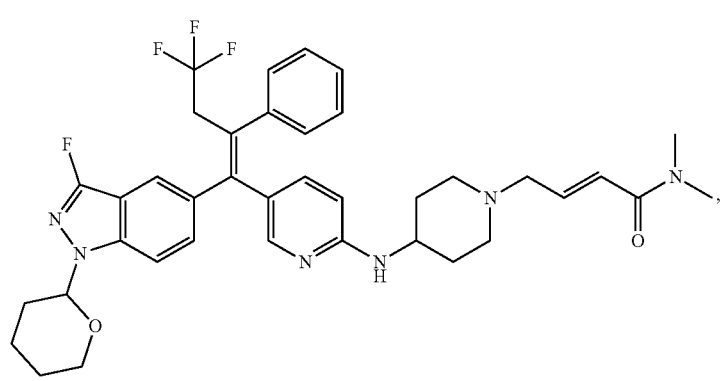
33e
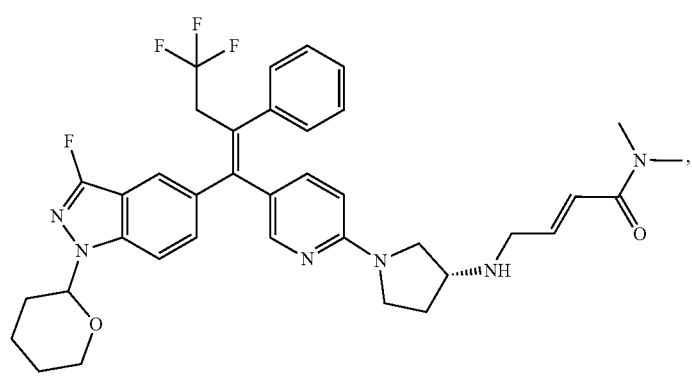
34e

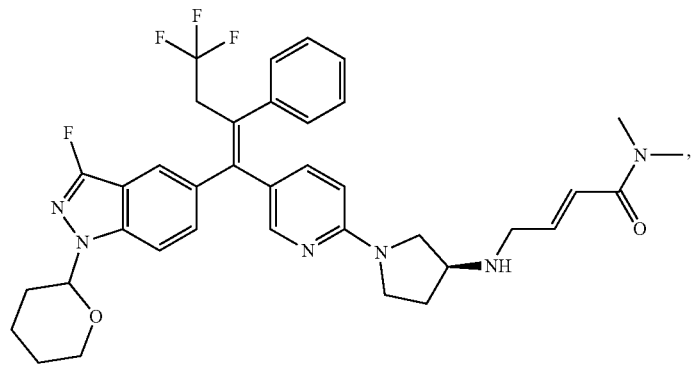
35e
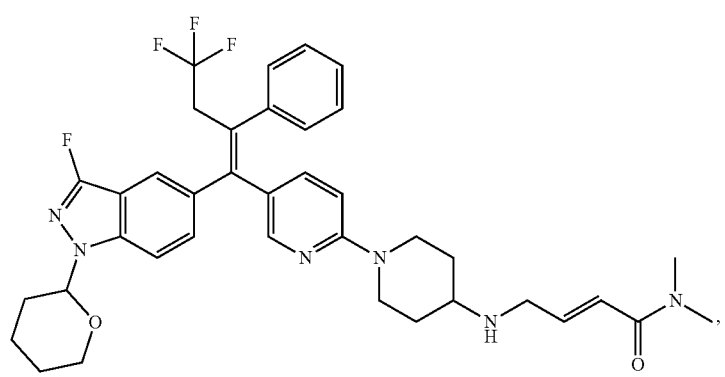
36e
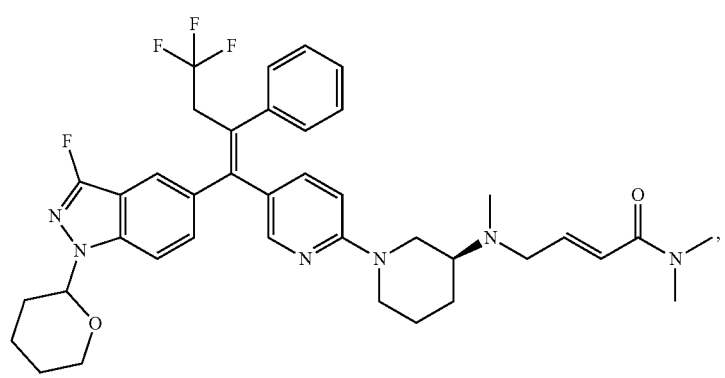
37f
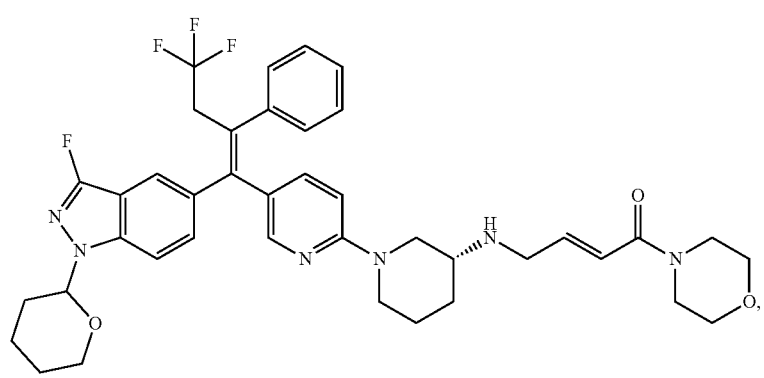
38c

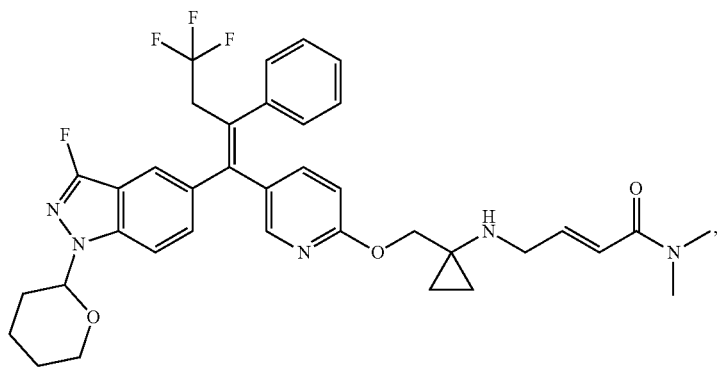
39a
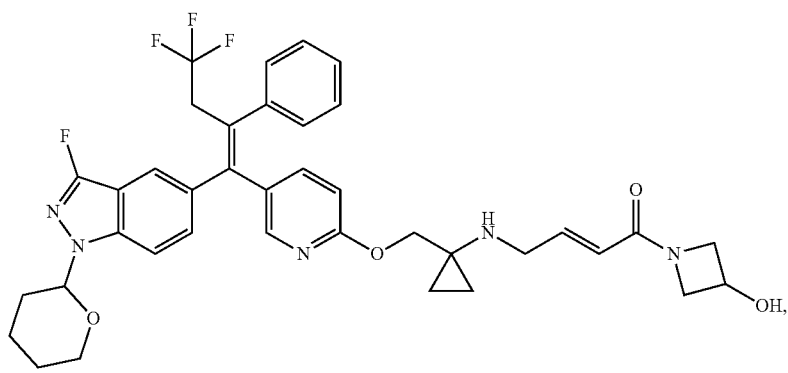
40b
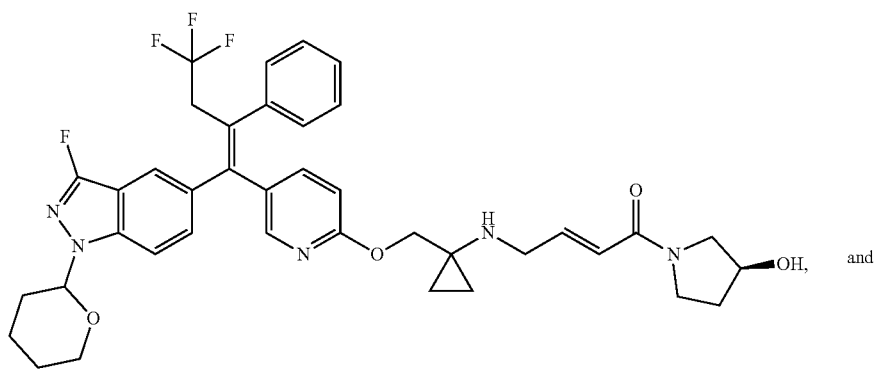
41b
and
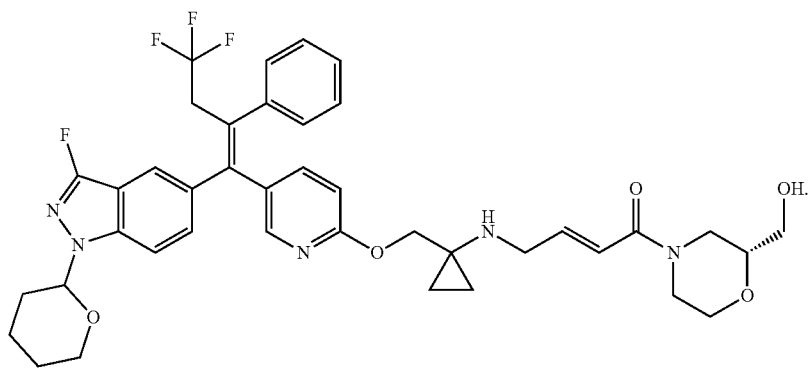
42b

16. A method for preparing the compound of formula (I) or the tautomer, mesomere, racemate, enantiomer, diastereomer thereof, or mixture thereof, or the pharmaceutically acceptable salt thereof according to claim 1, comprising a step of:

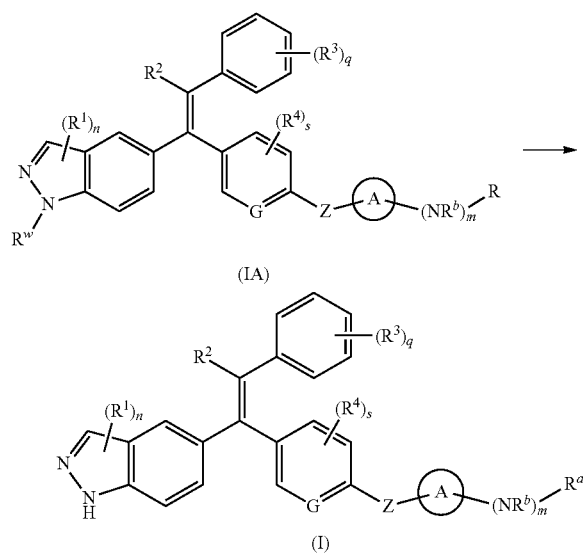

subjecting the compound of formula (IA) or the tautomer, mesomer, racemate, enantiomer, diastereomer thereof, or mixture thereof, or the pharmaceutically acceptable salt thereof to a deprotection reaction under an acidic condition to obtain the compound of formula (I) or the tautomer, mesomer, racemate, enantiomer, diastereomer thereof, or mixture thereof, or the pharmaceutically acceptable salt thereof;

wherein:

$R^w$ is an amino protecting group;

R is selected from the group consisting of —CH$_2$CH=CHC(O)NR$^8$R$^9$, —C(O)CH=CR$^{10}$R$^{11}$ and —C(O)C≡CR$^{12}$;

$R^8$ and $R^9$ are identical or different and are each independently selected from the group consisting of hydrogen atom, alkyl, haloalkyl, hydroxyalkyl, cycloalkyl, heterocyclyl, aryl and heteroaryl;

or, $R^8$ and $R^9$ together with the nitrogen atom to which they are attached form a heterocyclyl, wherein the heterocyclyl optionally contains in addition to one nitrogen atom, one to two identical or different heteroatoms selected from the group consisting of N, O and S, and the heterocyclyl is optionally substituted by one or more substituents selected from the group consisting of alkyl, alkoxy, halogen, amino, cyano, nitro, hydroxy, hydroxyalkyl, —COOR$^{16}$, cycloalkyl, heterocyclyl, aryl and heteroaryl;

$R^{10}$ and $R^{11}$ are identical or different and are each independently selected from the group consisting of hydrogen atom, halogen, alkyl, haloalkyl, alkoxy, cyano, amino, nitro, carboxy, formyl, hydroxy, hydroxyalkyl, cycloalkyl, heterocyclyl, aryl and heteroaryl;

$R^{12}$ is selected from the group consisting of hydrogen atom, alkyl, haloalkyl, hydroxyalkyl, cycloalkyl, heterocyclyl, aryl and heteroaryl;

$R^{16}$ is selected from the group consisting of hydrogen atom, alkyl, haloalkyl and hydroxyalkyl;

ring A, G, Z, $R^1$, $R^2$, $R^3$, $R^4$, $R^a$, $R^b$, n, m, s and q are as defined in claim 1.

17. A pharmaceutical composition, comprising a therapeutically effective amount of the compound of formula (I) or the tautomer, mesomer, racemate, enantiomer, diastereomer thereof, or mixture thereof, or the pharmaceutically acceptable salt thereof according to claim 1, and one or more pharmaceutically acceptable carriers, diluents or excipients.

18. A method of modulating an estrogen receptor in a subject in need thereof, the method comprising: administering to the subject the compound of formula (I), or the tautomer, mesomer, racemate, enantiomer, diastereomer thereof, or mixture thereof, or the pharmaceutically acceptable salt thereof according to claim 1.

19. A method of preventing and/or treating an estrogen receptor-mediated or an estrogen receptor-dependent disease or disorder in a subject in need thereof, the method comprising: administering the compound of formula (I), or the tautomer, mesomer, racemate, enantiomer, diastereomer thereof, or mixture thereof, or the pharmaceutically acceptable salt thereof according to claim 1 to athe subject in need thereof.

20. The method according to claim 19, wherein the estrogen receptor-mediated or the estrogen receptor-dependent disease or disorder is a cancer.

* * * * *